United States Patent
Kridel et al.

(10) Patent No.: US 10,071,076 B2
(45) Date of Patent: Sep. 11, 2018

(54) METHODS OF TREATING CANCER AND OTHER DISORDERS

(71) Applicant: Wake Forest University Health Sciences, Winston-Salem, NC (US)

(72) Inventors: Steven J. Kridel, Clemmons, NC (US); W. Todd Lowther, Pfafftown, NC (US); Herman H. Odens, Ooltewah, TN (US); Jeffrey D. Schmitt, Asheville, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 0 days.

(21) Appl. No.: 15/193,793

(22) Filed: Jun. 27, 2016

(65) Prior Publication Data

US 2016/0317496 A1 Nov. 3, 2016

Related U.S. Application Data

(63) Continuation of application No. 13/988,707, filed as application No. PCT/US2011/059527 on Nov. 7, 2011, now abandoned.

(60) Provisional application No. 61/412,915, filed on Nov. 12, 2010.

(51) Int. Cl.
  *A61K 31/416* (2006.01)
  *A61K 31/42* (2006.01)
  *C07D 231/56* (2006.01)
  *C07D 261/20* (2006.01)

(52) U.S. Cl.
  CPC .......... *A61K 31/416* (2013.01); *A61K 31/42* (2013.01); *C07D 231/56* (2013.01); *C07D 261/20* (2013.01)

(58) Field of Classification Search
  None
  See application file for complete search history.

(56) References Cited

U.S. PATENT DOCUMENTS

| | | |
|---|---|---|
| 6,680,299 B2 | 1/2004 | Or et al. |
| 6,680,322 B2 | 1/2004 | Castelhano et al. |
| 6,680,324 B2 | 1/2004 | Castelhano et al. |
| 2005/0181977 A1 | 8/2005 | Hunter et al. |
| 2009/0061031 A1 | 3/2009 | Lee-Huang et al. |
| 2009/0325877 A1 | 12/2009 | Grunt et al. |
| 2010/0022630 A1 | 1/2010 | Singh et al. |

OTHER PUBLICATIONS

Kridel SJ. Inhibitors of fatty acid synthase for prostate cancer. DTIC Report. May 2010.
Yang W et al. Fatty acid synthase is upregulated during HCV infection and regulates HCV entry and production. Hepatology. Nov. 2008; 48(5): 1396-1403.
Menendez JA et al. Fatty acid synthase: association with insulin resistance, Type 2 diabetes, and cancer. Clinical Chemistry. 2009: 55(3): 425-438.
Sharma S et al. Triclosan as a systemic antibacterial agent in a mouse model of acute bacterial challenge. Antimicrobial Agents and Chemotherapy. Dec. 2003; 47(12) 3859-3866.
International Search Report and Written Opinion, PCT/US2011/059527, dated Mar. 19, 2012.
Dörwald FZ. Side reactions in organic synthesis: A guide to successful synthesis design, Weinheim: Wiley-VCH Verlag GmbH & Co., KGaA, 2005, Preface.
Jordan VC. Tamoxifen: A most unlikely pioneering medicine. Nature Reviews: Drug Discovery. Mar. 2003; 2: 205-213.
Ko JH et al. Synthesis and biological evaluation of 5-arylamino-6-chloro-1H-indazole-4,7-diones as inhibitors of protein kinase B/Akt. Bioorganic & Medicinal Chemistry Letters. 2006; 16: 6001-6005.
Kuhajda FP. Fatty-acid synthase and human cancer: new perspectives on its role in tumor biology. Nutrition. 2000; 16: 202-208.
Hamadi et al. "Synthesis and Evolution of New Isoxazolo-1,4-Quinones of Biologic Interest" *Heterocyclic Communications* 12(6):457-462 (2006) (Abstract Only).
Jeganathan et al. "Selective reactions of azide-substituted α-diazo amides with olefins and alcohols using rhodium(II) catalysts" *The Journal of Organic Chemistry* 51(26):5362-5367 (1986) (Abstract Only).
Katritzky et al. "Rubber Chemicals Derived from Conjugate Addition. II. Synthesis of a Novel Class of Benzoquinone Diimines" *Rubber Chemistry and Technology* 74(5):927-945 (2001).
Kridel, Steven J. "Inhibitors of Fatty Acid Synthase for Prostate Cancer" report written by Wake Forest University under grant from the U.S. Army Medical Research and Materiel Command (44 pages) (report date: May 31, 2010) (made available to the public: May 2011).
Kridel et al. "Inhibitors of Fatty Acid Synthase for Prostate Cancer" report written by Wake Forest University under grant from the U.S. Army Medical Research and Materiel Command (13 pages) (report date: May 1, 2011) (made available to the public: Aug. 2011).

*Primary Examiner* — Kortney L. Klinkel
*Assistant Examiner* — William Y Lee
(74) *Attorney, Agent, or Firm* — Myers Bigel, P.A.

(57) ABSTRACT

Active compounds useful for inhibiting fatty acid synthase in a subject in need thereof are described. The active compounds are, in general, a 5-mercapto-1H-Indazole-4,7-dione or an analog thereof. The compounds are useful for treating subjects afflicted with, cancer, obesity, diabetes, a viral infection, a bacterial infection, a fungal infection, or a protozoal infection.

14 Claims, No Drawings

METHODS OF TREATING CANCER AND OTHER DISORDERS

RELATED APPLICATIONS

This application is a continuation of U.S. patent application Ser. No. 13/988,707, filed Sep. 9, 2013, now pending, which is a 35 U.S.C. § 371 national phase entry of PCT Application PCT/US2011/059527, filed Nov. 7, 2011, and published in English on May 18, 2012, as International Publication No. WO 2012/064632, and which claims the benefit under 35 U.S.C. § 119(e) of U.S. Provisional Patent Application No. 61/412,915, filed Nov. 12, 2010, the disclosure of each of which is incorporated herein by reference in its entirety.

GOVERNMENT SUPPORT

This invention was made with government support under grant numbers W81XWH-09-1-0204 and W81XWH-05-1-0065 awarded by the Department of Defense (DOD) and CA114104 awarded by the National Institutes of Health (NIH). The government has certain rights in the invention.

FIELD OF THE INVENTION

The present invention concerns methods of treatment, and compounds and compositions useful for carrying out such methods.

SUMMARY OF THE INVENTION

A first aspect of the present invention is a method of inhibiting fatty acid synthase in a subject in need thereof, comprising administering to said subject an active compound as described herein in a treatment-effective amount. Examples of subjects in need thereof include, but are not limited to, subjects afflicted with cancer, obesity, diabetes, viral infection, bacterial infection, fungal infection or protozoal infection.

A second aspect of the present invention is the use of an active compound as described herein for the preparation of a medicament for carrying out a method as described herein, such as for treating cancer, obesity, diabetes, viral infection, bacterial infection, fungal infection or protozoal infection.

A third aspect of the present invention is the use of an active compound as described herein for carrying out a method as described herein, such as for treating cancer, obesity, diabetes, viral infection, bacterial infection, fungal infection or protozoal infection.

A further aspect of the present invention is the use of an active compound, as described herein, in combination with one or more known medicaments to achieve additive or synergistic activity for treating cancer, obesity, diabetes, viral infection, bacterial infection, fungal infection or protozoal infection.

The foregoing and other objects and aspects of the present invention are explained in greater detail in the specification set forth below.

DETAILED DESCRIPTION OF PREFERRED EMBODIMENTS

The present invention is primarily concerned with the treatment of human subjects, but the invention may also be carried out on animal subjects, particularly mammalian subjects such as dogs, cats, livestock and horses for veterinary purposes. Human subjects may be male or female subjects and may be any age, including neonate, infant, juvenile, adolescent, adult, and geriatric subjects.

"Treat" as used herein refers to any type of treatment that imparts a benefit to a patient, particularly delaying or retarding the progression of the disease.

"Pharmaceutically acceptable" as used herein means that the compound or composition is suitable for administration to a subject to achieve the treatments described herein, without unduly deleterious side effects in light of the severity of the disease and necessity of the treatment.

"Concurrently" as used herein means sufficiently close in time to produce a combined effect (that is, concurrently may be simultaneously, or it may be two or more events occurring within a short time period before or after each other).

"Cancer" as used herein includes, but is not limited to, any cancers exhibiting elevated levels of fatty acid synthase as in epithelial cancers; the term "cancer" includes also breast cancer, lung cancer, prostate cancer, ovarian cancer, colon or colorectal cancer, liver cancer, skin cancer such as melanoma, brain cancer such as astrocytoma, pancreatic cancer, leukemia, lymphoma, etc.

"Diabetes" as used herein includes type I and type II diabetes.

"Bacterial infection" as used herein refers to any undesired infection of a subject with a gram negative or gram positive bacteria. Particular examples are infections by those bacteria set forth below.

"Gram-negative" bacteria are those that do not retain crystal violet dye after an alcohol wash in the Gram staining protocol. This is due to structural properties in the cell walls of the bacteria. Many genera and species of Gram-negative bacteria are pathogenic. Gram-negative bacteria include members of the phylum proteobacteria, which include genus members *Escherichia, Salmonella, Vibrio*, and *Helicobacter*. Examples of genera of biofilm-forming bacteria include, but are not limited to, *Pseudomonas, Bordetella, Vibrio, Haemophilus, Halomonas*, and *Acinetobacter*. Other genera include *Klebsiella, Proteus, Neisseria, Helicobacter, Brucella, Legionella, Campylobacter, Francisella, Pasteurella, Yersinia, Bartonella, Bacteroides, Streptobacillus, Spirillum, Moraxella* and *Shigella*. Examples of species of bacteria include *Pseudomonas aeuroginosa, Bordetella pertussis, Vibrio vulnificus, Haemophilus influenzae*, and *Halomonas pacifica*.

Gram-negative bacteria of the *Acinetobacter* genus belong to the phylum Gammaproteobacteria, order Pseudomonadalas, and family Moraxellaceae. Genus members include, but are not limited to, *Acinetobacter bumanni, Acinetobacter haemolyticus*, and *Acinetobacter lwoffi*. Various nosocomial infections that are especially prevalent in intensive care units implicate *Acinetobacter* species such as *Acinetobacter baumannii* and *Acinetobacter lwoffi*. *Acinetobacter baumanni* is a frequent cause of nosocomial pneumonia, and can also cause skin and wound infections and bacteremia. *Acinetobacter lwoffi* causes meningitis. The *Acinetobacter* species are resistant to many classes of antibiotics.

Examples of Gram-positive bacteria include, but are not limited to, bacteria of the genera *Listeria, Staphylococcus, Streptococcus, Bacillus, Corynebacterium, Peptostreptococcus*, and *Clostridium*. Species include, but not limited to, *Listeria monocytogenes, Staphylococcus aureus, Streptococcus pyogenes, Streptococcus pneumoniae, Bacillus cereus, Bacillus anthracis, Clostridium botulinum, Clostridium perfringens, Clostridium difficile, Clostridium tetani, Corynebacterium diphtheriae, Corynebacterium* ulcerans, and *Peptostreptococcus anaerobius*. Other bacterial genera include, but are not limited to, *Actinomyces, Propionibacterium, Nocardia* and *Streptomyces*. *Staphylococcus aureus* is a common cause of nosocomial infections, often found in post-surgical wound infections. *Staphylococcus aureus* can also cause a variety of other infections in humans (e.g., skin infections), as well as contribute to mastitis in dairy cows. Methicillin-resistant *Staphylococcus aureaus* (MRSA), in particular, is especially difficult to treat due to multiple drug resistances, including penicillins and cephalosporins. MRSA has become problematic in hospital settings, particularly among the more susceptible patients with open wounds, invasive devices, weakened immune systems, etc.

"Fungal infection" as used herein refers to any undesired infection of a subject with fungal cells, including but not limited to infections with *Aspergillus, Candida, Cryptococcus, Coccidioides, Tinea, Sporothrix, Blastomyces, Histoplasma, Pneumocystis* and *Saccharomyces*. Additionally, fungal cells include, but is not limited to, *Aspergillus fumigatus, Aspergillus flavus, Aspergillus niger, Aspergillus terreus, Aspergillus nidulans, Candida albicans, Coccidioides immitis, Cryptococcus neoformans, Tinea unguium, Tinea corporis, Tinea cruris, Sporothrix schenckii, Blastomyces dermatitidis, Histoplasma capsulatum, Histoplasma duboisii,* and *Saccharomyces cerevisiae.*

"Protozoal infection" as used herein refers to any undesired infection of a subject with protozoal cells, including but not limited to infection with *Leishmania, Kokzidioa, Trypanosoma, Chlamydia,* and *Rickettsia,* and more particularly infection with *Histoplasma capsulatum, Entamoeba histolytica, Trichomonas tenas, Trichomonas hominis, Trichomonas vaginalis, Trypanosoma gambiense, Trypanosoma rhodesiense, Trypanosoma cruzi, Leishmania donovani, Leishmania tropica, Leishmania braziliensis, Pneumocystis pneumonia, Enterobius vermicularis, Trichuris trichiura, Ascaris lumbricoides, Trichinella spiralis, Strongyloides stercoralis, Schistosoma japonicum, Schistosoma mansoni, Schistosoma haematobium,* etc.

"Viral infection" as used herein includes but is not limited to such as severe acute respiratory syndrome; coronavirus infection; influenza infection; SARS virus infection; an orthomyxovirus-coronavirus hybrid infection; Hepatitis C infection, RSV infection, etc.

"Obesity" as used herein refers not only to morbid obesity but any undesired elevation in weight or associated condition which may be the subject of medical treatment. (see, e.g., Sylvia Lee-Huang et al., US Patent Application No. 20090061031 (Mar. 5, 2009). Thus the treatment of obesity as described herein includes methods of treating, controlling or preventing obesity, or of reducing body weight, or of inhibiting fat accumulation, or of promoting fat burning and energy uncoupling in vivo, or of treating, controlling or preventing the onset of one or more obesity-related disorders or conditions, comprising administering an active agent as described herein. Obesity-related disorders or conditions that may be treated by the methods of the present invention include, but are not limited to, coronary artery disease, hypertension, stroke, peripheral vascular disease, insulin resistance, glucose intolerance, diabetes mellitus, hyperglycemia, hyperlipidemia, hypercholesteremia, hypertriglyceridemia, hyperinsulinemia, atherosclerosis, cellular proliferation and endothelial dysfunction, diabetic dyslipidemia, HIV-related lipodystrophy and metabolic syndrome, type II diabetes, diabetic complications including diabetic neuropathy, nephropathy, retinopathy or cataracts, heart failure, inflammation, thrombosis, congestive heart failure, any other asthmatic or pulmonary disease related to obesity and any other viral infection, infection related diseases and any other cardiovascular disease related to obesity or an overweight condition.

"Alkyl" as used herein alone or as part of another group, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. Alkyl groups as used herein may be lower alkyl. "Lower alkyl" as used herein, is a subset of alkyl, in some embodiments preferred, and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like.

The term "akyl" or "loweralkyl" is intended to include both substituted and unsubstituted alkyl or loweralkyl unless otherwise indicated and these groups may be substituted with groups selected from halo (e.g., haloalkyl), alkyl, haloalkyl, alkenyl, alkynyl, cycloalkyl, cycloalkylalkyl, aryl, arylalkyl, heterocyclo, heterocycloalkyl, hydroxyl, alkoxy (thereby creating a polyalkoxy such as polyethylene glycol), alkenyloxy, alkynyloxy, haloalkoxy, cycloalkoxy, cycloalkylalkyloxy, aryloxy, arylalkyloxy, heterocylooxy, heterocylolalkyloxy, mercapto, alkyl-$S(O)_m$, haloalkyl-$S(O)_m$, alkenyl-$S(O)_m$, alkynyl-$S(O)_m$, cycloalkyl-$S(O)_m$, cycloalkylalkyl-$S(O)_m$, aryl-$S(O)_m$, arylalkyl-$S(O)_m$, heterocyclo-$S(O)_m$, heterocycloalkyl-$S(O)_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Alkenyl" as used herein alone or as part of another group, refers to a straight or branched chain hydrocarbon containing from 1 to 10 carbon atoms (or in loweralkenyl 1 to 4 carbon atoms) which include 1 to 4 double bonds in the normal chain. Representative examples of alkenyl include, but are not limited to, vinyl, 2-propenyl, 3-butenyl, 2-butenyl, 4-pentenyl, 3-pentenyl, 2-hexenyl, 3-hexenyl, 2,4-heptadiene, and the like. The term "alkenyl" or "loweralkenyl" is intended to include both substituted and unsubstituted alkenyl or loweralkenyl unless otherwise indicated and these groups may be substituted with groups as described in connection with alkyl and loweralkyl above.

"Alkynyl" as used herein alone or as part of another group, refers to a straight or branched chain hydrocarbon containing from 1 to 10 carbon atoms (or in loweralkynyl 1 to 4 carbon atoms) which include 1 triple bond in the normal chain Representative examples of alkynyl include, but are not limited to, 2-propynyl, 3-butynyl, 2-butynyl, 4-pentynyl, 3-pentynyl, and the like. The term "alkynyl" or "loweralkynyl" is intended to include both substituted and unsubstituted alkynyl or loweralknynyl unless otherwise indicated and these groups may be substituted with the same groups as set forth in connection with alkyl and loweralkyl above.

"Cycloalkyl" as used herein alone or as part of another group, refers to a saturated or partially unsaturated cyclic hydrocarbon group containing from 3, 4 or 5 to 6, 7 or 8 carbons (which carbons may be replaced in a heterocyclic group as discussed below). Representative examples of cycloalkyl include, cyclopropyl, cyclobutyl, cyclopentyl, cyclohexyl, cycloheptyl, and cyclooctyl. These rings may be optionally substituted with additional substituents as described herein such as halo or loweralkyl. The term "cycloalkyl" is generic and intended to include heterocyclic groups as discussed below unless specified otherwise.

"Heterocyclic group" or "heterocyclo" as used herein alone or as part of another group, refers to an aliphatic (e.g., fully or partially saturated heterocyclo) or aromatic (e.g., heteroaryl) monocyclic- or a bicyclic-ring system. Monocyclic ring systems are exemplified by any 5 or 6 membered ring containing 1, 2, 3, or 4 heteroatoms independently selected from oxygen, nitrogen and sulfur. The 5 membered ring has from 0-2 double bonds and the 6 membered ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, thiopyranopyridine, and the like. These rings include quaternized derivatives thereof and may be optionally substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Aryl" as used herein alone or as part of another group, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like. The term "aryl" is intended to include both substituted and unsubstituted aryl unless otherwise indicated and these groups may be substituted with the same groups as set forth in connection with alkyl and loweralkyl above.

"Arylalkyl" as used herein alone or as part of another group, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

"Heteroaryl" as used herein is as described in connection with heterocyclo above.

"Alkoxy" as used herein alone or as part of another group, refers to an alkyl or loweralkyl group, as defined herein (and thus including substituted versions such as polyalkoxy), appended to the parent molecular moiety through an oxy group, —O—. Representative examples of alkoxy include, but are not limited to, methoxy, ethoxy, propoxy, 2-propoxy, butoxy, tert-butoxy, pentyloxy, hexyloxy and the like.

"Halo" as used herein refers to any suitable halogen, including —F, —Cl, —Br, and —I.

"Mercapto" as used herein refers to an —SH group.

"Azido" as used herein refers to an —N$_3$ group.

"Cyano" as used herein refers to a —CN group.

"Formyl" as used herein refers to a —C(O)H group.

"Carboxylic acid" as used herein refers to a —C(O)OH group.

"Hydroxyl" as used herein refers to an —OH group.

"Nitro" as used herein refers to an —NO$_2$ group.

"Acyl" as used herein alone or as part of another group refers to a —C(O)R radical, where R is any suitable substituent such as aryl, alkyl, alkenyl, alkynyl, cycloalkyl or other suitable substituent as described herein.

"Alkylthio" as used herein alone or as part of another group, refers to an alkyl group, as defined herein, appended to the parent molecular moiety through a thio or mercapto moiety, as defined herein. Representative examples of alkylthio include, but are not limited, methylthio, ethylthio, tert-butylthio, hexylthio, and the like.

"Amino" as used herein means the radical —NH$_2$.

"Alkylamino" as used herein alone or as part of another group means the radical —NHR, where R is an alkyl group.

"Arylalkylamino" as used herein alone or as part of another group means the radical —NHR, where R is an arylalkyl group.

"Disubstituted-amino" as used herein alone or as part of another group means the radical —NR$_a$R$_b$, where R$_a$ and R$_b$ are independently selected from the groups alkyl, haloalkyl, alkenyl, alkynyl, cycloalkyl, cycloalkylalkyl, aryl, arylalkyl, heterocyclo, heterocycloalkyl.

"Acylamino" as used herein alone or as part of another group means the radical —NR$_a$R$_b$, where R$_a$ is an acyl group as defined herein and R$_b$ is selected from the groups hydrogen, alkyl, haloalkyl, alkenyl, alkynyl, cycloalkyl, cycloalkylalkyl, aryl, arylalkyl, heterocyclo, heterocycloalkyl.

"Acyloxy" as used herein alone or as part of another group means the radical —OR, where R is an acyl group as defined herein.

"Ester" as used herein alone or as part of another group refers to a —C(O)OR radical, where R is any suitable substituent such as alkyl, cycloalkyl, alkenyl, alkynyl or aryl.

"Amide" as used herein alone or as part of another group refers to a —C(O)NR$_a$R$_b$ radical, where R$_a$ and R$_b$ are any suitable substituent such as alkyl, cycloalkyl, alkenyl, alkynyl or aryl.

"Sulfoxyl" as used herein refers to a compound of the formula —S(O)R, where R is any suitable substituent such as alkyl, cycloalkyl, alkenyl, alkynyl or aryl.

"Sulfonyl" as used herein refers to a compound of the formula —S(O)(O)R, where R is any suitable substituent such as alkyl, cycloalkyl, alkenyl, alkynyl or aryl.

"Sulfonate" as used herein refers to a compound of the formula —S(O)(O)OR, where R is any suitable substituent such as alkyl, cycloalkyl, alkenyl, alkynyl or aryl.

"Sulfonic acid" as used herein refers to a compound of the formula —S(O)(O)OH.

"Sulfonamide" as used herein alone or as part of another group refers to a —S(O)$_2$NR$_a$R$_b$ radical, where R$_a$ and R$_b$ are any suitable substituent such as H, alkyl, cycloalkyl, alkenyl, alkynyl or aryl.

"Thio" and "mercapto" as used herein refers to a compound of the formula —SR, where R is any suitable substituent such as alkyl, cycloalkyl, alkenyl, alkynyl or aryl.

"Urea" as used herein alone or as part of another group refers to an N(R$_c$)C(O)NR$_a$R$_b$ radical, where R$_a$, R$_b$ and R$_c$ are any suitable substituent such as H, alkyl, cycloalkyl, alkenyl, alkynyl or aryl.

"Alkoxyacylamino" as used herein alone or as part of another group refers to an —N(R$_a$)C(O)OR$_b$ radical, where R$_a$, R$_b$ are any suitable substituent such as H, alkyl, cycloalkyl, alkenyl, alkynyl or aryl.

"Aminoacyloxy" as used herein alone or as part of another group refers to an —OC(O)NR$_a$R$_b$ radical, where R$_a$ and R$_b$ are any suitable substituent such as H, alkyl, cycloalkyl, alkenyl, alkynyl or aryl.

1. Active Compounds.

Active compounds of the present invention are, in general, fatty acid synthase (FASN) inhibitors and analogs thereof, particularly compounds that bind specifically or stereospecifically to the thioesterase domain of mammalian (e.g., human) FASN. Examples of such compounds include compounds of Formula Ia, Ib and Ic:

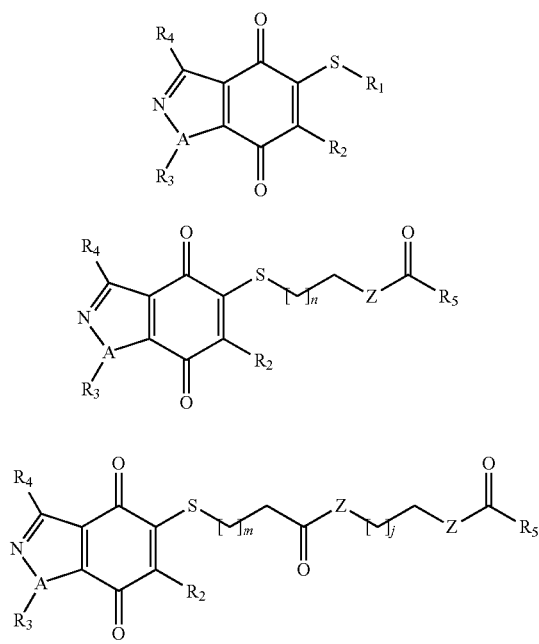

where:
each Z is independently selected from the group consisting of N, O, S and CH$_2$;
A is O (then R$_3$ is null) or N
n=1-5; m=1-5; j=1-4
E is N, CH or CH$_2$;
R$_1$, R$_2$, R$_3$, R$_4$, and R$_5$ individually can represent H, lower straight-chain alkyl (e.g. alkyl groups containing one to ten carbon atoms, such as methyl, ethyl or hexyl) or branched chain lower alkyl, aromatic (e.g. phenyl, naphthyl) substituted aromatic, heteroaromatic (e.g., pyridyl, pyrimidinyl, pyrazole, imidizole, triazole, oxazole, isoxazole, thiazole, isothiazole, oxadiazole, thiadiazole, pyridazine, triazine, indole, indazole, benzoisoxazole, benzoxazole, benzoisothiazole, benzothiazole), substituted heteroaromatic, benzyl, substituted benzyl.

R$_1$, R$_2$, R$_3$, R$_4$, and R$_5$ individually can also represent —(CH$_2$)$_n$—Ar, where n is preferably 1 to 3 and Ar is aromatic, substituted aromatic, heteroaromatic or substituted heteroaromatic. A and B individually can also represent —OR, —SR, —NR$_2$ (where R individually represents H, straight chain or branched chain lower alkoxy, aromatic, substituted aromatic, heteroaromatic, substituted heteroaromatic), halogen, aldehyde, carboxylic acid, —COOR, —CONHR, —CONR$_2$, —OCONHR, —OCONR$_2$, —NCONHR, —NCONR$_2$, —SCONR$_2$.

R$_1$, R$_2$, R$_3$, R$_4$, and R$_5$ can also be individually selected from —(CH$_2$)$_n$—R', (where R' individually represents H, straight chain or branched chain lower alkoxy, aromatic, substituted aromatic, heteroaromatic, substituted heteroaromatic, halogen, aldehyde, carboxylic acid, —COOR, —CONHR, —CONR$_2$, —OCONHR, —OCONR$_2$, —NCONHR, —NCONR$_2$, —SCONR$_2$ (where R individually represents H, straight chain or branched chain lower alkoxy, aromatic, substituted aromatic, heteroaromatic, substituted heteroaromatic).

In some embodiments, R$_1$, R$_2$, R$_3$, R$_4$, and R$_5$ are each independently selected from the group consisting of: H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, and aminoacyloxy.

In other embodiments R$_1$, R$_2$, R$_3$, R$_4$, and R$_5$ can also be pantetheine or a pantetheine derivative; examples include, but are not limited to the foregoing examples in formulas IIa, IIb and IIc:

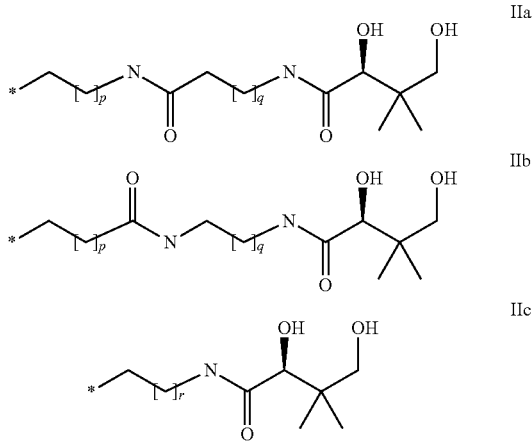

where:
p=1-5; m=0-5; r=1-8;
the asterisk to left of the structures above denotes the attachment point.

Particular examples of active compounds of the present invention include, but are not limited to, those set forth in the following Table 1, and pharmaceutically acceptable salts or prodrugs thereof.
TABLE 1
Example Active Compounds
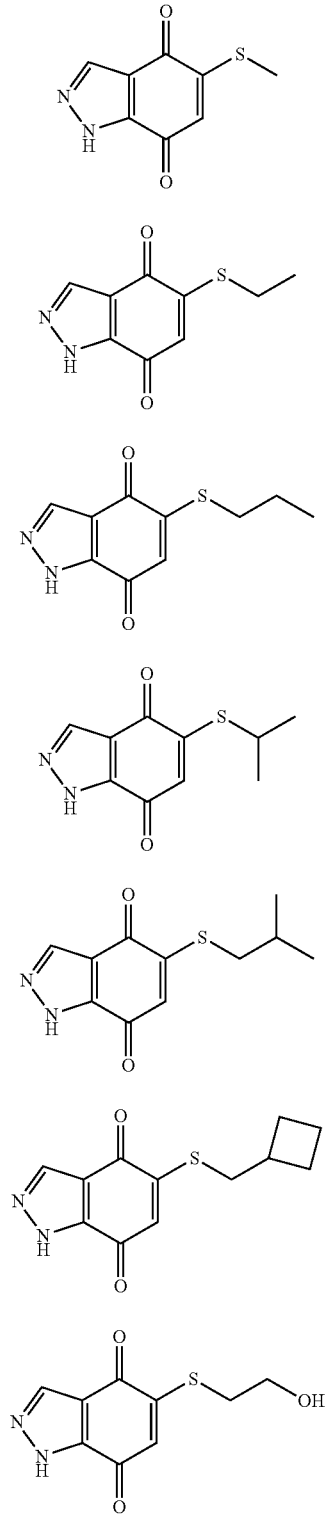
TABLE 1-continued
Example Active Compounds
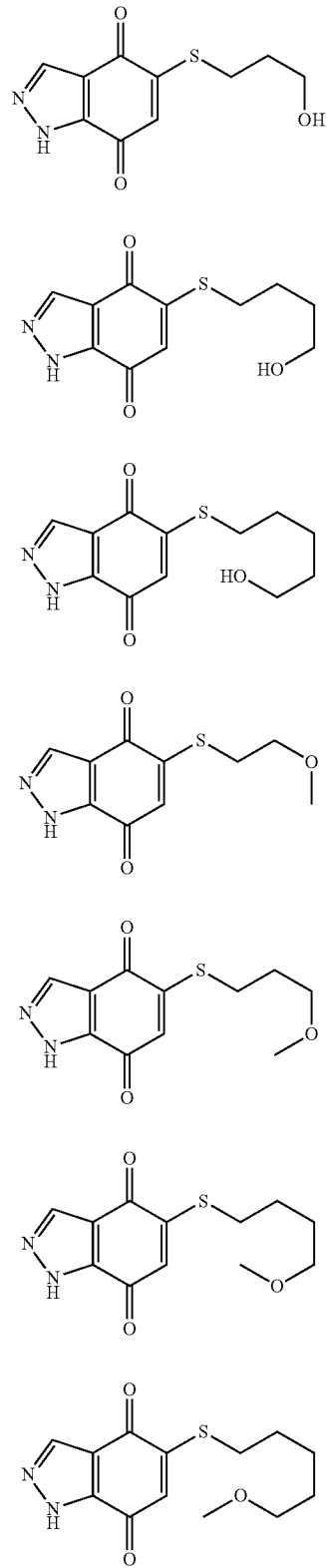

TABLE 1-continued
Example Active Compounds
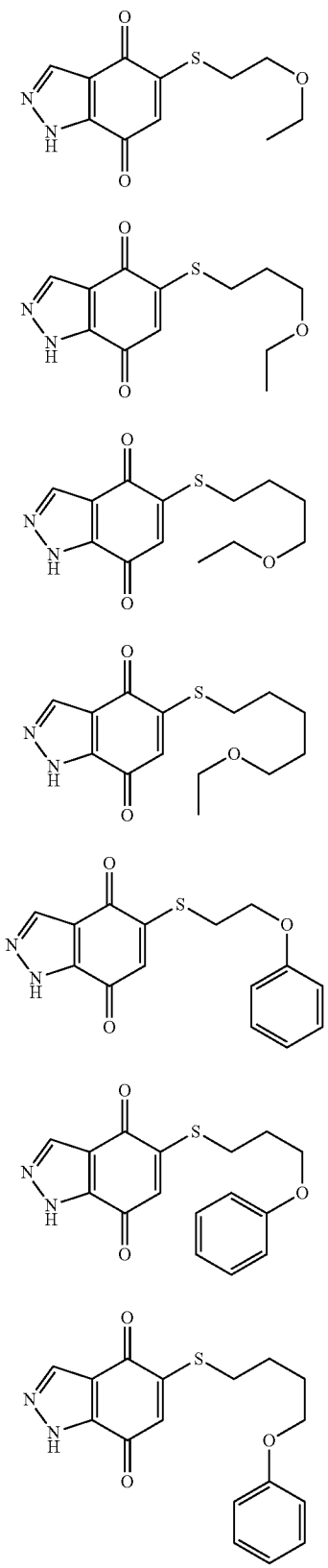
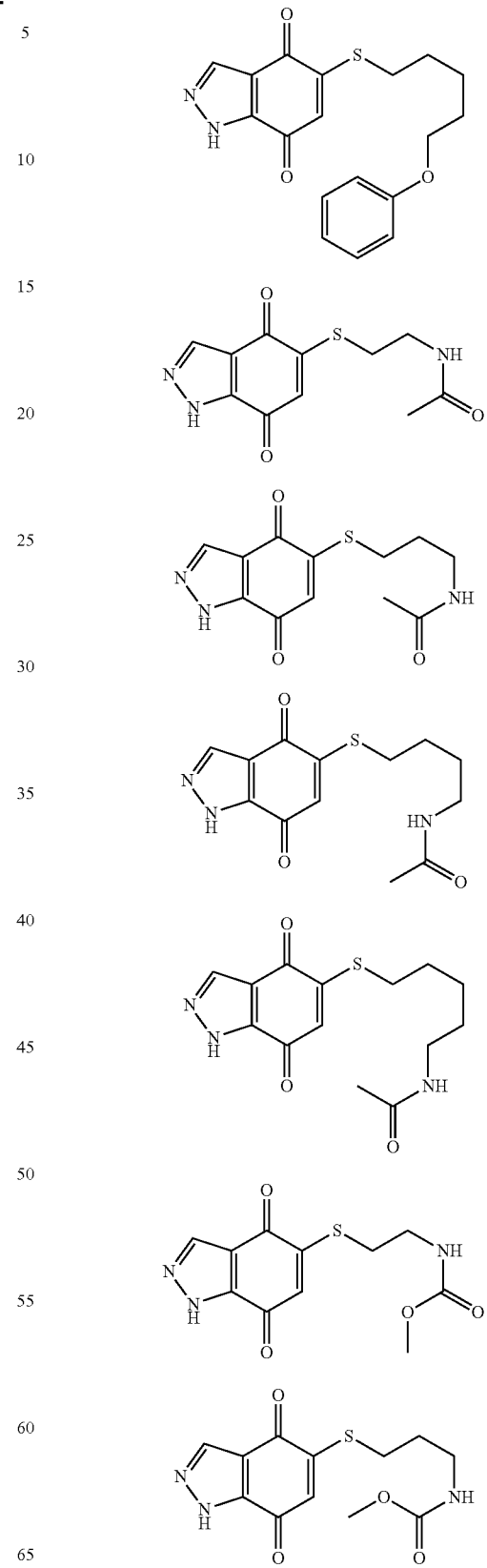

TABLE 1-continued
Example Active Compounds
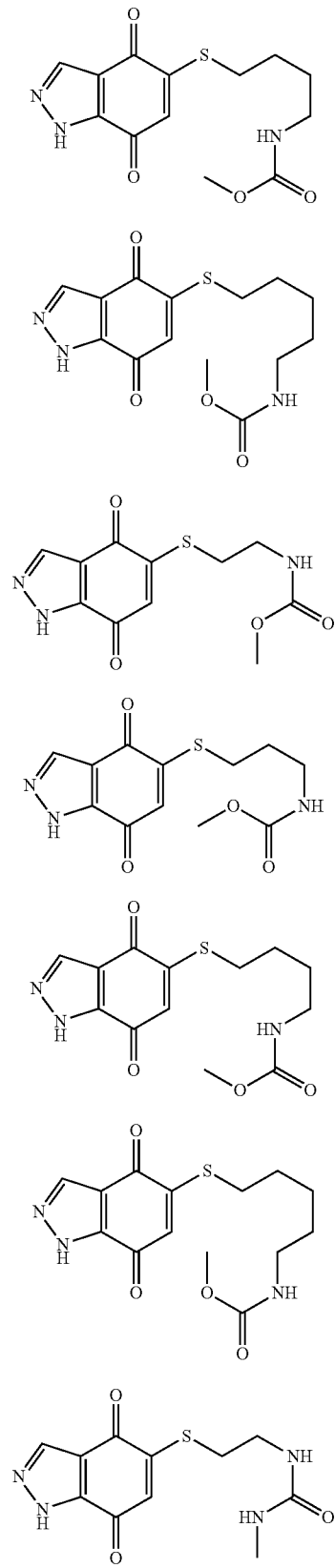
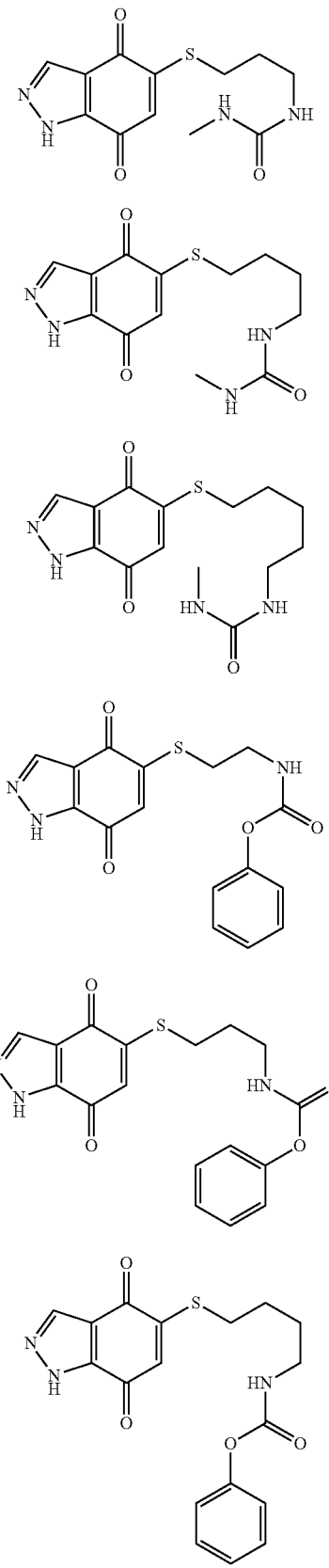

TABLE 1-continued
Example Active Compounds
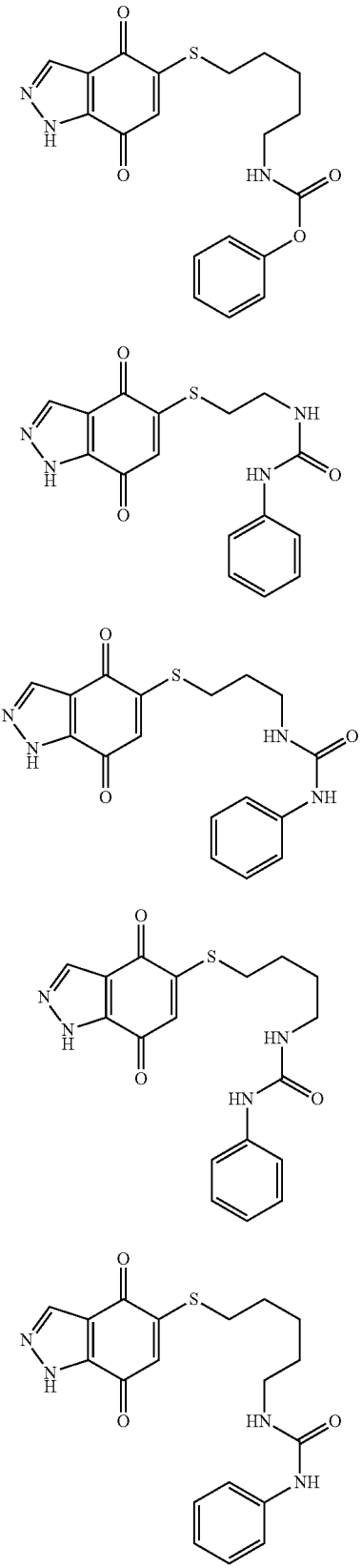
TABLE 1-continued
Example Active Compounds
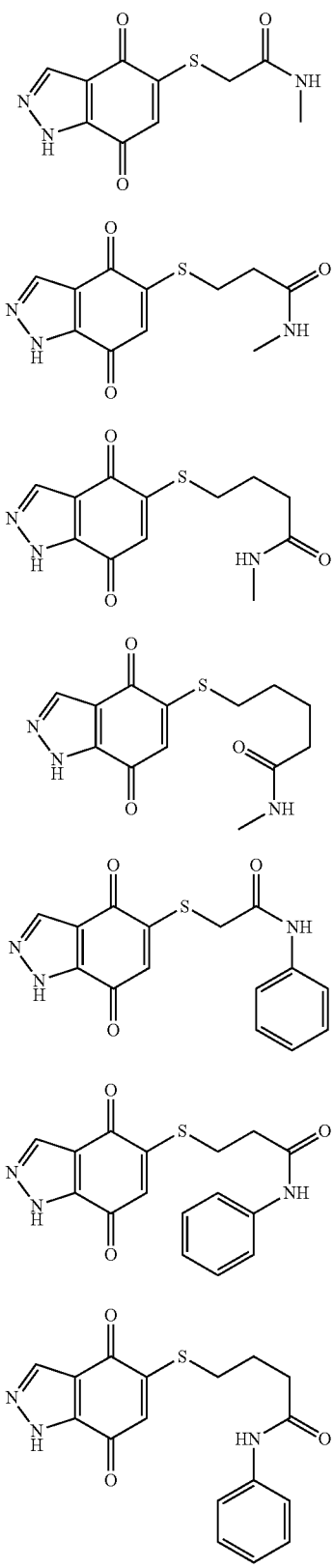

TABLE 1-continued
Example Active Compounds
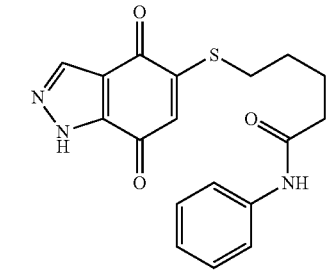
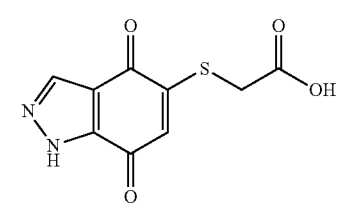
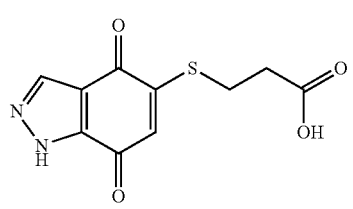 [SMILES: O=C(O)CCSC1=CC(=O)c2[nH]ncc2C1=O]
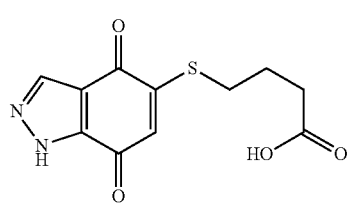 [SMILES: O=C(O)CCCSC1=CC(=O)c2[nH]ncc2C1=O]
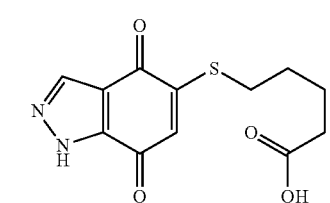 [SMILES: O=C(O)CCCCSC1=CC(=O)c2[nH]ncc2C1=O]
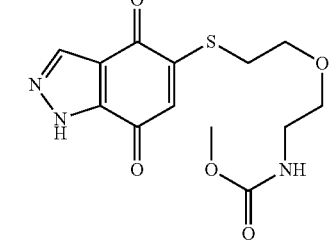
TABLE 1-continued
Example Active Compounds
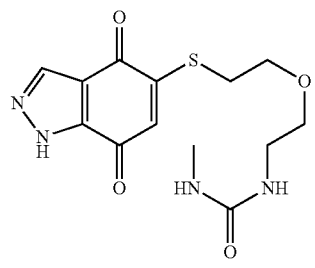 [SMILES: CNC(=O)NCCOCCSC1=CC(=O)c2[nH]ncc2C1=O]
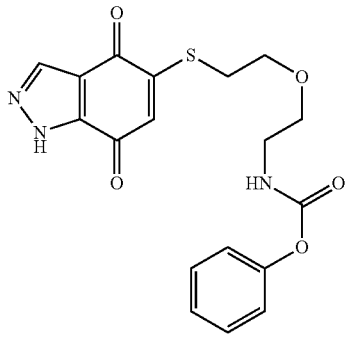
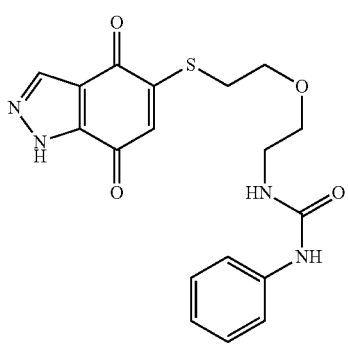
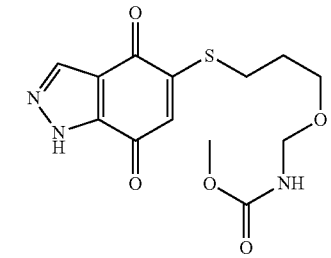 [SMILES: COC(=O)NCOCCCSC1=CC(=O)c2[nH]ncc2C1=O]
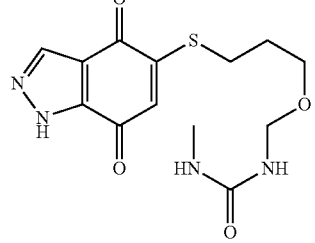

TABLE 1-continued
Example Active Compounds
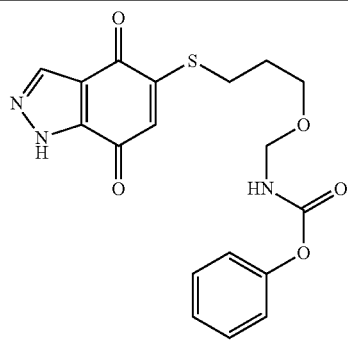
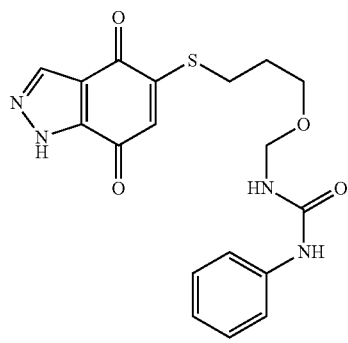
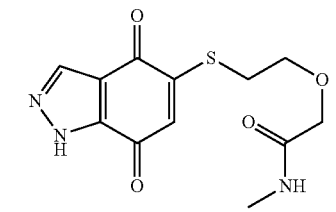 [SMILES: CNC(=O)COCCSC1=CC(=O)c2[nH]ncc2C1=O]
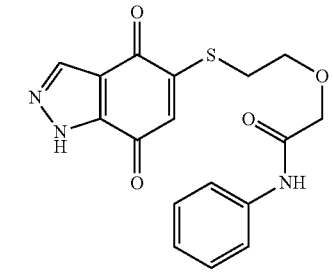 [SMILES: O=C(COCCSC1=CC(=O)c2[nH]ncc2C1=O)Nc1ccccc1]
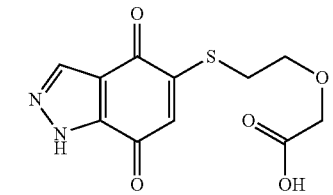 [SMILES: O=C(O)COCCSC1=CC(=O)c2[nH]ncc2C1=O]
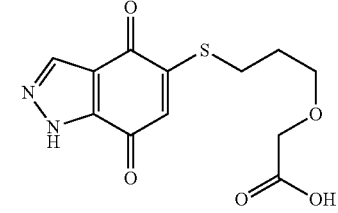
TABLE 1-continued
Example Active Compounds
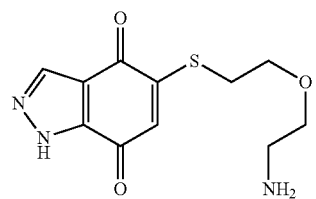
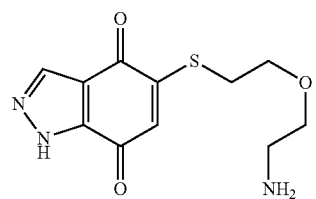 [SMILES: NCCOCCSC1=CC(=O)c2[nH]ncc2C1=O]
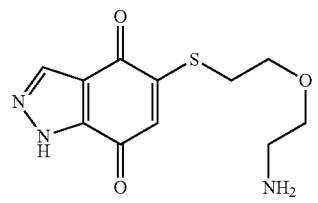 [SMILES: NCCOCCSC1=CC(=O)c2[nH]ncc2C1=O]
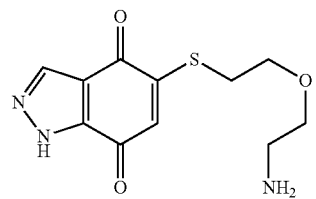
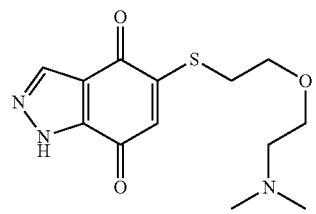
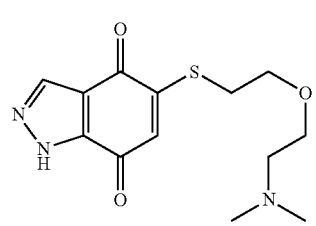
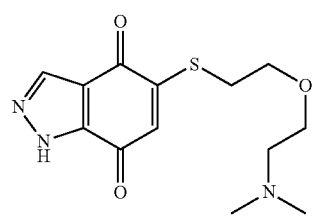

TABLE 1-continued
Example Active Compounds
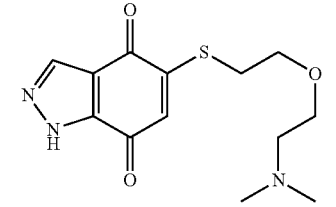
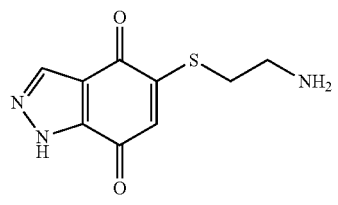 [SMILES: NCCSC1=CC(=O)c2[nH]ncc2C1=O]
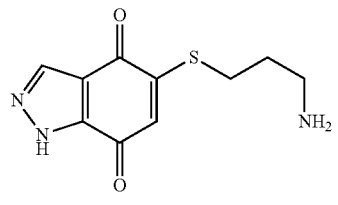 [SMILES: NCCCSC1=CC(=O)c2[nH]ncc2C1=O]
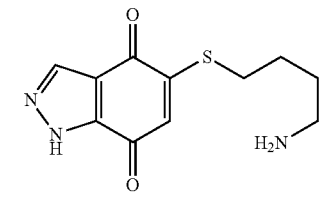
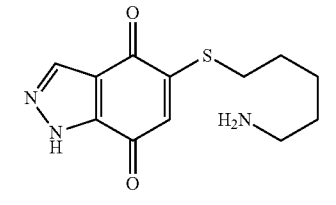 [SMILES: NCCCCCSC1=CC(=O)c2[nH]ncc2C1=O]
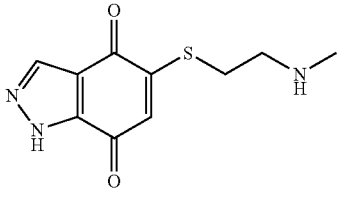
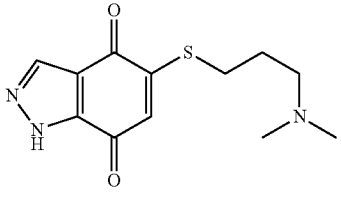
TABLE 1-continued
Example Active Compounds
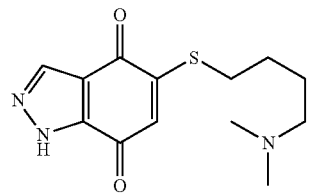
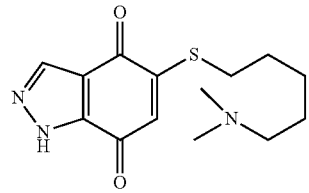
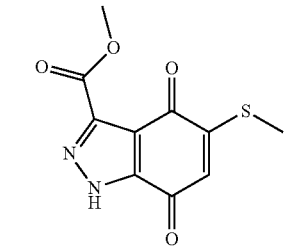 [SMILES: COC(=O)c1n[nH]c2c1C(=O)C(SC)=CC2=O]
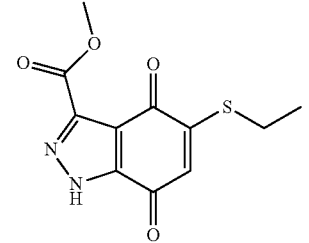 [SMILES: CCSC1=CC(=O)c2[nH]nc(C(=O)OC)c2C1=O]
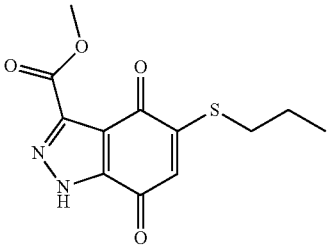 [SMILES: CCCSC1=CC(=O)c2[nH]nc(C(=O)OC)c2C1=O]
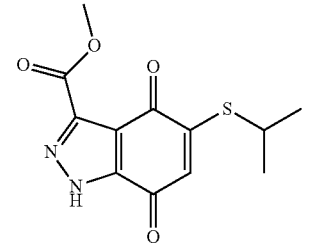 [SMILES: COC(=O)c1n[nH]c2c1C(=O)C(SC(C)C)=CC2=O]

TABLE 1-continued
Example Active Compounds
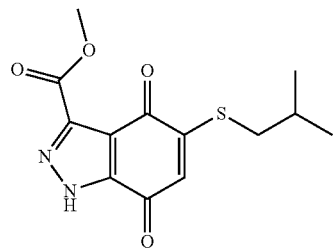
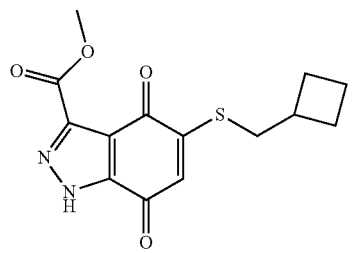 [SMILES: COC(=O)c1n[nH]c2c1C(=O)C(SCC1CCC1)=CC2=O]
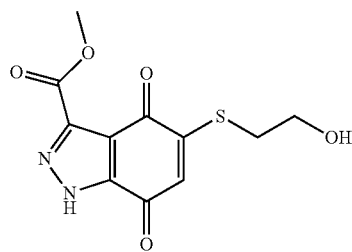 [SMILES: COC(=O)c1n[nH]c2c1C(=O)C(SCCO)=CC2=O]
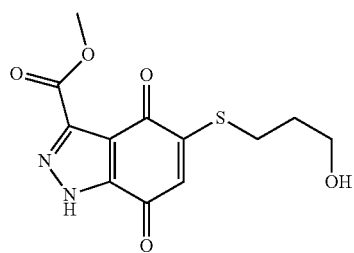 [SMILES: COC(=O)c1n[nH]c2c1C(=O)C(SCCCO)=CC2=O]
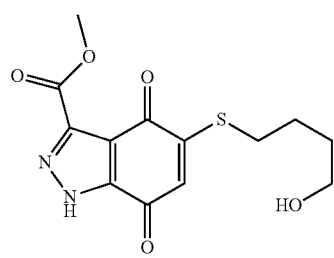
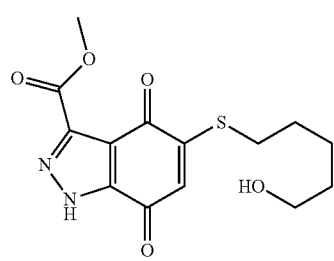
TABLE 1-continued
Example Active Compounds
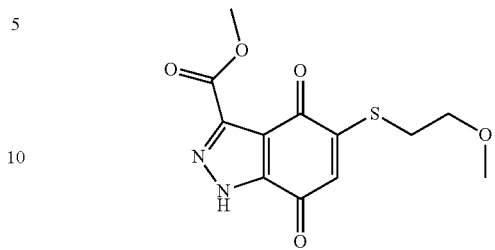
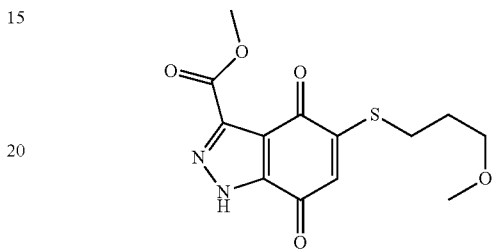
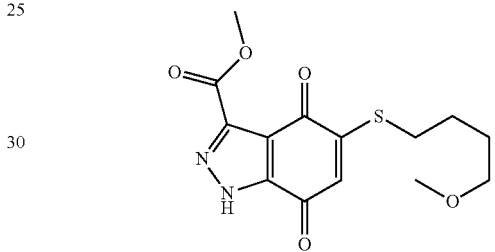
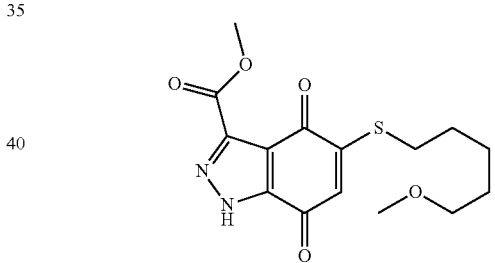
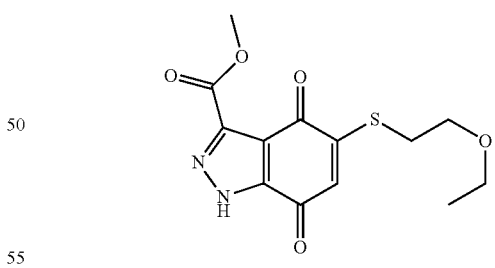
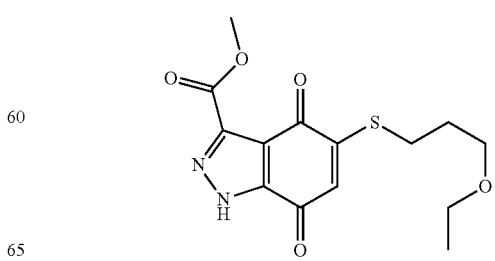

TABLE 1-continued
Example Active Compounds
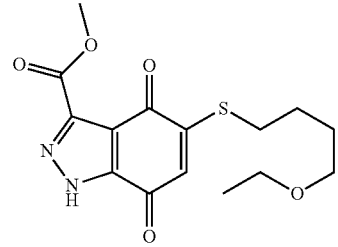
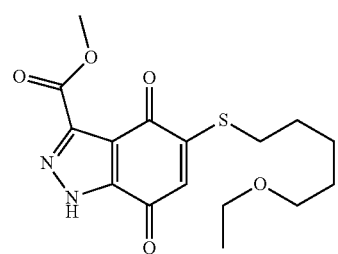 [SMILES: CCOCCCCCSC1=CC(=O)c2[nH]nc(C(=O)OC)c2C1=O]
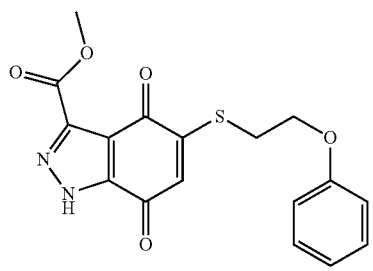 [SMILES: COC(=O)c1n[nH]c2c1C(=O)C(SCCOc1ccccc1)=CC2=O]
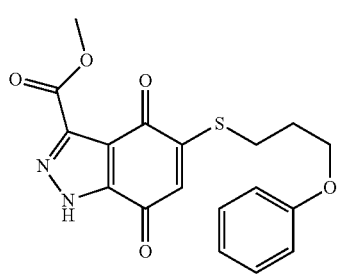
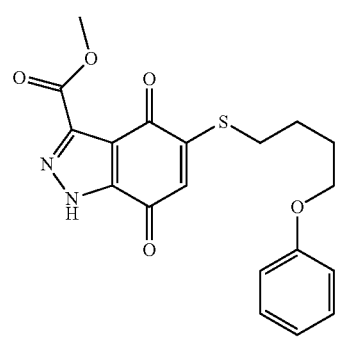
TABLE 1-continued
Example Active Compounds
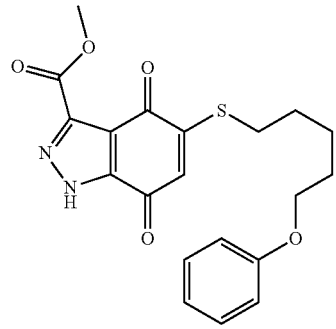 [SMILES: COC(=O)c1n[nH]c2c1C(=O)C(SCCCCCOc1ccccc1)=CC2=O]
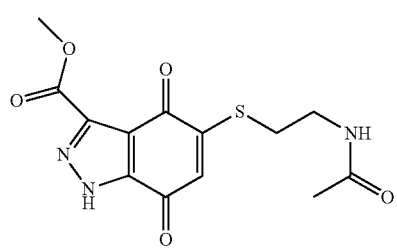 [SMILES: COC(=O)c1n[nH]c2c1C(=O)C(SCCNC(C)=O)=CC2=O]
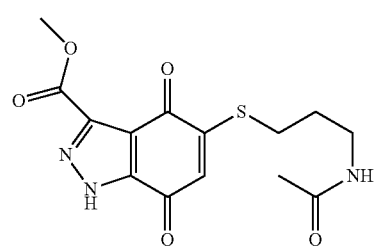 [SMILES: COC(=O)c1n[nH]c2c1C(=O)C(SCCCNC(C)=O)=CC2=O]
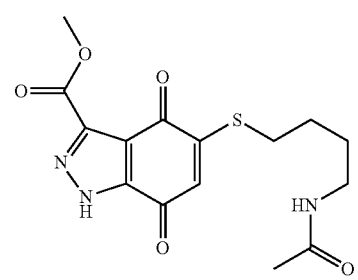 [SMILES: COC(=O)c1n[nH]c2c1C(=O)C(SCCCCNC(C)=O)=CC2=O]
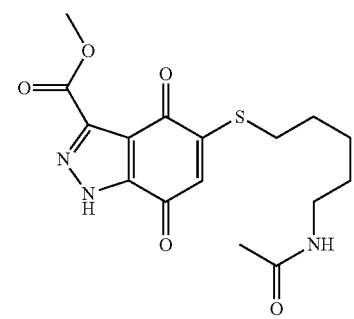 [SMILES: COC(=O)c1n[nH]c2c1C(=O)C(SCCCCCNC(C)=O)=CC2=O]

TABLE 1-continued
Example Active Compounds
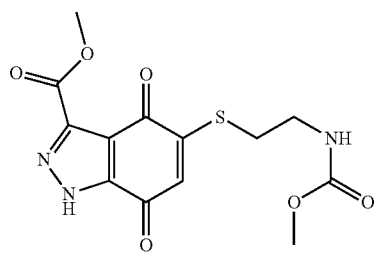
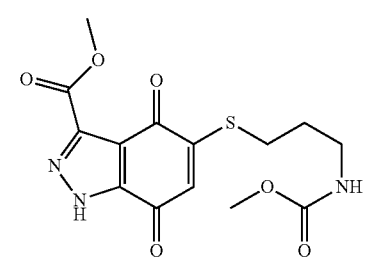 [SMILES: COC(=O)NCCCSC1=CC(=O)c2[nH]nc(C(=O)OC)c2C1=O]
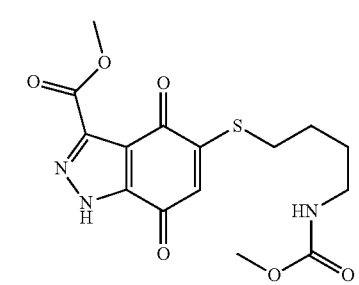
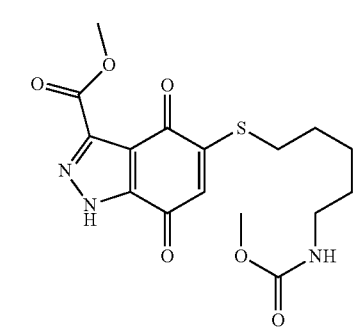 [SMILES: COC(=O)NCCCCCSC1=CC(=O)c2[nH]nc(C(=O)OC)c2C1=O]
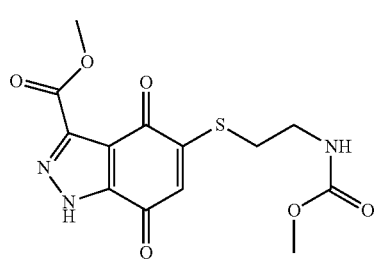
TABLE 1-continued
Example Active Compounds
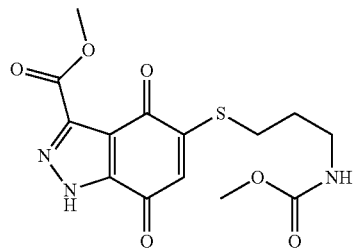 [SMILES: COC(=O)NCCCSC1=CC(=O)c2[nH]nc(C(=O)OC)c2C1=O]
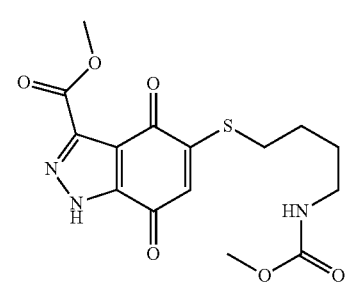
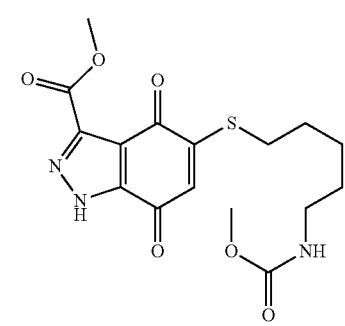 [SMILES: COC(=O)NCCCCCSC1=CC(=O)c2[nH]nc(C(=O)OC)c2C1=O]
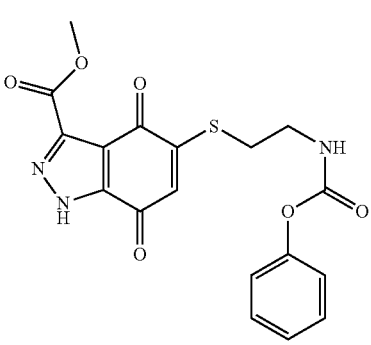 [SMILES: COC(=O)c1n[nH]c2c1C(=O)C(SCCNC(=O)Oc1ccccc1)=CC2=O]
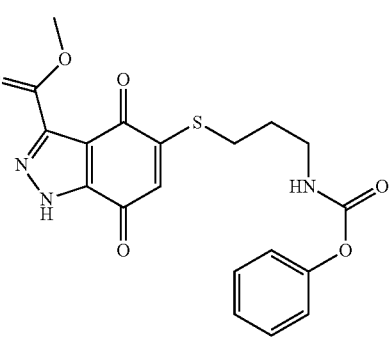

TABLE 1-continued
Example Active Compounds
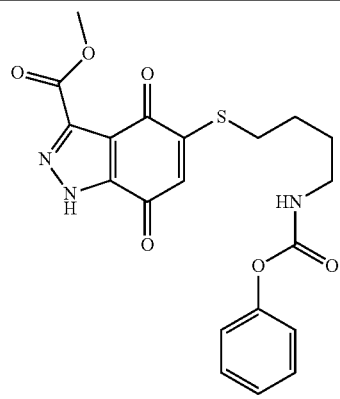
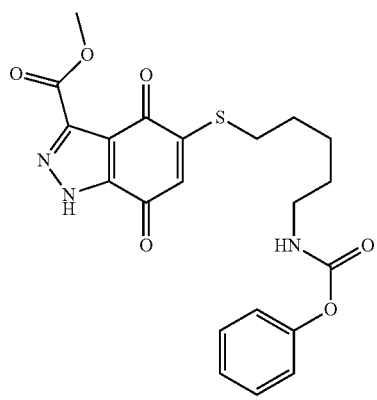
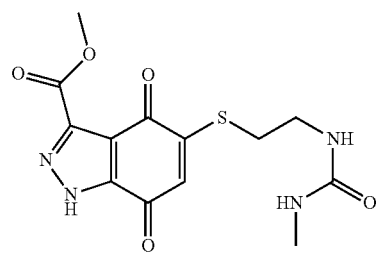
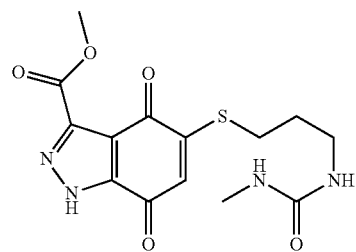 [SMILES: CNC(=O)NCCCSC1=CC(=O)c2[nH]nc(C(=O)OC)c2C1=O]
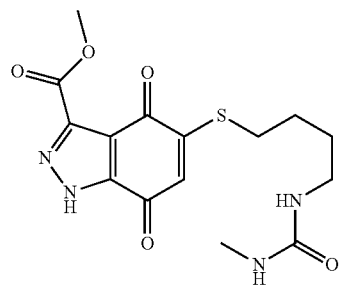 [SMILES: CNC(=O)NCCCCSC1=CC(=O)c2[nH]nc(C(=O)OC)c2C1=O]
TABLE 1-continued
Example Active Compounds
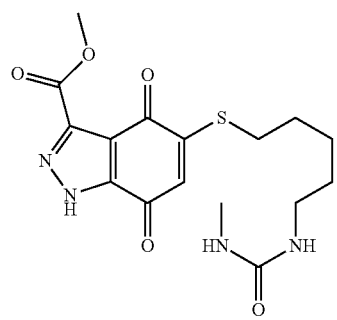 [SMILES: CNC(=O)NCCCCCSC1=CC(=O)c2[nH]nc(C(=O)OC)c2C1=O]
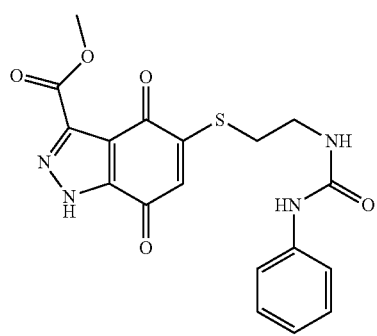 [SMILES: COC(=O)c1n[nH]c2c1C(=O)C(SCCNC(=O)Nc1ccccc1)=CC2=O]
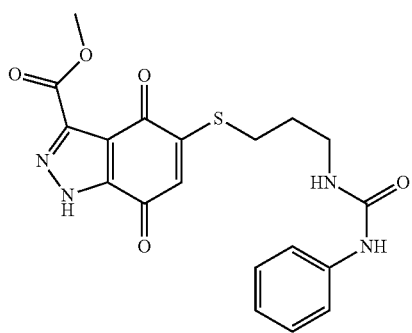
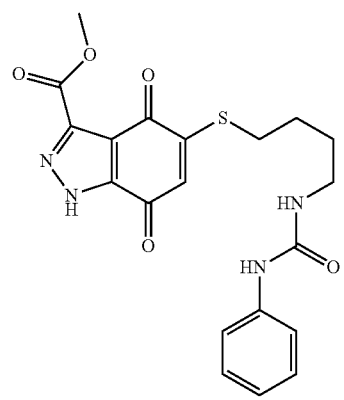

TABLE 1-continued

Example Active Compounds

TABLE 1-continued
Example Active Compounds
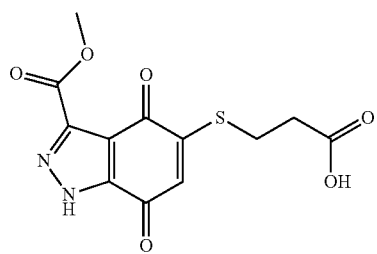 [SMILES: COC(=O)c1n[nH]c2c1C(=O)C(SCCC(=O)O)=CC2=O]
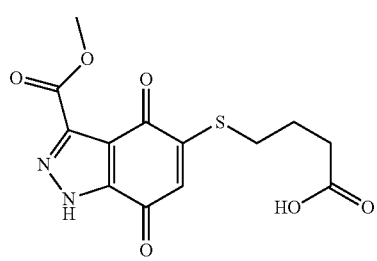
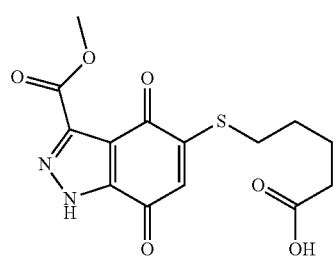 [SMILES: COC(=O)c1n[nH]c2c1C(=O)C(SCCCCC(=O)O)=CC2=O]
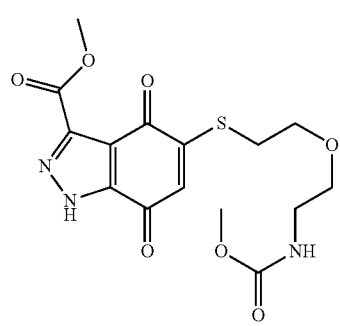 [SMILES: COC(=O)NCCOCCSC1=CC(=O)c2[nH]nc(C(=O)OC)c2C1=O]
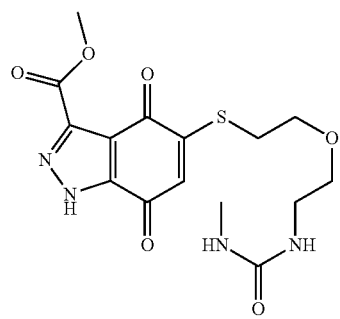 [SMILES: CNC(=O)NCCOCCSC1=CC(=O)c2[nH]nc(C(=O)OC)c2C1=O]
TABLE 1-continued
Example Active Compounds
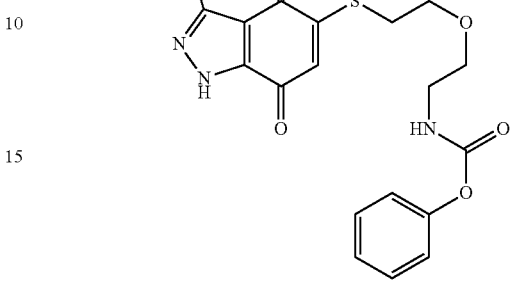
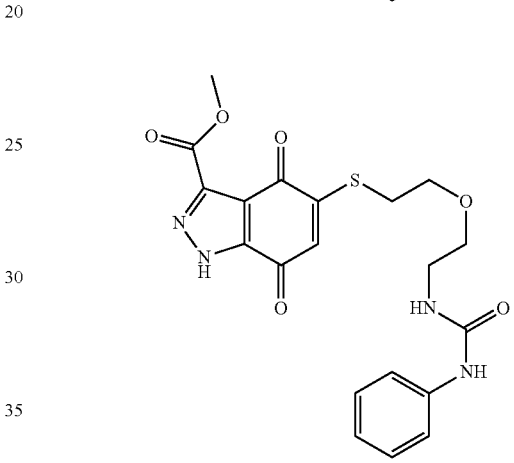
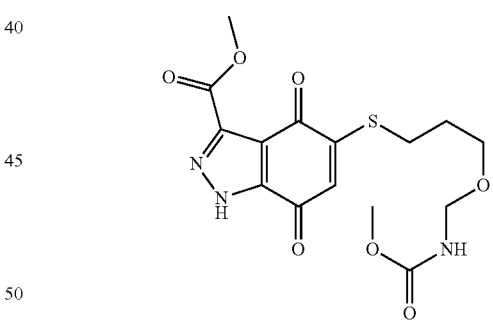
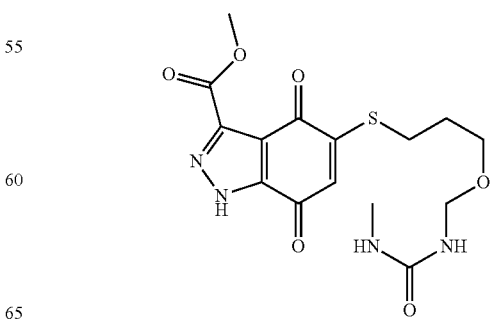

TABLE 1-continued
Example Active Compounds
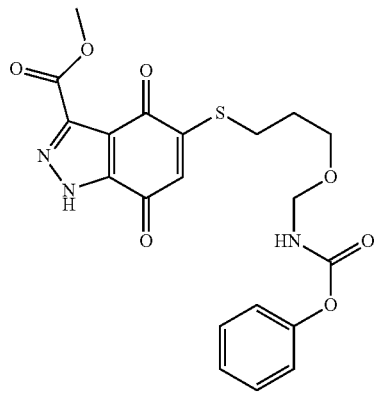
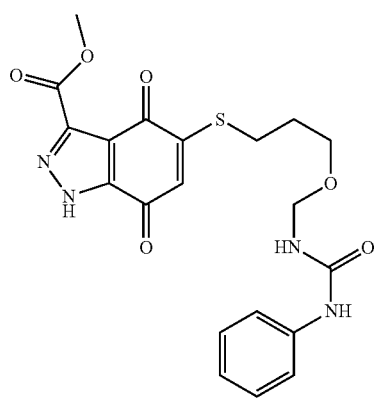
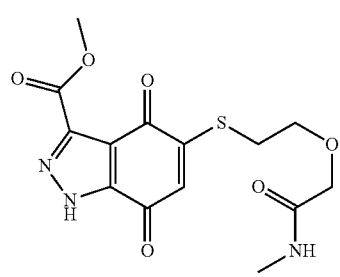
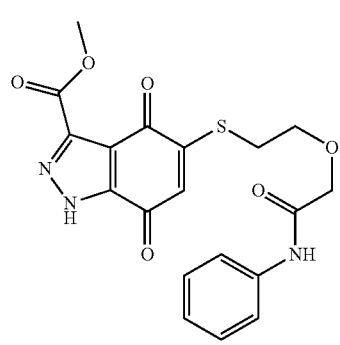 [SMILES: COC(=O)c1n[nH]c2c1C(=O)C(SCCOCC(=O)Nc1ccccc1)=CC2=O]

TABLE 1-continued
Example Active Compounds
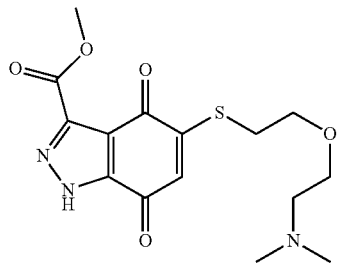 [SMILES: COC(=O)c1n[nH]c2c1C(=O)C(SCCOCCN(C)C)=CC2=O]
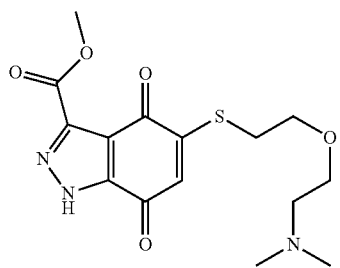 [SMILES: COC(=O)c1n[nH]c2c1C(=O)C(SCCOCCN(C)C)=CC2=O]
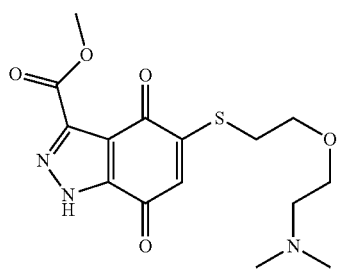 [SMILES: COC(=O)c1n[nH]c2c1C(=O)C(SCCOCCN(C)C)=CC2=O]
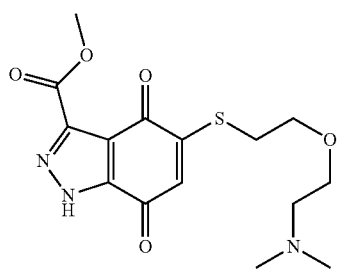 [SMILES: COC(=O)c1n[nH]c2c1C(=O)C(SCCOCCN(C)C)=CC2=O]
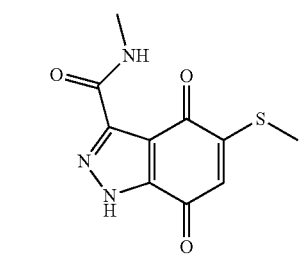 [SMILES: CNC(=O)c1n[nH]c2c1C(=O)C(SC)=CC2=O]
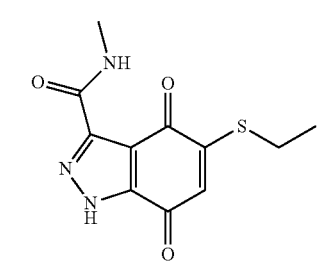
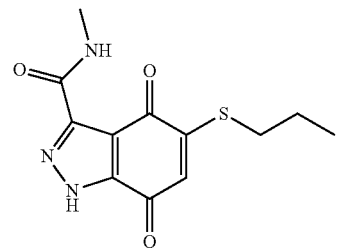 [SMILES: CCCSC1=CC(=O)c2[nH]nc(C(=O)NC)c2C1=O]
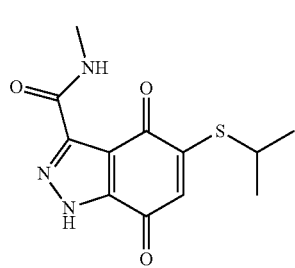 [SMILES: CNC(=O)c1n[nH]c2c1C(=O)C(SC(C)C)=CC2=O]
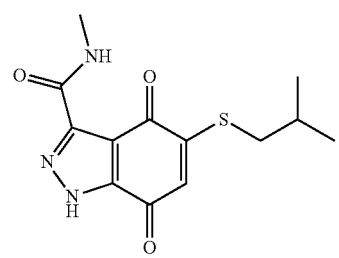 [SMILES: CNC(=O)c1n[nH]c2c1C(=O)C(SCC(C)C)=CC2=O]
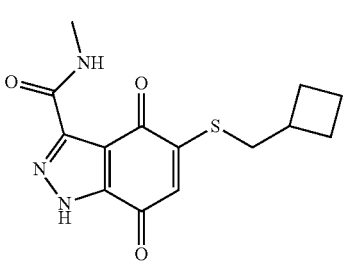 [SMILES: CNC(=O)c1n[nH]c2c1C(=O)C(SCC1CCC1)=CC2=O]
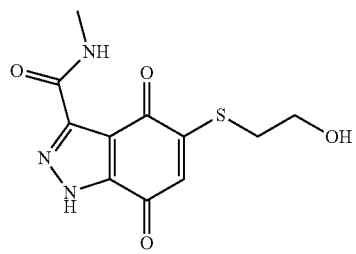
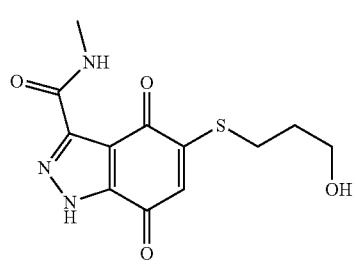

TABLE 1-continued
Example Active Compounds
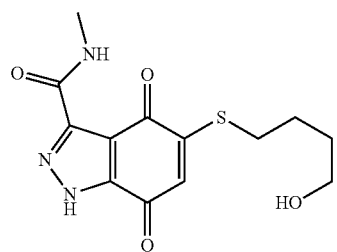 [SMILES: CNC(=O)c1n[nH]c2c1C(=O)C(SCCCCO)=CC2=O]
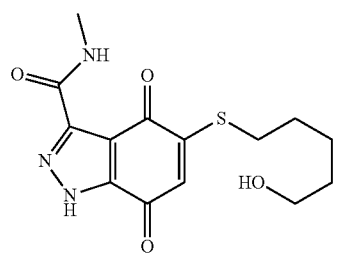 [SMILES: CNC(=O)c1n[nH]c2c1C(=O)C(SCCCCCO)=CC2=O]
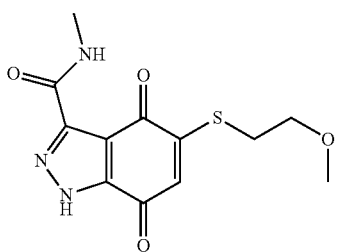
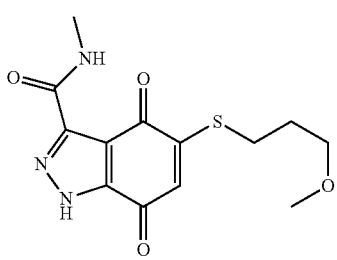 [SMILES: CNC(=O)c1n[nH]c2c1C(=O)C(SCCCOC)=CC2=O]
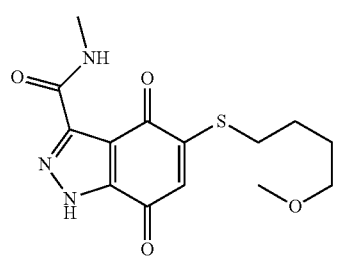 [SMILES: CNC(=O)c1n[nH]c2c1C(=O)C(SCCCCOC)=CC2=O]
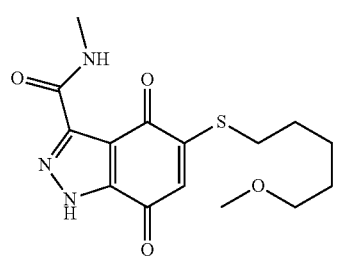
TABLE 1-continued
Example Active Compounds
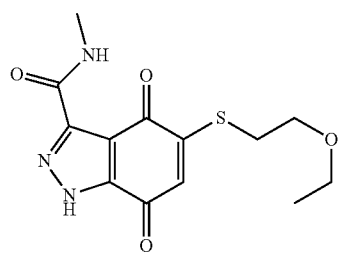
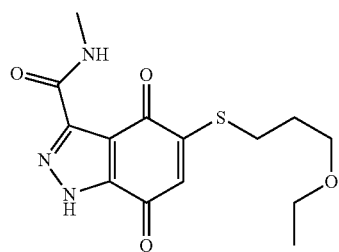
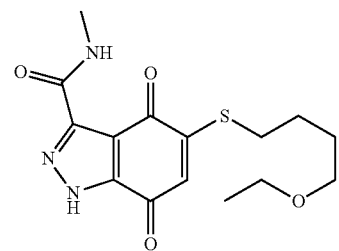 [SMILES: CCOCCCCSC1=CC(=O)c2[nH]nc(C(=O)NC)c2C1=O]
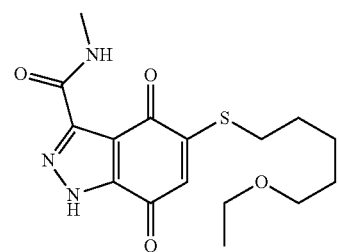 [SMILES: CCOCCCCCSC1=CC(=O)c2[nH]nc(C(=O)NC)c2C1=O]
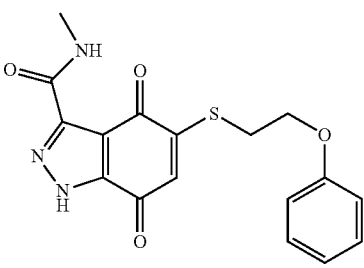 [SMILES: CNC(=O)c1n[nH]c2c1C(=O)C(SCCOc1ccccc1)=CC2=O]
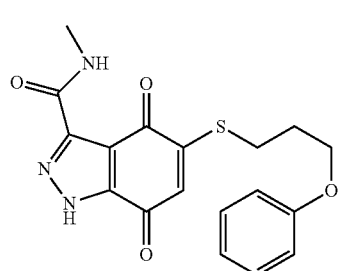

TABLE 1-continued
Example Active Compounds
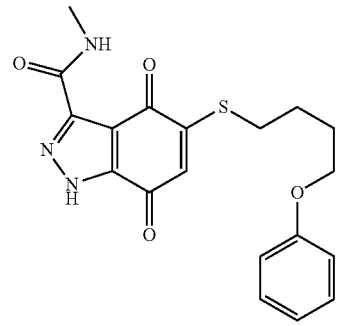 [SMILES: CNC(=O)c1n[nH]c2c1C(=O)C(SCCCCOc1ccccc1)=CC2=O]
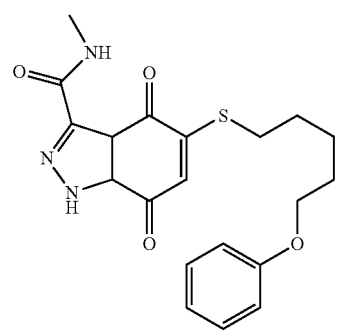 [SMILES: CNC(=O)C1=NNC2C(=O)C=C(SCCCCCOc3ccccc3)C(=O)C12]
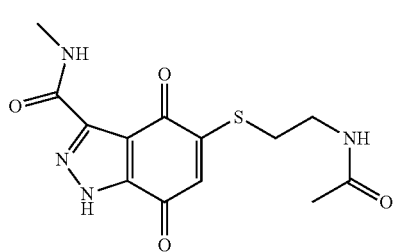 [SMILES: CNC(=O)c1n[nH]c2c1C(=O)C(SCCNC(C)=O)=CC2=O]
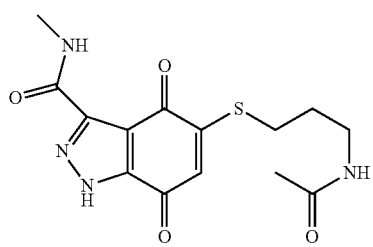 [SMILES: CNC(=O)c1n[nH]c2c1C(=O)C(SCCCNC(C)=O)=CC2=O]
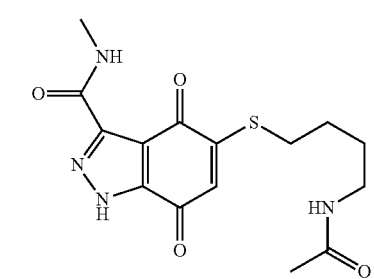
TABLE 1-continued
Example Active Compounds
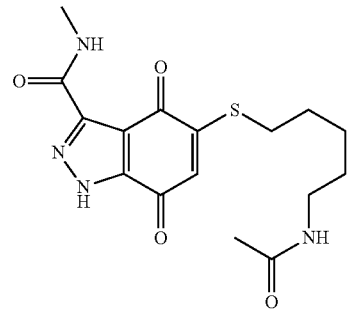
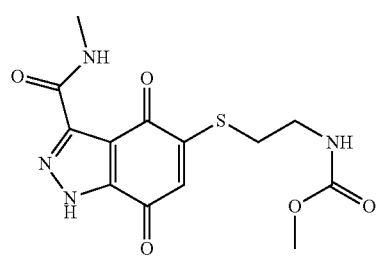 [SMILES: CNC(=O)c1n[nH]c2c1C(=O)C(SCCNC(=O)OC)=CC2=O]
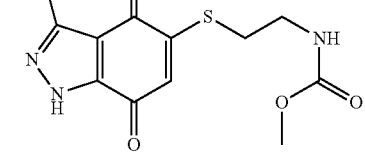
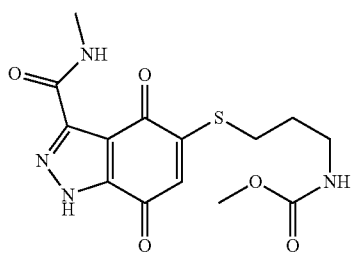 [SMILES: CNC(=O)c1n[nH]c2c1C(=O)C(SCCCNC(=O)OC)=CC2=O]
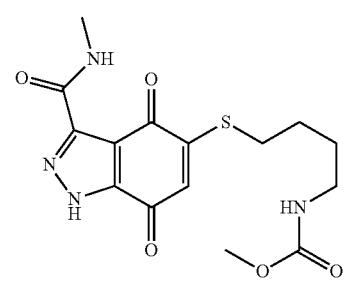 [SMILES: CNC(=O)c1n[nH]c2c1C(=O)C(SCCCCNC(=O)OC)=CC2=O]
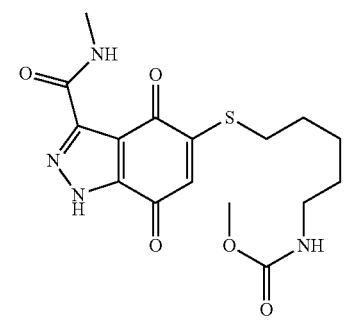 [SMILES: CNC(=O)c1n[nH]c2c1C(=O)C(SCCCCCNC(=O)OC)=CC2=O]

TABLE 1-continued

Example Active Compounds

TABLE 1-continued

Example Active Compounds

TABLE 1-continued
Example Active Compounds
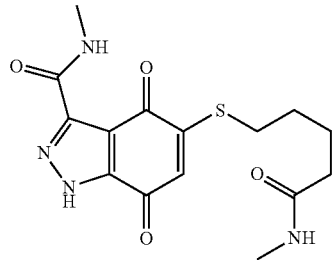 [SMILES: CNC(=O)CCCCSC1=CC(=O)c2[nH]nc(C(=O)NC)c2C1=O]
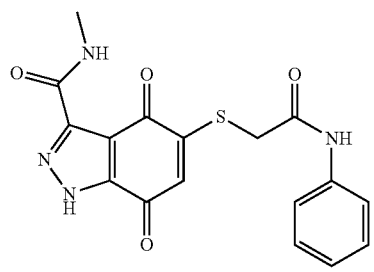
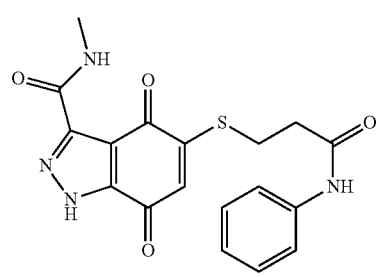
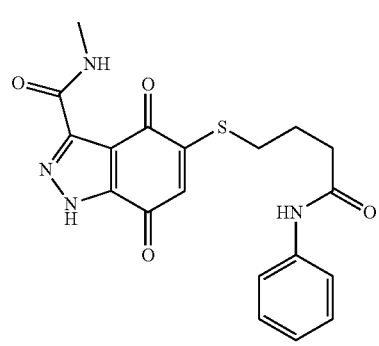
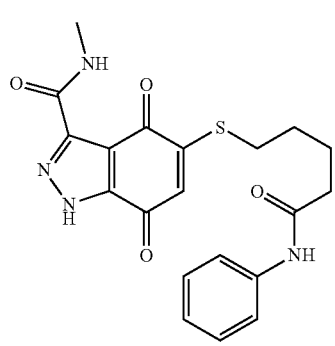 [SMILES: CNC(=O)c1n[nH]c2c1C(=O)C(SCCCCC(=O)Nc1ccccc1)=CC2=O]
TABLE 1-continued
Example Active Compounds
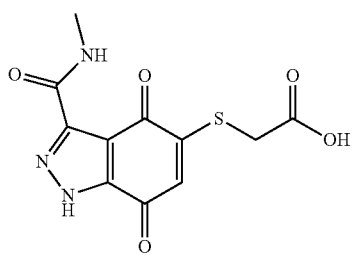
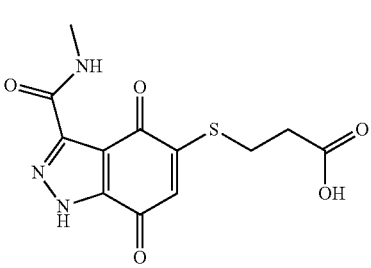
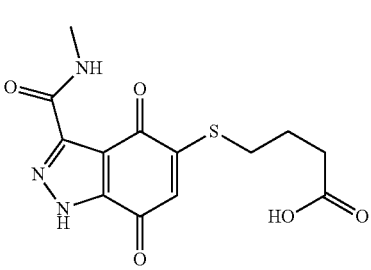
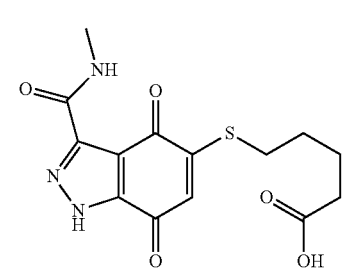 [SMILES: CNC(=O)c1n[nH]c2c1C(=O)C(SCCCCC(=O)O)=CC2=O]
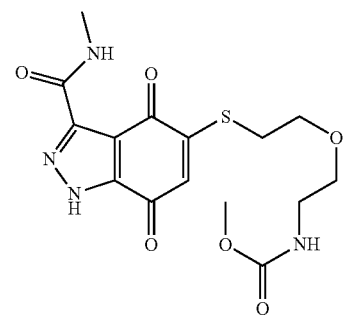

TABLE 1-continued

Example Active Compounds

TABLE 1-continued

Example Active Compounds

TABLE 1-continued
Example Active Compounds
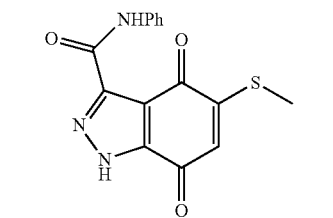
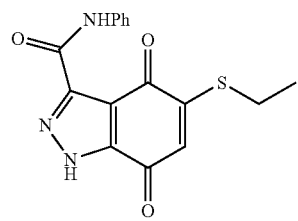
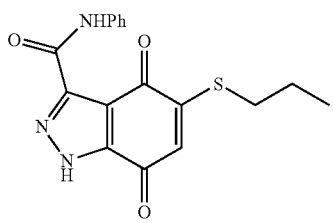
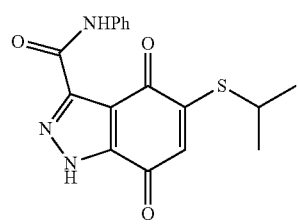
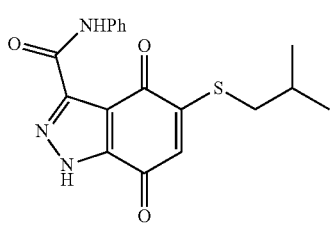
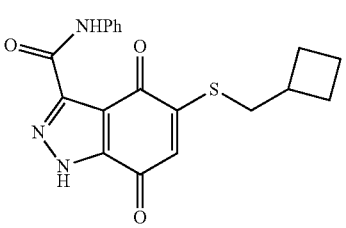
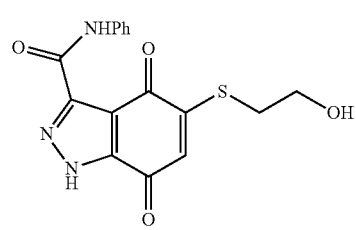
TABLE 1-continued
Example Active Compounds
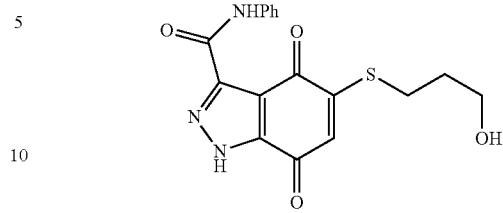
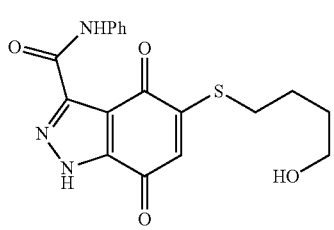
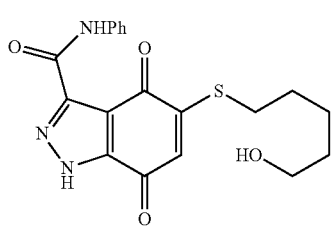
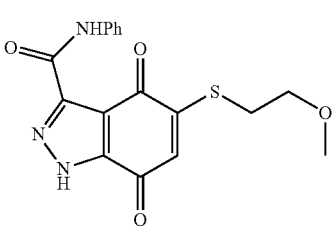
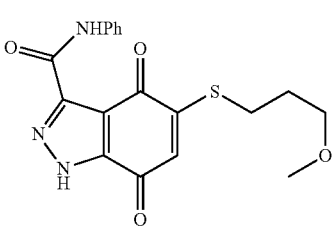
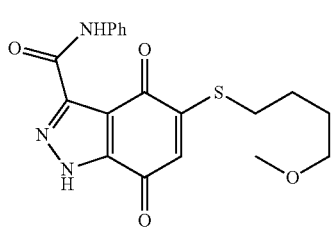

TABLE 1-continued
Example Active Compounds
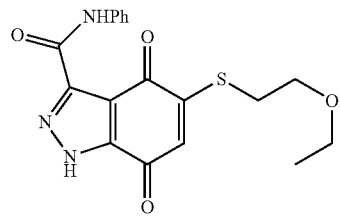
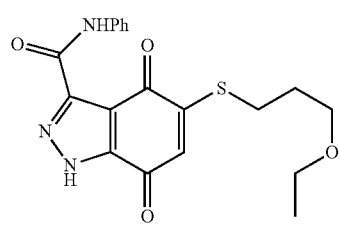
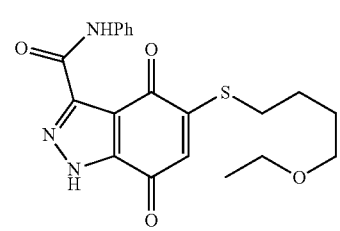
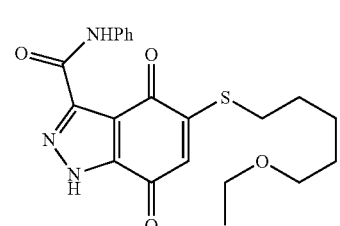
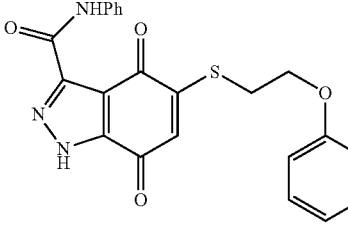
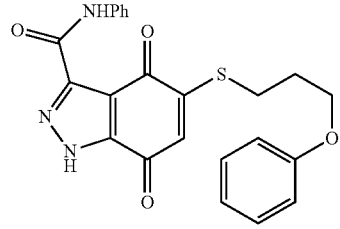
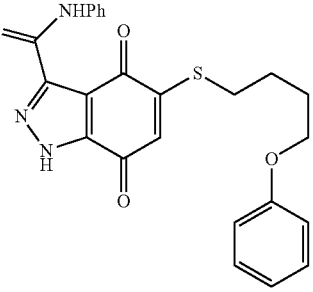
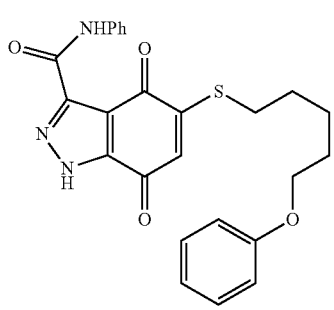
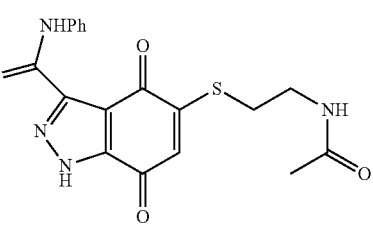
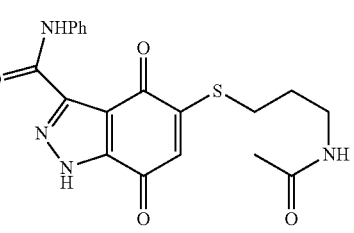
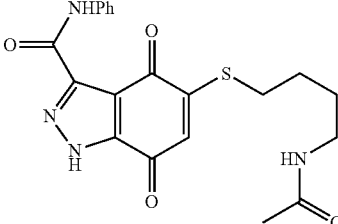
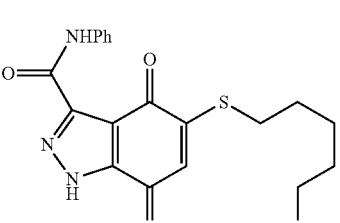

TABLE 1-continued
Example Active Compounds
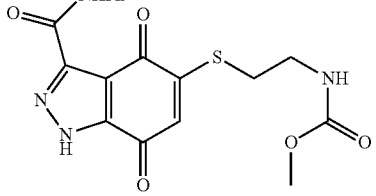
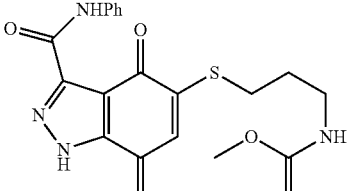
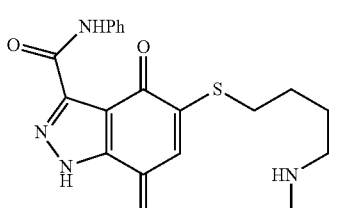
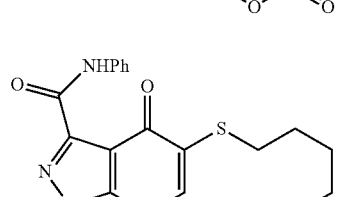
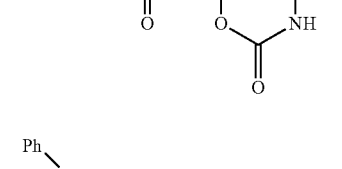
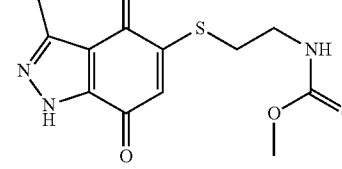
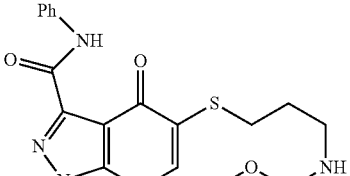

TABLE 1-continued
Example Active Compounds
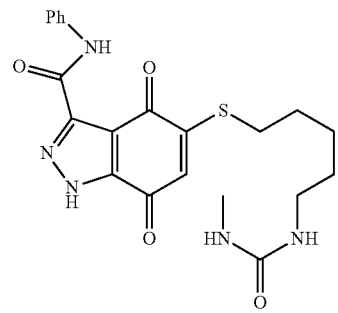 [SMILES: CNC(=O)NCCCCCSC1=CC(=O)c2[nH]nc(C(=O)Nc3ccccc3)c2C1=O]
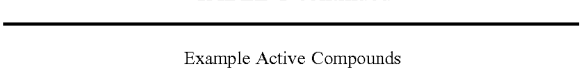
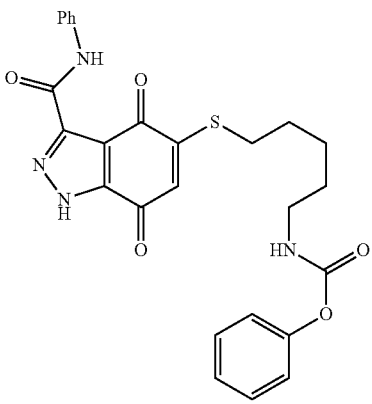 [SMILES: O=C(NCCCCCSC1=CC(=O)c2[nH]nc(C(=O)Nc3ccccc3)c2C1=O)Oc1ccccc1]
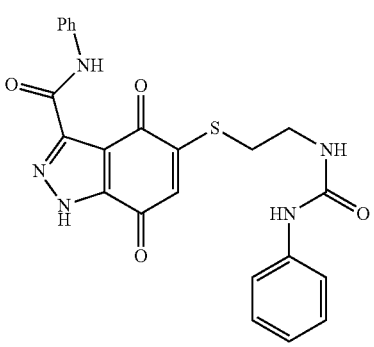 [SMILES: O=C(NCCSC1=CC(=O)c2[nH]nc(C(=O)Nc3ccccc3)c2C1=O)Nc1ccccc1]
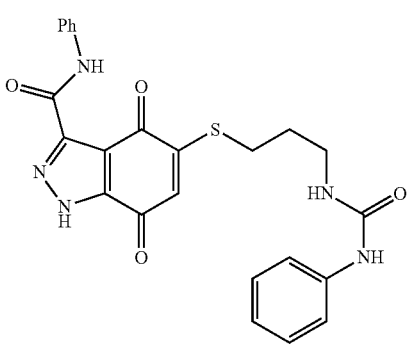
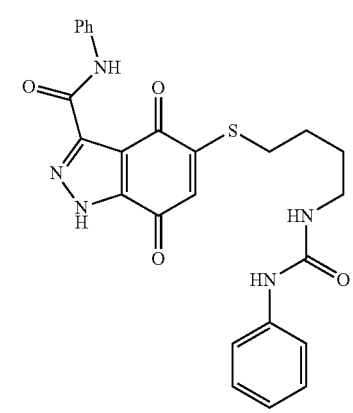

TABLE 1-continued

Example Active Compounds

TABLE 1-continued

Example Active Compounds

TABLE 1-continued

Example Active Compounds

TABLE 1-continued

Example Active Compounds

TABLE 1-continued
Example Active Compounds
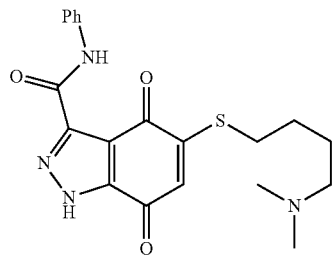 [SMILES: CN(C)CCCCSC1=CC(=O)c2[nH]nc(C(=O)Nc3ccccc3)c2C1=O]
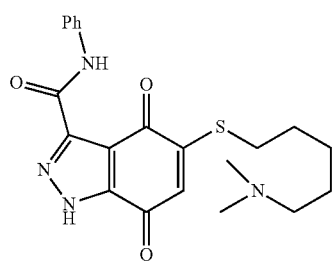 [SMILES: CN(C)CCCCCSC1=CC(=O)c2[nH]nc(C(=O)Nc3ccccc3)c2C1=O]
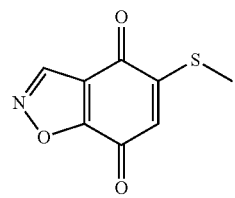
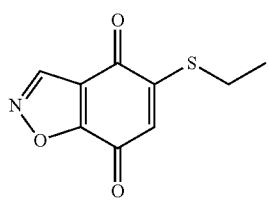
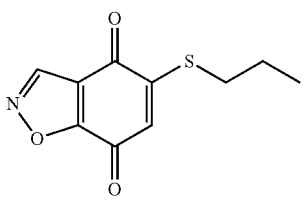
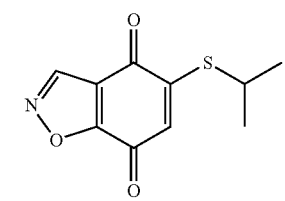
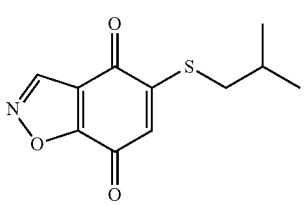 [SMILES: CC(C)CSC1=CC(=O)c2oncc2C1=O]
TABLE 1-continued
Example Active Compounds
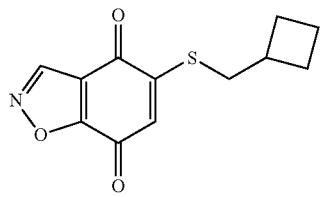 [SMILES: O=C1C(SCC2CCC2)=CC(=O)c2oncc21]
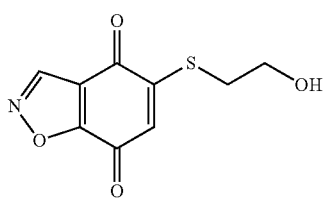 [SMILES: O=C1C(SCCO)=CC(=O)c2oncc21]
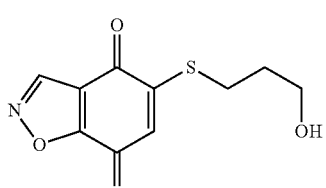
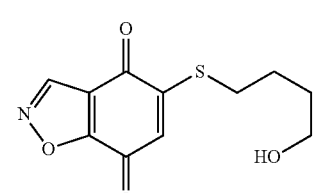
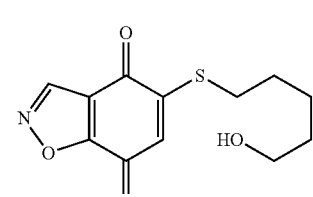
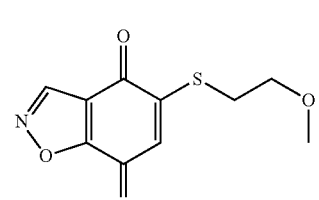
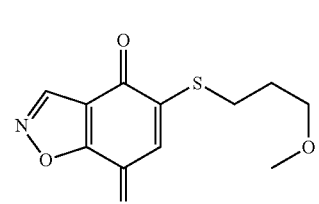

TABLE 1-continued
Example Active Compounds
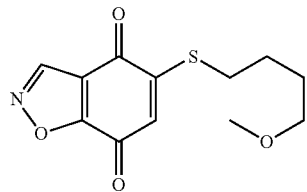 [SMILES: COCCCCSC1=CC(=O)c2oncc2C1=O]
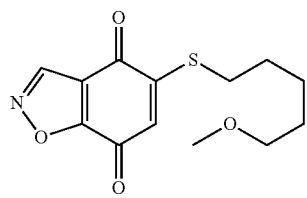 [SMILES: COCCCCCSC1=CC(=O)c2oncc2C1=O]
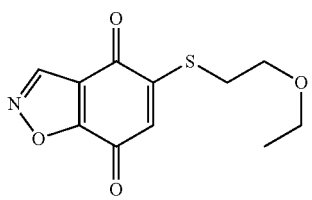 [SMILES: CCOCCSC1=CC(=O)c2oncc2C1=O]
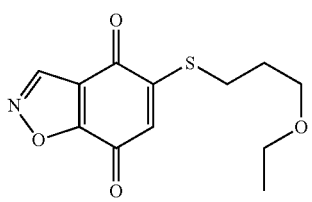 [SMILES: CCOCCCSC1=CC(=O)c2oncc2C1=O]
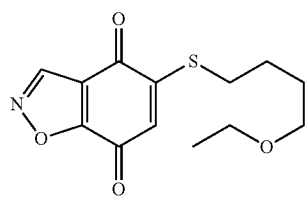 [SMILES: CCOCCCCSC1=CC(=O)c2oncc2C1=O]
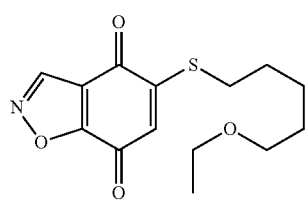 [SMILES: CCOCCCCCSC1=CC(=O)c2oncc2C1=O]
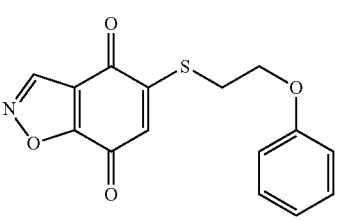
TABLE 1-continued
Example Active Compounds
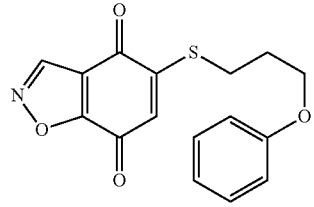
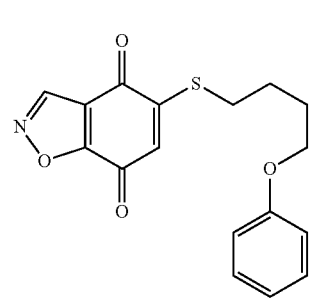 [SMILES: O=C1C(SCCCCOc2ccccc2)=CC(=O)c2oncc21]
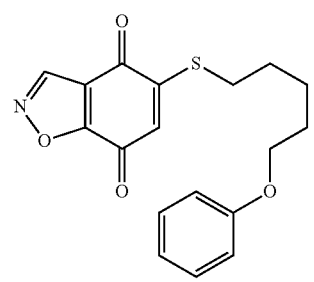 [SMILES: O=C1C(SCCCCCOc2ccccc2)=CC(=O)c2oncc21]
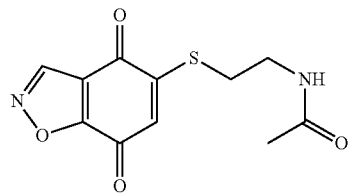 [SMILES: CC(=O)NCCSC1=CC(=O)c2oncc2C1=O]
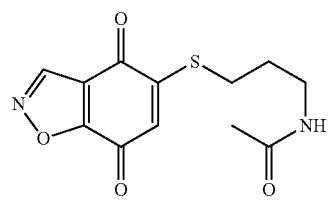 [SMILES: CC(=O)NCCCSC1=CC(=O)c2oncc2C1=O]
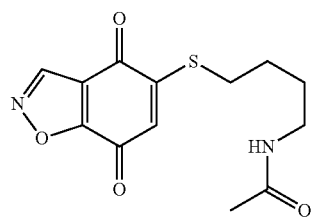 [SMILES: CC(=O)NCCCCSC1=CC(=O)c2oncc2C1=O]

TABLE 1-continued
Example Active Compounds
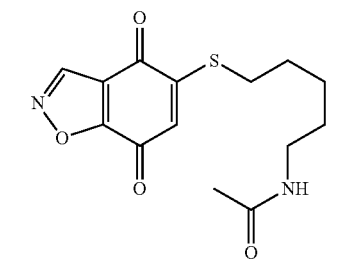 [SMILES: CC(=O)NCCCCCSC1=CC(=O)c2oncc2C1=O]
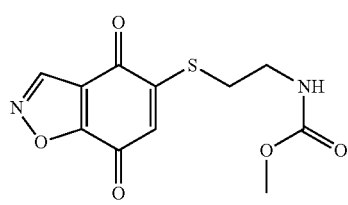 [SMILES: COC(=O)NCCSC1=CC(=O)c2oncc2C1=O]
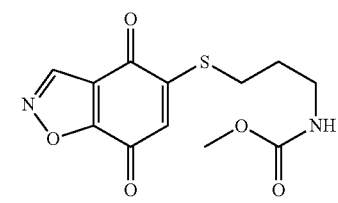 [SMILES: COC(=O)NCCCSC1=CC(=O)c2oncc2C1=O]
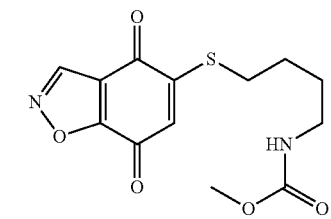 [SMILES: COC(=O)NCCCCSC1=CC(=O)c2oncc2C1=O]
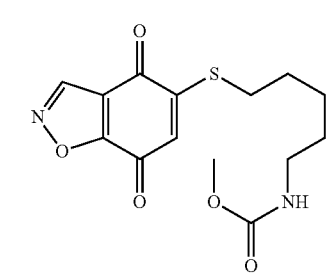 [SMILES: COC(=O)NCCCCCSC1=CC(=O)c2oncc2C1=O]
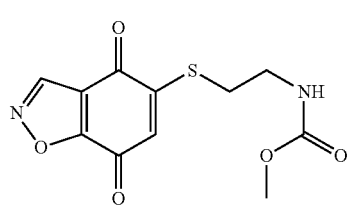 [SMILES: COC(=O)NCCSC1=CC(=O)c2oncc2C1=O]
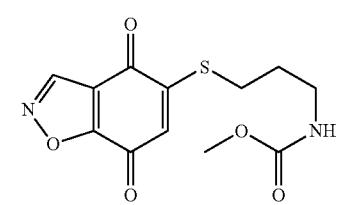 [SMILES: COC(=O)NCCCSC1=CC(=O)c2oncc2C1=O]
TABLE 1-continued
Example Active Compounds
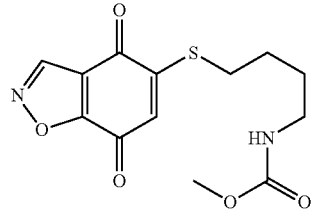
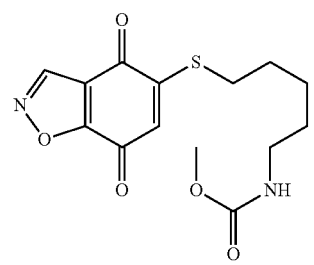 [SMILES: COC(=O)NCCCCCSC1=CC(=O)c2oncc2C1=O]
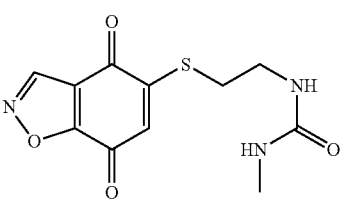 [SMILES: CNC(=O)NCCSC1=CC(=O)c2oncc2C1=O]
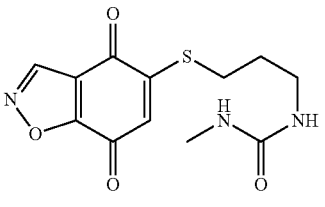 [SMILES: CNC(=O)NCCCSC1=CC(=O)c2oncc2C1=O]
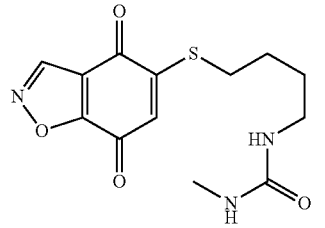
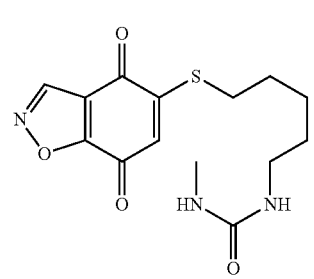 [SMILES: CNC(=O)NCCCCCSC1=CC(=O)c2oncc2C1=O]
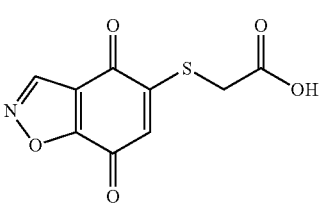 [SMILES: O=C(O)CSC1=CC(=O)c2oncc2C1=O]

TABLE 1-continued
Example Active Compounds
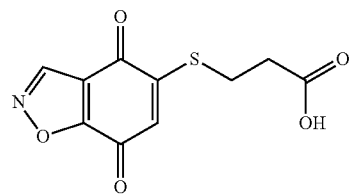 [SMILES: O=C(O)CCSC1=CC(=O)c2oncc2C1=O]
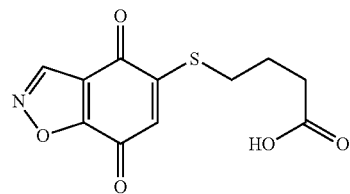
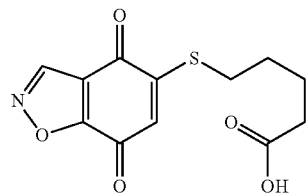 [SMILES: O=C(O)CCCCSC1=CC(=O)c2oncc2C1=O]
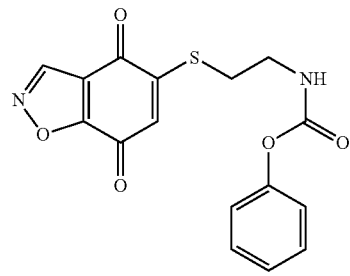 [SMILES: O=C(NCCSC1=CC(=O)c2oncc2C1=O)Oc1ccccc1]
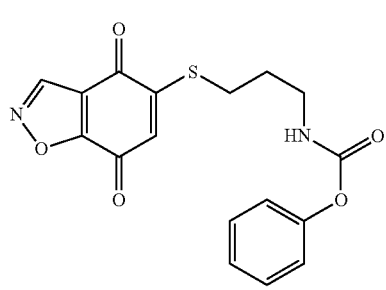
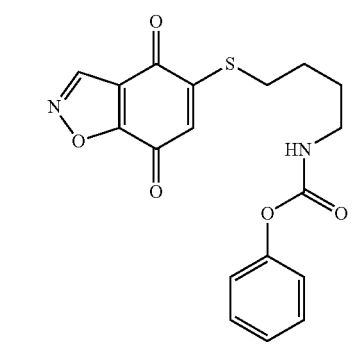 [SMILES: O=C(NCCCCSC1=CC(=O)c2oncc2C1=O)Oc1ccccc1]
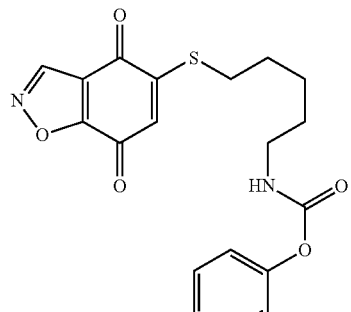
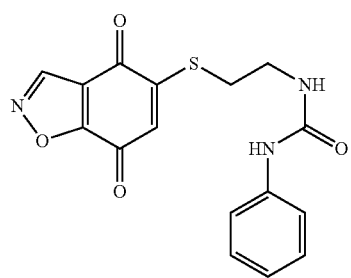 [SMILES: O=C(NCCSC1=CC(=O)c2oncc2C1=O)Nc1ccccc1]
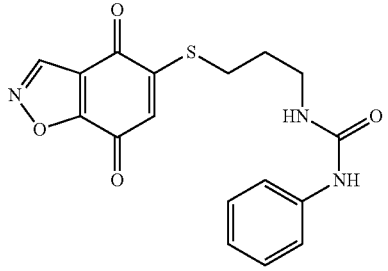
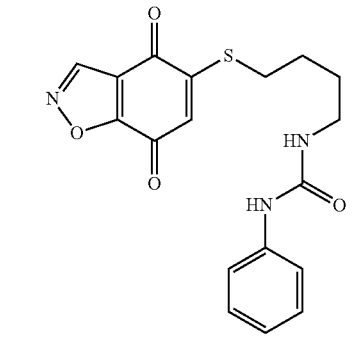 [SMILES: O=C(NCCCCSC1=CC(=O)c2oncc2C1=O)Nc1ccccc1]
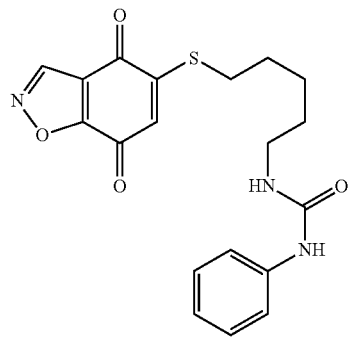

TABLE 1-continued
Example Active Compounds
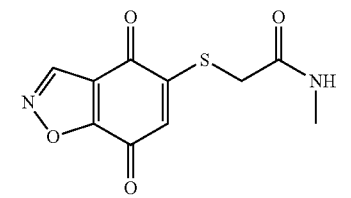
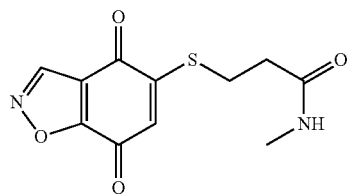 [SMILES: CNC(=O)CCSC1=CC(=O)c2oncc2C1=O]
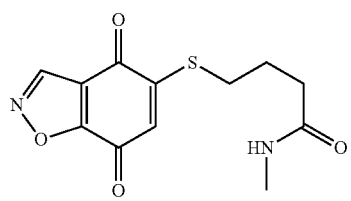 [SMILES: CNC(=O)CCCSC1=CC(=O)c2oncc2C1=O]
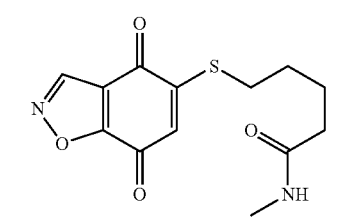 [SMILES: CNC(=O)CCCCSC1=CC(=O)c2oncc2C1=O]
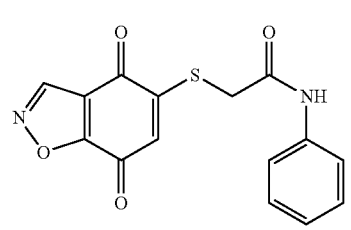
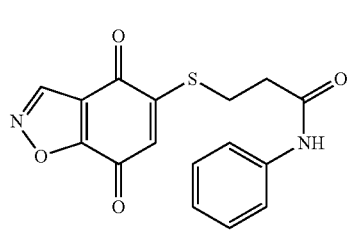
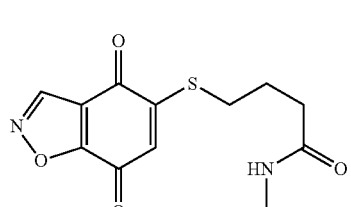
TABLE 1-continued
Example Active Compounds
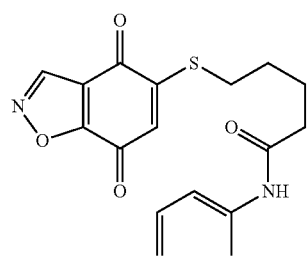 [SMILES: C=C/C=C(\C)NC(=O)CCCCSC1=CC(=O)c2oncc2C1=O]
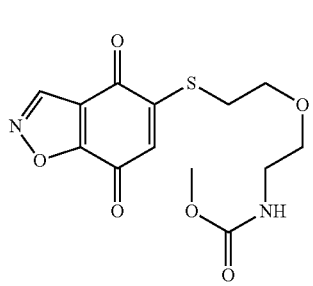 [SMILES: COC(=O)NCCOCCSC1=CC(=O)c2oncc2C1=O]
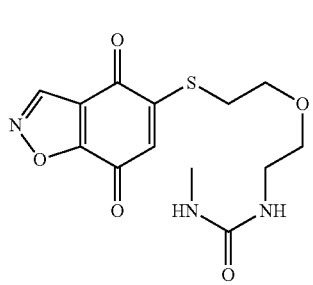 [SMILES: CNC(=O)NCCOCCSC1=CC(=O)c2oncc2C1=O]
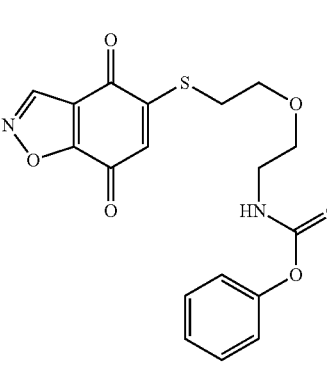
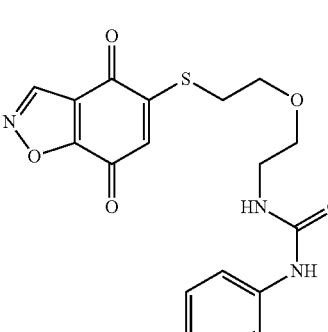

TABLE 1-continued
Example Active Compounds
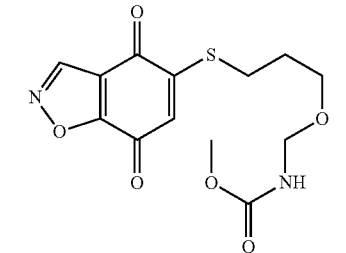 [SMILES: COC(=O)NCOCCCSC1=CC(=O)c2oncc2C1=O]
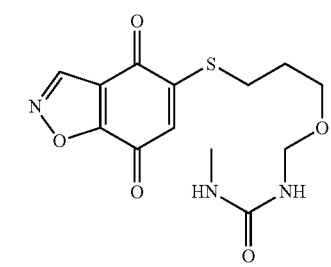 [SMILES: CNC(=O)NCOCCCSC1=CC(=O)c2oncc2C1=O]
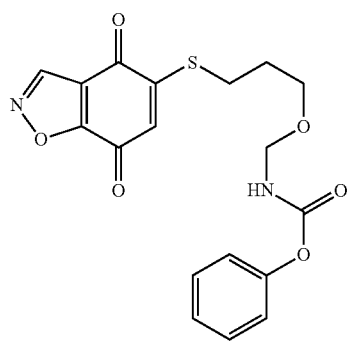 [SMILES: O=C(NCOCCCSC1=CC(=O)c2oncc2C1=O)Oc1ccccc1]
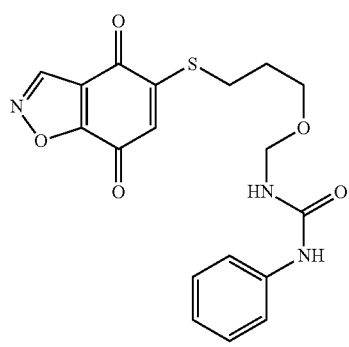
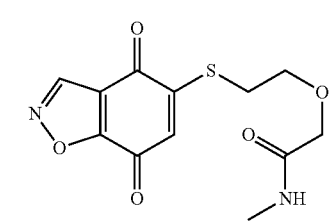 [SMILES: CNC(=O)COCCSC1=CC(=O)c2oncc2C1=O]
TABLE 1-continued
Example Active Compounds
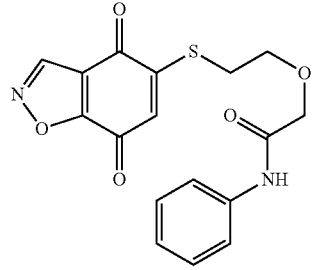
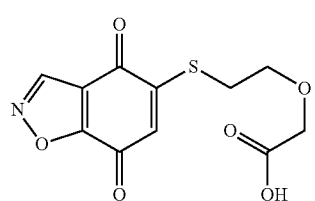 [SMILES: O=C(O)COCCSC1=CC(=O)c2oncc2C1=O]
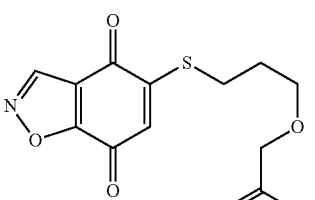
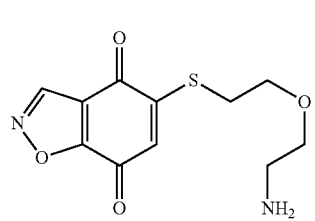
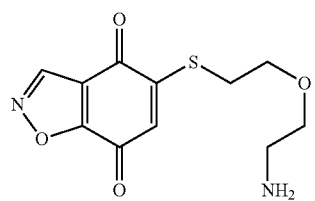 [SMILES: NCCOCCSC1=CC(=O)c2oncc2C1=O]
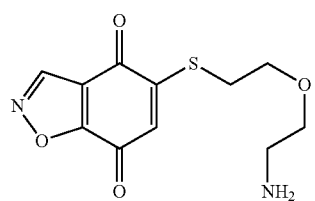
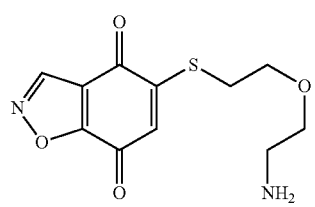

TABLE 1-continued

Example Active Compounds

TABLE 1-continued
Example Active Compounds
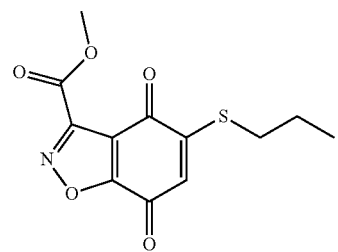 [SMILES: CCCSC1=CC(=O)c2onc(C(=O)OC)c2C1=O]
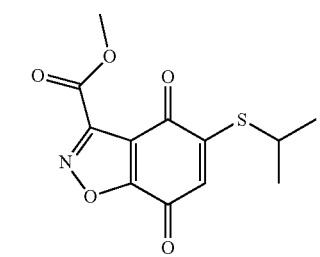 [SMILES: COC(=O)c1noc2c1C(=O)C(SC(C)C)=CC2=O]
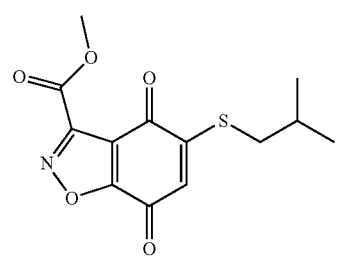 [SMILES: COC(=O)c1noc2c1C(=O)C(SCC(C)C)=CC2=O]
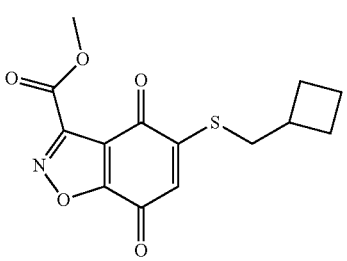 [SMILES: COC(=O)c1noc2c1C(=O)C(SCC1CCC1)=CC2=O]
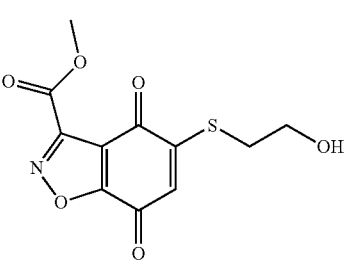 [SMILES: COC(=O)c1noc2c1C(=O)C(SCCO)=CC2=O]
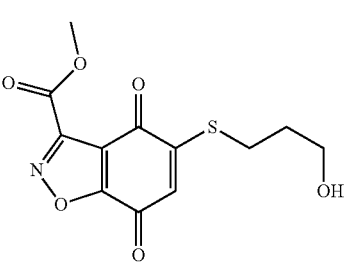 [SMILES: COC(=O)c1noc2c1C(=O)C(SCCCO)=CC2=O]
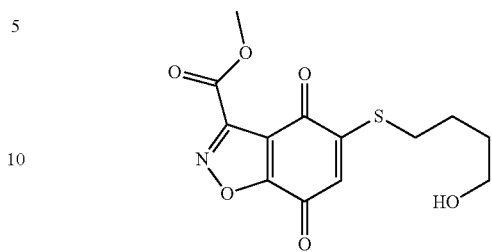
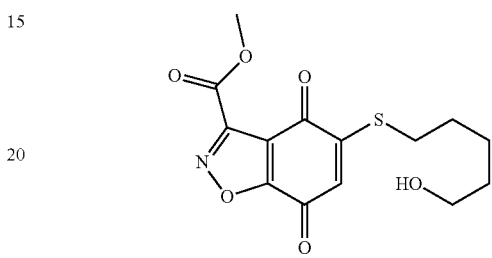
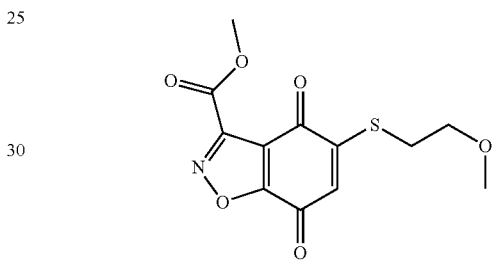
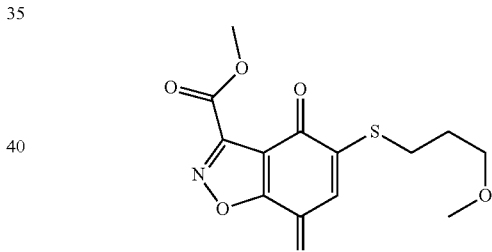
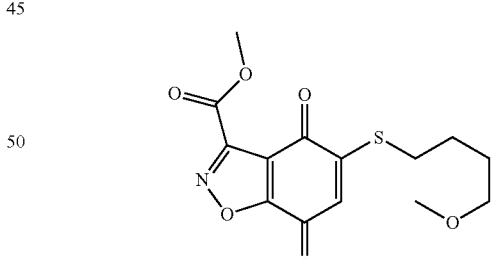
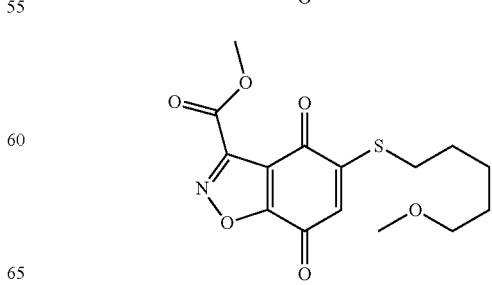

TABLE 1-continued
Example Active Compounds
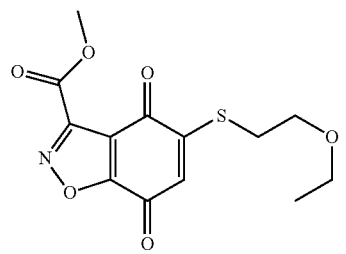 [SMILES: CCOCCSC1=CC(=O)c2onc(C(=O)OC)c2C1=O]
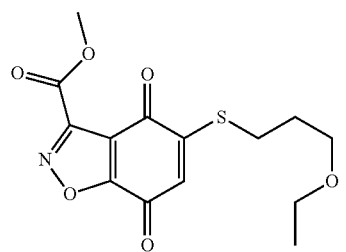 [SMILES: CCOCCCSC1=CC(=O)c2onc(C(=O)OC)c2C1=O]
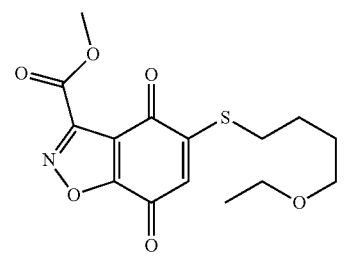 [SMILES: CCOCCCCSC1=CC(=O)c2onc(C(=O)OC)c2C1=O]
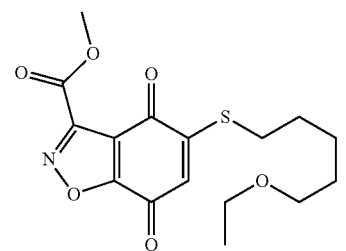 [SMILES: CCOCCCCCSC1=CC(=O)c2onc(C(=O)OC)c2C1=O]
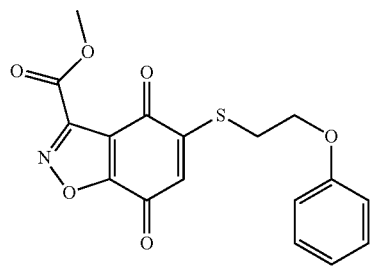 [SMILES: COC(=O)c1noc2c1C(=O)C(SCCOc1ccccc1)=CC2=O]
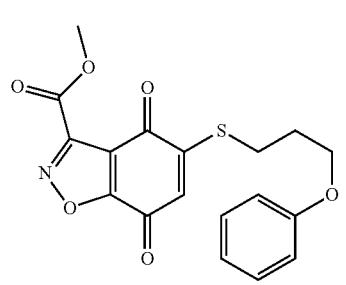 [SMILES: COC(=O)c1noc2c1C(=O)C(SCCCOc1ccccc1)=CC2=O]
TABLE 1-continued
Example Active Compounds
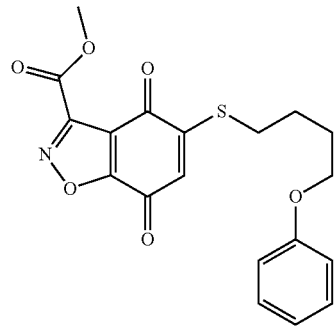 [SMILES: COC(=O)c1noc2c1C(=O)C(SCCCCOc1ccccc1)=CC2=O]
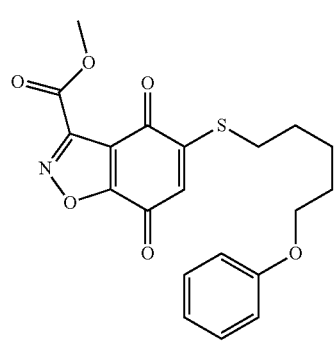 [SMILES: COC(=O)c1noc2c1C(=O)C(SCCCCCOc1ccccc1)=CC2=O]
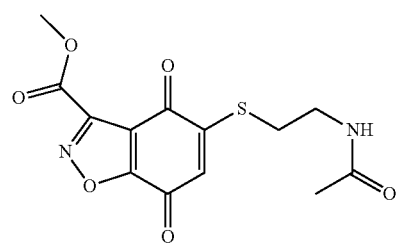
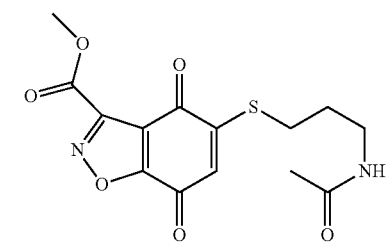 [SMILES: COC(=O)c1noc2c1C(=O)C(SCCCNC(C)=O)=CC2=O]
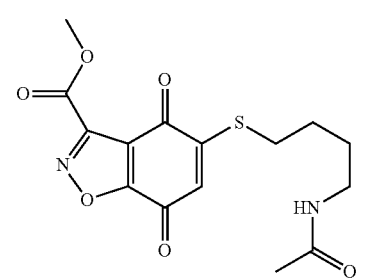 [SMILES: COC(=O)c1noc2c1C(=O)C(SCCCCNC(C)=O)=CC2=O]

TABLE 1-continued

Example Active Compounds

TABLE 1-continued
Example Active Compounds
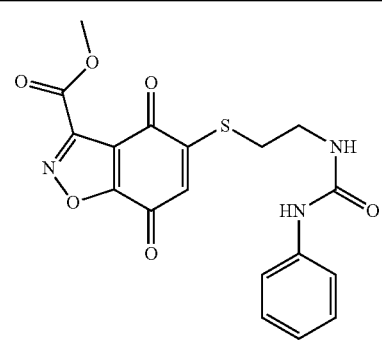
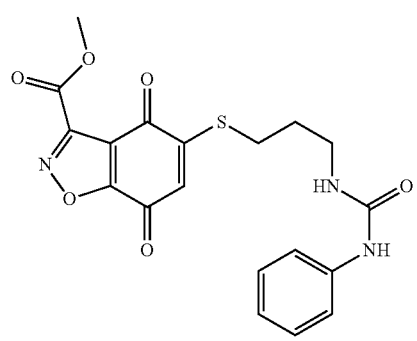
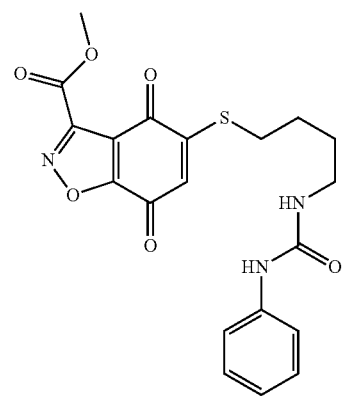
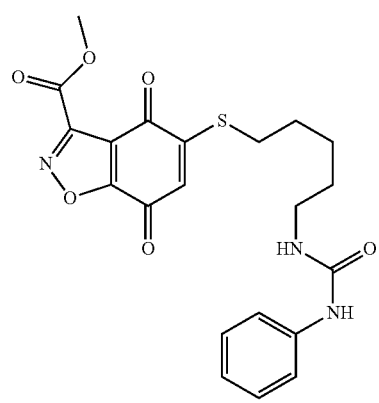
TABLE 1-continued
Example Active Compounds
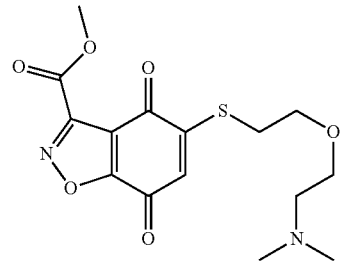
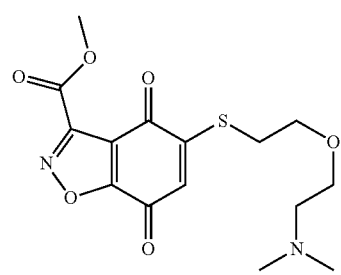
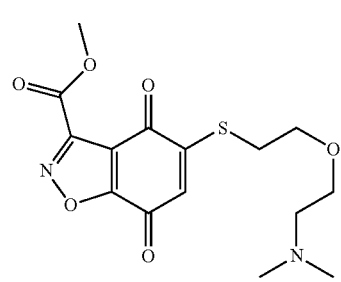
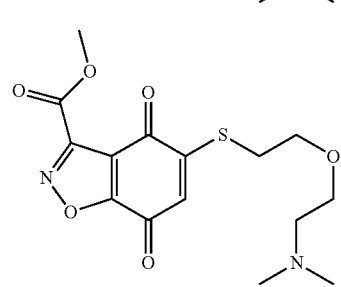
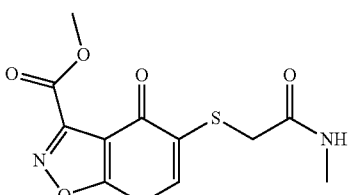
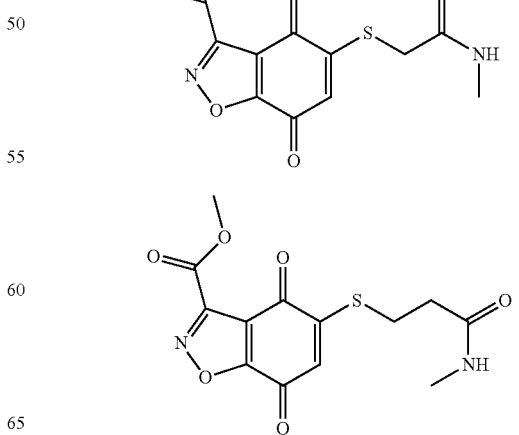

TABLE 1-continued
Example Active Compounds
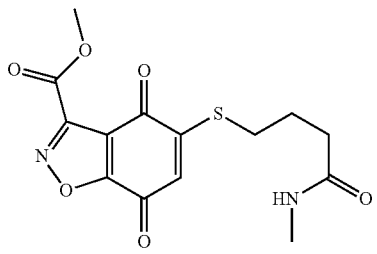
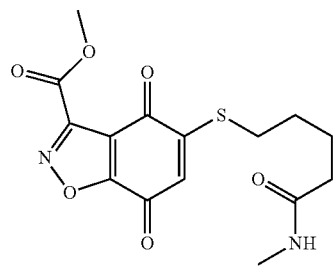 [SMILES: CNC(=O)CCCCSC1=CC(=O)c2onc(C(=O)OC)c2C1=O]
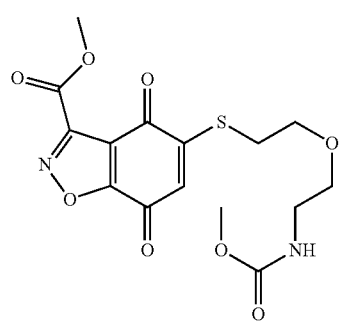 [SMILES: COC(=O)NCCOCCSC1=CC(=O)c2onc(C(=O)OC)c2C1=O]
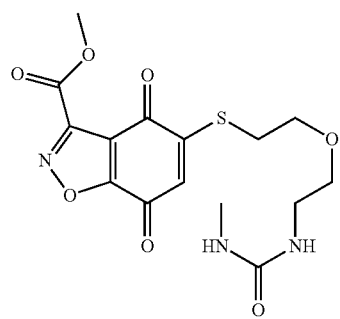 [SMILES: CNC(=O)NCCOCCSC1=CC(=O)c2onc(C(=O)OC)c2C1=O]
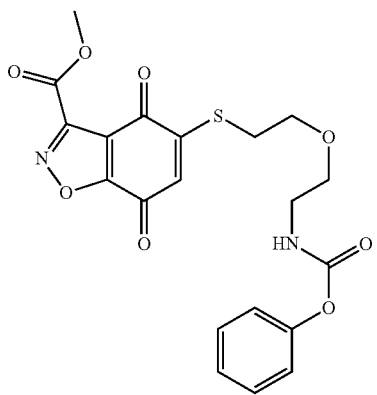
TABLE 1-continued
Example Active Compounds
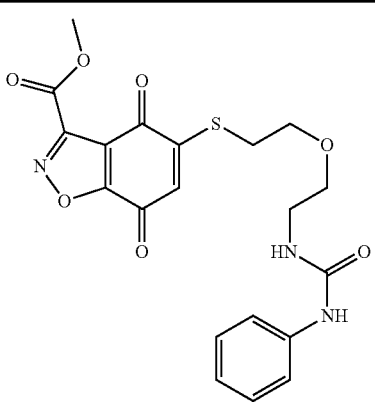
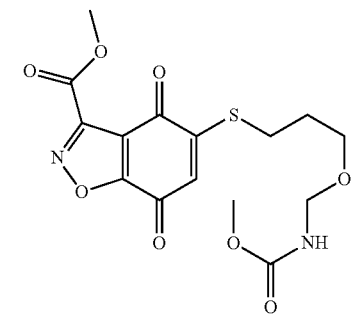
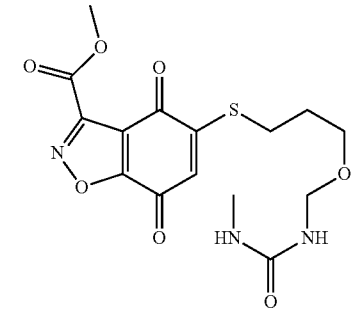
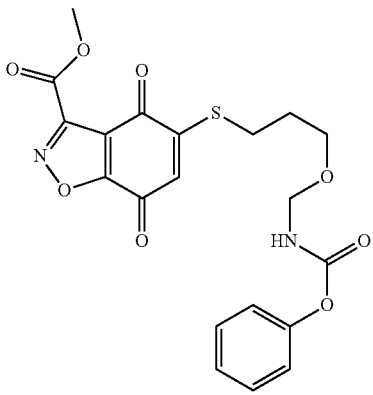 [SMILES: COC(=O)c1noc2c1C(=O)C(SCCCOCNC(=O)Oc1ccccc1)=CC2=O]

TABLE 1-continued
Example Active Compounds
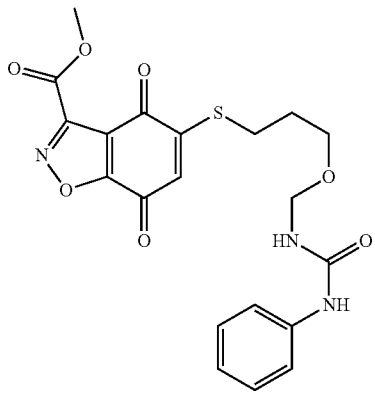
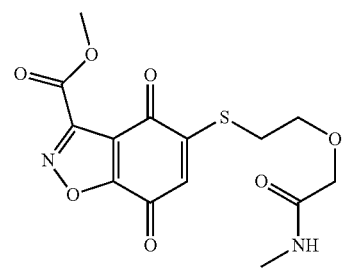 [SMILES: CNC(=O)COCCSC1=CC(=O)c2onc(C(=O)OC)c2C1=O]
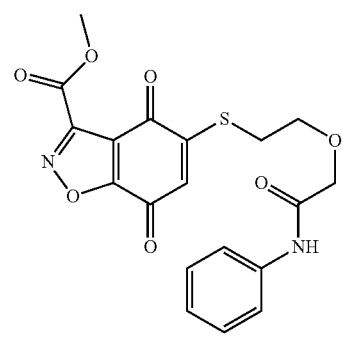 [SMILES: COC(=O)c1noc2c1C(=O)C(SCCOCC(=O)Nc1ccccc1)=CC2=O]
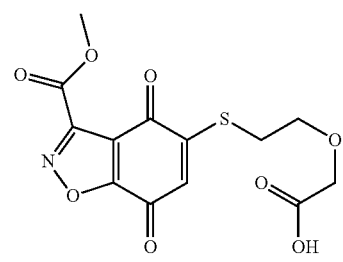 [SMILES: COC(=O)c1noc2c1C(=O)C(SCCOCC(=O)O)=CC2=O]
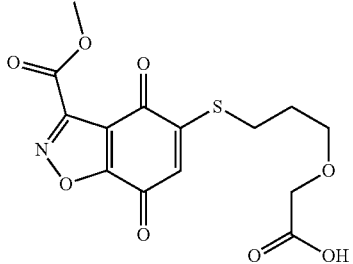 [SMILES: COC(=O)c1noc2c1C(=O)C(SCCCOCC(=O)O)=CC2=O]
TABLE 1-continued
Example Active Compounds
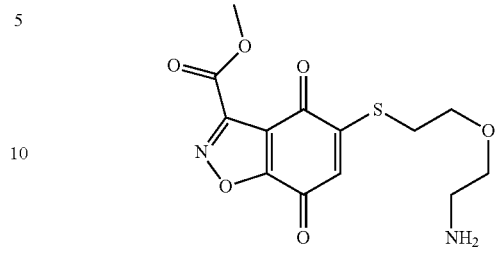
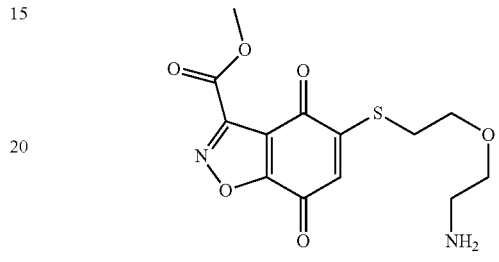
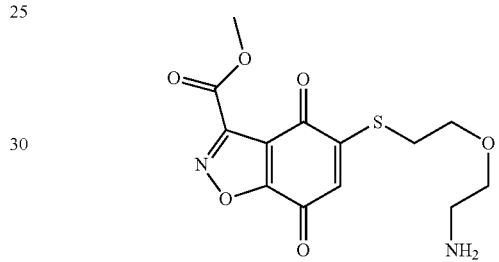
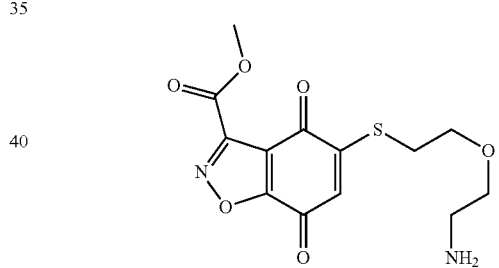
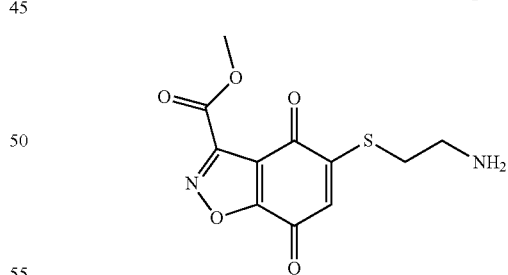
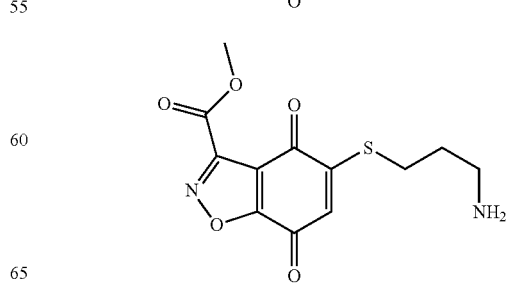

TABLE 1-continued
Example Active Compounds
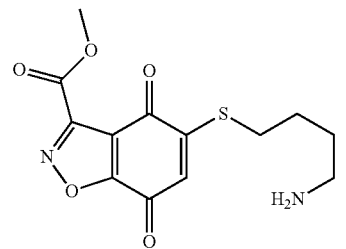 [SMILES: COC(=O)c1noc2c1C(=O)C(SCCCCN)=CC2=O]
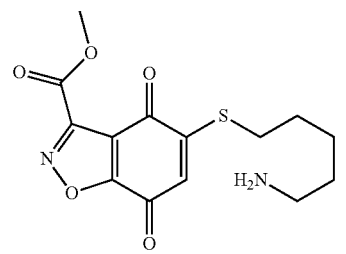 [SMILES: COC(=O)c1noc2c1C(=O)C(SCCCCCN)=CC2=O]
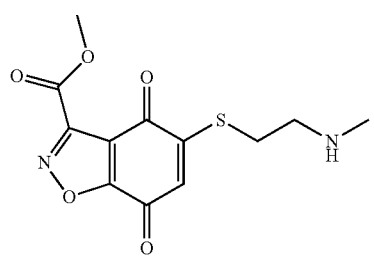 [SMILES: CNCCSC1=CC(=O)c2onc(C(=O)OC)c2C1=O]
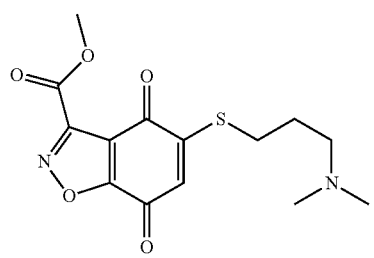 [SMILES: COC(=O)c1noc2c1C(=O)C(SCCCN(C)C)=CC2=O]
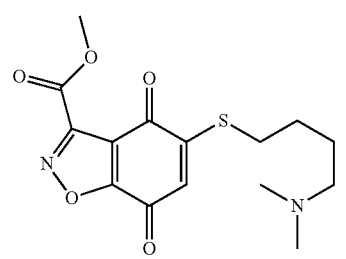 [SMILES: COC(=O)c1noc2c1C(=O)C(SCCCCN(C)C)=CC2=O]
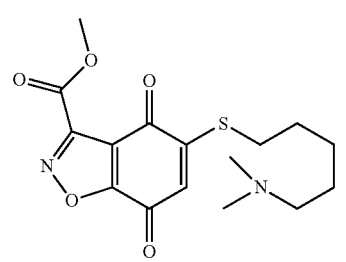 [SMILES: COC(=O)c1noc2c1C(=O)C(SCCCCCN(C)C)=CC2=O]
TABLE 1-continued
Example Active Compounds
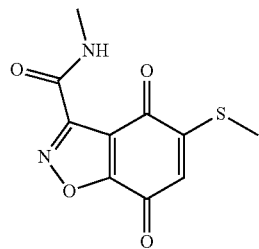 [SMILES: CNC(=O)c1noc2c1C(=O)C(SC)=CC2=O]
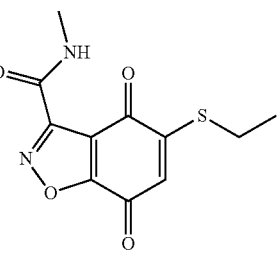
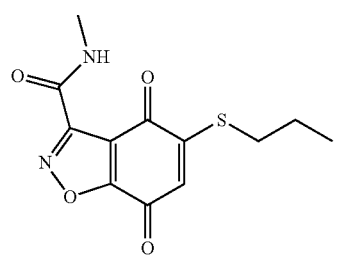 [SMILES: CCCSC1=CC(=O)c2onc(C(=O)NC)c2C1=O]
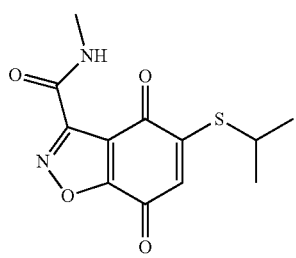 [SMILES: CNC(=O)c1noc2c1C(=O)C(SC(C)C)=CC2=O]
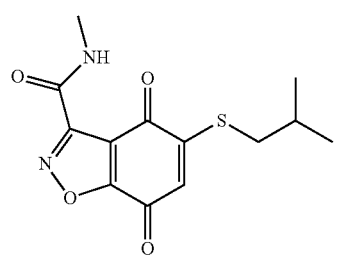 [SMILES: CNC(=O)c1noc2c1C(=O)C(SCC(C)C)=CC2=O]
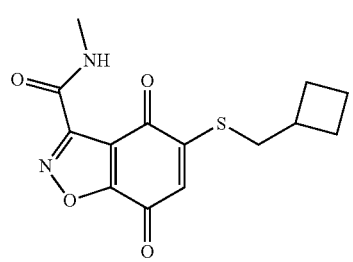 [SMILES: CNC(=O)c1noc2c1C(=O)C(SCC1CCC1)=CC2=O]

TABLE 1-continued
Example Active Compounds
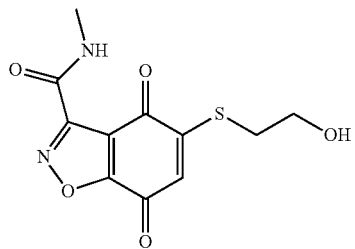 [SMILES: CNC(=O)c1noc2c1C(=O)C(SCCO)=CC2=O]
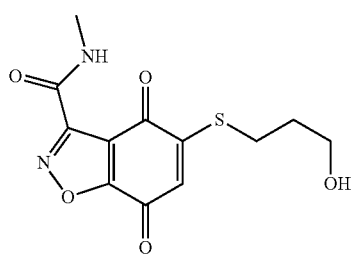 [SMILES: CNC(=O)c1noc2c1C(=O)C(SCCCO)=CC2=O]
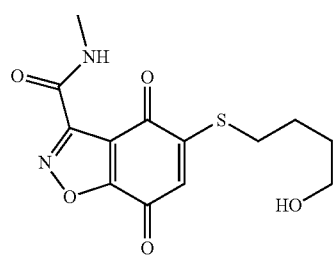 [SMILES: CNC(=O)c1noc2c1C(=O)C(SCCCCO)=CC2=O]
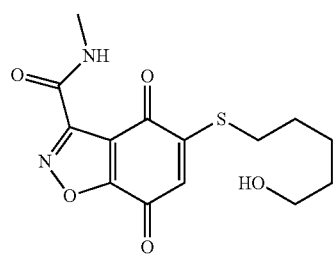 [SMILES: CNC(=O)c1noc2c1C(=O)C(SCCCCCO)=CC2=O]
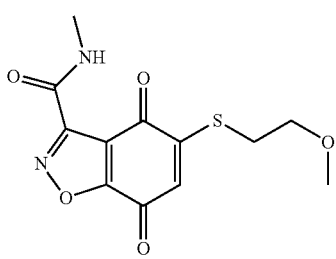 [SMILES: CNC(=O)c1noc2c1C(=O)C(SCCOC)=CC2=O]
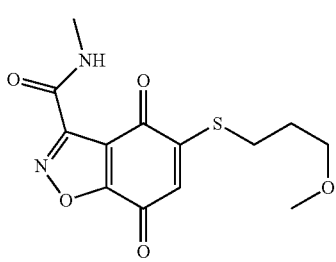 [SMILES: CNC(=O)c1noc2c1C(=O)C(SCCCOC)=CC2=O]
TABLE 1-continued
Example Active Compounds
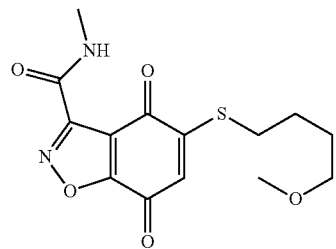 [SMILES: CNC(=O)c1noc2c1C(=O)C(SCCCCOC)=CC2=O]
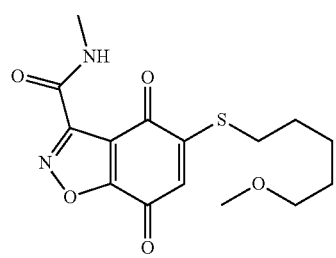 [SMILES: CNC(=O)c1noc2c1C(=O)C(SCCCCCOC)=CC2=O]
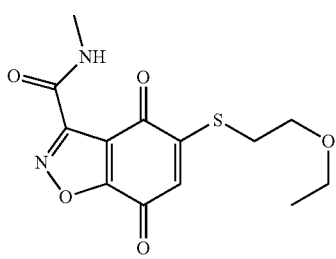
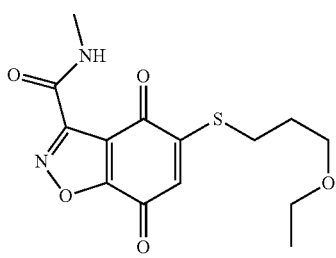
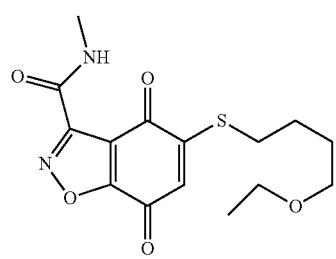 [SMILES: CCOCCCCSC1=CC(=O)c2onc(C(=O)NC)c2C1=O]
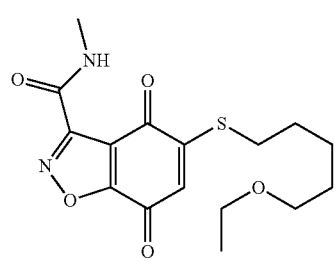 [SMILES: CCOCCCCCSC1=CC(=O)c2onc(C(=O)NC)c2C1=O]

TABLE 1-continued
Example Active Compounds
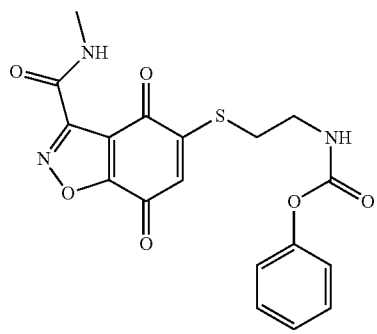
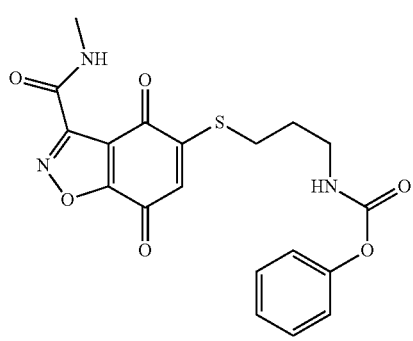
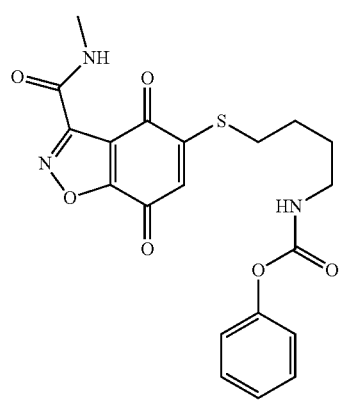 [SMILES: CNC(=O)c1noc2c1C(=O)C(SCCCCNC(=O)Oc1ccccc1)=CC2=O]
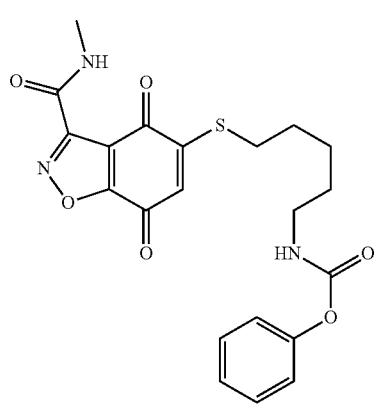
TABLE 1-continued
Example Active Compounds
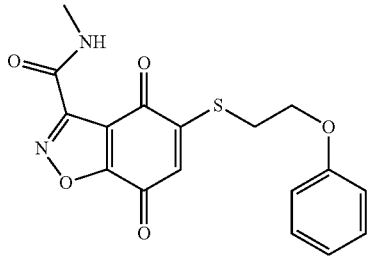 [SMILES: CNC(=O)c1noc2c1C(=O)C(SCCOc1ccccc1)=CC2=O]
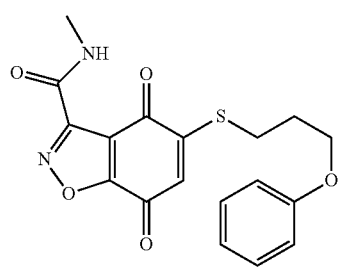 [SMILES: CNC(=O)c1noc2c1C(=O)C(SCCCOc1ccccc1)=CC2=O]
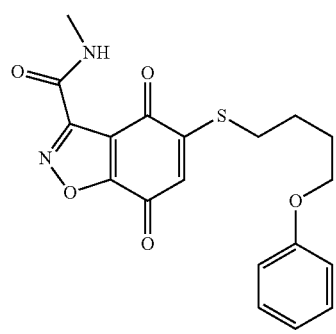 [SMILES: CNC(=O)c1noc2c1C(=O)C(SCCCCOc1ccccc1)=CC2=O]
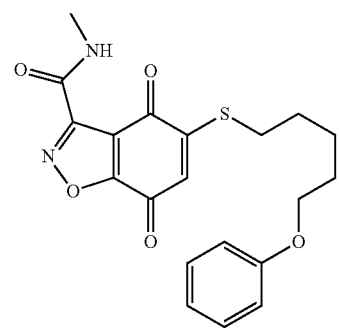 [SMILES: CNC(=O)c1noc2c1C(=O)C(SCCCCCOc1ccccc1)=CC2=O]
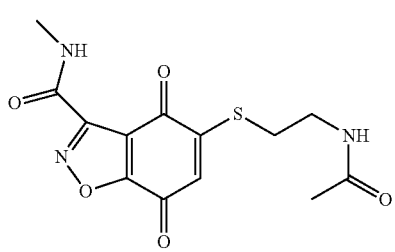 [SMILES: CNC(=O)c1noc2c1C(=O)C(SCCNC(C)=O)=CC2=O]

TABLE 1-continued
Example Active Compounds
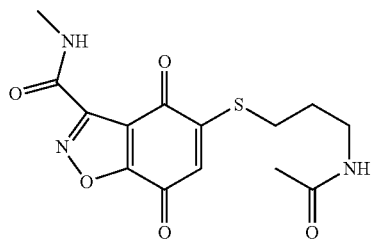 [SMILES: CNC(=O)c1noc2c1C(=O)C(SCCCNC(C)=O)=CC2=O]
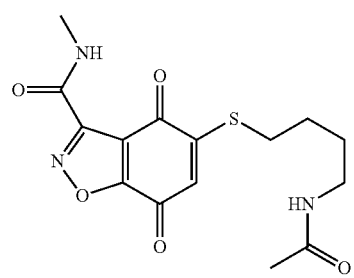 [SMILES: CNC(=O)c1noc2c1C(=O)C(SCCCCNC(C)=O)=CC2=O]
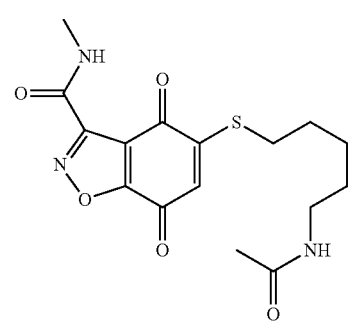 [SMILES: CNC(=O)c1noc2c1C(=O)C(SCCCCCNC(C)=O)=CC2=O]
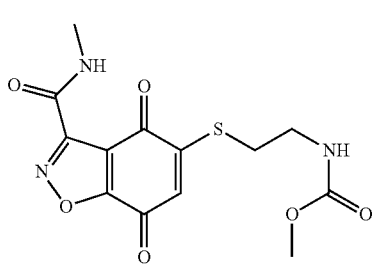
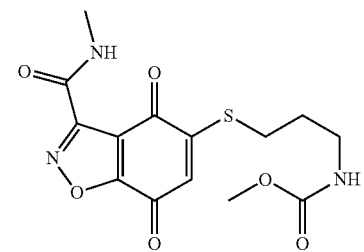 [SMILES: CNC(=O)c1noc2c1C(=O)C(SCCCNC(=O)OC)=CC2=O]
TABLE 1-continued
Example Active Compounds
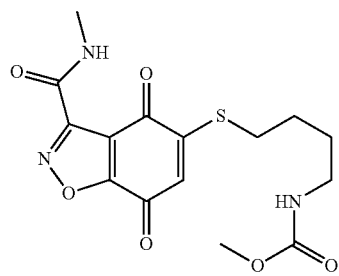 [SMILES: CNC(=O)c1noc2c1C(=O)C(SCCCCNC(=O)OC)=CC2=O]
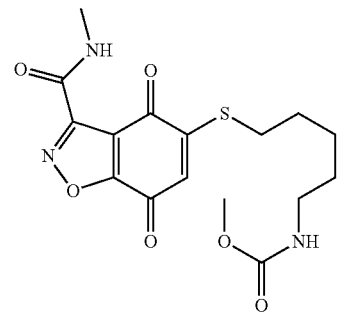 [SMILES: CNC(=O)c1noc2c1C(=O)C(SCCCCCNC(=O)OC)=CC2=O]
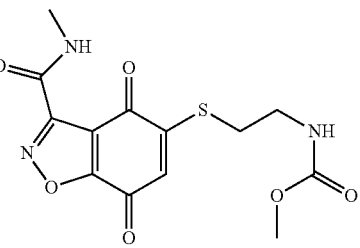
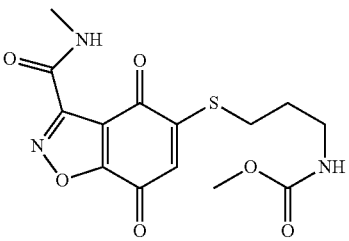 [SMILES: CNC(=O)c1noc2c1C(=O)C(SCCCNC(=O)OC)=CC2=O]
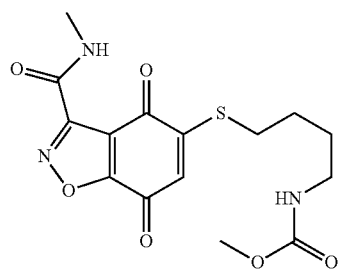 [SMILES: CNC(=O)c1noc2c1C(=O)C(SCCCCNC(=O)OC)=CC2=O]

TABLE 1-continued
Example Active Compounds
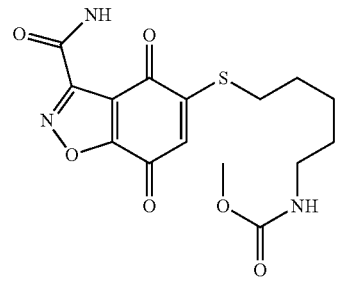 [SMILES: COC(=O)NCCCCCSC1=CC(=O)c2onc(C(N)=O)c2C1=O]
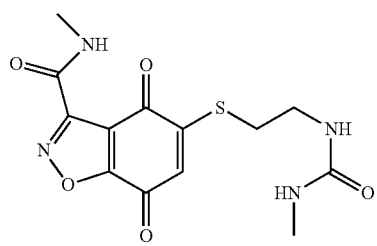 [SMILES: CNC(=O)NCCSC1=CC(=O)c2onc(C(=O)NC)c2C1=O]
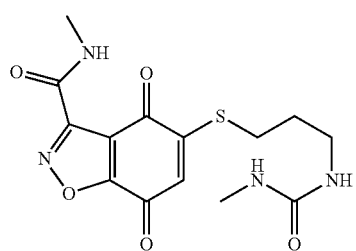 [SMILES: CNC(=O)NCCCSC1=CC(=O)c2onc(C(=O)NC)c2C1=O]
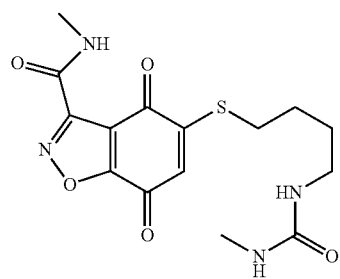 [SMILES: CNC(=O)NCCCCSC1=CC(=O)c2onc(C(=O)NC)c2C1=O]
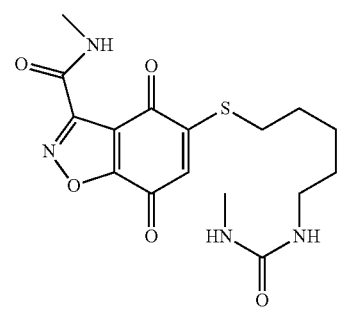 [SMILES: CNC(=O)NCCCCCSC1=CC(=O)c2onc(C(=O)NC)c2C1=O]
TABLE 1-continued
Example Active Compounds
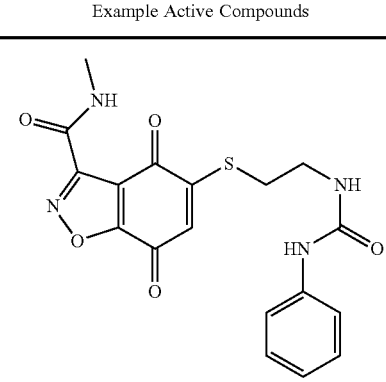
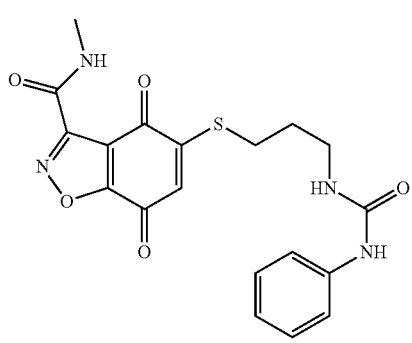
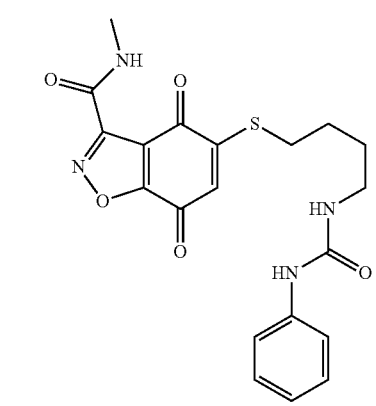
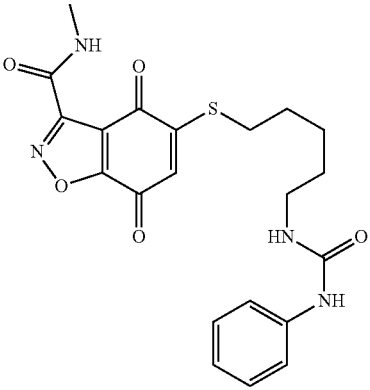 [SMILES: CNC(=O)c1noc2c1C(=O)C(SCCCCCNC(=O)Nc1ccccc1)=CC2=O]

TABLE 1-continued

Example Active Compounds

TABLE 1-continued
Example Active Compounds
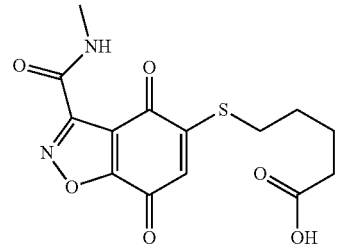 [SMILES: CNC(=O)c1noc2c1C(=O)C(SCCCCC(=O)O)=CC2=O]
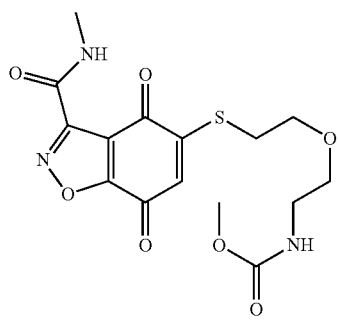 [SMILES: CNC(=O)c1noc2c1C(=O)C(SCCOCCNC(=O)OC)=CC2=O]
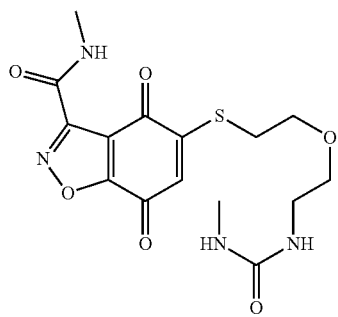 [SMILES: CNC(=O)NCCOCCSC1=CC(=O)c2onc(C(=O)NC)c2C1=O]
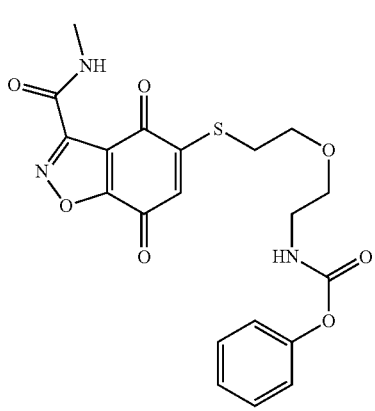
TABLE 1-continued
Example Active Compounds
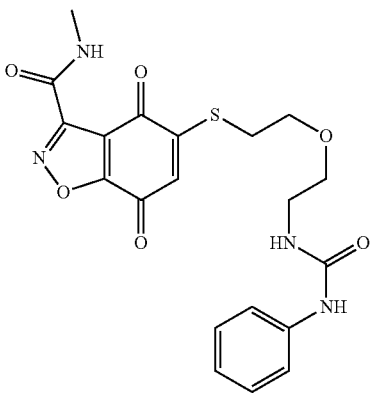 [SMILES: CNC(=O)c1noc2c1C(=O)C(SCCOCCNC(=O)Nc1ccccc1)=CC2=O]
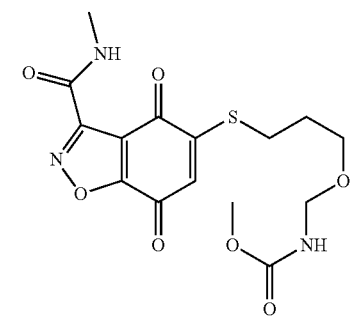
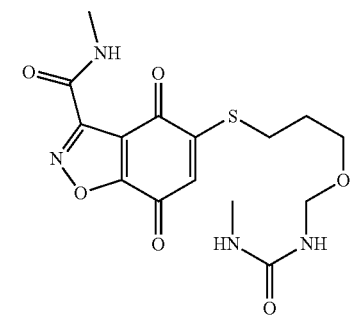
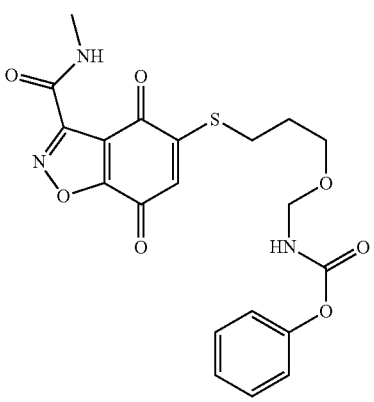 [SMILES: CNC(=O)c1noc2c1C(=O)C(SCCCOCNC(=O)Oc1ccccc1)=CC2=O]

TABLE 1-continued
Example Active Compounds
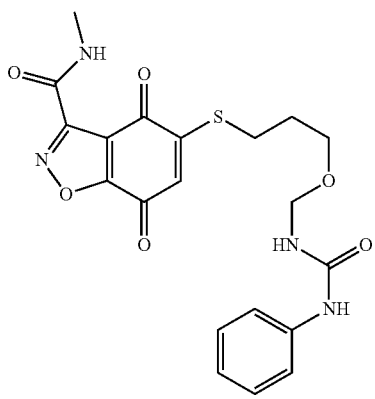
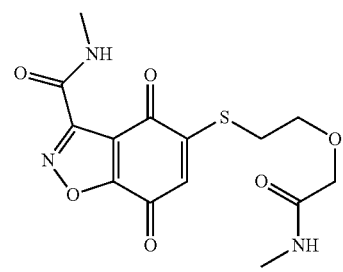
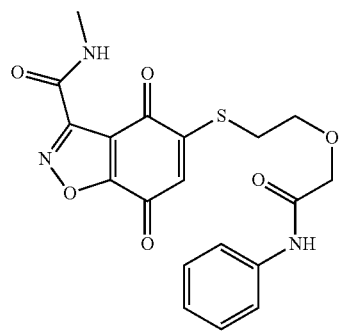 [SMILES: CNC(=O)c1noc2c1C(=O)C(SCCOCC(=O)Nc1ccccc1)=CC2=O]
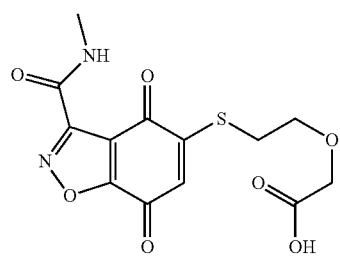 [SMILES: CNC(=O)c1noc2c1C(=O)C(SCCOCC(=O)O)=CC2=O]
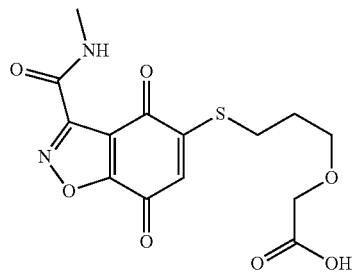 [SMILES: CNC(=O)c1noc2c1C(=O)C(SCCCOCC(=O)O)=CC2=O]
TABLE 1-continued
Example Active Compounds
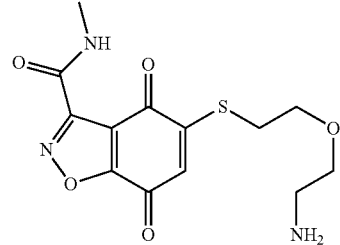 [SMILES: CNC(=O)c1noc2c1C(=O)C(SCCOCCN)=CC2=O]
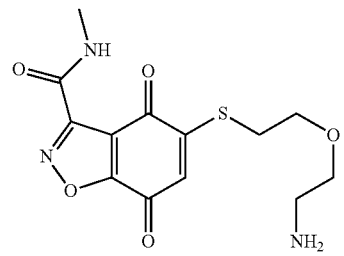
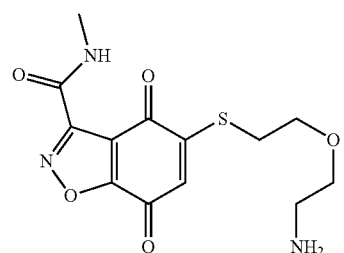
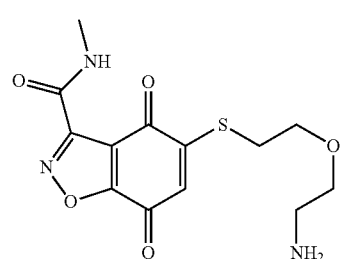
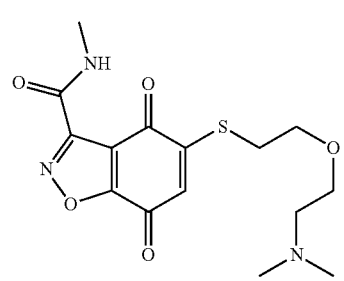
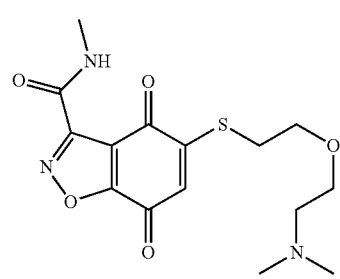

TABLE 1-continued
Example Active Compounds
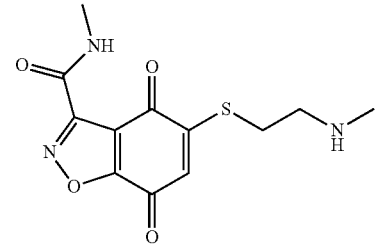
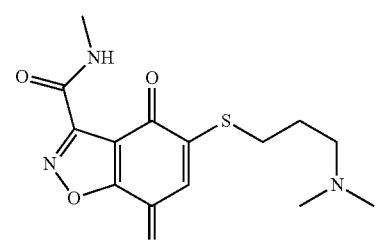
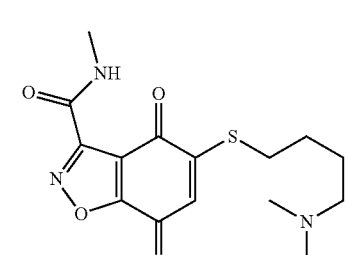
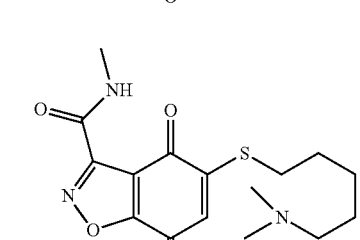
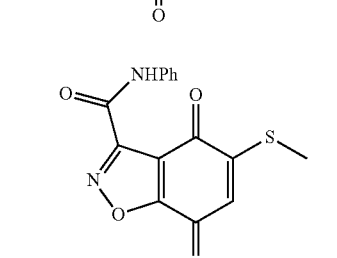
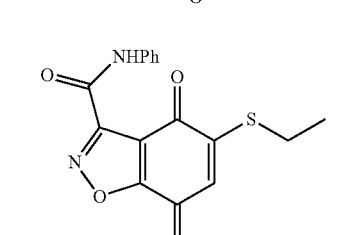
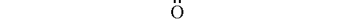

TABLE 1-continued
Example Active Compounds
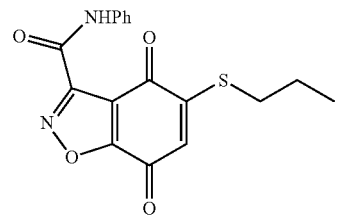
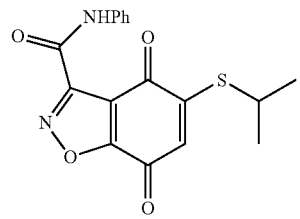
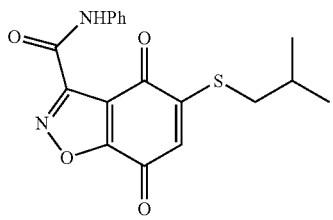
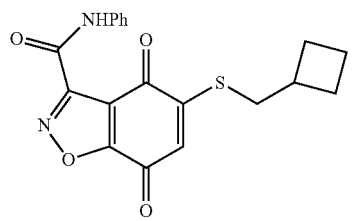
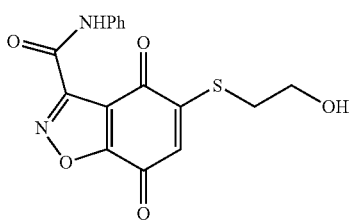
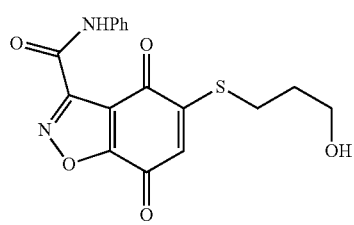
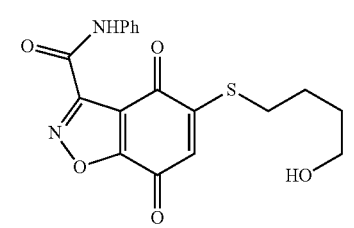
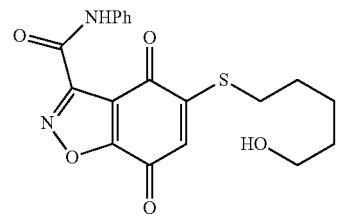
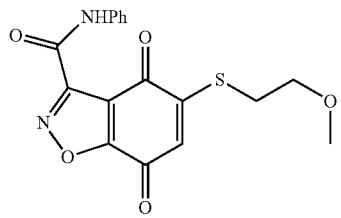
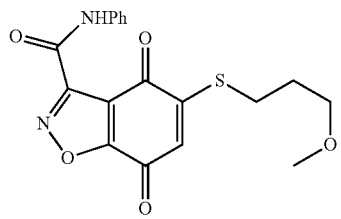
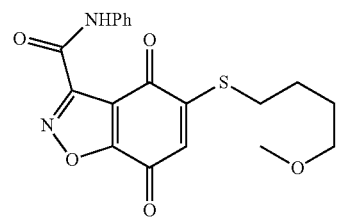
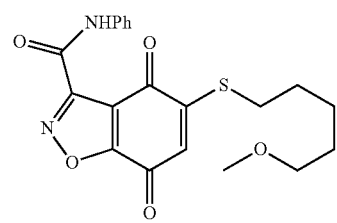
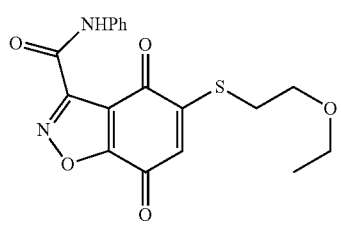
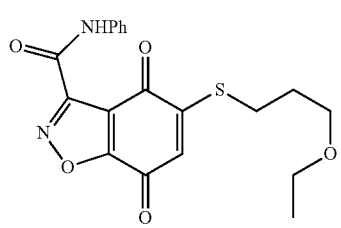

TABLE 1-continued
Example Active Compounds
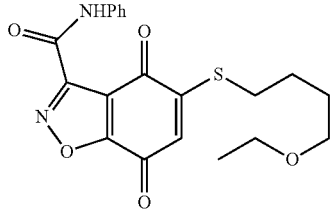
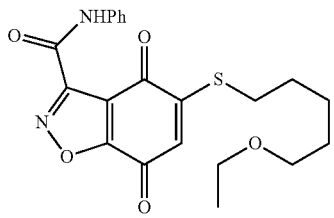
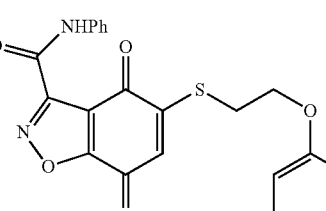
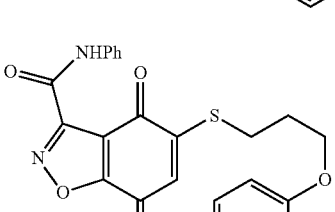
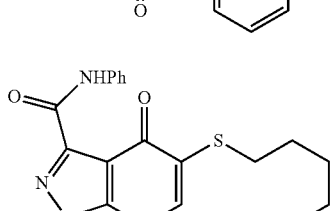
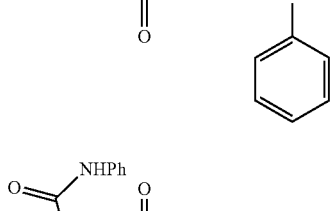
TABLE 1-continued
Example Active Compounds
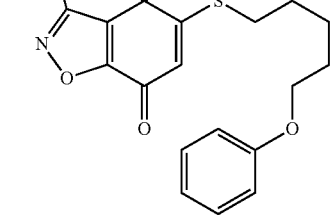
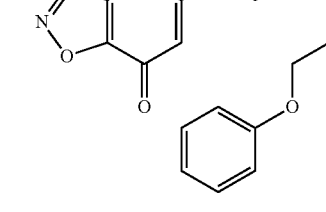
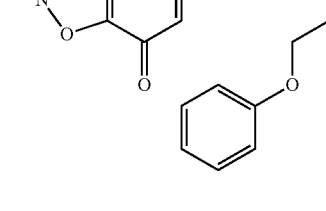
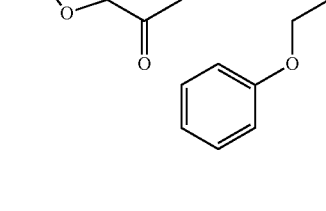
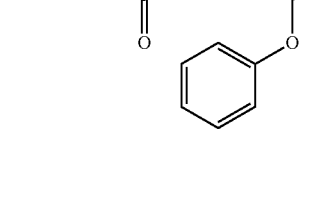
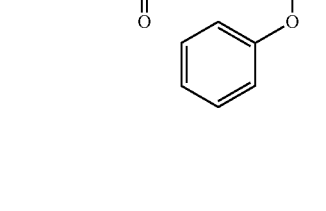

TABLE 1-continued
Example Active Compounds
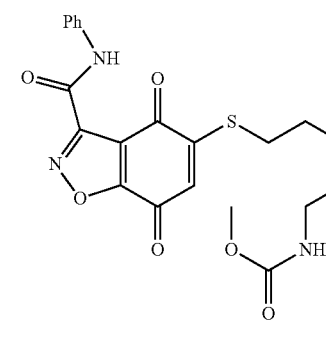

TABLE 1-continued
Example Active Compounds
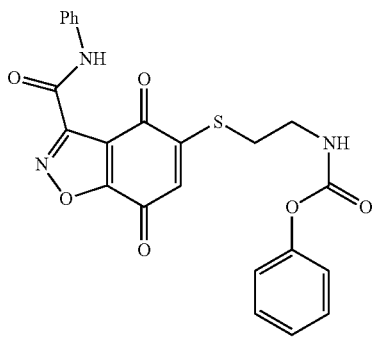
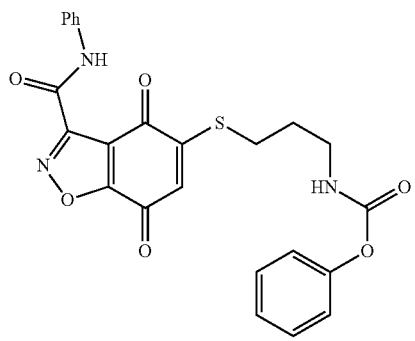
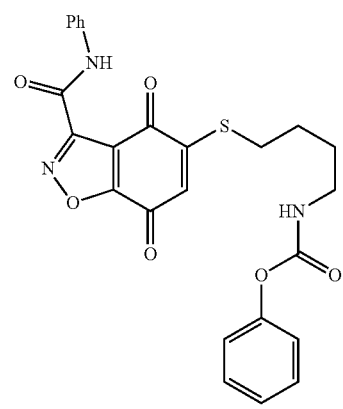 [SMILES: O=C(NCCCCSC1=CC(=O)c2onc(C(=O)Nc3ccccc3)c2C1=O)Oc1ccccc1]
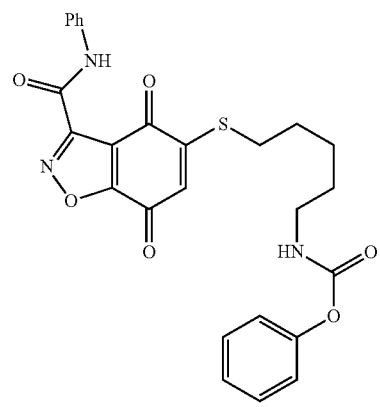 [SMILES: O=C(NCCCCCSC1=CC(=O)c2onc(C(=O)Nc3ccccc3)c2C1=O)Oc1ccccc1]
TABLE 1-continued
Example Active Compounds
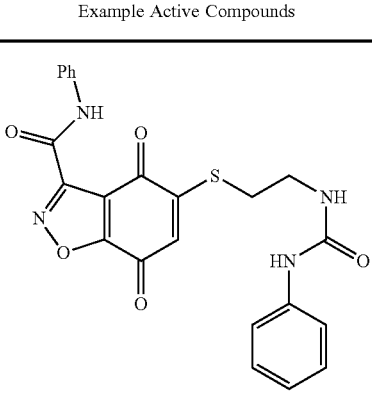
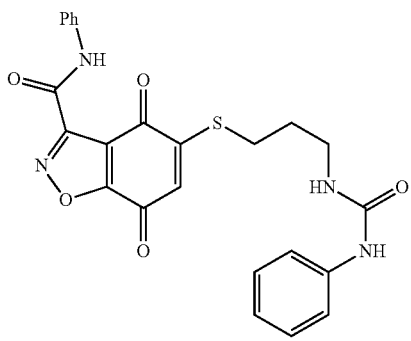
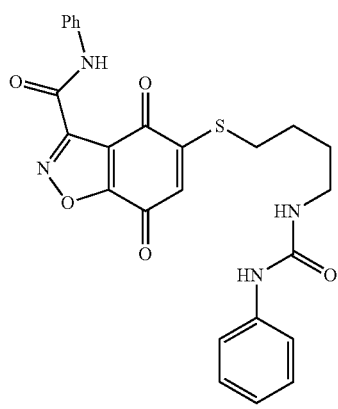
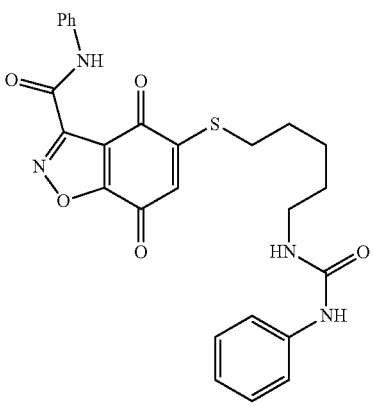 [SMILES: O=C(NCCCCCSC1=CC(=O)c2onc(C(=O)Nc3ccccc3)c2C1=O)Nc1ccccc1]

TABLE 1-continued
Example Active Compounds
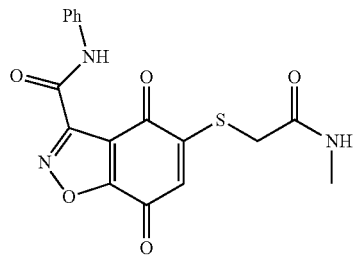 [SMILES: CNC(=O)CSC1=CC(=O)c2onc(C(=O)Nc3ccccc3)c2C1=O]
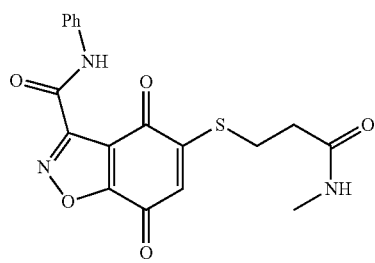
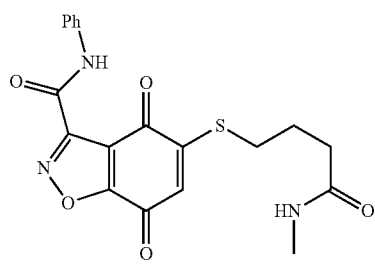
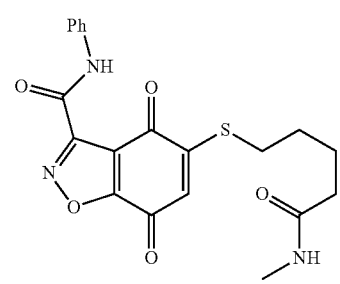 [SMILES: CNC(=O)CCCCSC1=CC(=O)c2onc(C(=O)Nc3ccccc3)c2C1=O]
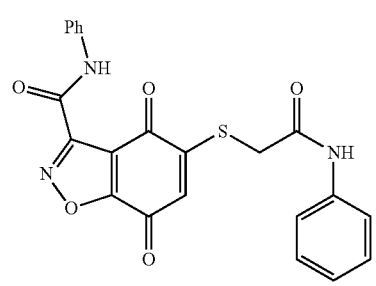
TABLE 1-continued
Example Active Compounds
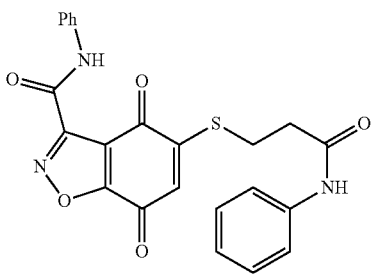 [SMILES: O=C(CCSC1=CC(=O)c2onc(C(=O)Nc3ccccc3)c2C1=O)Nc1ccccc1]
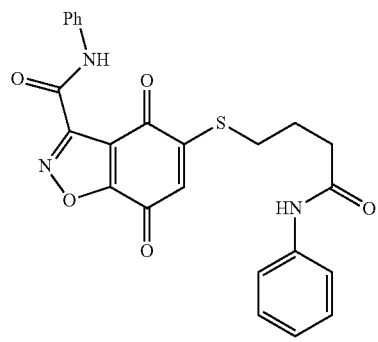 [SMILES: O=C(CCCSC1=CC(=O)c2onc(C(=O)Nc3ccccc3)c2C1=O)Nc1ccccc1]
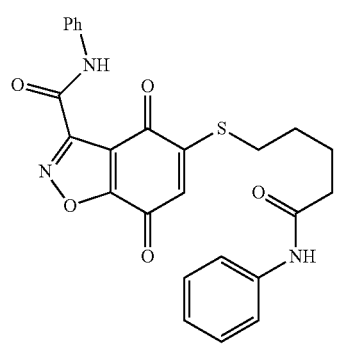 [SMILES: O=C(CCCCSC1=CC(=O)c2onc(C(=O)Nc3ccccc3)c2C1=O)Nc1ccccc1]
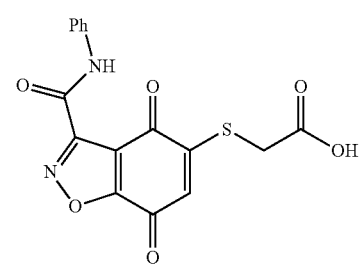
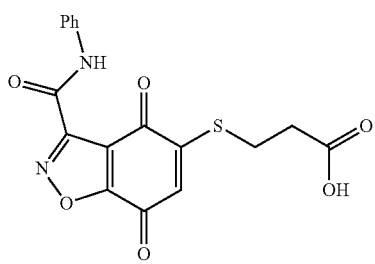 [SMILES: O=C(O)CCSC1=CC(=O)c2onc(C(=O)Nc3ccccc3)c2C1=O]

TABLE 1-continued
Example Active Compounds
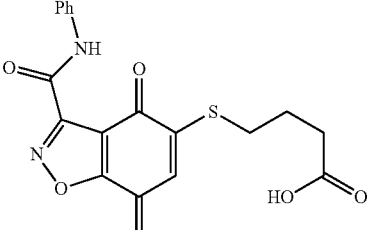
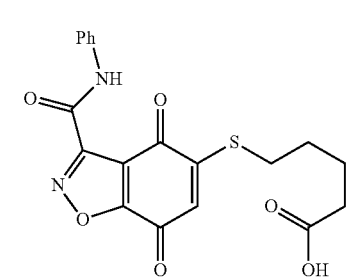 [SMILES: O=C(O)CCCCSC1=CC(=O)c2onc(C(=O)Nc3ccccc3)c2C1=O]
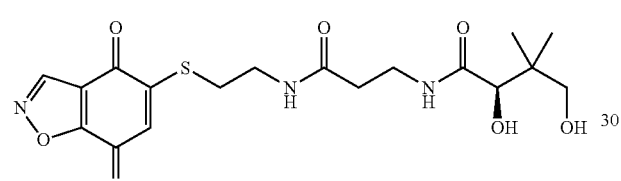
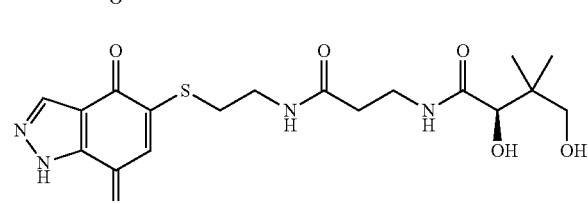
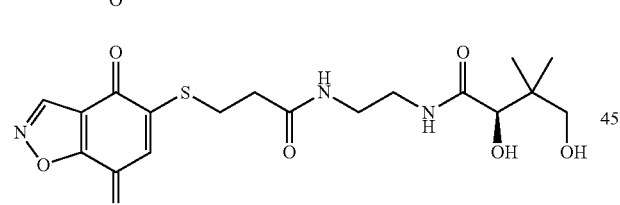
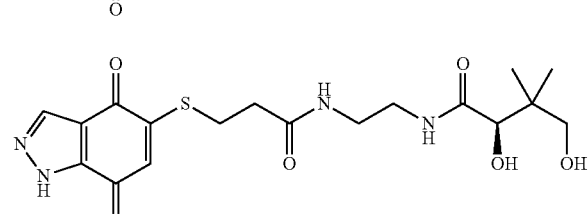
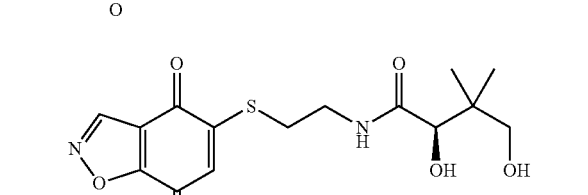
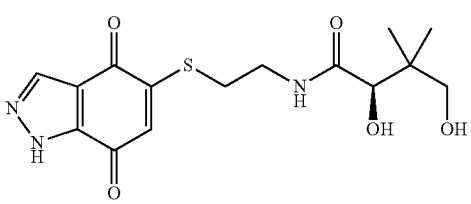
TABLE 1-continued
Example Active Compounds
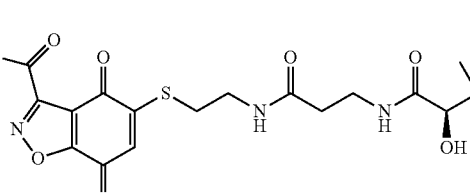
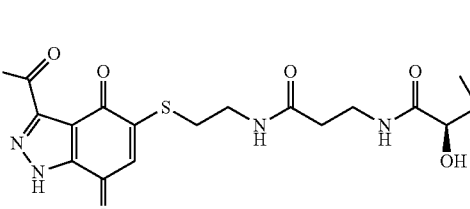
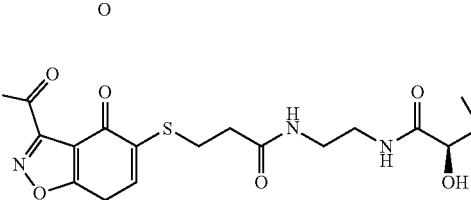
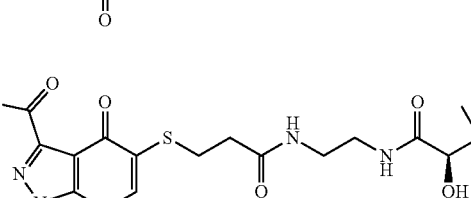
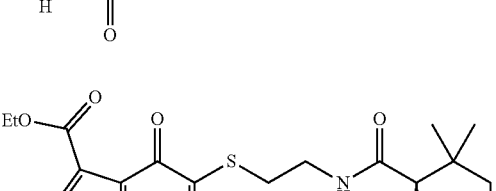
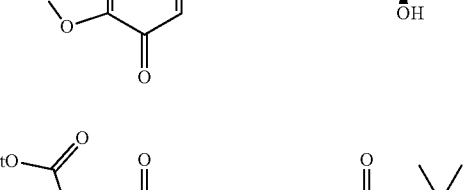
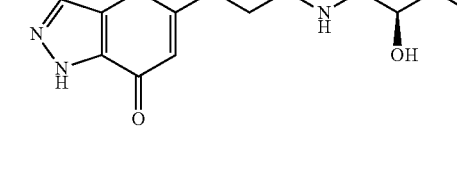

TABLE 1-continued

Example Active Compounds

[Chemical structures of example active compounds]

2. Pharmaceutical Formulations.

The active compounds disclosed herein can, as noted above, be prepared in the form of their pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

Active compounds of the present invention may be prepared as pharmaceutically acceptable prodrugs. Such prodrugs are those which are, within the scope of sound medical judgment, suitable for use in contact with the tissues of humans and lower animals without undue toxicity, irritation, allergic response and the like, commensurate with a reasonable risk/benefit ratio, and effective for their intended use, as well as the zwitterionic forms, where possible, of the compounds of the invention. The term "prodrug" refers to compounds that are rapidly transformed in vivo to yield the parent compound of the above formulae, for example, by hydrolysis in blood. A thorough discussion is provided in T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein. See also U.S. Pat. No. 6,680,299. Examples include a prodrug that is metabolized in vivo by a subject to an active drug having an activity of active compounds as described herein, wherein the prodrug is an ester of an alcohol or carboxylic acid group, if such a group is present in the compound; an acetal or ketal of an alcohol group, if such a group is present in the compound; an N-Mannich base or an imine of an amine group, if such a group is present in the compound; or a Schiff base, oxime, acetal, enol ester, oxazolidine, or thiazolidine of a carbonyl group, if such a group is present in the compound, such as described in U.S. Pat. No. 6,680,324 and U.S. Pat. No. 6,680,322.

The active compounds described above may be formulated for administration in a pharmaceutical carrier in accordance with known techniques. See, e.g., Remington, *The Science and Practice of Pharmacy* ($9^{th}$ Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well known techniques of pharmacy comprising admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active compound(s), which preparations are preferably isotonic with the blood of the intended recipient. These preparations may contain antioxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising an active compound(s), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis/tris buffer (pH 6) or ethanol/water and contain from 0.1 to 0.2M active ingredient.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the compounds disclosed herein or salts thereof, may be lyophilized to produce a lyophilizate which may be reconstituted with a pharmaceutically acceptable carrier, such as water, to regenerate a liposomal suspension.

Other pharmaceutical compositions may be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidyl cholines, and lecithin.

In addition to active compound(s), the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

Dosage and Routes of Administration.

As noted above, the present invention provides pharmaceutical formulations comprising the active compounds (including the pharmaceutically acceptable salts thereof), in pharmaceutically acceptable carriers for oral, rectal, topical, buccal, parenteral, intramuscular, intradermal, or intravenous, and transdermal administration.

The therapeutically effective dosage of any specific compound, the use of which is in the scope of present invention, will vary somewhat from compound to compound, and patient to patient, and will depend upon the condition of the patient and the route of delivery. As a general proposition, a dosage from about 0.1 to about 50 mg/kg will have therapeutic efficacy, with all weights being calculated based upon the weight of the active compound, including the cases where a salt is employed. Toxicity concerns at the higher level may restrict intravenous dosages to a lower level such as up to about 10 mg/kg, with all weights being calculated based upon the weight of the active base, including the cases where a salt is employed. A dosage from about 10 mg/kg to about 50 mg/kg may be employed for oral administration. Typically, a dosage from about 0.5 mg/kg to 5 mg/kg may be employed for intramuscular injection.

Depending upon the disorder being treated, the compounds described herein may be administered alone or concurrently with one or more additional active agent useful for treating the disease or condition with which the patient is afflicted. Examples of additional active agents include, but are not limited to, those set forth in paragraphs 0065 through 0387 of W. Hunter, D. Gravett, et al., US Patent Application Publication No. 20050181977 (Published Aug. 18, 2005) (assigned to Angiotech International AG) the disclosure of which is incorporated by reference herein in its entirety.

The present invention is explained in greater detail in the following non-limiting Examples.

Example 1

5-mercapto-benzo[d]isoxazole-4,7-diones and 5-mercapto-1H-indazole-4,7-diones

Table 2 below shows structure-activity relationships of 5-mercapto-benzo[d]isoxazole-4,7-diones and 5-mercapto-1H-indazole-4,7-diones synthesized in our laboratory. These compounds (a) inhibit the recombinant thioesterase domain of FASN; some show marked ability to (b) inhibit FASN in living cells, as evidenced by the inhibition of $^{14}$C-acetate uptake; some also show marked ability to (c) inhibit in vitro cancer cell growth.

SCHEME 1

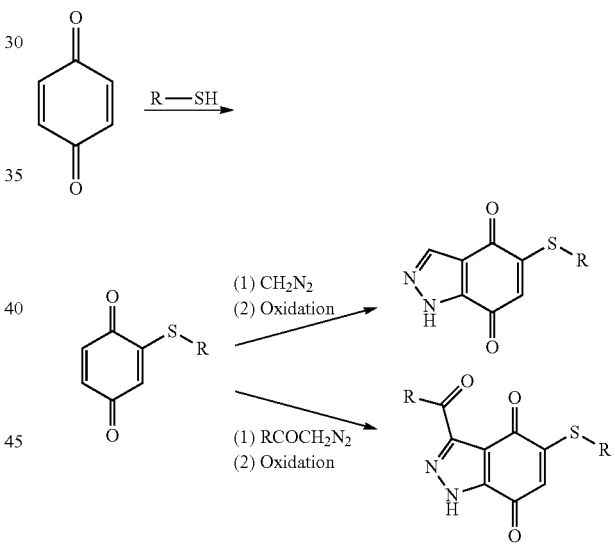

An overall synthetic approach for 5-mercapto-1H-indazole-4,7-diones and other analogs thereof is shown in Scheme 1. The upper scheme describes the synthesis of targets where $R_4$=H. Briefly 1,4-benzoquinone is reacted with desired mercaptan according to the method of Katritzky, A. R.; Odens, H. H.; et al (Rubber Chemistry and Technology, vol 74 (5), pp. 915-925 (2001)). The resulting 2-mercapto-1,4-benzoquinone is then treated with diazomethane prepared in situ and in the presence of and oxidating agent such as 2,3-dichloro-5,6-dicyano-1,4-benzoquinone (DDQ) to yield the desired indazole. The lower scheme describes the synthesis of targets where $R_4$ as described in Markush structures Ia, Ib and Ic is COOEt. Similarly, 1,4-benzoquinone is reacted with desired mercaptan according to the method of Katritzky, A. R.; Odens, H. H.; et al (Rubber Chemistry and Technology, vol 74 (5), pp. 915-925, (2001)). The resulting 2-mercapto-1,4-benzoquinone is then treated with diazomethane derivative prepared by the method of Watt (J. Org. Chem. vol 51, pp. 5362-536 (1986)) in the presence of an oxidizing agent (DDQ) to yield the desired indazole compound.

SCHEME 2

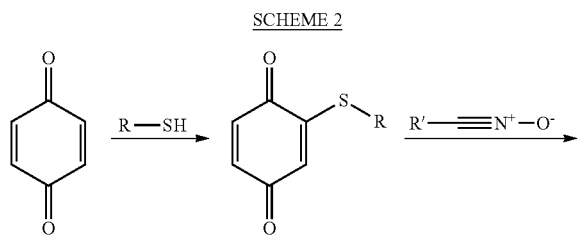

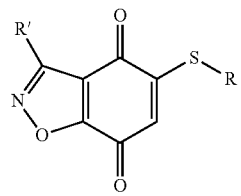

An overall synthetic approach for 5-mercapto-benzo[d]isoxazole-4,7-diones and other analogs thereof is shown in Scheme 2. Briefly 1,4-benzoquinone is reacted with desired mercaptan according to the method of Katritzky, A. R.; Odens, H. H.; et al (Rubber Chemistry and Technology, vol 74 (5), 915-925 (2001)) followed by addition of a nitrile oxide derivative prepared by the method of Hamadi and Msaddek (Heterocyclic Communications, Vol 12 (6), pp. 457-462 (2006)).

| Compound Structure | Number | recombinant thioesterase % Inhibition (10 µM) TE1 | TE2 | approx, $IC_{50}$ TE1 (µM) | approx, tion of $^{14}C$- $IC_{50}$ TE2 (µM) | % inhibition of $^{14}C$-acetate incorp. PC3 cells | cell cells PC3 | MTS assay ($IC_{50}$) survival, tumor DU-145 | normal cells FS-4 |
|---|---|---|---|---|---|---|---|---|---|
| (structure: Ph, OH, N-O, OMe, OH) | TPI-00401-00-A | 40.00 | 55.88 | NA | NA | 29.1 | 33 | >50 | ND |
| (structure: ethyl ester, indazole, S-ethyl) | TPI-00402-00-A | 66.63 | 95.73 | 2.35 | 0.56 | 90.4 | 18.75 | 40 | 20.9 |
| (structure: ethyl ester, indazole, S) | TPI-00403-00-A | 69.35 | 79.27 | 3.90 | 2.42 | 97 ($IC_{50}$ = 6.75 µM) | 3.25 | 15.6 | 9.15 |
| (structure: ethyl ester, indazole, S-CH2-C(O)OMe) | TPI-00405-00-A | 69.52 | 96.82 | 2.78 | 0.41 | ND | ND | ND | ND |

-continued
| Compound Structure | Number | recombinant thioesterase % Inhibition (10 μM) TE1 | TE2 | approx, IC$_{50}$ TE1 (μM) | approx, IC$_{50}$ TE2 (μM) | % inhibition of $^{14}$C-acetate incorp. PC3 cells | cell survival, PC3 cells | cell survival, tumor DU-145 | MTS assay (IC$_{50}$) normal cells FS-4 |
|---|---|---|---|---|---|---|---|---|---|
| 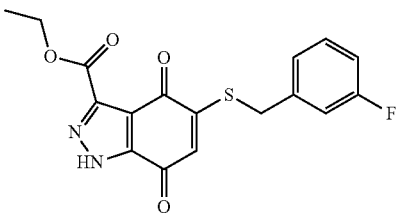 [SMILES: CCOC(=O)c1n[nH]c2c1C(=O)C(SCc1cccc(F)c1)=CC2=O] | TPI-00406-00-A | 73.64 | 96.01 | NA | NA | 37.7 | ND | ND | ND |
| 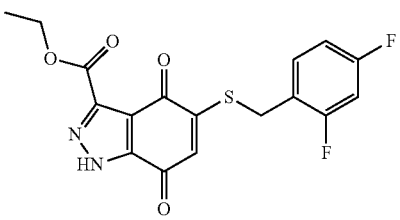 [SMILES: CCOC(=O)c1n[nH]c2c1C(=O)C(SCc1ccc(F)cc1F)=CC2=O] | TPI-00407-00-A | 65.96 | 94.89 | NA | NA | 37.8 | ND | ND | ND |
| 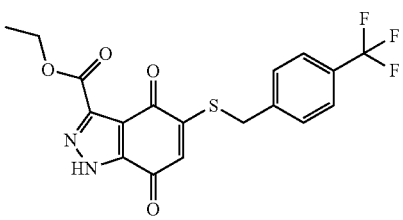 [SMILES: CCOC(=O)c1n[nH]c2c1C(=O)C(SCc1ccc(C(F)(F)F)cc1)=CC2=O] | TPI-00408-00-A | 67.87 | 96.18 | NA | NA | 89.9 | 18.5 | ND | 22.5 |
| 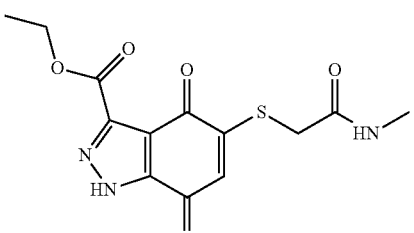 | TPI-00409-00-A | 53.50 | 92.17 | NA | NA | 0 | ND | ND | ND |
| 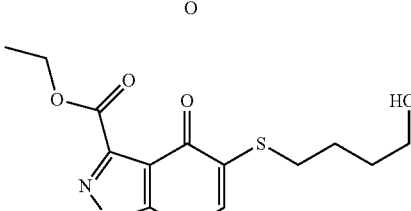 | TPI-00410-00-A | 59.61 | 91.67 | NA | NA | 1.85 | ND | ND | ND |
| 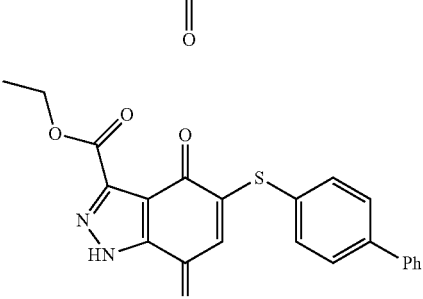 | TPI-00411-00-A | 70.51 | 97.43 | NA | NA | 0.75 | ND | ND | ND |

| Compound Structure | Number | recombinant thioesterase | | approx, IC$_{50}$ TE1 (μM) | IC$_{50}$ TE2 (μM) | % inhibition of $^{14}$C-acetate incorp. PC3 cells | cell survival, cells PC3 | cell survival, tumor DU-145 | MTS assay (IC$_{50}$) normal cells FS-4 |
|---|---|---|---|---|---|---|---|---|---|
| | | % Inhibition (10 μM) TE1 | TE2 | | | | | | |
| (ethyl indazole-dione with 3-methoxyphenylthio) | TPI-00412-00-A | 81.63 | 97.98 | NA | NA | 9.95 | ND | ND | ND |
| (ethyl indazole-dione with 2-(2-methoxyethoxy)ethylthio) | TPI-00413-00-A | 50.23 | 94.78 | NA | NA | 20.2 | ND | ND | ND |
| (ethyl indazole-dione with cyclopentylthio) | TPI-00414-00-A | 52.21 | 86.40 | NA | NA | 92.4 | 25 | ND | 33 |
| (ethyl indazole-dione with phenylthio) | TPI-00415-00-A | 79.69 | 97.46 | NA | NA | 7.05 | ND | ND | ND |
| (ethyl indazole-dione with 4-methoxybenzylthio) | TPI-00416-00-A | 64.31 | 96.49 | NA | NA | 89.9 | 25.8 | ND | 33 |
| (ethyl indazole-dione with 4-chlorobenzylthio) | TPI-00417-00-A | 74.81 | 97.85 | NA | NA | 96.1 | 13.8 | ND | 21 |

-continued
| Compound Structure | Number | recombinant thioesterase | | approx, IC50 TE1 (μM) | IC50 TE2 (μM) | % inhibition of 14C-acetate incorp. PC3 cells | cells PC3 | cell survival, tumor DU-145 | MTS assay (IC50) normal cells FS-4 |
|---|---|---|---|---|---|---|---|---|---|
| | | % Inhibition (10 μM) | | | | | | | |
| | | TE1 | TE2 | | | | | | |
| 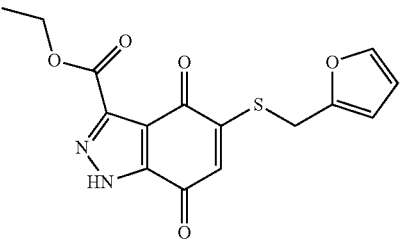 [SMILES: CCOC(=O)c1n[nH]c2c1C(=O)C(SCc1ccco1)=CC2=O] | TPI-00418-00-A | 65.54 | 95.92 | NA | NA | 92.2 | 31.7 | ND | 37 |
| 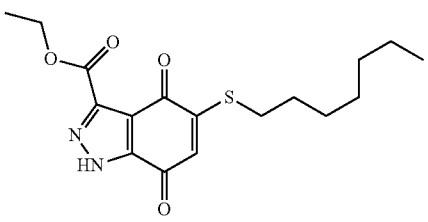 [SMILES: CCCCCCCSC1=CC(=O)c2[nH]nc(C(=O)OCC)c2C1=O] | TPI-00419-00-A | 66.19 | 95.79 | NA | NA | 67.95 | 32 | ND | 50 |
| 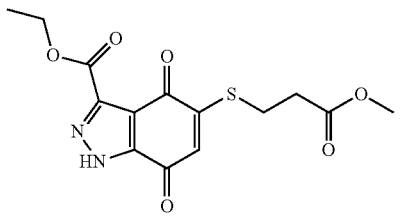 [SMILES: CCOC(=O)c1n[nH]c2c1C(=O)C(SCCC(=O)OC)=CC2=O] | TPI-00420-00-A | 61.96 | 95.35 | NA | NA | 68.5 | 37.5 | ND | 42 |
| 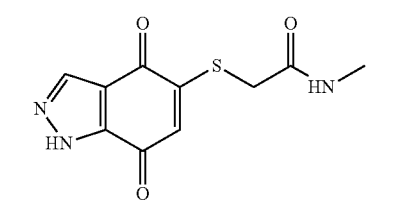 [SMILES: CNC(=O)CSC1=CC(=O)c2[nH]ncc2C1=O] | TPI-00421-00-A | 100.00 | 100.00 | 1.02 | NA | 70 | 17.9 | ND | 41 |
| 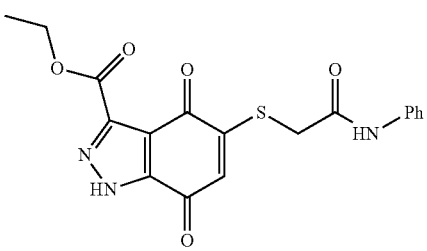 [SMILES: CCOC(=O)c1n[nH]c2c1C(=O)C(SCC(=O)Nc1ccccc1)=CC2=O] | TPI-00422-00-A | 22.92 | 86.76 | NA | NA | 0 | 48 | ND | >50 |
| 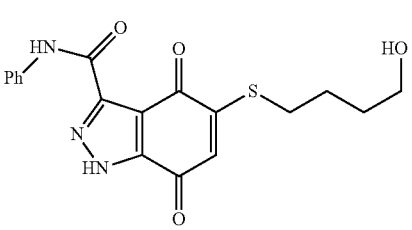 [SMILES: O=C(Nc1ccccc1)c1n[nH]c2c1C(=O)C(SCCCCO)=CC2=O] | TPI-00423-00-A | 79.75 | 97.99 | NA | NA | 87.25 | 20 | ND | 25 |

-continued

| Compound Structure | Number | recombinant thioesterase | | approx. IC₅₀ TE1 (μM) | IC₅₀ TE2 (μM) | % inhibition of ¹⁴C-acetate incorp. PC3 cells | cell survival, tumor PC3 | cell survival, tumor DU-145 | MTS assay (IC₅₀) normal cells FS-4 |
|---|---|---|---|---|---|---|---|---|---|
| | | % Inhibition (10 μM) TE1 | TE2 | | | | | | |
| (structure shown) | TPI-00424-00-A | 92.59 | 100.00 | NA | NA | 0 | 27 | ND | 50 |

Key to Table 2:
Recombinant Thioesterase Inhibition Assay.

Briefly, recombinant FASN-TE (250 nM, 100 mM TRIS pH 7.4, 50 mM NaCl, 1 mM EDTA) was pre-incubated with inhibitors for 30 min at 37° C. prior to the addition of fluorogenic substrate, 4-methylumbelliferyl heptanoate (4-MUH, 120 μM) (56); the reaction was then monitored by following the increase in fluorescence using a Tecan Safire² 96-well plate reader using 350/450 excitation/emission wavelengths. The IC₅₀ values are then determined for each compound in the series.

Inhibition of ¹⁴C-Acetate Incorporation in PC3 Cells.

This test ensures that the compound(s) target intracellular FASN correctly. The ability to inhibit FASN activity in cells will be performed by metabolic labeling of newly synthesized fatty acids with ¹⁴C-acetate, as we have described previously. Briefly, PC-3 cells were seeded in 24-well plates at 50,000 cells per well. After 48 hours media was replaced with fresh media containing either drug or DMSO vehicle. As with the toxicity assay described below, the IC₅₀ for the ability to inhibit FASN will also be determined. Cells will be incubated with a dose of each derivative compound that reflects the IC₅₀'s determined in the MTS assays. After two hours, 1 μCi of ¹⁴C-acetate was added to each well for a two hour labeling period. The cells are then washed with PBS and collected by trypsinization. Lipids were finally isolated by Folch extraction and quantified by scintillation counting. The IC₅₀ value for each compound against FASN in cells can then be determined.

MTS Cell Survival Assay.

Prostate tumor (PC3, DU145) and normal fibroblast controls (FS-4) cells were individually seeded in 96-well plates at a density of 4,000 cells per well. After 48 hours the cells are be treated with a dose of each compound (1-50 μM) or DMSO vehicle in fresh media. Cell viability of each cell line was then determined after 24, 48 and 72 hours of treatment with each compound by MTS assay (Roche). MTS assays provide a relative measure of cell viability based on the ability of mitochondria to metabolize a tetrazolium substrate to a colored formazan product. Viability is determined by colorimetric readout at 492 nm and determined relative to vehicle only treated cells. The IC₅₀ for each drug, at each time point, will be determined by curve fitting.

The foregoing is illustrative of the present invention, and is not to be construed as limiting thereof. The invention is defined by the following claims, with equivalents of the claims to be included therein.

What is claimed is:

1. A method of reversibly or irreversibly inhibiting fatty acid synthase in a subject in need thereof, comprising administering to said subject an active compound in a treatment-effective amount to reversibly or irreversibly inhibit fatty acid synthase in said subject; wherein said active compound is selected from the group consisting of compounds of Formula Ia, Ib, and Ic, and pharmaceutically acceptable salts or prodrugs thereof:

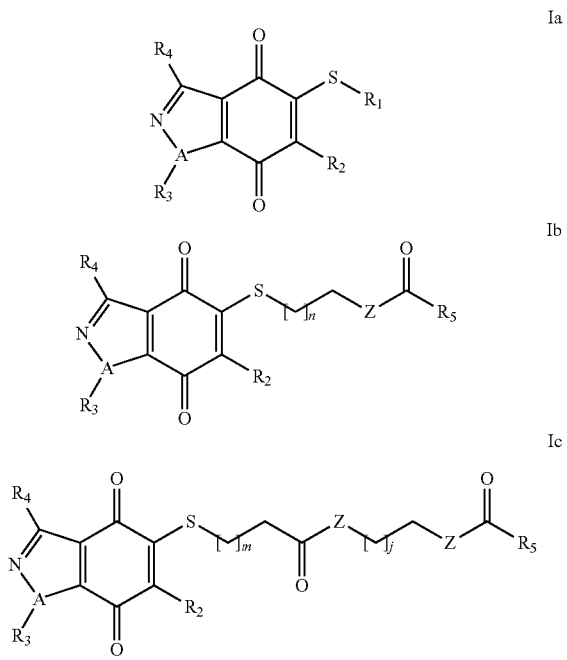

wherein:
each Z is independently selected from the group consisting of N, O, S and CH₂;
A is O (then R₃ is null) or N;
n=1-5; m=1-5; j=1-4; and
R₁, R₂, R₃, R₄, and R₅ are each independently selected from the group consisting of H, lower straight-chain alkyl or branched chain lower alkyl, aromatic, substituted aromatic, heteroaromatic, substituted heteroaromatic, benzyl, substituted benzyl, —(CH₂)ₚ—Ar, where p is 1 to 3 and Ar is aromatic, substituted aromatic, heteroaromatic or substituted heteroaromatic, and —(CH$_2$)$_p$—R', where p is 1 to 3 and R' is H, straight chain or branched chain lower alkoxy, aromatic, substituted aromatic, heteroaromatic, substituted heteroaromatic, halogen, aldehyde, carboxylic acid, —COOR", —CONHR", —CONR"$_2$, —OCONHR", —OCONR"$_2$, —NCONHR", —NCONR"$_2$, or —SCONR"$_2$, and where each R" is independently H, straight chain or branched chain lower alkoxy, aromatic, substituted aromatic, heteroaromatic, or substituted heteroaromatic.

2. The method of claim 1, wherein said subject is afflicted with cancer.

3. The method of claim 1, wherein said subject is afflicted with obesity.

4. The method of claim 1, wherein said subject is afflicted with diabetes.

5. The method of claim 1, wherein said subject is afflicted with a viral infection.

6. The method of claim 1, wherein said subject is afflicted with a bacterial infection.

7. The method of claim 1, wherein said subject is afflicted with a fungal infection.

8. The method of claim 1, wherein said subject is afflicted with a protozoal infection.

9. The method of claim 1, wherein said active compound is selected from the group consisting of the compounds of Table 1 below

TABLE 1

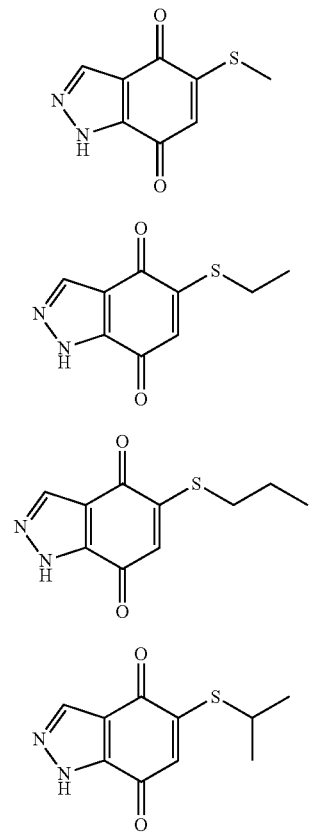

TABLE 1-continued

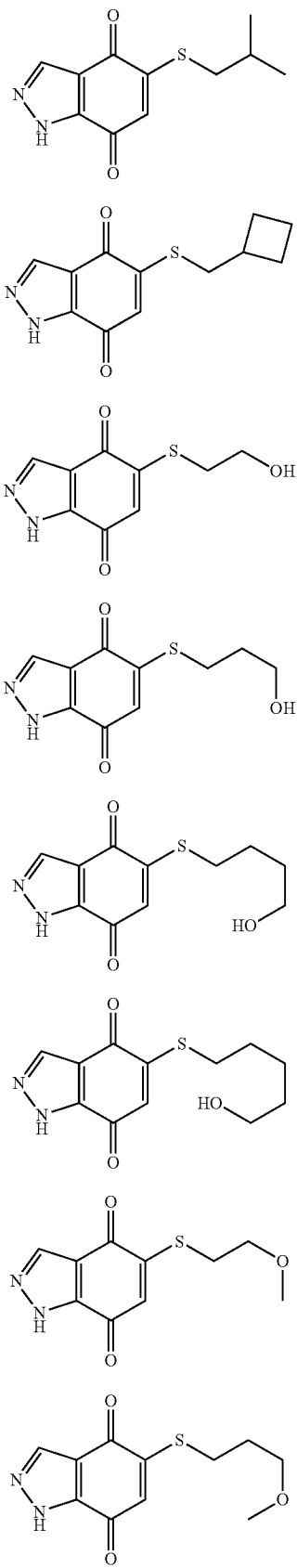

TABLE 1-continued
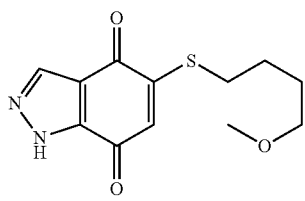 [SMILES: COCCCCSC1=CC(=O)c2[nH]ncc2C1=O]
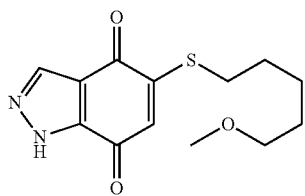 [SMILES: COCCCCCSC1=CC(=O)c2[nH]ncc2C1=O]
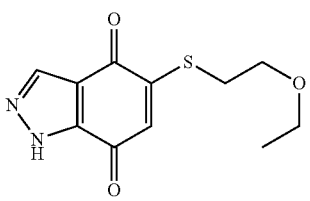 [SMILES: CCOCCSC1=CC(=O)c2[nH]ncc2C1=O]
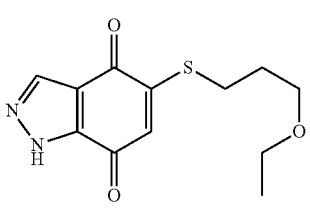 [SMILES: CCOCCCSC1=CC(=O)c2[nH]ncc2C1=O]
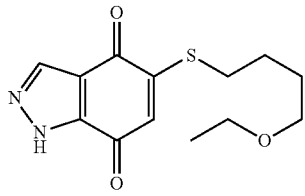
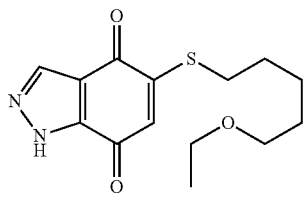 [SMILES: CCOCCCCCSC1=CC(=O)c2[nH]ncc2C1=O]
TABLE 1-continued
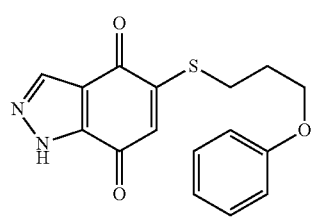 [SMILES: O=C1C(SCCCOc2ccccc2)=CC(=O)c2[nH]ncc21]
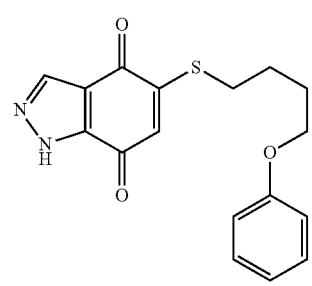 [SMILES: O=C1C(SCCCCOc2ccccc2)=CC(=O)c2[nH]ncc21]
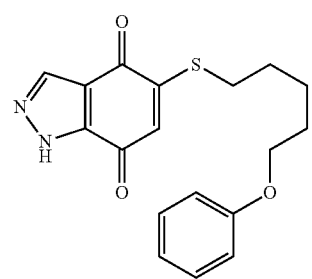
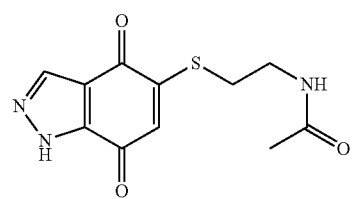 [SMILES: CC(=O)NCCSC1=CC(=O)c2[nH]ncc2C1=O]
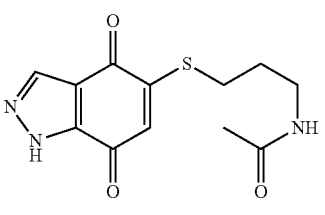 [SMILES: CC(=O)NCCCSC1=CC(=O)c2[nH]ncc2C1=O]
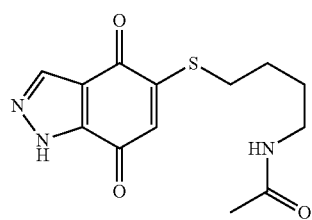 [SMILES: CC(=O)NCCCCSC1=CC(=O)c2[nH]ncc2C1=O]

TABLE 1-continued
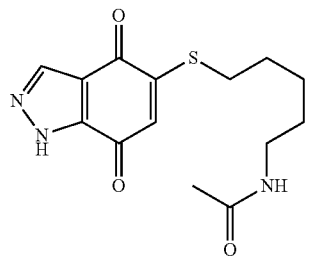 [SMILES: CC(=O)NCCCCCSC1=CC(=O)c2[nH]ncc2C1=O]
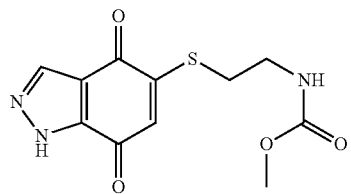 [SMILES: COC(=O)NCCSC1=CC(=O)c2[nH]ncc2C1=O]
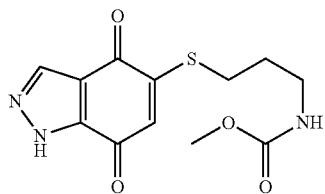
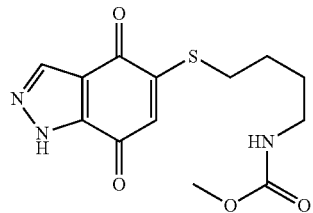
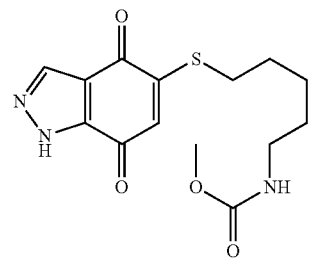 [SMILES: COC(=O)NCCCCCSC1=CC(=O)c2[nH]ncc2C1=O]
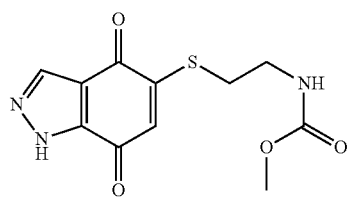
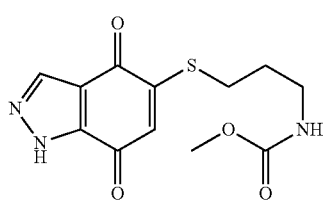 [SMILES: COC(=O)NCCCSC1=CC(=O)c2[nH]ncc2C1=O]
TABLE 1-continued
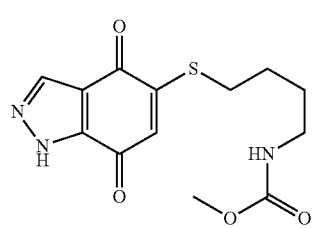
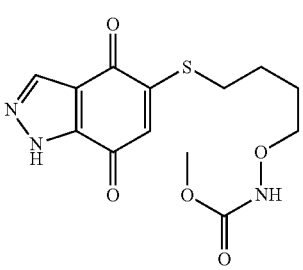 [SMILES: COC(=O)NOCCCCSC1=CC(=O)c2[nH]ncc2C1=O]
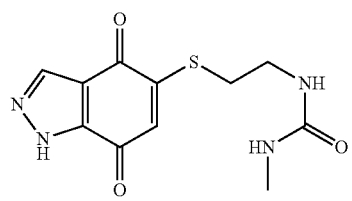
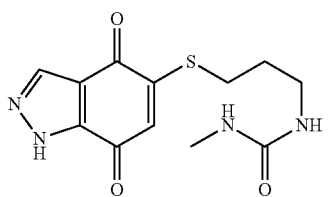 [SMILES: CNC(=O)NCCCSC1=CC(=O)c2[nH]ncc2C1=O]
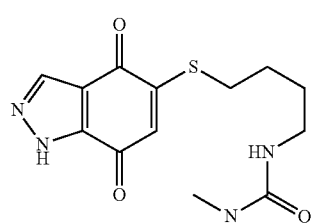
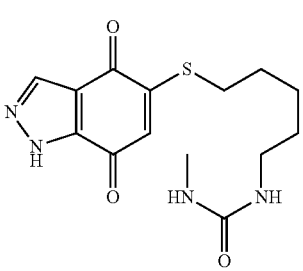 [SMILES: CNC(=O)NCCCCCSC1=CC(=O)c2[nH]ncc2C1=O]

TABLE 1-continued
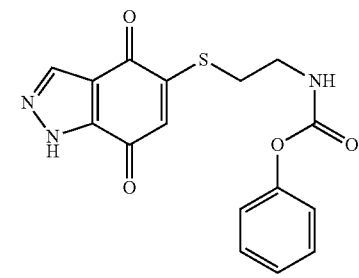 [SMILES: O=C(NCCSC1=CC(=O)c2[nH]ncc2C1=O)Oc1ccccc1]
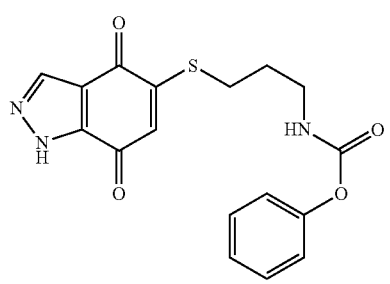 [SMILES: O=C(NCCCSC1=CC(=O)c2[nH]ncc2C1=O)Oc1ccccc1]
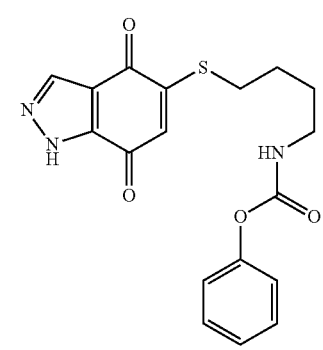
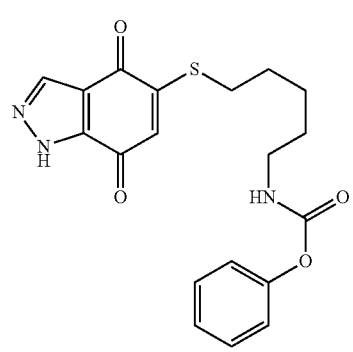 [SMILES: O=C(NCCCCCSC1=CC(=O)c2[nH]ncc2C1=O)Oc1ccccc1]
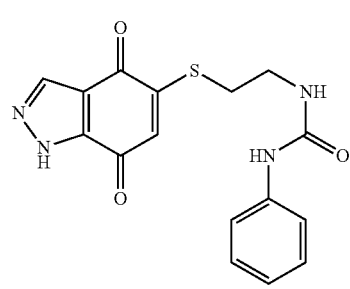 [SMILES: O=C(NCCSC1=CC(=O)c2[nH]ncc2C1=O)Nc1ccccc1]
TABLE 1-continued
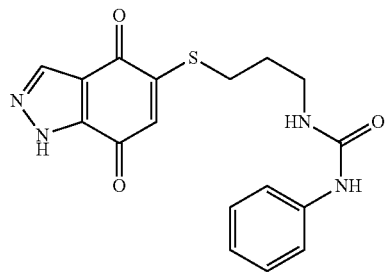 [SMILES: O=C(NCCCSC1=CC(=O)c2[nH]ncc2C1=O)Nc1ccccc1]
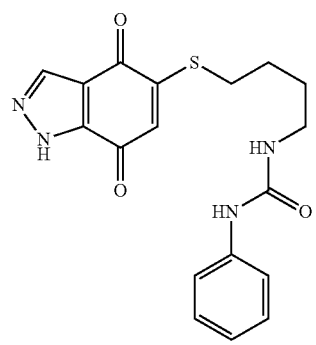 [SMILES: O=C(NCCCCSC1=CC(=O)c2[nH]ncc2C1=O)Nc1ccccc1]
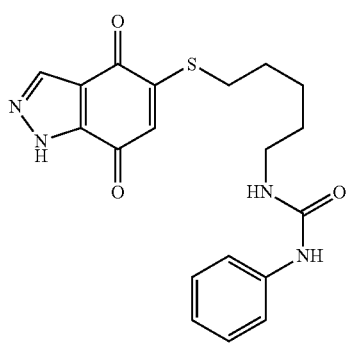 [SMILES: O=C(NCCCCCSC1=CC(=O)c2[nH]ncc2C1=O)Nc1ccccc1]
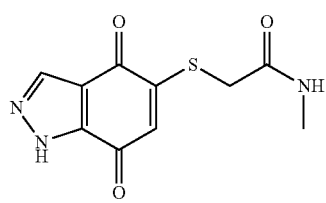 [SMILES: CNC(=O)CSC1=CC(=O)c2[nH]ncc2C1=O]
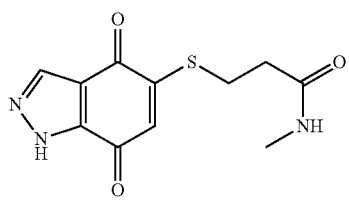 [SMILES: CNC(=O)CCSC1=CC(=O)c2[nH]ncc2C1=O]
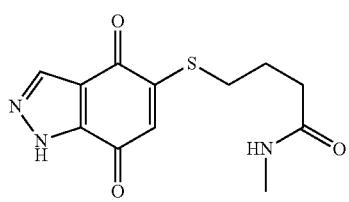

TABLE 1-continued
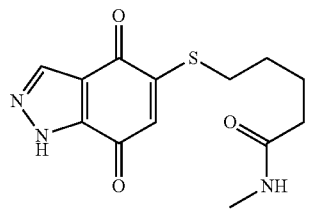 [SMILES: CNC(=O)CCCCSC1=CC(=O)c2[nH]ncc2C1=O]
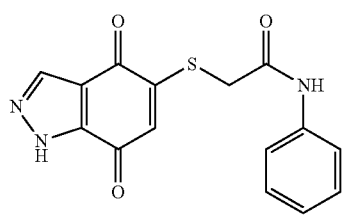 [SMILES: O=C(CSC1=CC(=O)c2[nH]ncc2C1=O)Nc1ccccc1]
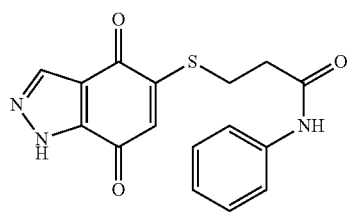 [SMILES: O=C(CCSC1=CC(=O)c2[nH]ncc2C1=O)Nc1ccccc1]
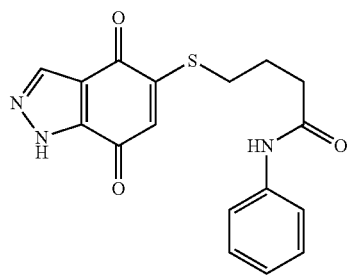 [SMILES: O=C(CCCSC1=CC(=O)c2[nH]ncc2C1=O)Nc1ccccc1]
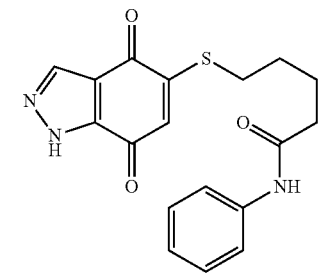 [SMILES: O=C(CCCCSC1=CC(=O)c2[nH]ncc2C1=O)Nc1ccccc1]
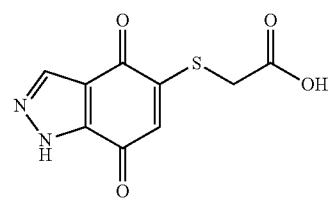
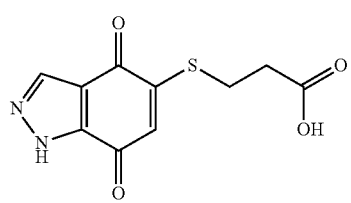 [SMILES: O=C(O)CCSC1=CC(=O)c2[nH]ncc2C1=O]
TABLE 1-continued
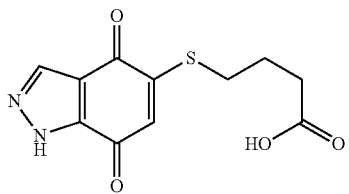 [SMILES: O=C(O)CCCSC1=CC(=O)c2[nH]ncc2C1=O]
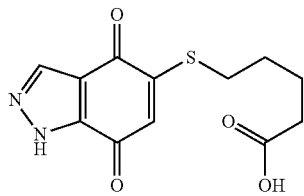 [SMILES: O=C(O)CCCCSC1=CC(=O)c2[nH]ncc2C1=O]
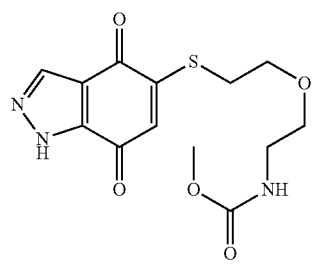
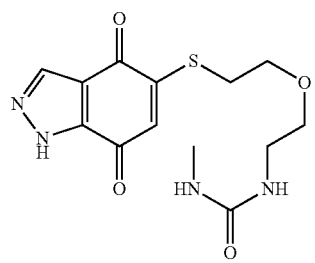 [SMILES: CNC(=O)NCCOCCSC1=CC(=O)c2[nH]ncc2C1=O]
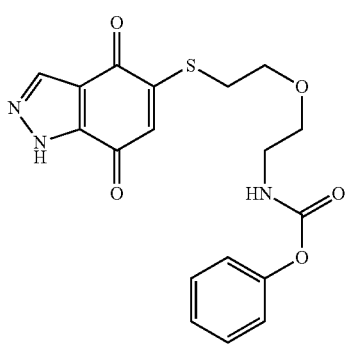 [SMILES: O=C(NCCOCCSC1=CC(=O)c2[nH]ncc2C1=O)Oc1ccccc1]
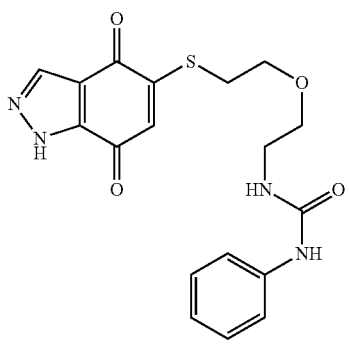 [SMILES: O=C(NCCOCCSC1=CC(=O)c2[nH]ncc2C1=O)Nc1ccccc1]

TABLE 1-continued
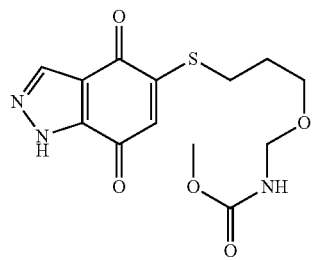 [SMILES: COC(=O)NCOCCCSC1=CC(=O)c2[nH]ncc2C1=O]
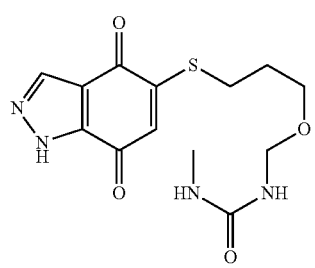 [SMILES: CNC(=O)NCOCCCSC1=CC(=O)c2[nH]ncc2C1=O]
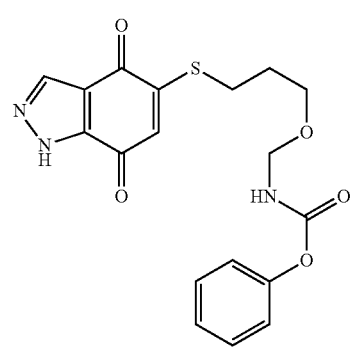 [SMILES: O=C(NCOCCCSC1=CC(=O)c2[nH]ncc2C1=O)Oc1ccccc1]
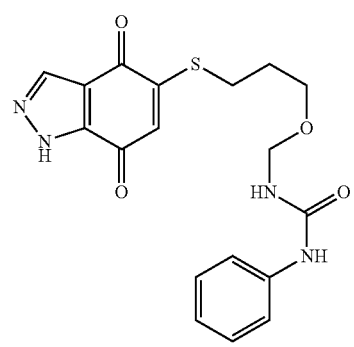 [SMILES: O=C(NCOCCCSC1=CC(=O)c2[nH]ncc2C1=O)Nc1ccccc1]
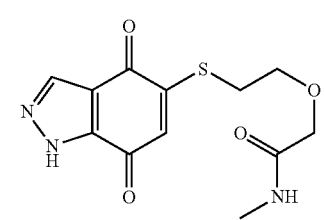 [SMILES: CNC(=O)COCCSC1=CC(=O)c2[nH]ncc2C1=O]
TABLE 1-continued
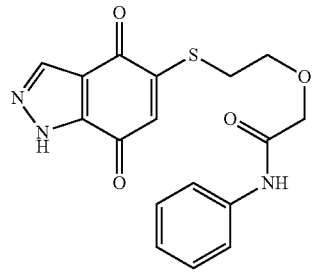 [SMILES: O=C(COCCSC1=CC(=O)c2[nH]ncc2C1=O)Nc1ccccc1]
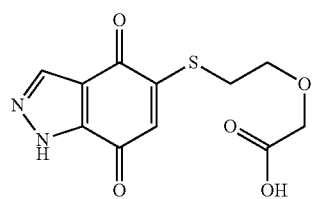 [SMILES: O=C(O)COCCSC1=CC(=O)c2[nH]ncc2C1=O]
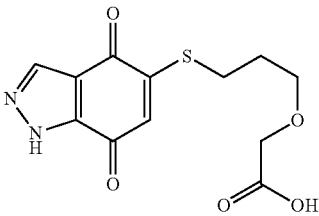 [SMILES: O=C(O)COCCCSC1=CC(=O)c2[nH]ncc2C1=O]
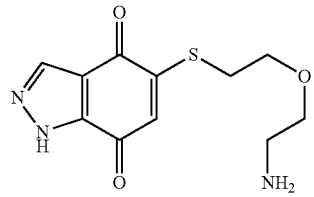 [SMILES: NCCOCCSC1=CC(=O)c2[nH]ncc2C1=O]
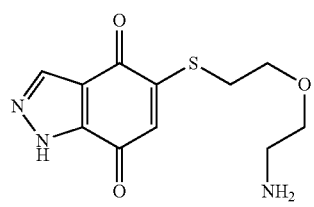
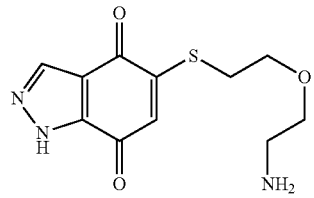
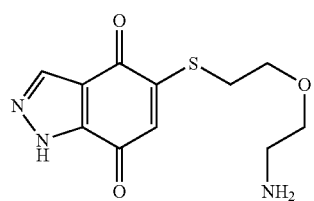 [SMILES: NCCOCCSC1=CC(=O)c2[nH]ncc2C1=O]

TABLE 1-continued
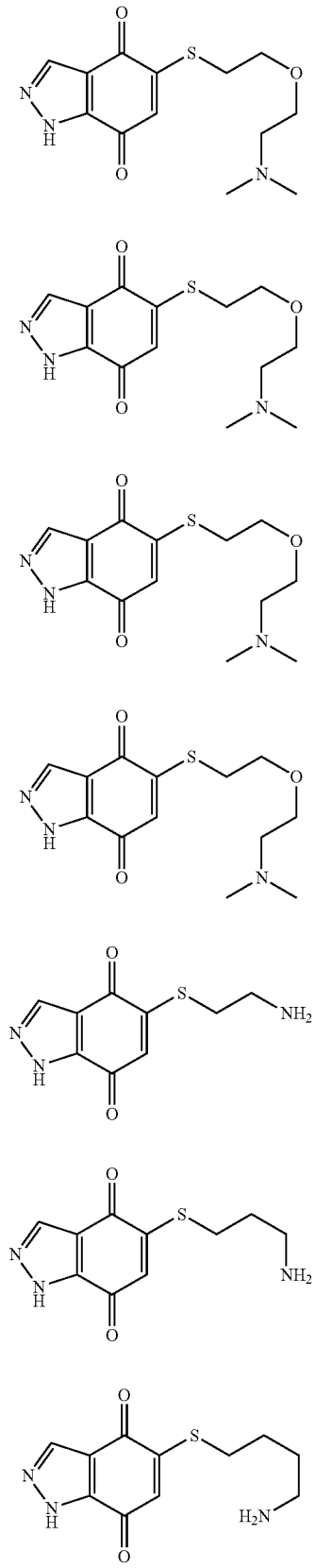
TABLE 1-continued
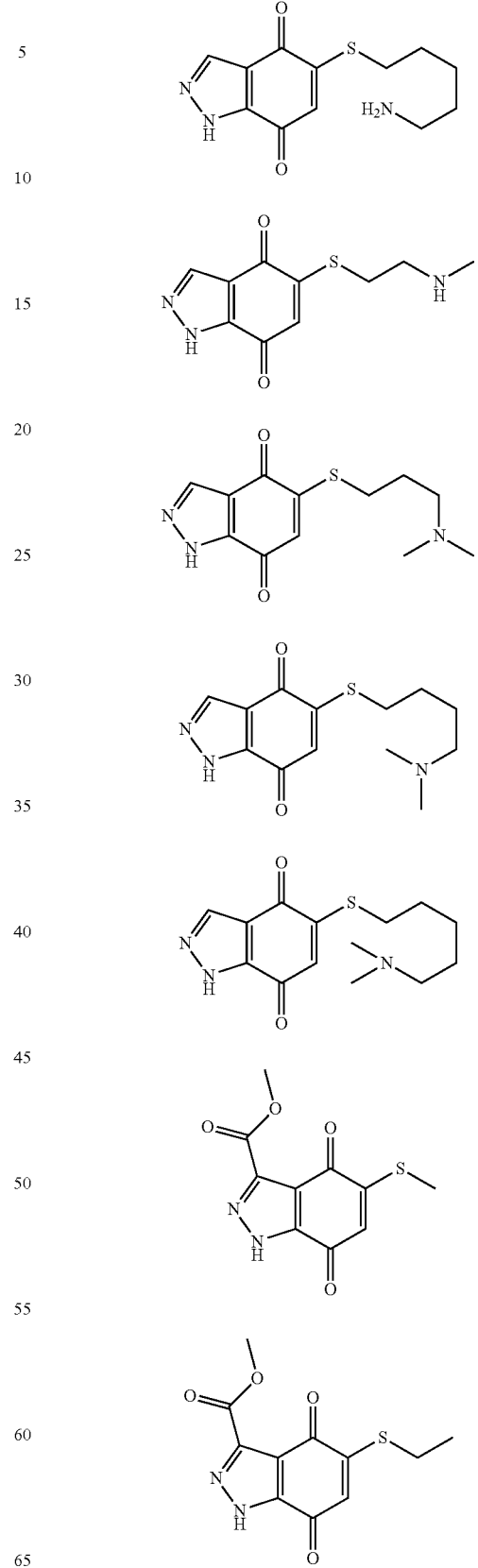

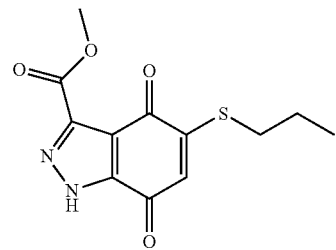 [SMILES: CCCSC1=CC(=O)c2[nH]nc(C(=O)OC)c2C1=O]
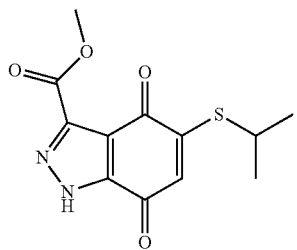 [SMILES: COC(=O)c1n[nH]c2c1C(=O)C(SC(C)C)=CC2=O]
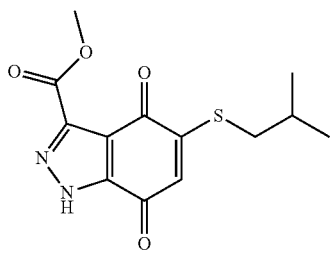 [SMILES: COC(=O)c1n[nH]c2c1C(=O)C(SCC(C)C)=CC2=O]
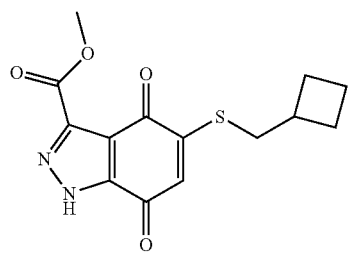 [SMILES: COC(=O)c1n[nH]c2c1C(=O)C(SCC1CCC1)=CC2=O]
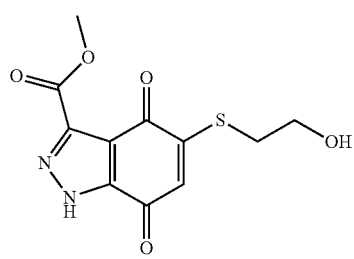 [SMILES: COC(=O)c1n[nH]c2c1C(=O)C(SCCO)=CC2=O]
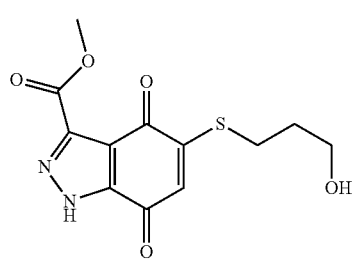 [SMILES: COC(=O)c1n[nH]c2c1C(=O)C(SCCCO)=CC2=O]
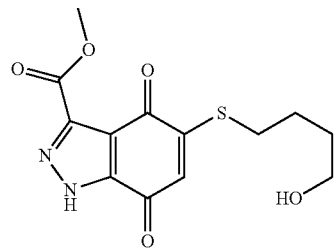 [SMILES: COC(=O)c1n[nH]c2c1C(=O)C(SCCCCO)=CC2=O]
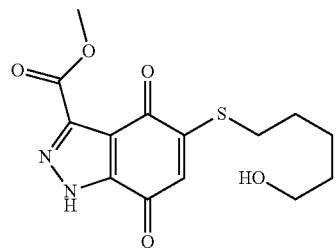 [SMILES: COC(=O)c1n[nH]c2c1C(=O)C(SCCCCCO)=CC2=O]
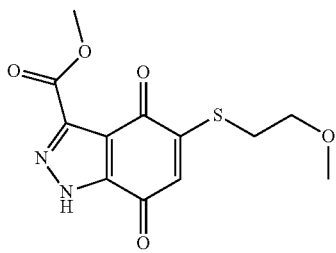
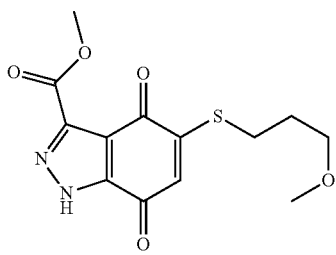
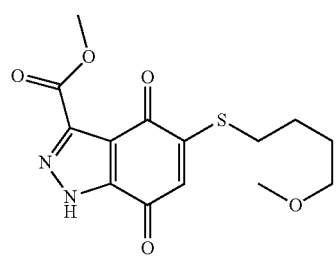 [SMILES: COCCCCSC1=CC(=O)c2[nH]nc(C(=O)OC)c2C1=O]
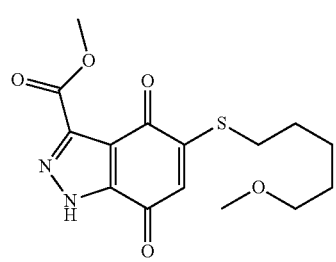 [SMILES: COCCCCCSC1=CC(=O)c2[nH]nc(C(=O)OC)c2C1=O]

TABLE 1-continued
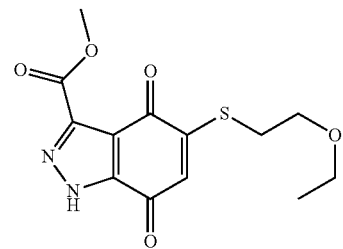 [SMILES: CCOCCSC1=CC(=O)c2[nH]nc(C(=O)OC)c2C1=O]
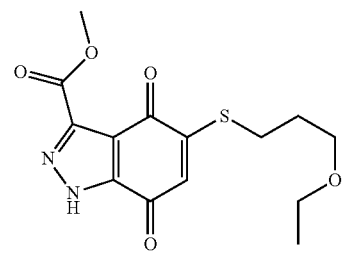 [SMILES: CCOCCCSC1=CC(=O)c2[nH]nc(C(=O)OC)c2C1=O]
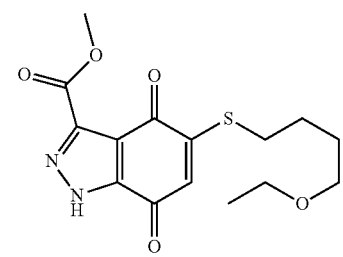 [SMILES: CCOCCCCSC1=CC(=O)c2[nH]nc(C(=O)OC)c2C1=O]
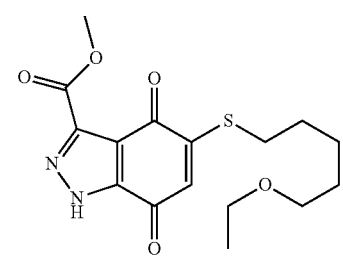 [SMILES: CCOCCCCCSC1=CC(=O)c2[nH]nc(C(=O)OC)c2C1=O]
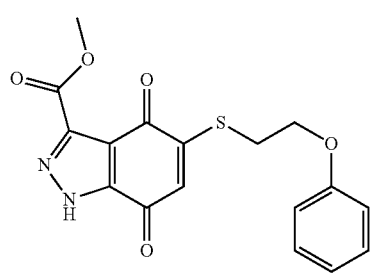 [SMILES: COC(=O)c1n[nH]c2c1C(=O)C(SCCOc1ccccc1)=CC2=O]
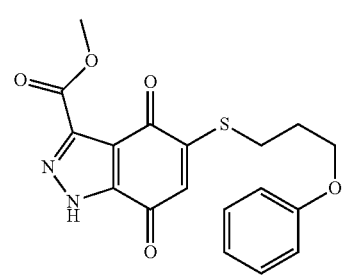 [SMILES: COC(=O)c1n[nH]c2c1C(=O)C(SCCCOc1ccccc1)=CC2=O]
TABLE 1-continued
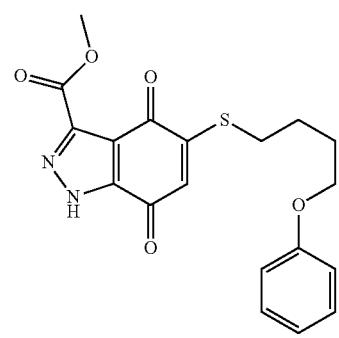 [SMILES: COC(=O)c1n[nH]c2c1C(=O)C(SCCCCOc1ccccc1)=CC2=O]
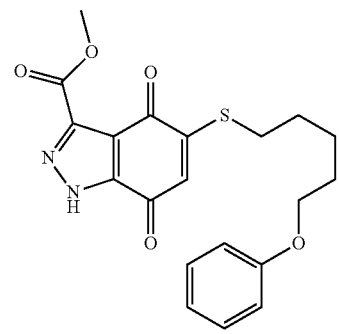 [SMILES: COC(=O)c1n[nH]c2c1C(=O)C(SCCCCCOc1ccccc1)=CC2=O]
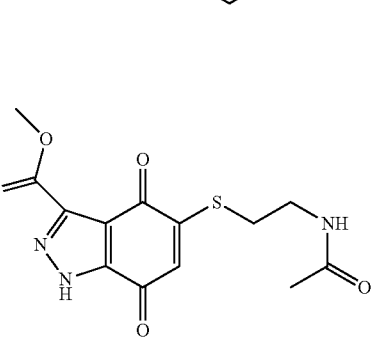
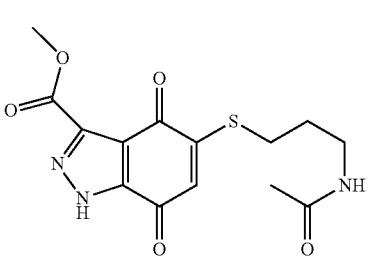 [SMILES: COC(=O)c1n[nH]c2c1C(=O)C(SCCCNC(C)=O)=CC2=O]
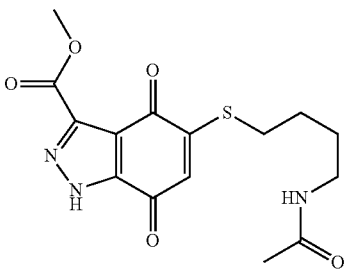 [SMILES: COC(=O)c1n[nH]c2c1C(=O)C(SCCCCNC(C)=O)=CC2=O]

TABLE 1-continued
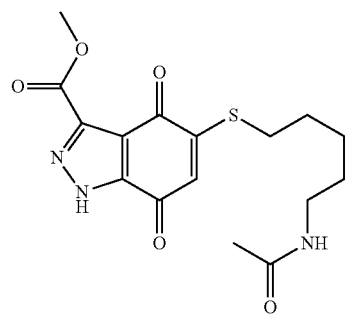 [SMILES: COC(=O)c1n[nH]c2c1C(=O)C(SCCCCCNC(C)=O)=CC2=O]
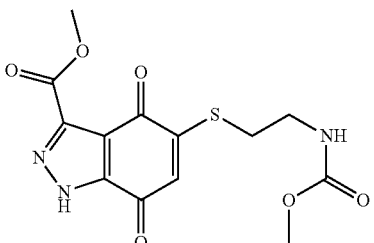
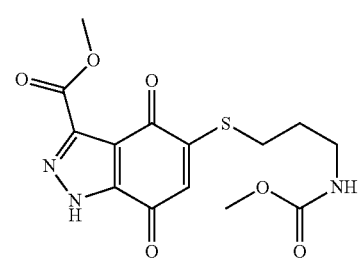 [SMILES: COC(=O)NCCCSC1=CC(=O)c2[nH]nc(C(=O)OC)c2C1=O]
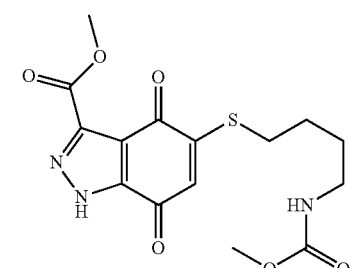
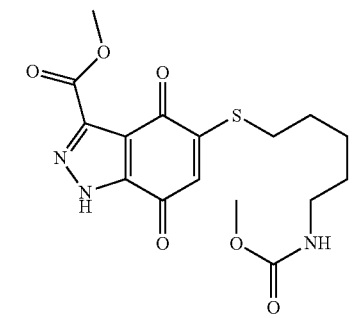 [SMILES: COC(=O)NCCCCCSC1=CC(=O)c2[nH]nc(C(=O)OC)c2C1=O]
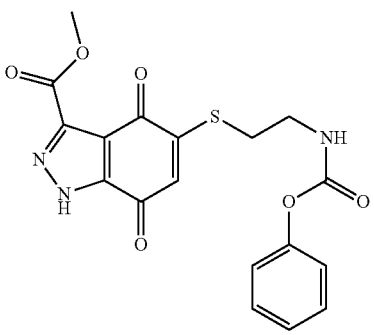 [SMILES: COC(=O)c1n[nH]c2c1C(=O)C(SCCNC(=O)Oc1ccccc1)=CC2=O]

TABLE 1-continued
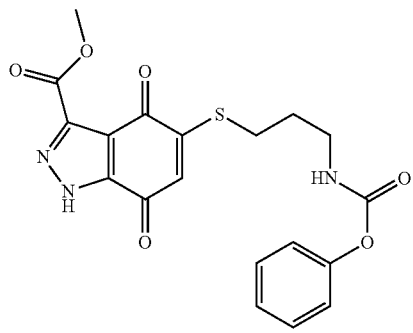 [SMILES: COC(=O)c1n[nH]c2c1C(=O)C(SCCCNC(=O)Oc1ccccc1)=CC2=O]
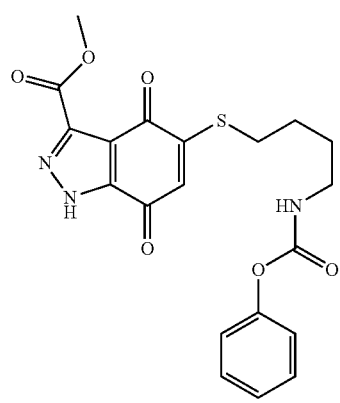 [SMILES: COC(=O)c1n[nH]c2c1C(=O)C(SCCCCNC(=O)Oc1ccccc1)=CC2=O]
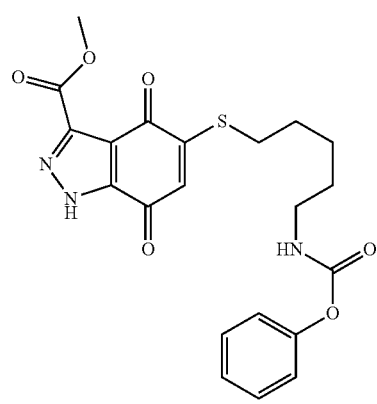 [SMILES: COC(=O)c1n[nH]c2c1C(=O)C(SCCCCCNC(=O)Oc1ccccc1)=CC2=O]
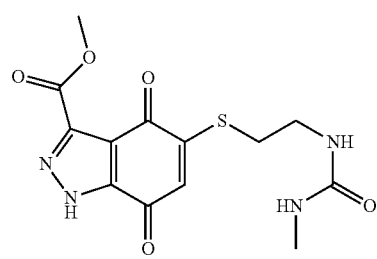 [SMILES: CNC(=O)NCCSC1=CC(=O)c2[nH]nc(C(=O)OC)c2C1=O]
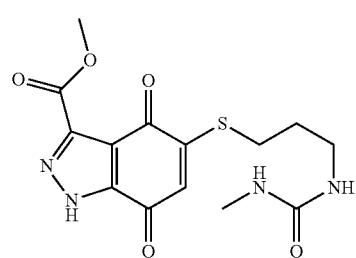 [SMILES: CNC(=O)NCCCSC1=CC(=O)c2[nH]nc(C(=O)OC)c2C1=O]
TABLE 1-continued
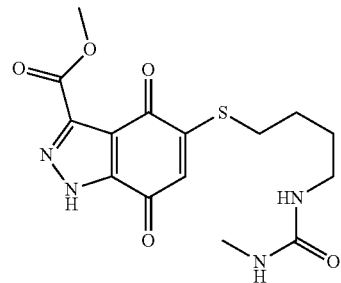
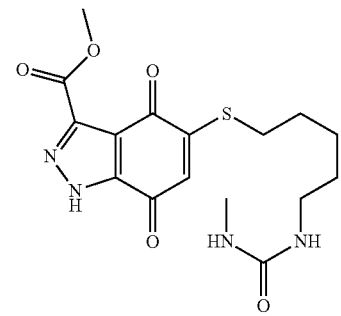 [SMILES: CNC(=O)NCCCCCSC1=CC(=O)c2[nH]nc(C(=O)OC)c2C1=O]
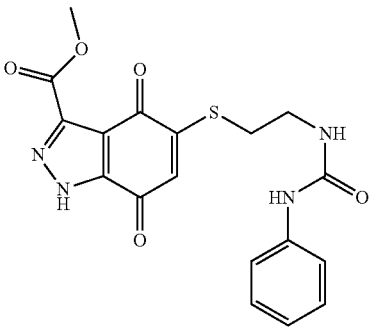 [SMILES: COC(=O)c1n[nH]c2c1C(=O)C(SCCNC(=O)Nc1ccccc1)=CC2=O]
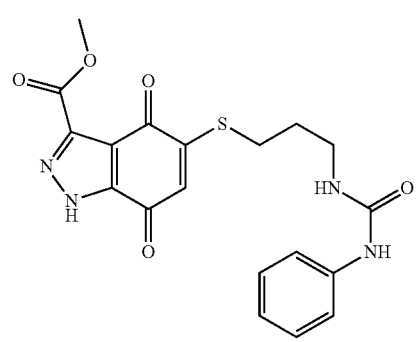 [SMILES: COC(=O)c1n[nH]c2c1C(=O)C(SCCCNC(=O)Nc1ccccc1)=CC2=O]

TABLE 1-continued
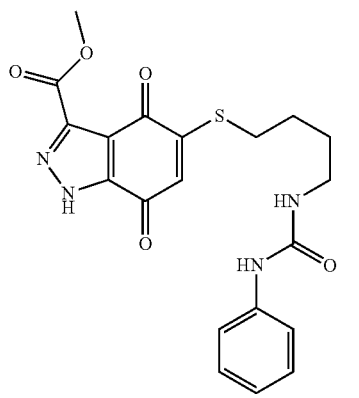 [SMILES: COC(=O)c1n[nH]c2c1C(=O)C(SCCCCNC(=O)Nc1ccccc1)=CC2=O]
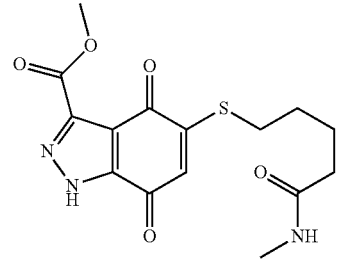 [SMILES: CNC(=O)CCCCSC1=CC(=O)c2[nH]nc(C(=O)OC)c2C1=O]
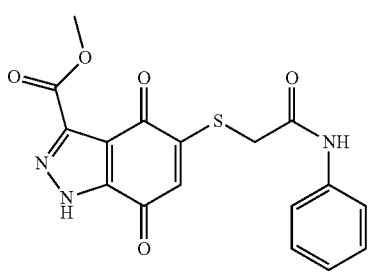 [SMILES: COC(=O)c1n[nH]c2c1C(=O)C(SCC(=O)Nc1ccccc1)=CC2=O]
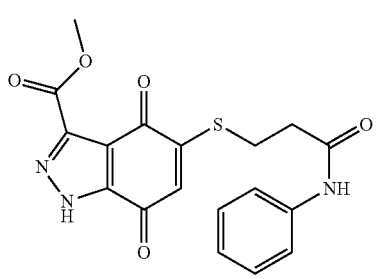 [SMILES: COC(=O)c1n[nH]c2c1C(=O)C(SCCC(=O)Nc1ccccc1)=CC2=O]
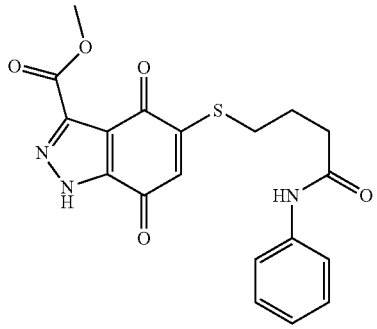 [SMILES: COC(=O)c1n[nH]c2c1C(=O)C(SCCCC(=O)Nc1ccccc1)=CC2=O]
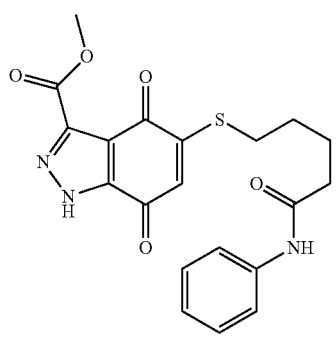 [SMILES: COC(=O)c1n[nH]c2c1C(=O)C(SCCCCC(=O)Nc1ccccc1)=CC2=O]

TABLE 1-continued
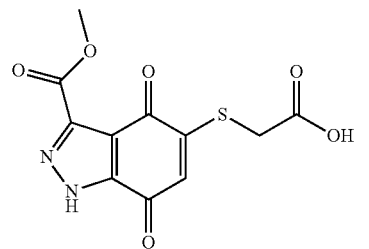
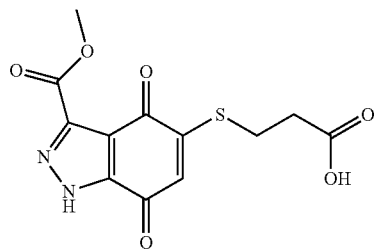 [SMILES: COC(=O)c1n[nH]c2c1C(=O)C(SCCC(=O)O)=CC2=O]
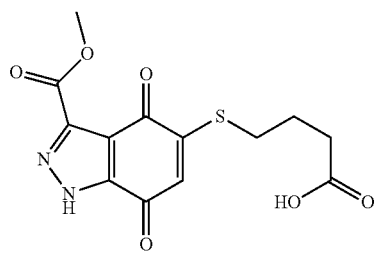 [SMILES: COC(=O)c1n[nH]c2c1C(=O)C(SCCCC(=O)O)=CC2=O]
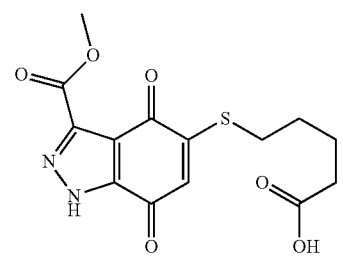 [SMILES: COC(=O)c1n[nH]c2c1C(=O)C(SCCCCC(=O)O)=CC2=O]
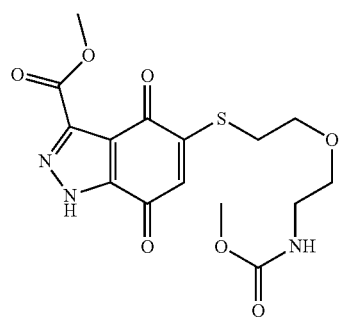 [SMILES: COC(=O)NCCOCCSC1=CC(=O)c2[nH]nc(C(=O)OC)c2C1=O]
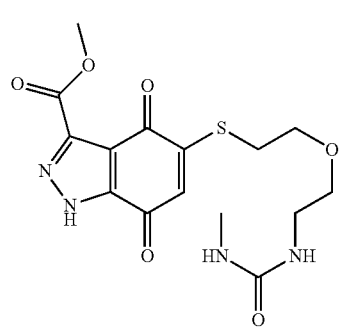 [SMILES: CNC(=O)NCCOCCSC1=CC(=O)c2[nH]nc(C(=O)OC)c2C1=O]
TABLE 1-continued
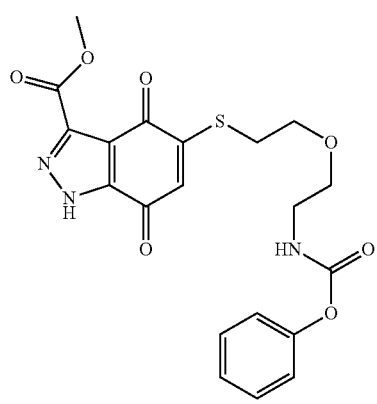 [SMILES: COC(=O)c1n[nH]c2c1C(=O)C(SCCOCCNC(=O)Oc1ccccc1)=CC2=O]

TABLE 1-continued
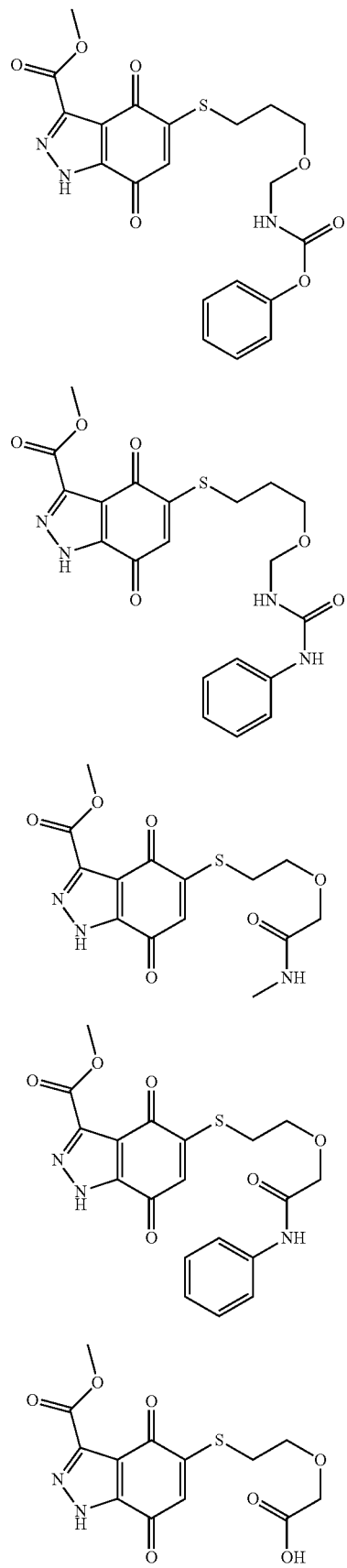
TABLE 1-continued
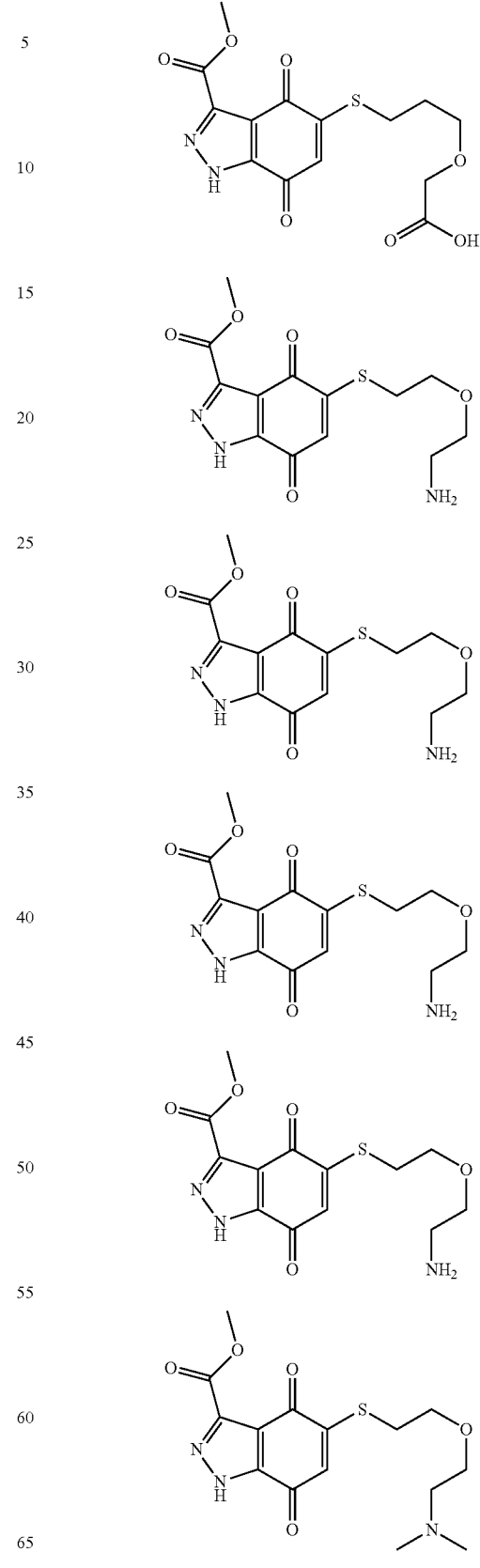

TABLE 1-continued
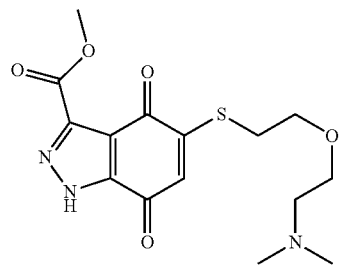 [SMILES: COC(=O)c1n[nH]c2c1C(=O)C(SCCOCCN(C)C)=CC2=O]
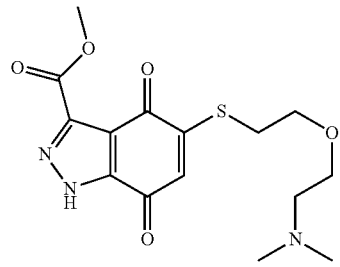 [SMILES: COC(=O)c1n[nH]c2c1C(=O)C(SCCOCCN(C)C)=CC2=O]
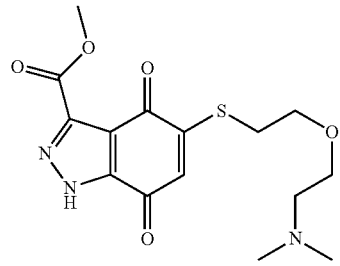 [SMILES: COC(=O)c1n[nH]c2c1C(=O)C(SCCOCCN(C)C)=CC2=O]
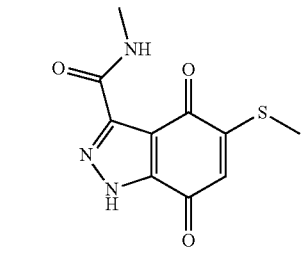 [SMILES: CNC(=O)c1n[nH]c2c1C(=O)C(SC)=CC2=O]
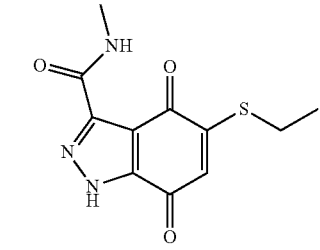 [SMILES: CCSC1=CC(=O)c2[nH]nc(C(=O)NC)c2C1=O]
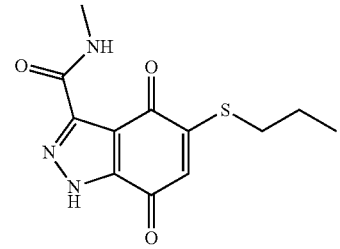 [SMILES: CCCSC1=CC(=O)c2[nH]nc(C(=O)NC)c2C1=O]
TABLE 1-continued
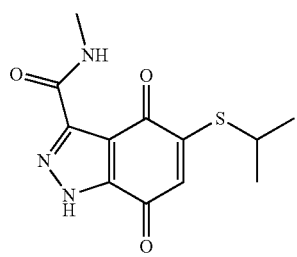 [SMILES: CNC(=O)c1n[nH]c2c1C(=O)C(SC(C)C)=CC2=O]
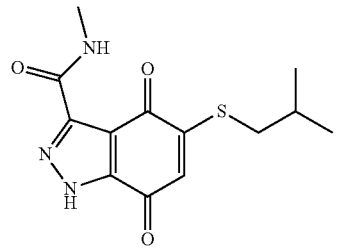 [SMILES: CNC(=O)c1n[nH]c2c1C(=O)C(SCC(C)C)=CC2=O]
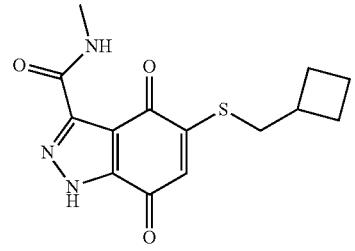
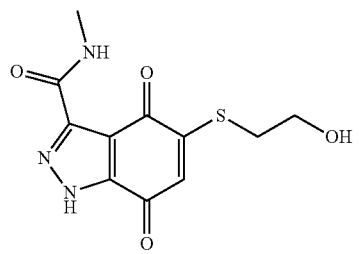 [SMILES: CNC(=O)c1n[nH]c2c1C(=O)C(SCCO)=CC2=O]
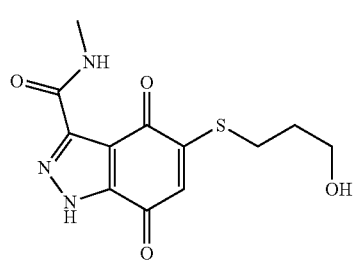 [SMILES: CNC(=O)c1n[nH]c2c1C(=O)C(SCCCO)=CC2=O]
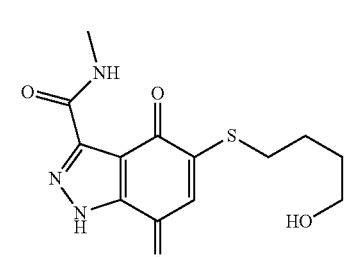

TABLE 1-continued
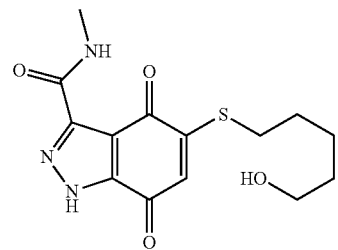
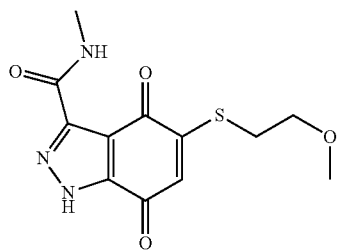 [SMILES: CNC(=O)c1n[nH]c2c1C(=O)C(SCCOC)=CC2=O]
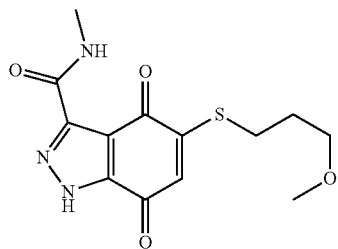 [SMILES: CNC(=O)c1n[nH]c2c1C(=O)C(SCCCOC)=CC2=O]
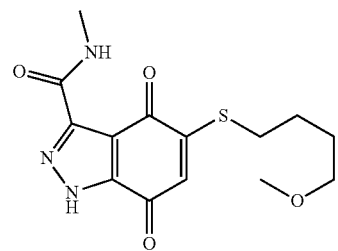 [SMILES: CNC(=O)c1n[nH]c2c1C(=O)C(SCCCCOC)=CC2=O]
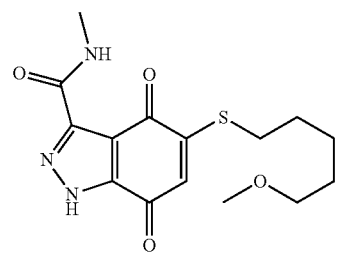
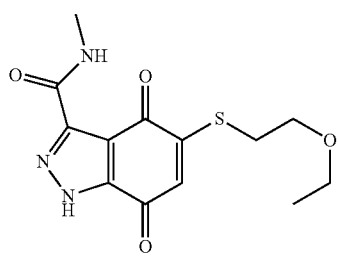 [SMILES: CCOCCSC1=CC(=O)c2[nH]nc(C(=O)NC)c2C1=O]
TABLE 1-continued
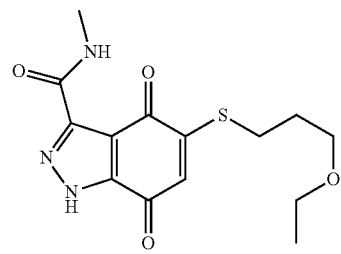 [SMILES: CCOCCCSC1=CC(=O)c2[nH]nc(C(=O)NC)c2C1=O]
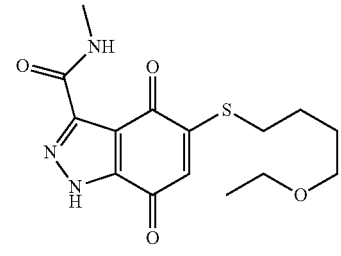 [SMILES: CCOCCCCSC1=CC(=O)c2[nH]nc(C(=O)NC)c2C1=O]
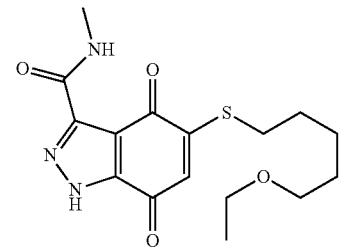 [SMILES: CCOCCCCCSC1=CC(=O)c2[nH]nc(C(=O)NC)c2C1=O]
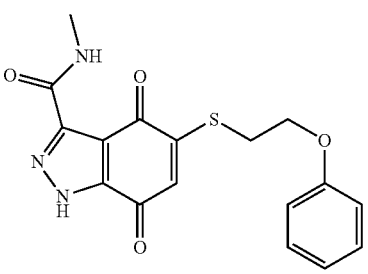 [SMILES: CNC(=O)c1n[nH]c2c1C(=O)C(SCCOc1ccccc1)=CC2=O]
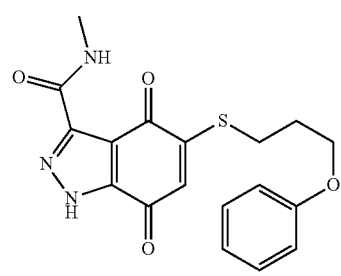
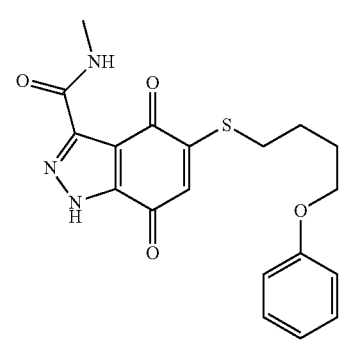 [SMILES: CNC(=O)c1n[nH]c2c1C(=O)C(SCCCCOc1ccccc1)=CC2=O]

TABLE 1-continued
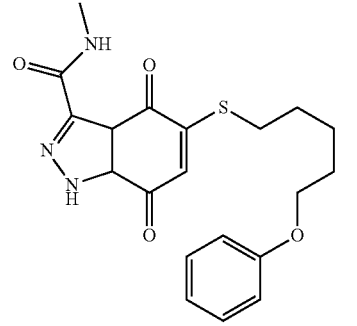 [SMILES: CNC(=O)C1=NNC2C(=O)C=C(SCCCCCOc3ccccc3)C(=O)C12]
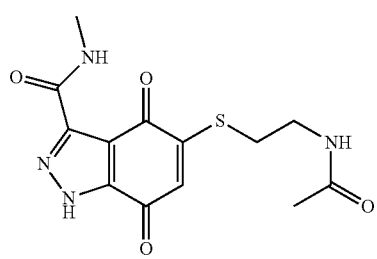 [SMILES: CNC(=O)c1n[nH]c2c1C(=O)C(SCCNC(C)=O)=CC2=O]
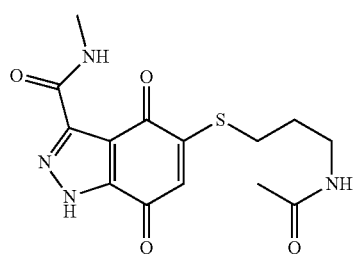 [SMILES: CNC(=O)c1n[nH]c2c1C(=O)C(SCCCNC(C)=O)=CC2=O]
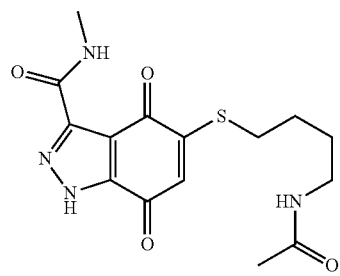 [SMILES: CNC(=O)c1n[nH]c2c1C(=O)C(SCCCCNC(C)=O)=CC2=O]
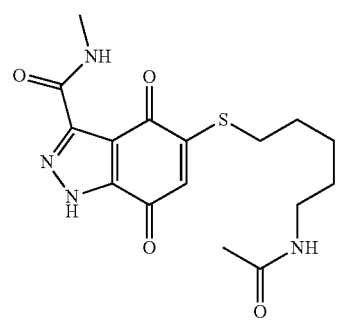 [SMILES: CNC(=O)c1n[nH]c2c1C(=O)C(SCCCCCNC(C)=O)=CC2=O]
TABLE 1-continued
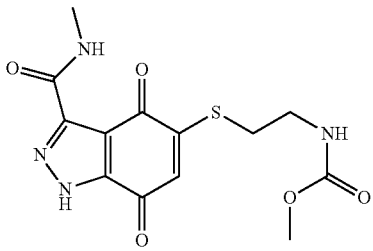 [SMILES: CNC(=O)c1n[nH]c2c1C(=O)C(SCCNC(=O)OC)=CC2=O]
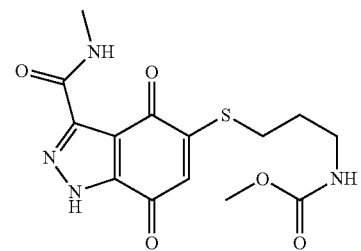 [SMILES: CNC(=O)c1n[nH]c2c1C(=O)C(SCCCNC(=O)OC)=CC2=O]
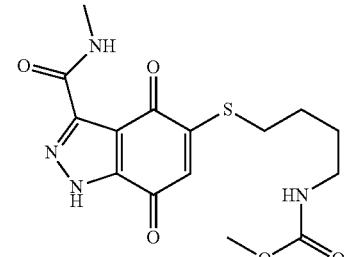
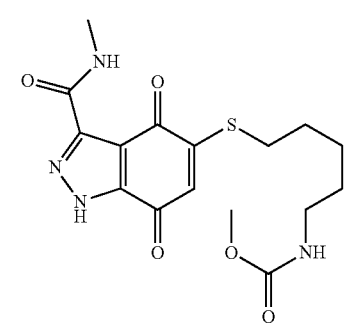
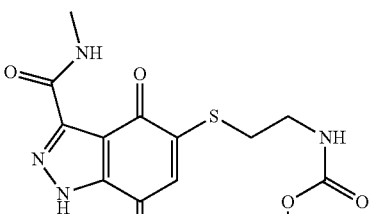
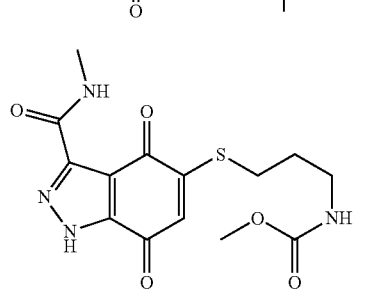

TABLE 1-continued

TABLE 1-continued

TABLE 1-continued
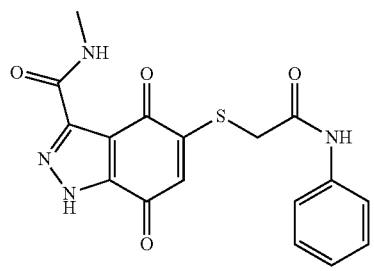 [SMILES: CNC(=O)c1n[nH]c2c1C(=O)C(SCC(=O)Nc1ccccc1)=CC2=O]
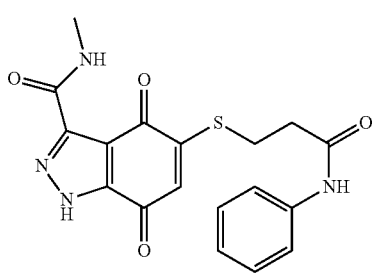 [SMILES: CNC(=O)c1n[nH]c2c1C(=O)C(SCCC(=O)Nc1ccccc1)=CC2=O]
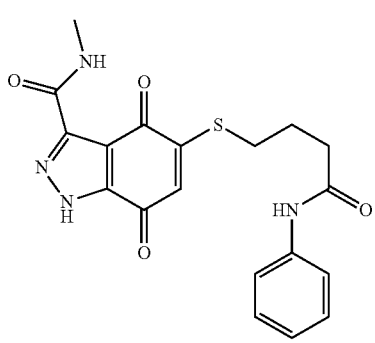 [SMILES: CNC(=O)c1n[nH]c2c1C(=O)C(SCCCC(=O)Nc1ccccc1)=CC2=O]
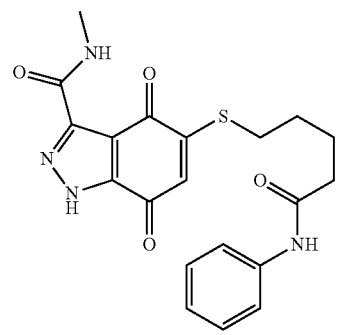
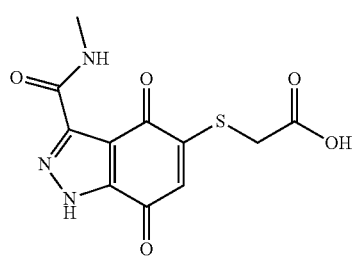
TABLE 1-continued
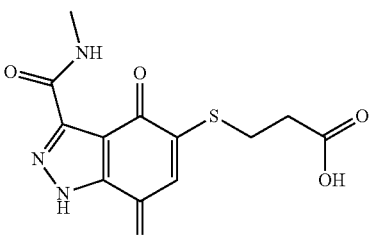
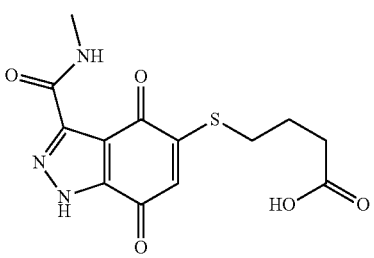 [SMILES: CNC(=O)c1n[nH]c2c1C(=O)C(SCCCC(=O)O)=CC2=O]
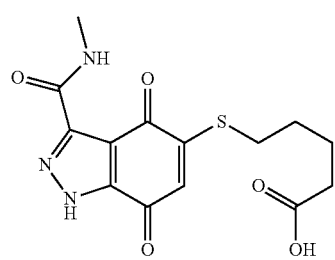 [SMILES: CNC(=O)c1n[nH]c2c1C(=O)C(SCCCCC(=O)O)=CC2=O]
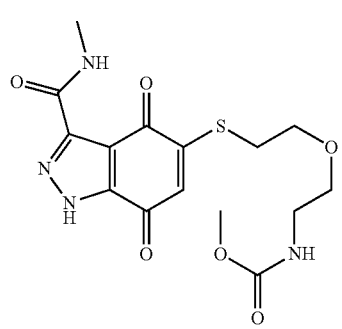
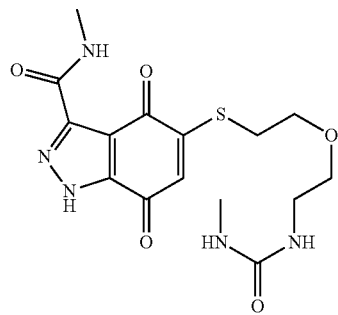

TABLE 1-continued
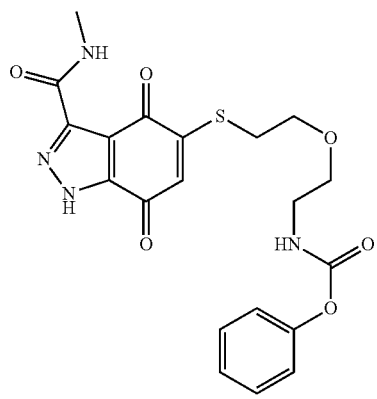 [SMILES: CNC(=O)c1n[nH]c2c1C(=O)C(SCCOCCNC(=O)Oc1ccccc1)=CC2=O]
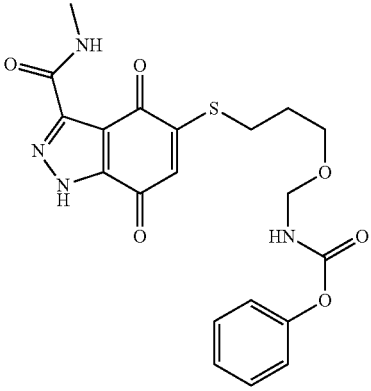 [SMILES: CNC(=O)c1n[nH]c2c1C(=O)C(SCCCOCNC(=O)Oc1ccccc1)=CC2=O]

TABLE 1-continued
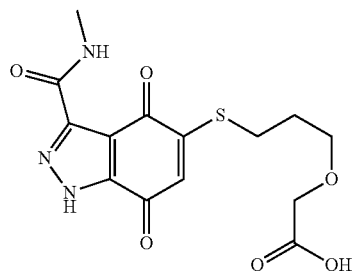 [SMILES: CNC(=O)c1n[nH]c2c1C(=O)C(SCCCOCC(=O)O)=CC2=O]
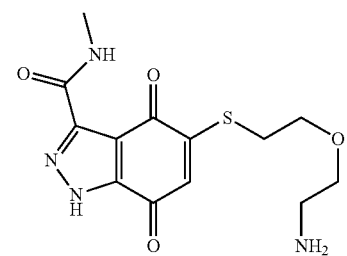 [SMILES: CNC(=O)c1n[nH]c2c1C(=O)C(SCCOCCN)=CC2=O]
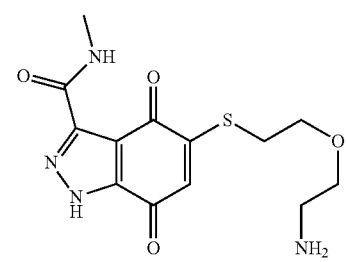 [SMILES: CNC(=O)c1n[nH]c2c1C(=O)C(SCCOCCN)=CC2=O]
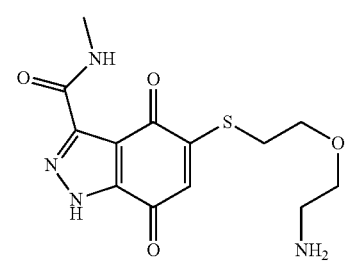 [SMILES: CNC(=O)c1n[nH]c2c1C(=O)C(SCCOCCN)=CC2=O]
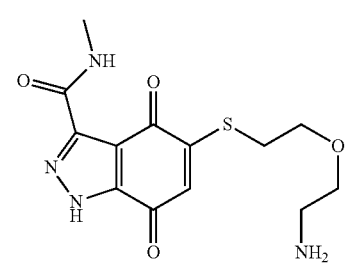 [SMILES: CNC(=O)c1n[nH]c2c1C(=O)C(SCCOCCN)=CC2=O]
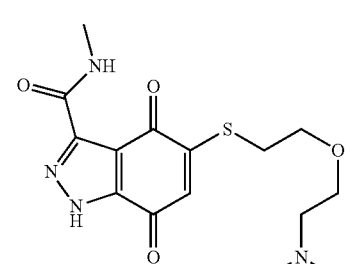
TABLE 1-continued
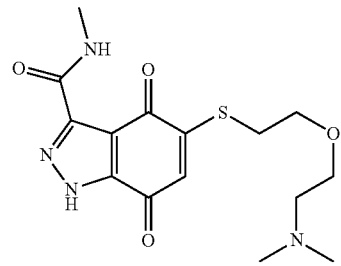
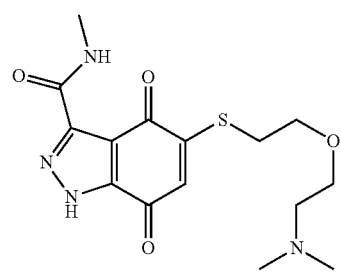 [SMILES: CNC(=O)c1n[nH]c2c1C(=O)C(SCCOCCN(C)C)=CC2=O]
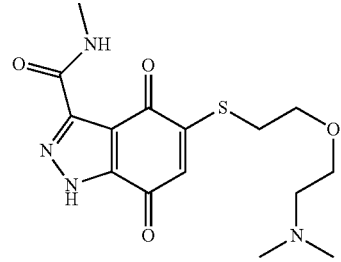
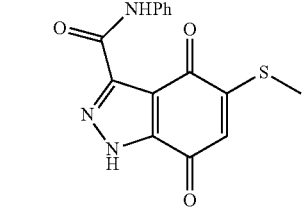
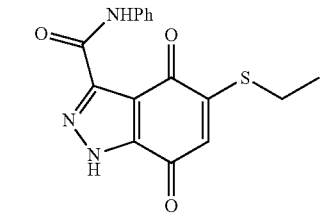
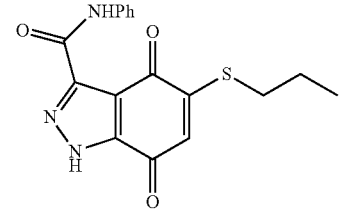

TABLE 1-continued
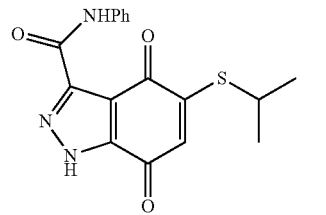
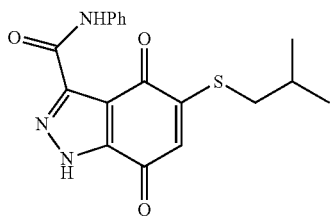
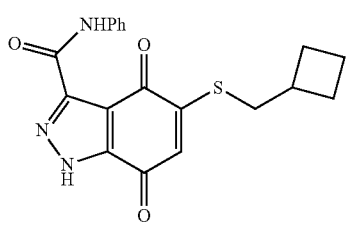
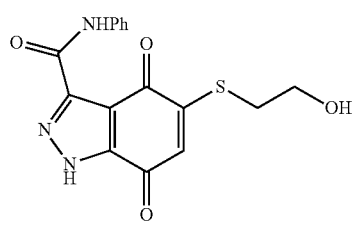
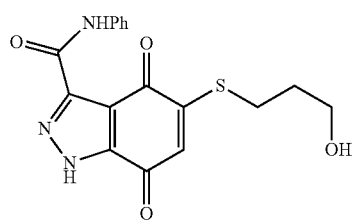
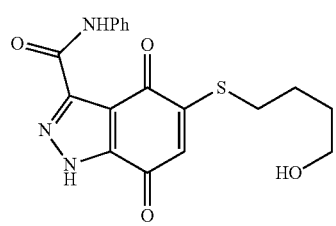
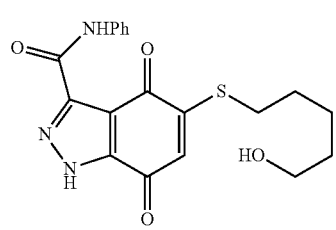
TABLE 1-continued
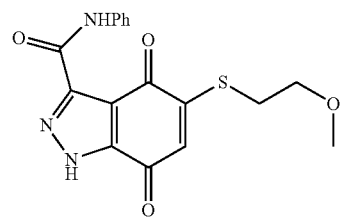
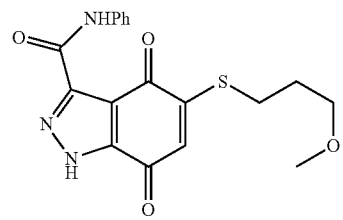
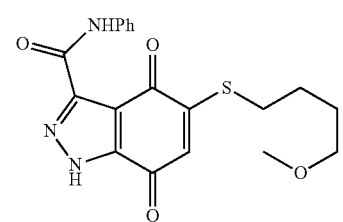
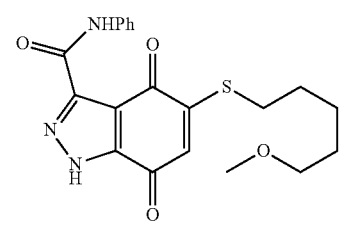
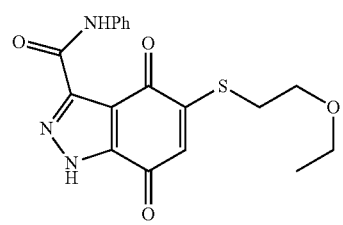
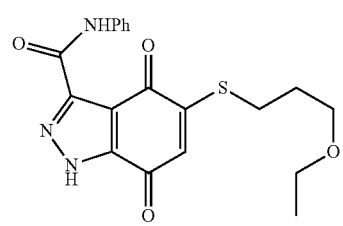
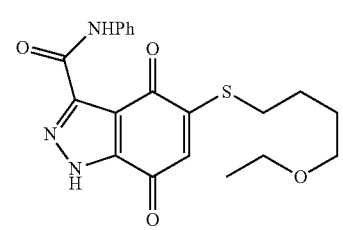

TABLE 1-continued
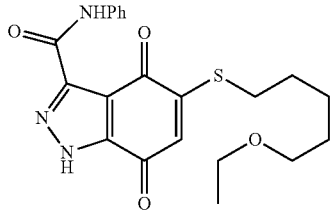
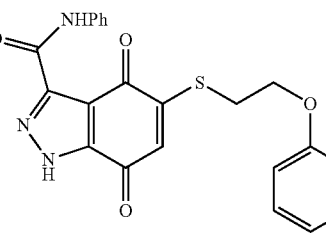
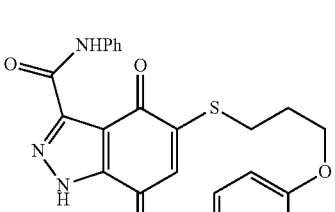
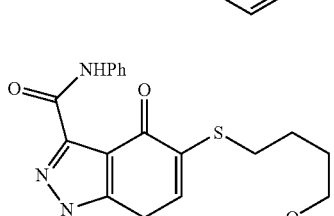
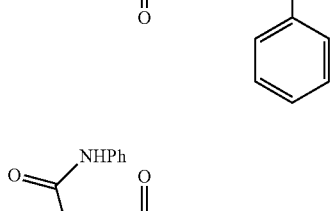
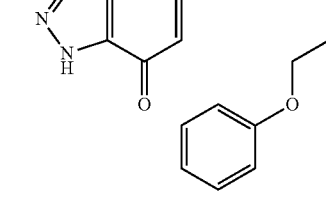
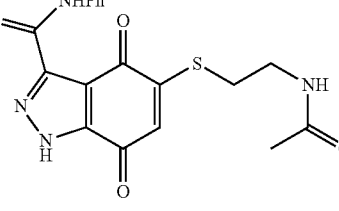
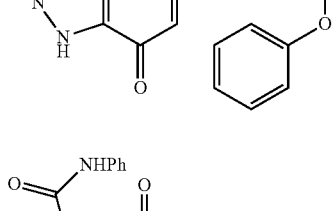
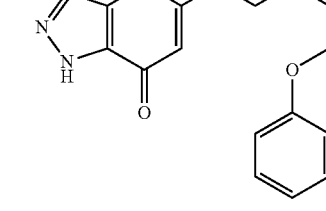
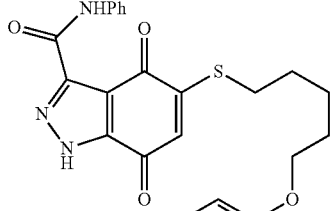
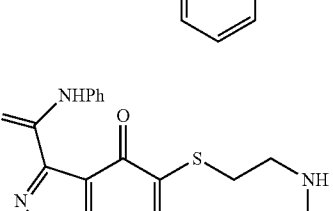
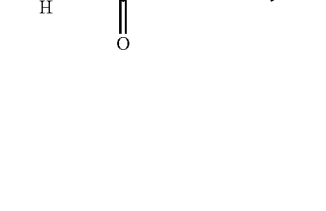

TABLE 1-continued
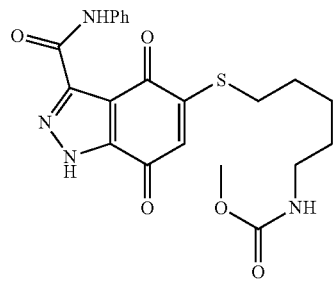
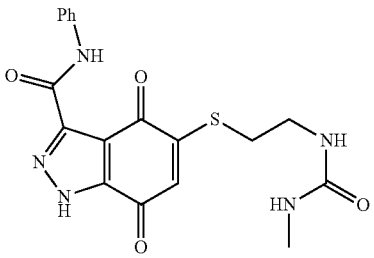 [SMILES: CNC(=O)NCCSC1=CC(=O)c2[nH]nc(C(=O)Nc3ccccc3)c2C1=O]
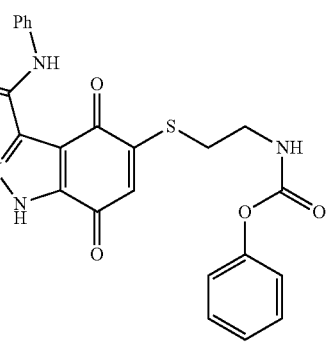

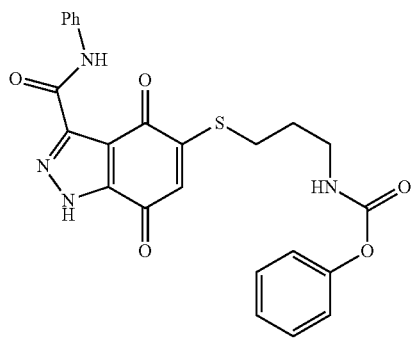 [SMILES: O=C(NCCCSC1=CC(=O)c2[nH]nc(C(=O)Nc3ccccc3)c2C1=O)Oc1ccccc1]
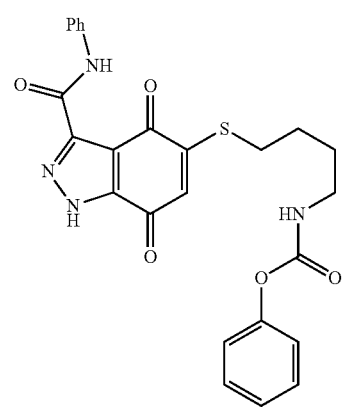 [SMILES: O=C(NCCCCSC1=CC(=O)c2[nH]nc(C(=O)Nc3ccccc3)c2C1=O)Oc1ccccc1]
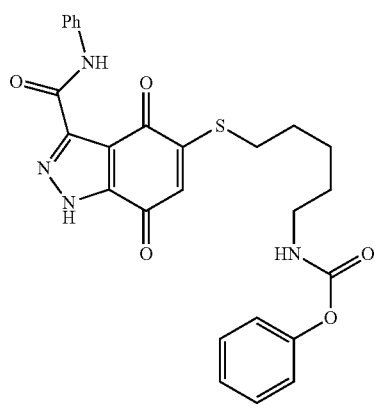
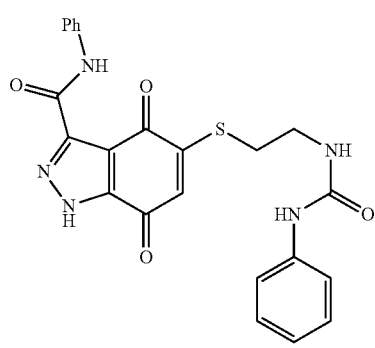 [SMILES: O=C(NCCSC1=CC(=O)c2[nH]nc(C(=O)Nc3ccccc3)c2C1=O)Nc1ccccc1]
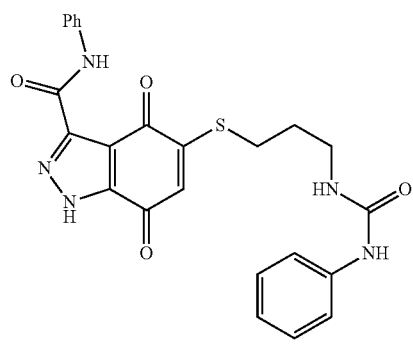 [SMILES: O=C(NCCCSC1=CC(=O)c2[nH]nc(C(=O)Nc3ccccc3)c2C1=O)Nc1ccccc1]
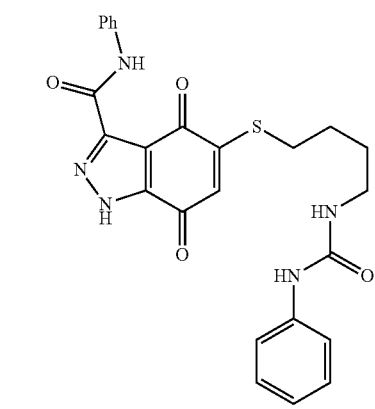
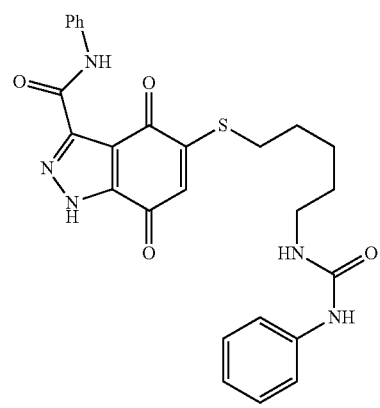 [SMILES: O=C(NCCCCCSC1=CC(=O)c2[nH]nc(C(=O)Nc3ccccc3)c2C1=O)Nc1ccccc1]
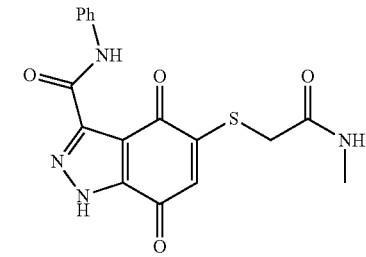

TABLE 1-continued
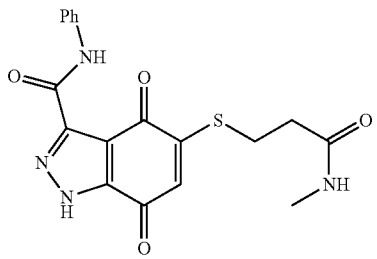 [SMILES: CNC(=O)CCSC1=CC(=O)c2[nH]nc(C(=O)Nc3ccccc3)c2C1=O]
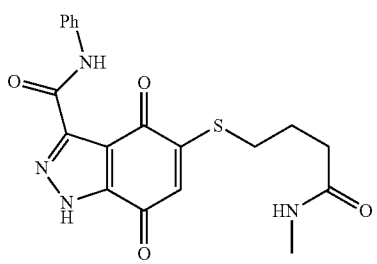 [SMILES: CNC(=O)CCCSC1=CC(=O)c2[nH]nc(C(=O)Nc3ccccc3)c2C1=O]
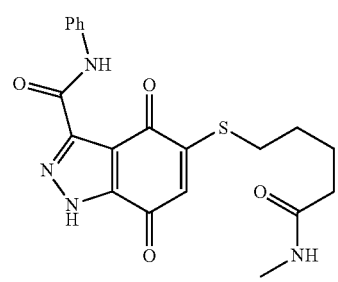 [SMILES: CNC(=O)CCCCSC1=CC(=O)c2[nH]nc(C(=O)Nc3ccccc3)c2C1=O]
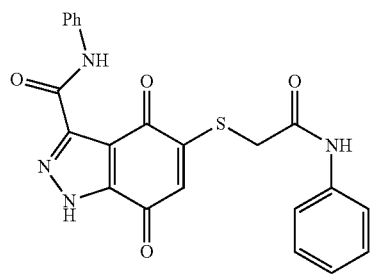 [SMILES: O=C(CSC1=CC(=O)c2[nH]nc(C(=O)Nc3ccccc3)c2C1=O)Nc1ccccc1]
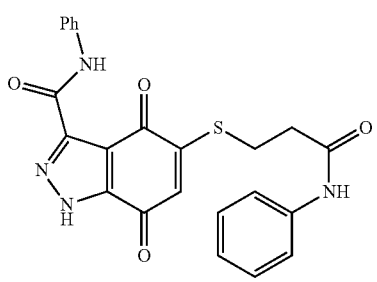 [SMILES: O=C(CCSC1=CC(=O)c2[nH]nc(C(=O)Nc3ccccc3)c2C1=O)Nc1ccccc1]
TABLE 1-continued
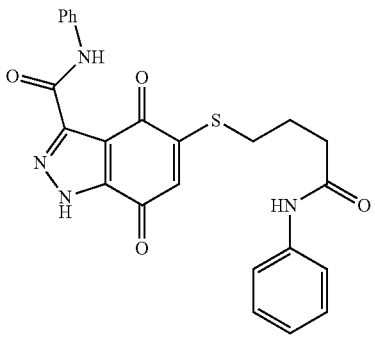
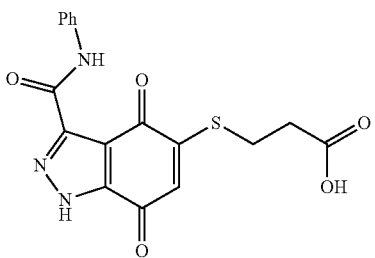 [SMILES: O=C(O)CCSC1=CC(=O)c2[nH]nc(C(=O)Nc3ccccc3)c2C1=O]
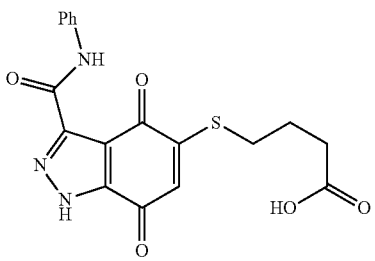 [SMILES: O=C(O)CCCSC1=CC(=O)c2[nH]nc(C(=O)Nc3ccccc3)c2C1=O]

TABLE 1-continued
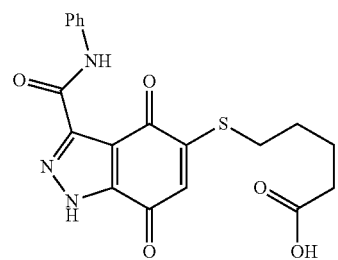 [SMILES: O=C(O)CCCCSC1=CC(=O)c2[nH]nc(C(=O)Nc3ccccc3)c2C1=O]
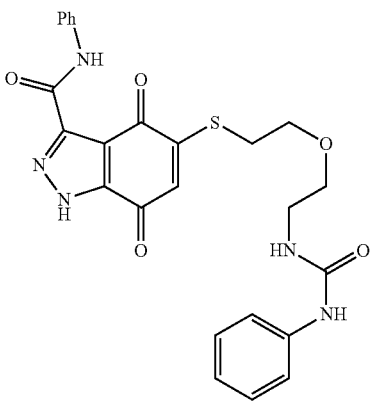
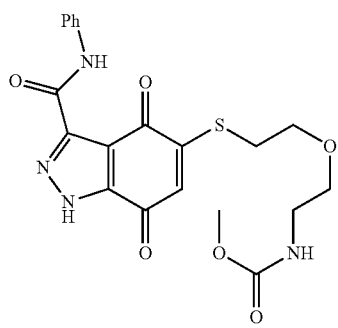 [SMILES: COC(=O)NCCOCCSC1=CC(=O)c2[nH]nc(C(=O)Nc3ccccc3)c2C1=O]
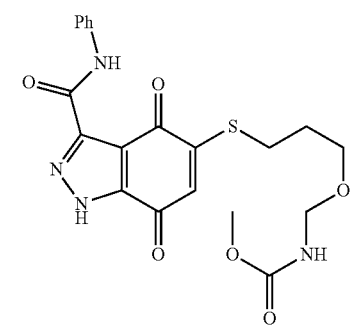
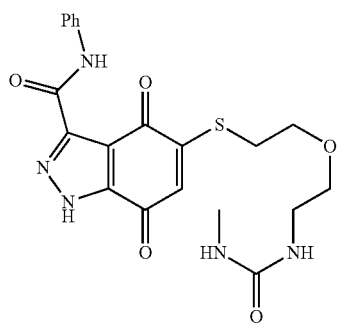 [SMILES: CNC(=O)NCCOCCSC1=CC(=O)c2[nH]nc(C(=O)Nc3ccccc3)c2C1=O]
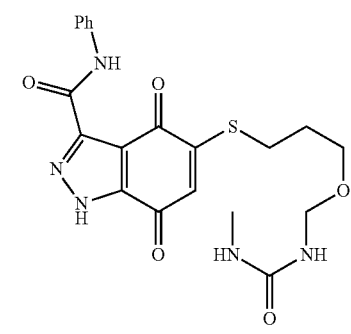
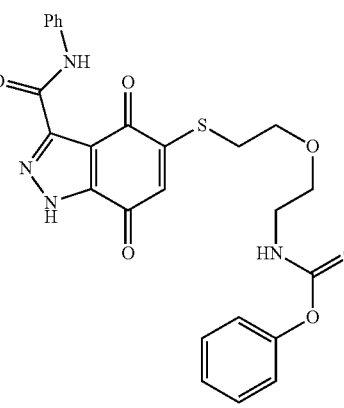
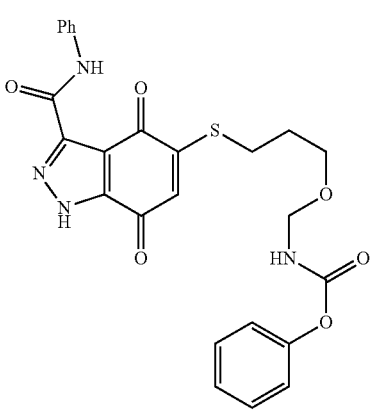 [SMILES: O=C(NCOCCCSC1=CC(=O)c2[nH]nc(C(=O)Nc3ccccc3)c2C1=O)Oc1ccccc1]

TABLE 1-continued
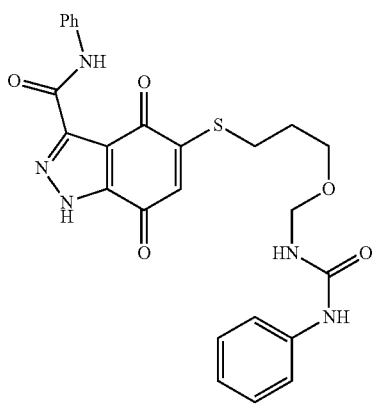 [SMILES: O=C(NCOCCCSC1=CC(=O)c2[nH]nc(C(=O)Nc3ccccc3)c2C1=O)Nc1ccccc1]
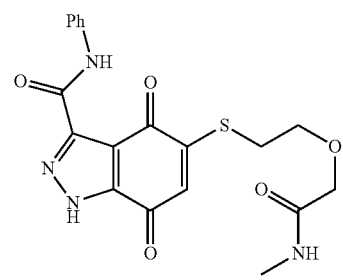 [SMILES: CNC(=O)COCCSC1=CC(=O)c2[nH]nc(C(=O)Nc3ccccc3)c2C1=O]
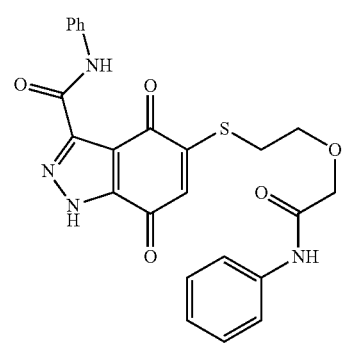 [SMILES: O=C(COCCSC1=CC(=O)c2[nH]nc(C(=O)Nc3ccccc3)c2C1=O)Nc1ccccc1]
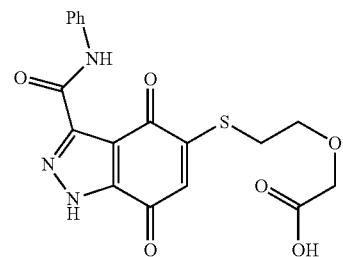 [SMILES: O=C(O)COCCSC1=CC(=O)c2[nH]nc(C(=O)Nc3ccccc3)c2C1=O]
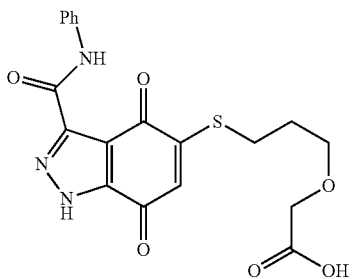 [SMILES: O=C(O)COCCCSC1=CC(=O)c2[nH]nc(C(=O)Nc3ccccc3)c2C1=O]
TABLE 1-continued
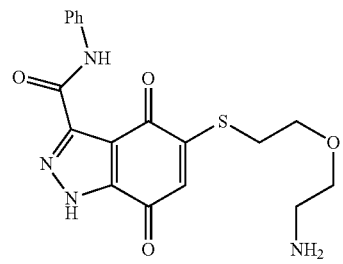 [SMILES: NCCOCCSC1=CC(=O)c2[nH]nc(C(=O)Nc3ccccc3)c2C1=O]
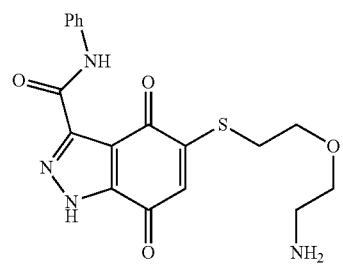 [SMILES: NCCOCCSC1=CC(=O)c2[nH]nc(C(=O)Nc3ccccc3)c2C1=O]
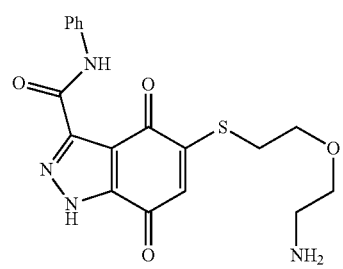 [SMILES: NCCOCCSC1=CC(=O)c2[nH]nc(C(=O)Nc3ccccc3)c2C1=O]
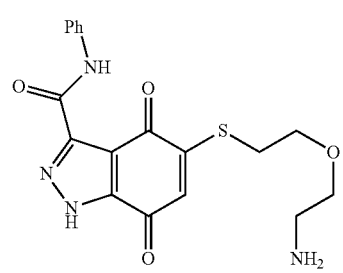 [SMILES: NCCOCCSC1=CC(=O)c2[nH]nc(C(=O)Nc3ccccc3)c2C1=O]
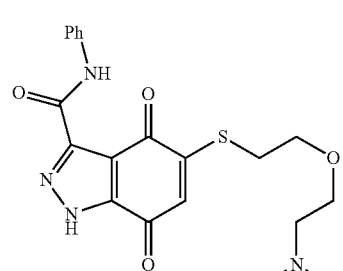
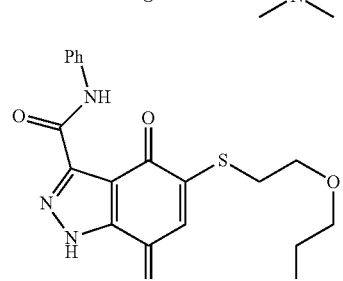

TABLE 1-continued
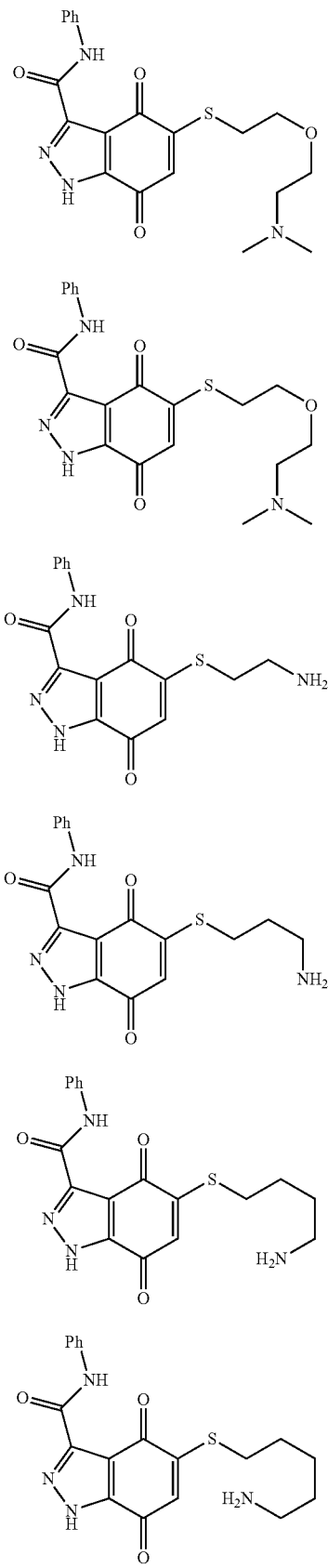
TABLE 1-continued
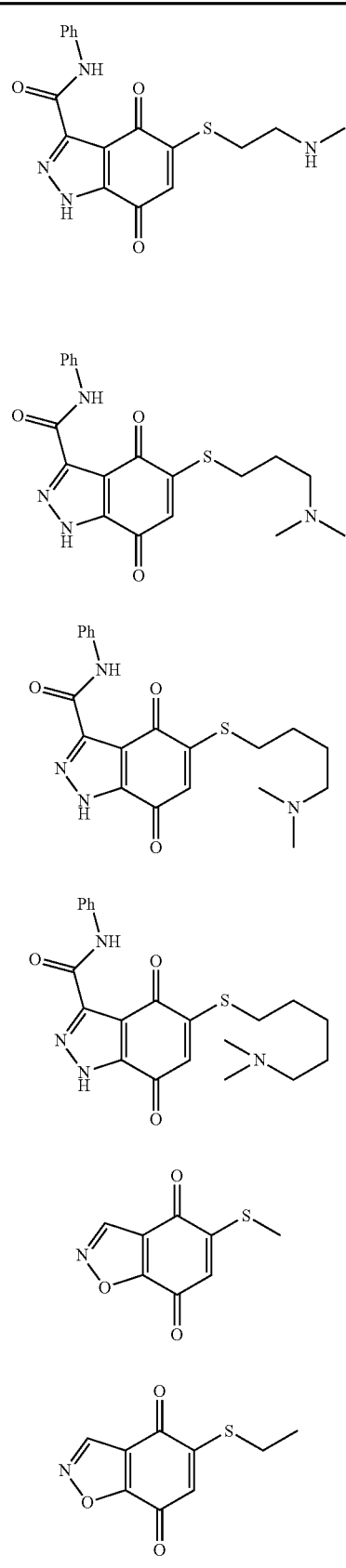

TABLE 1-continued
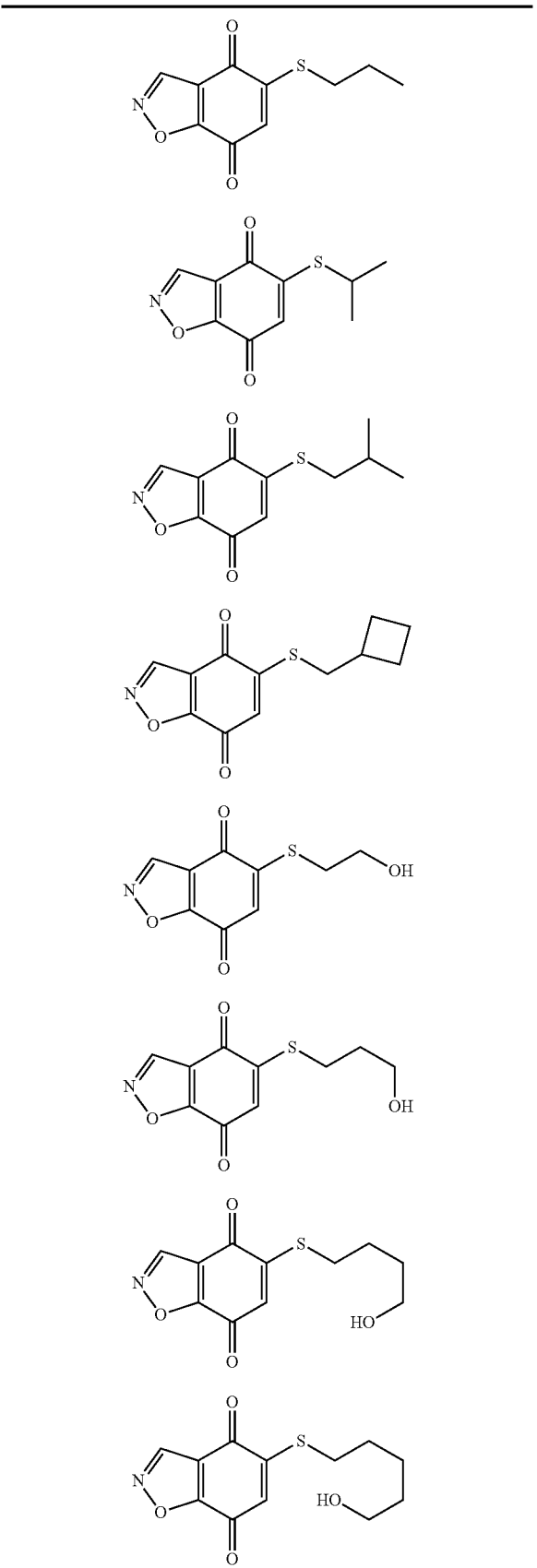
TABLE 1-continued
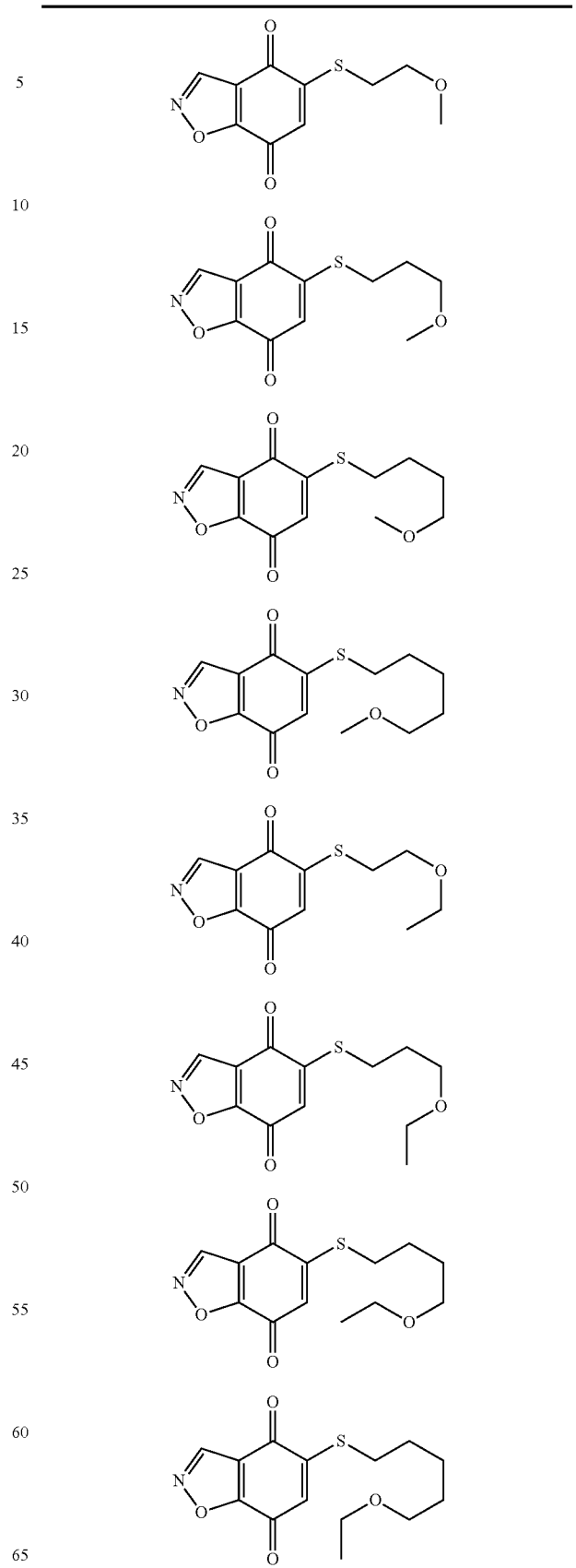

TABLE 1-continued
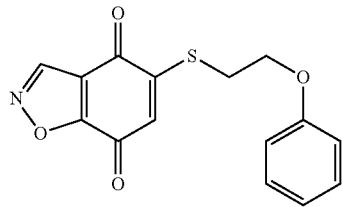 [SMILES: O=C1C(SCCOc2ccccc2)=CC(=O)c2oncc21]
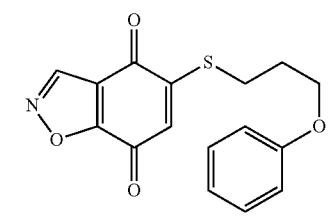 [SMILES: O=C1C(SCCCOc2ccccc2)=CC(=O)c2oncc21]
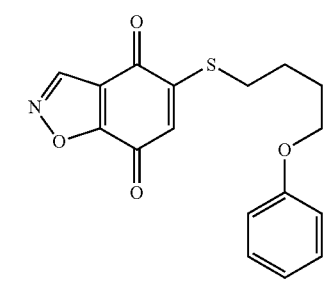 [SMILES: O=C1C(SCCCCOc2ccccc2)=CC(=O)c2oncc21]
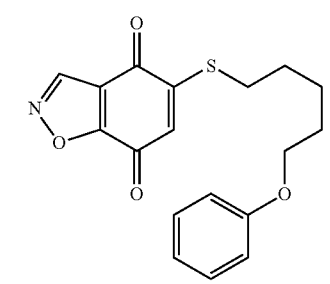 [SMILES: O=C1C(SCCCCCOc2ccccc2)=CC(=O)c2oncc21]
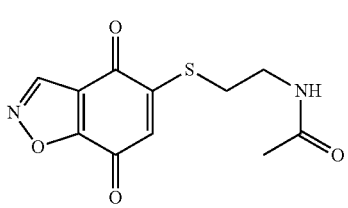
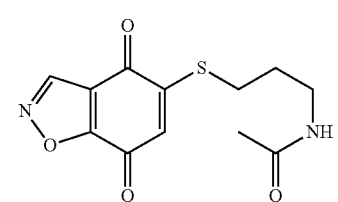 [SMILES: CC(=O)NCCCSC1=CC(=O)c2oncc2C1=O]
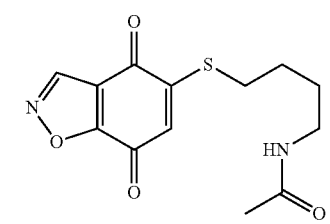 [SMILES: CC(=O)NCCCCSC1=CC(=O)c2oncc2C1=O]
TABLE 1-continued
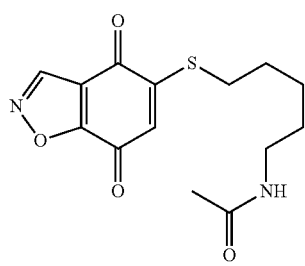 [SMILES: CC(=O)NCCCCCSC1=CC(=O)c2oncc2C1=O]
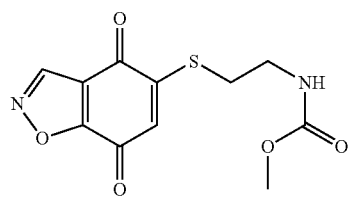 [SMILES: COC(=O)NCCSC1=CC(=O)c2oncc2C1=O]
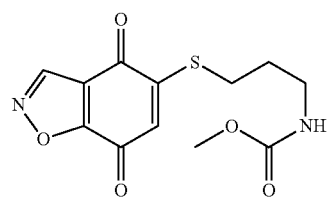 [SMILES: COC(=O)NCCCSC1=CC(=O)c2oncc2C1=O]
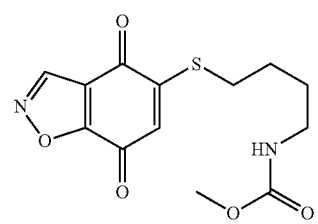
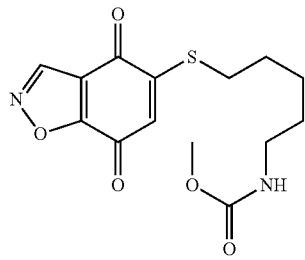 [SMILES: COC(=O)NCCCCCSC1=CC(=O)c2oncc2C1=O]
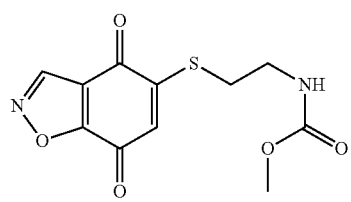 [SMILES: COC(=O)NCCSC1=CC(=O)c2oncc2C1=O]
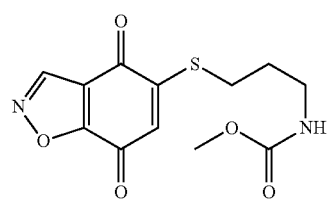 [SMILES: COC(=O)NCCCSC1=CC(=O)c2oncc2C1=O]

TABLE 1-continued
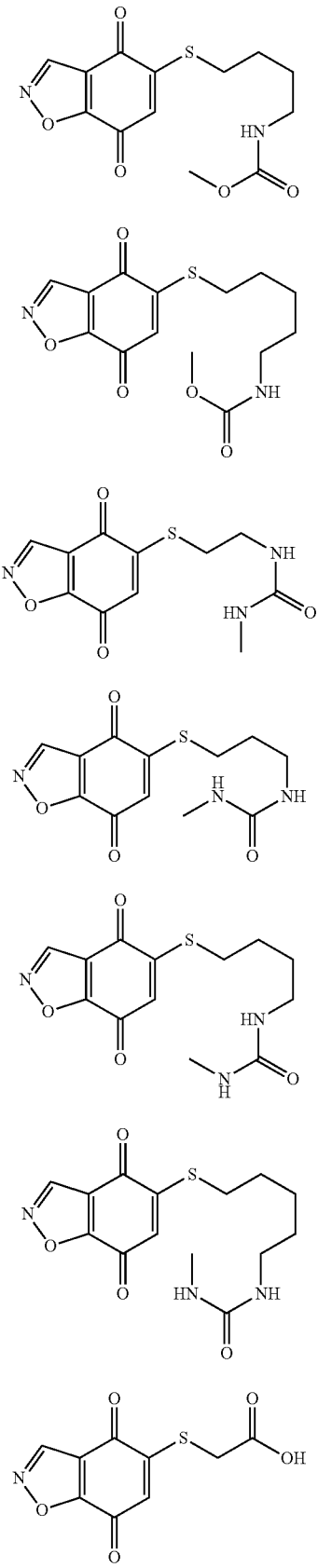
TABLE 1-continued
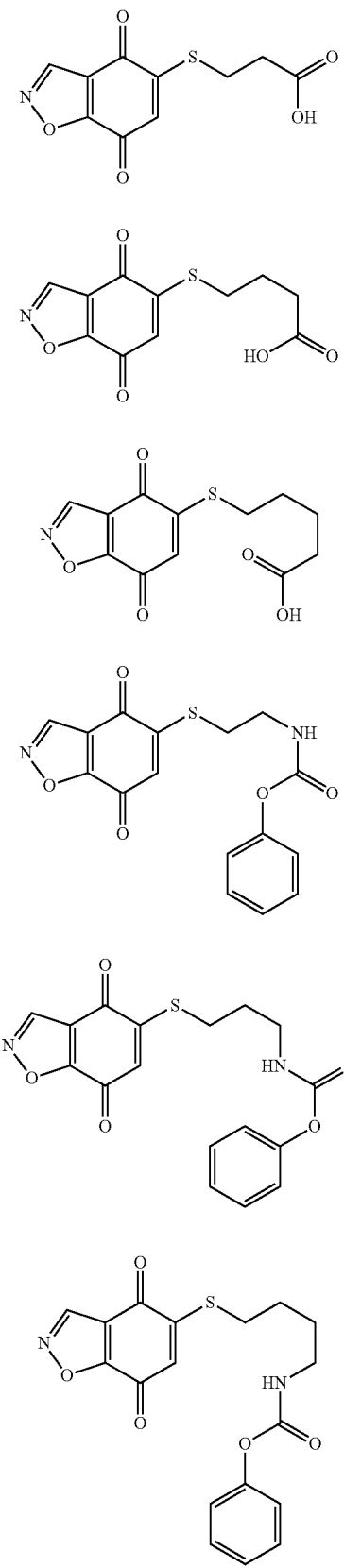

207
TABLE 1-continued
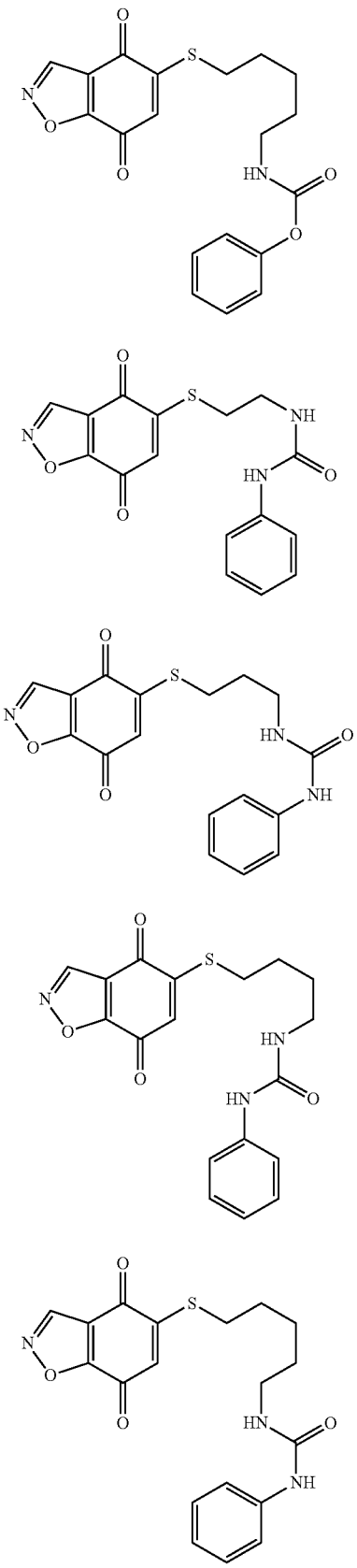
208
TABLE 1-continued
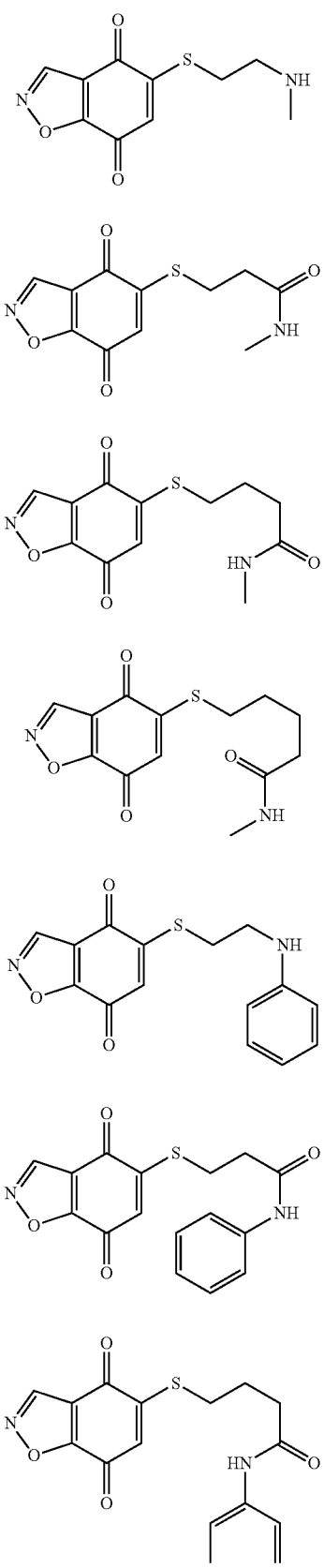

TABLE 1-continued
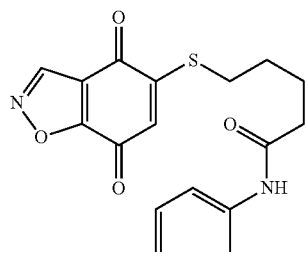 [SMILES: C=C/C=C(\C)NC(=O)CCCCSC1=CC(=O)c2oncc2C1=O]
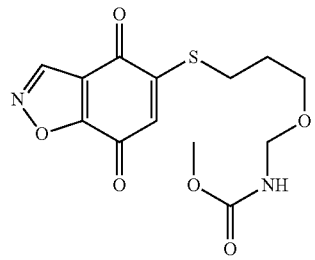

US 10,071,076 B2
TABLE 1-continued
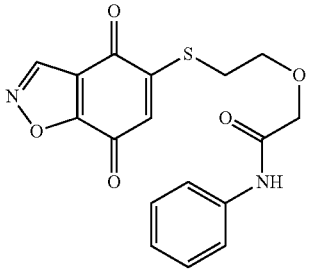 [SMILES: O=C(COCCSC1=CC(=O)c2oncc2C1=O)Nc1ccccc1]
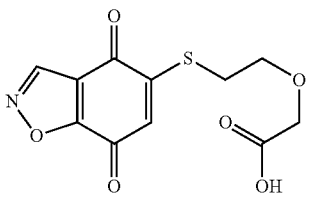 [SMILES: O=C(O)COCCSC1=CC(=O)c2oncc2C1=O]
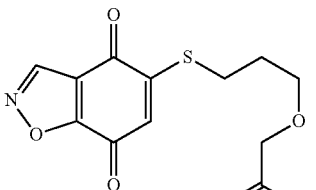
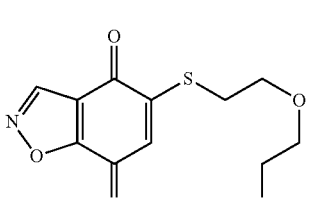
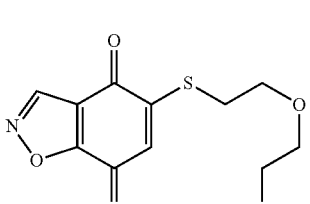
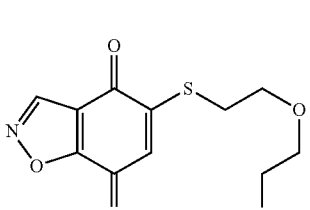
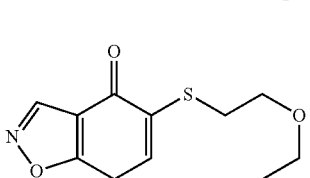
TABLE 1-continued
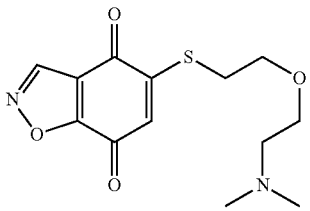

TABLE 1-continued
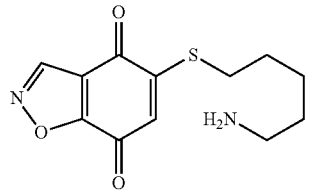 [SMILES: NCCCCCSC1=CC(=O)c2oncc2C1=O]
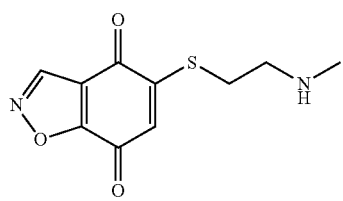 [SMILES: CNCCSC1=CC(=O)c2oncc2C1=O]
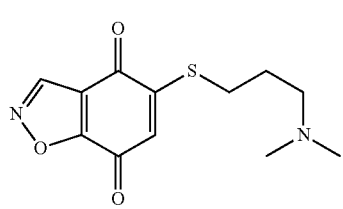 [SMILES: CN(C)CCCSC1=CC(=O)c2oncc2C1=O]
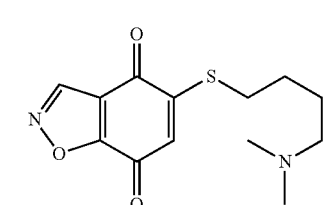
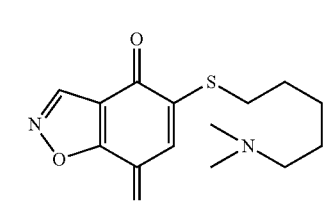
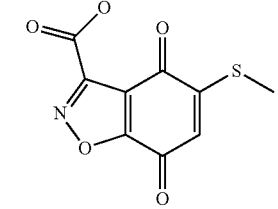 [SMILES: CSC1=CC(=O)c2onc(C(=O)O)c2C1=O]
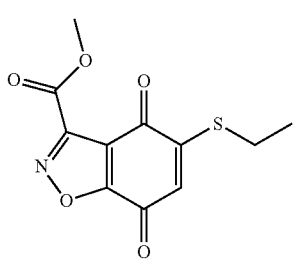 [SMILES: CCSC1=CC(=O)c2onc(C(=O)OC)c2C1=O]
TABLE 1-continued
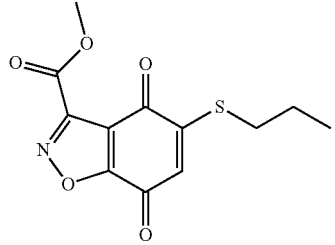 [SMILES: CCCSC1=CC(=O)c2onc(C(=O)OC)c2C1=O]
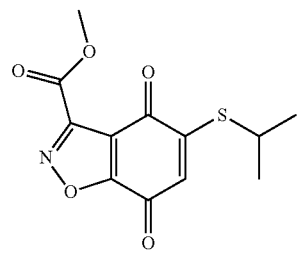 [SMILES: COC(=O)c1noc2c1C(=O)C(SC(C)C)=CC2=O]
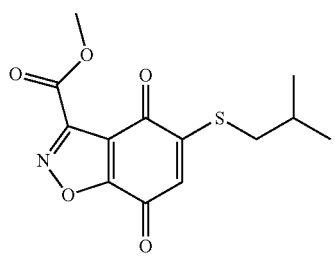 [SMILES: COC(=O)c1noc2c1C(=O)C(SCC(C)C)=CC2=O]
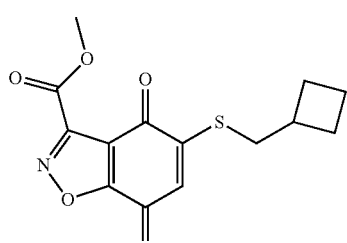
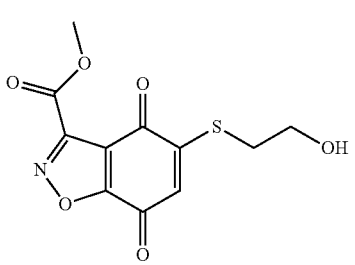 [SMILES: COC(=O)c1noc2c1C(=O)C(SCCO)=CC2=O]
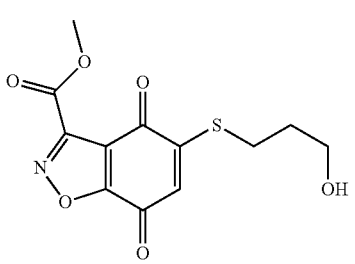 [SMILES: COC(=O)c1noc2c1C(=O)C(SCCCO)=CC2=O]

TABLE 1-continued
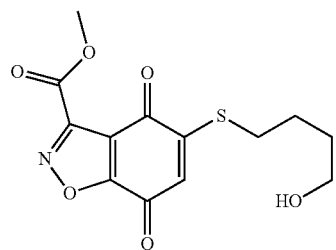 [SMILES: COC(=O)c1noc2c1C(=O)C(SCCCCO)=CC2=O]
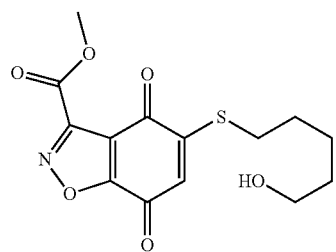 [SMILES: COC(=O)c1noc2c1C(=O)C(SCCCCCO)=CC2=O]
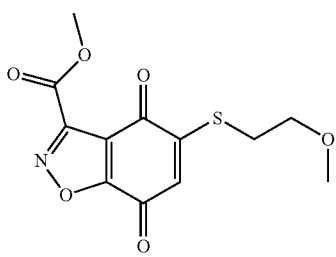 [SMILES: COCCSC1=CC(=O)c2onc(C(=O)OC)c2C1=O]
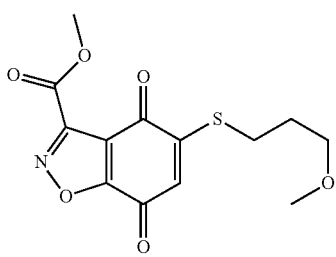 [SMILES: COCCCSC1=CC(=O)c2onc(C(=O)OC)c2C1=O]
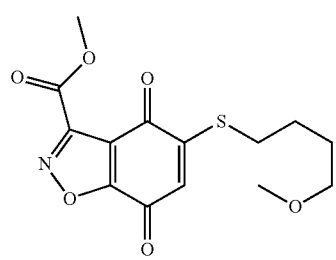 [SMILES: COCCCCSC1=CC(=O)c2onc(C(=O)OC)c2C1=O]
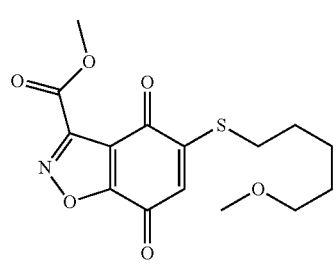 [SMILES: COCCCCCSC1=CC(=O)c2onc(C(=O)OC)c2C1=O]
TABLE 1-continued
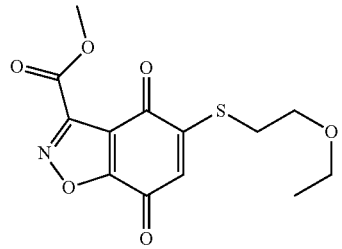
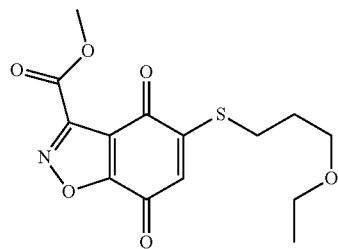
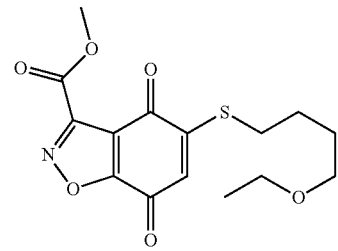 [SMILES: CCOCCCCSC1=CC(=O)c2onc(C(=O)OC)c2C1=O]
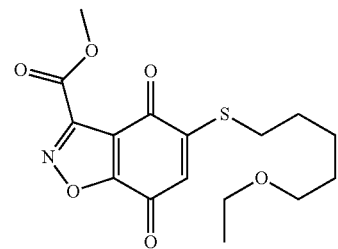 [SMILES: CCOCCCCCSC1=CC(=O)c2onc(C(=O)OC)c2C1=O]
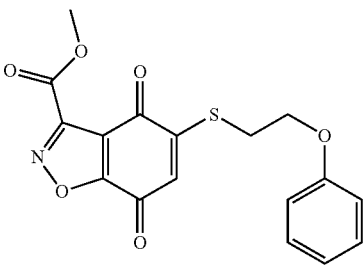 [SMILES: COC(=O)c1noc2c1C(=O)C(SCCOc1ccccc1)=CC2=O]
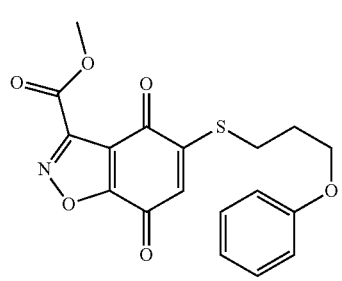

TABLE 1-continued
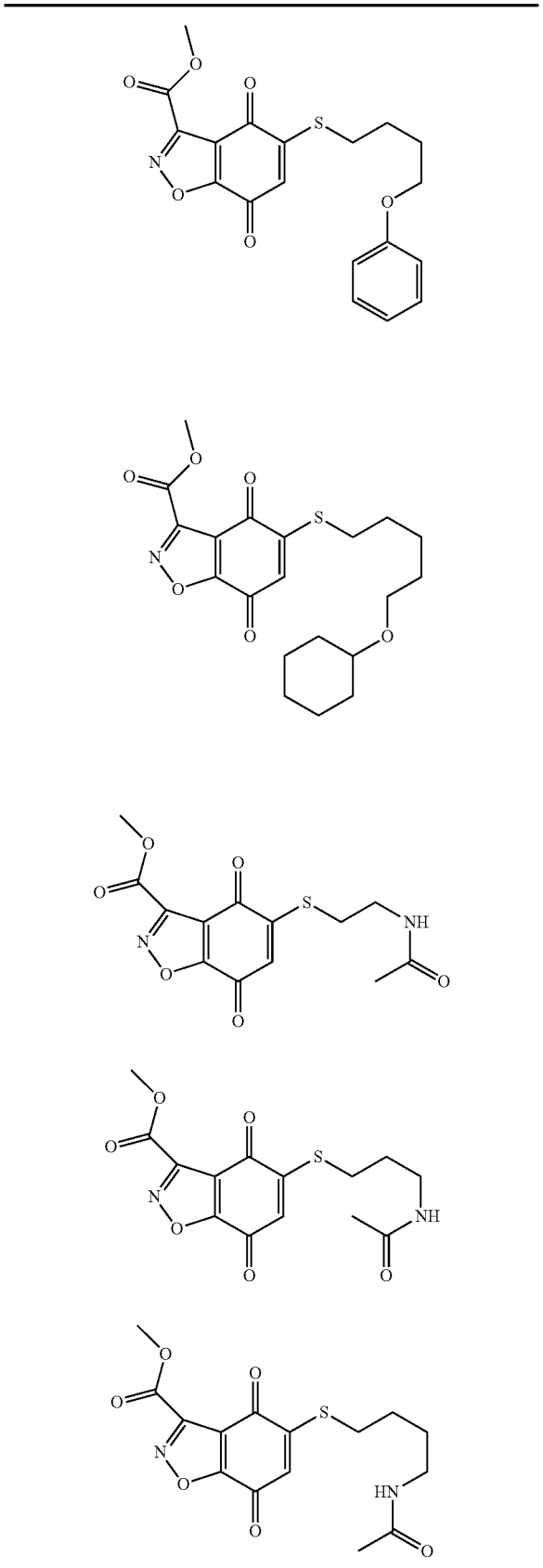
TABLE 1-continued
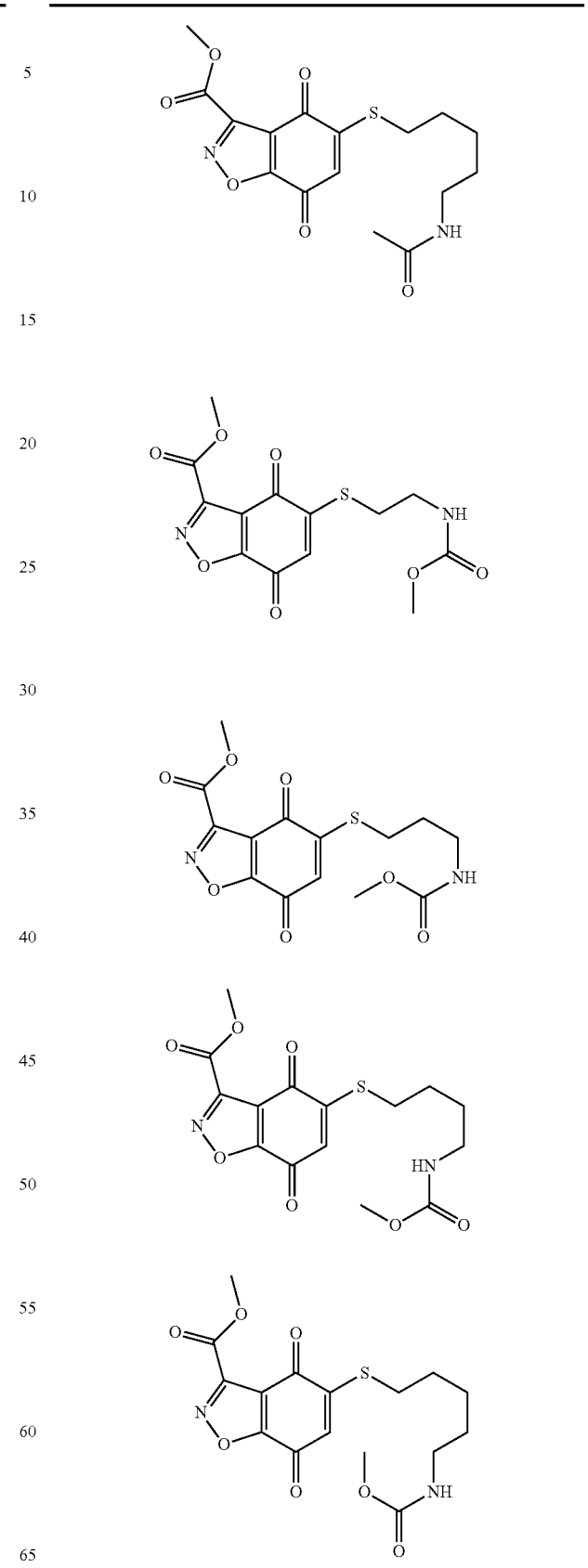

TABLE 1-continued
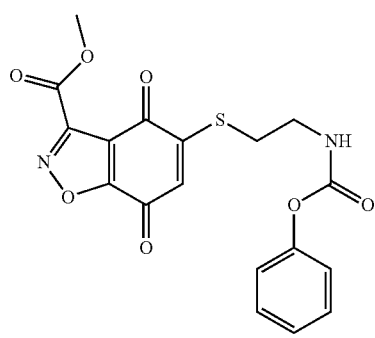 [SMILES: COC(=O)c1noc2c1C(=O)C(SCCNC(=O)Oc1ccccc1)=CC2=O]
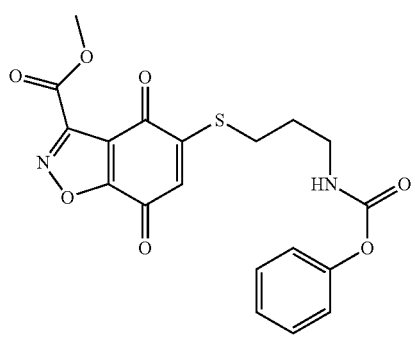 [SMILES: COC(=O)c1noc2c1C(=O)C(SCCCNC(=O)Oc1ccccc1)=CC2=O]
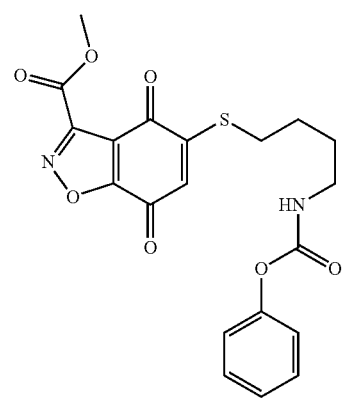 [SMILES: COC(=O)c1noc2c1C(=O)C(SCCCCNC(=O)Oc1ccccc1)=CC2=O]
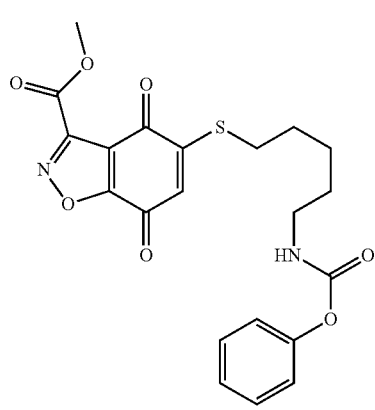 [SMILES: COC(=O)c1noc2c1C(=O)C(SCCCCCNC(=O)Oc1ccccc1)=CC2=O]
TABLE 1-continued
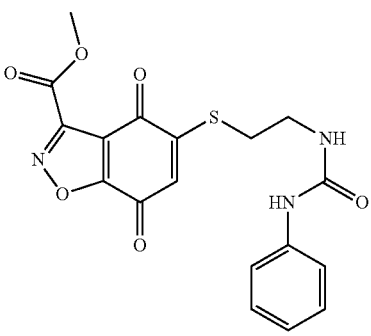
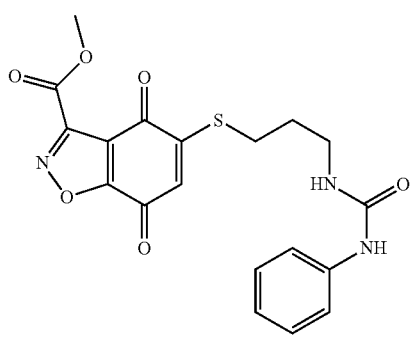 [SMILES: COC(=O)c1noc2c1C(=O)C(SCCCNC(=O)Nc1ccccc1)=CC2=O]
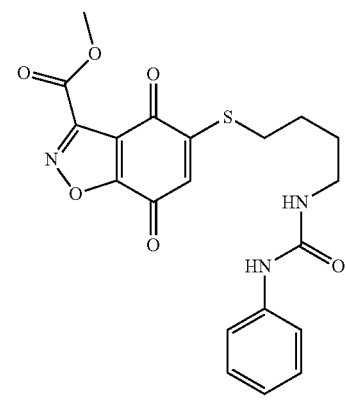
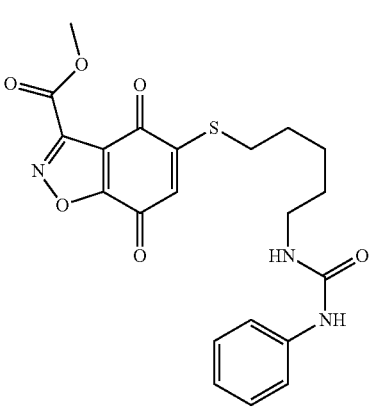 [SMILES: COC(=O)c1noc2c1C(=O)C(SCCCCCNC(=O)Nc1ccccc1)=CC2=O]

TABLE 1-continued
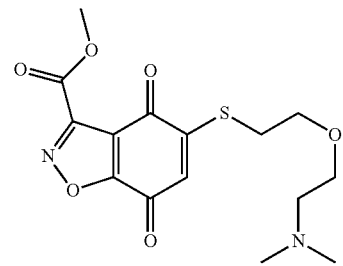 [SMILES: COC(=O)c1noc2c1C(=O)C(SCCOCCN(C)C)=CC2=O]
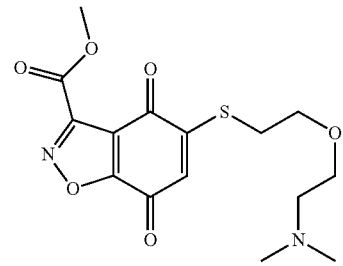 [SMILES: COC(=O)c1noc2c1C(=O)C(SCCOCCN(C)C)=CC2=O]
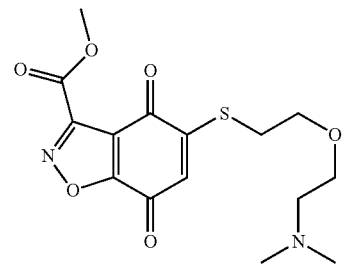 [SMILES: COC(=O)c1noc2c1C(=O)C(SCCOCCN(C)C)=CC2=O]
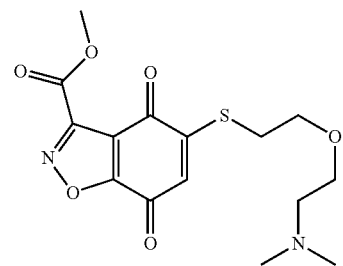 [SMILES: COC(=O)c1noc2c1C(=O)C(SCCOCCN(C)C)=CC2=O]
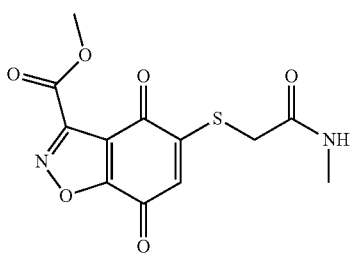
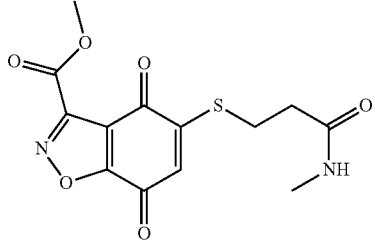 [SMILES: CNC(=O)CCSC1=CC(=O)c2onc(C(=O)OC)c2C1=O]
TABLE 1-continued
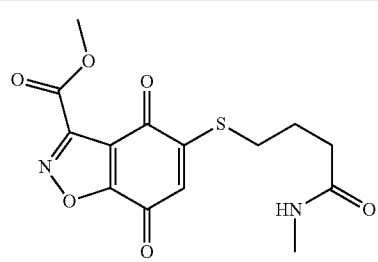 [SMILES: CNC(=O)CCCSC1=CC(=O)c2onc(C(=O)OC)c2C1=O]
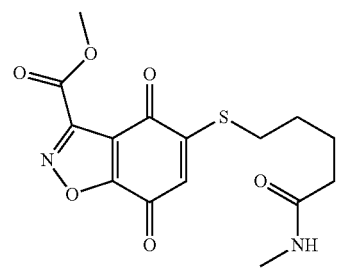 [SMILES: CNC(=O)CCCCSC1=CC(=O)c2onc(C(=O)OC)c2C1=O]
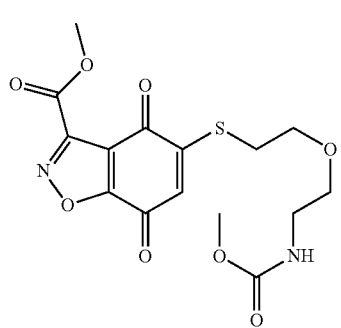
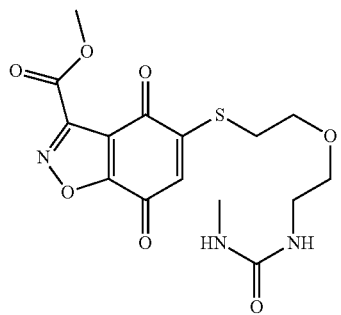
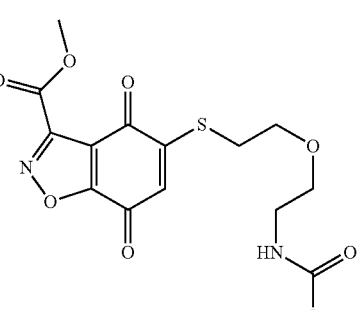
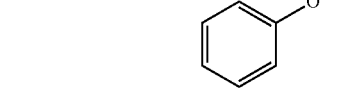

| 223 | 224 |
|---|---|
| 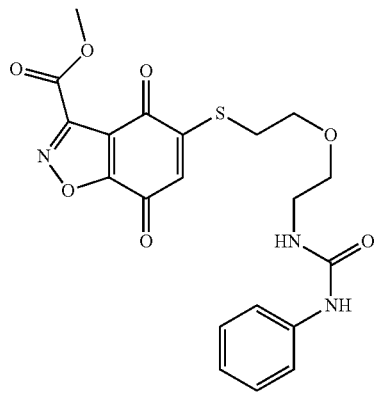 [SMILES: COC(=O)c1noc2c1C(=O)C(SCCOCCNC(=O)Oc1ccccc1)=CC2=O] | 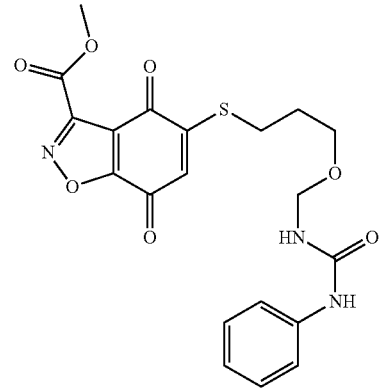 |
| 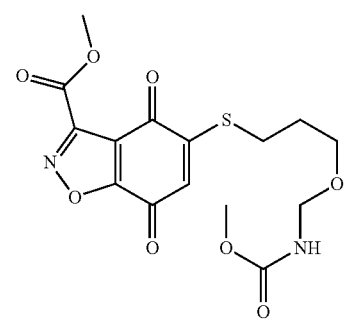 [SMILES: COC(=O)NCOCCCSC1=CC(=O)c2onc(C(=O)OC)c2C1=O] | 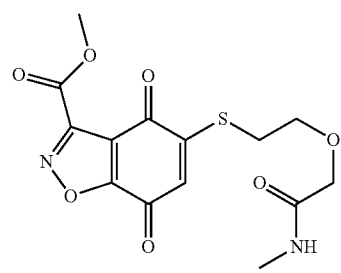 |
| | 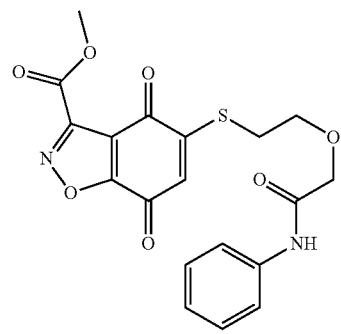 |
| 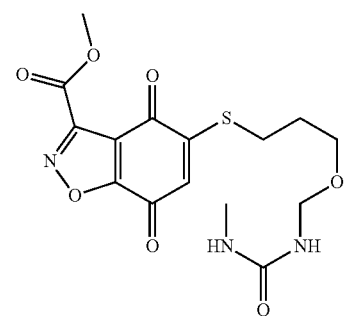 [SMILES: CNC(=O)NCOCCCSC1=CC(=O)c2onc(C(=O)OC)c2C1=O] | |
| | 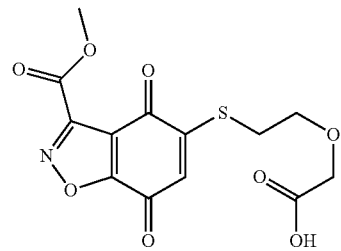 |
| 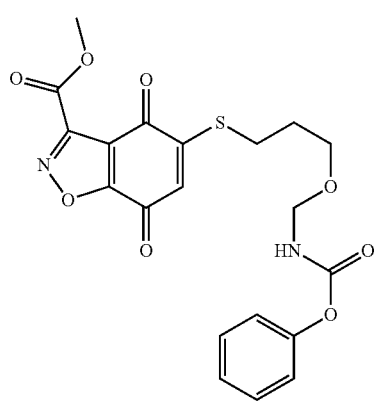 [SMILES: COC(=O)c1noc2c1C(=O)C(SCCCOCNC(=O)Oc1ccccc1)=CC2=O] | 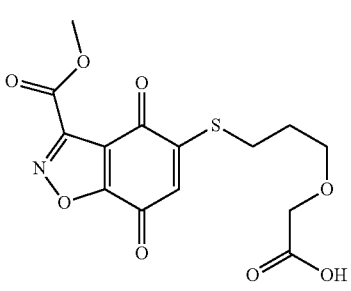 [SMILES: COC(=O)c1noc2c1C(=O)C(SCCCOCC(=O)O)=CC2=O] |

TABLE 1-continued
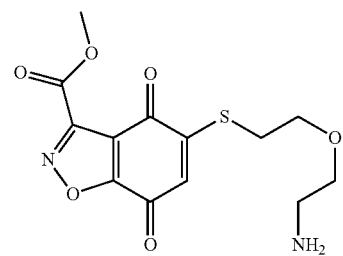 [SMILES: COC(=O)c1noc2c1C(=O)C(SCCOCCN)=CC2=O]
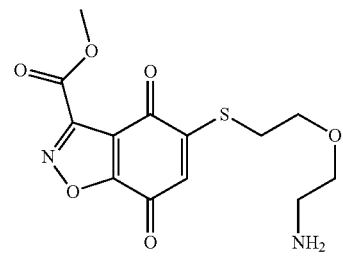
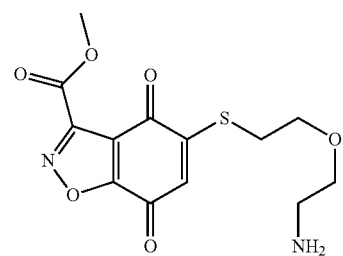 [SMILES: COC(=O)c1noc2c1C(=O)C(SCCOCCN)=CC2=O]
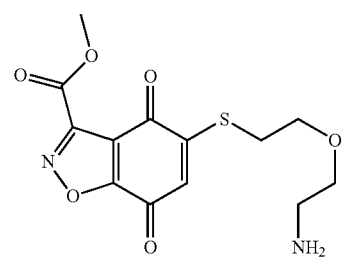 [SMILES: COC(=O)c1noc2c1C(=O)C(SCCOCCN)=CC2=O]
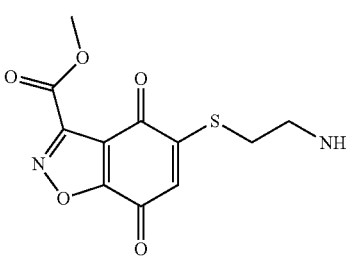
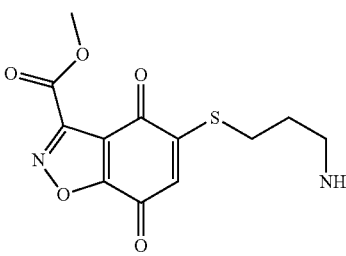
TABLE 1-continued
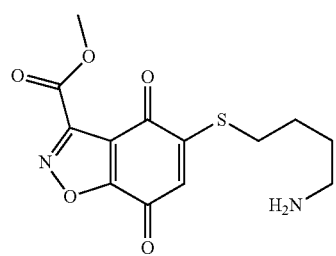 [SMILES: COC(=O)c1noc2c1C(=O)C(SCCCCN)=CC2=O]
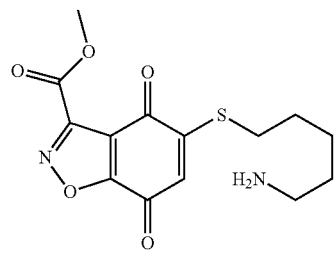 [SMILES: COC(=O)c1noc2c1C(=O)C(SCCCCCN)=CC2=O]
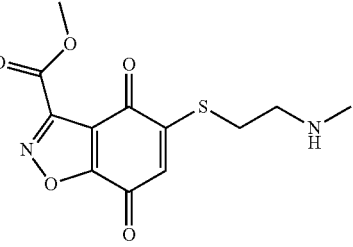
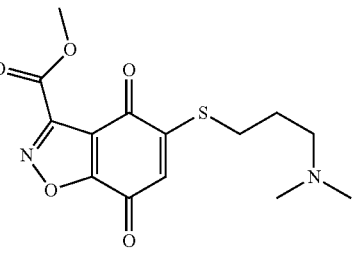
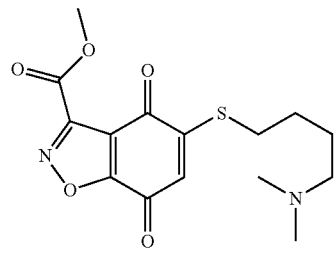 [SMILES: COC(=O)c1noc2c1C(=O)C(SCCCCN(C)C)=CC2=O]
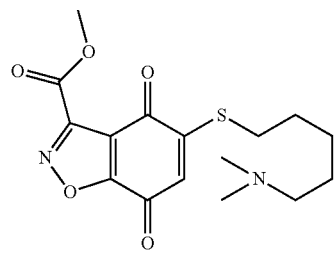 [SMILES: COC(=O)c1noc2c1C(=O)C(SCCCCCN(C)C)=CC2=O]

TABLE 1-continued
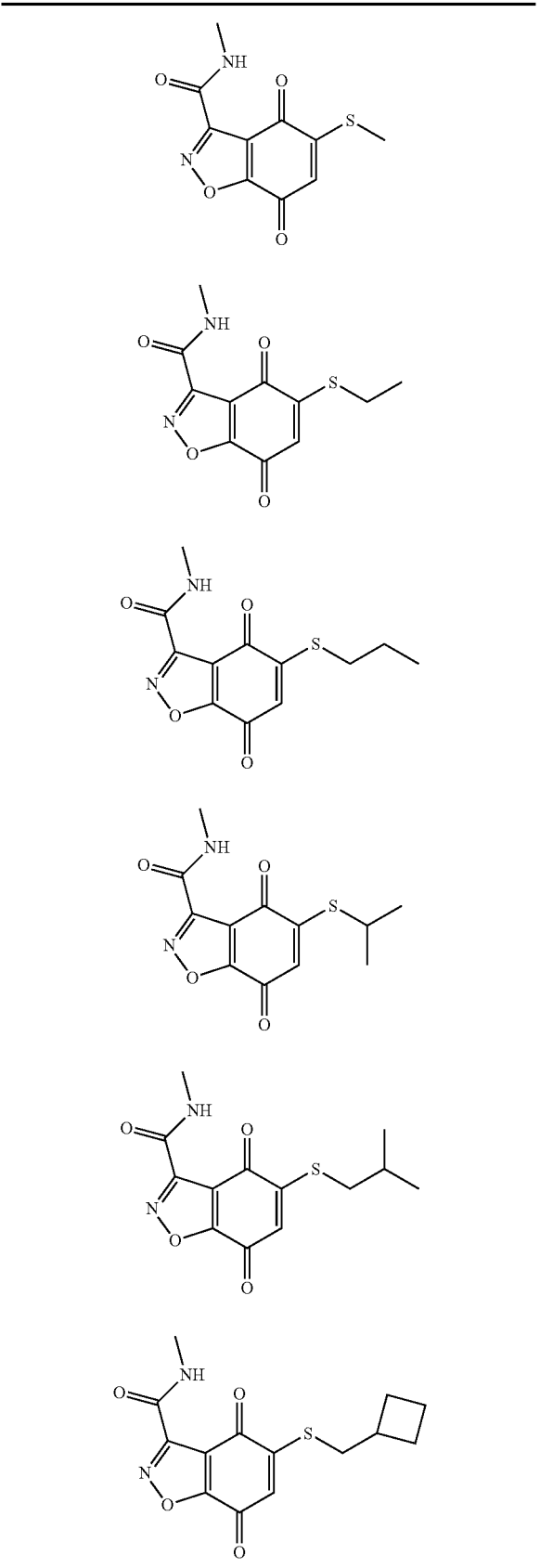
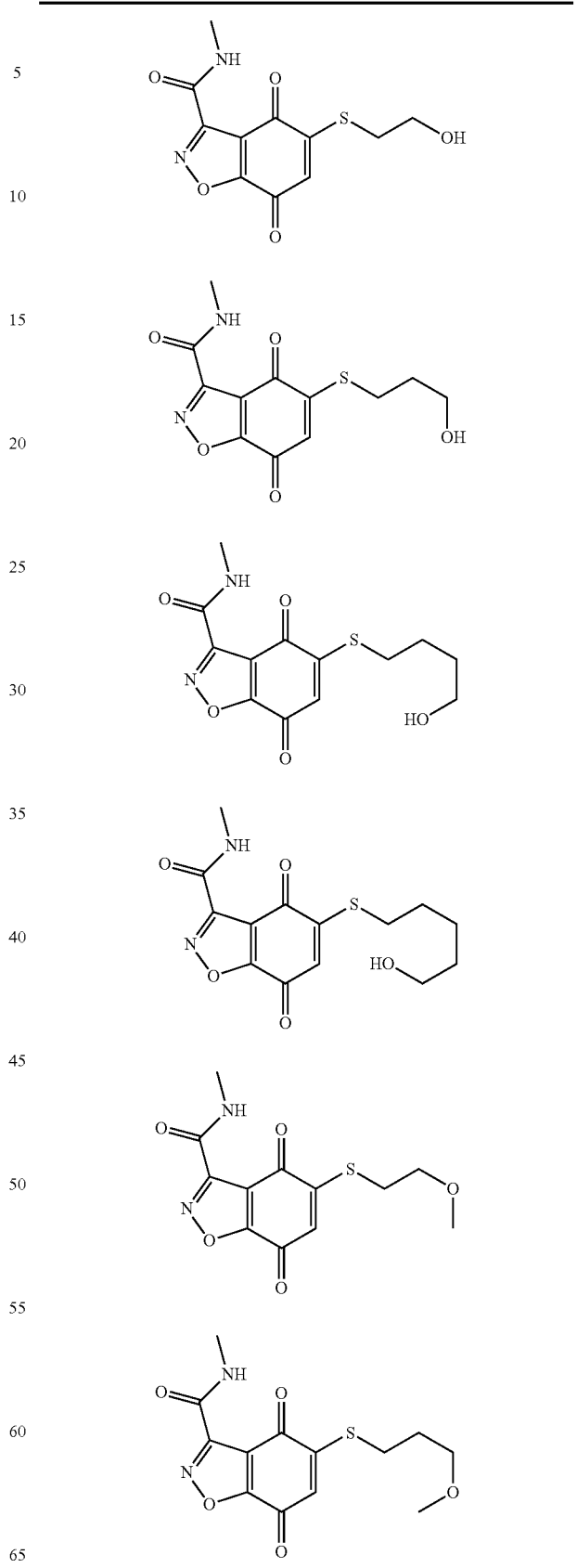

TABLE 1-continued
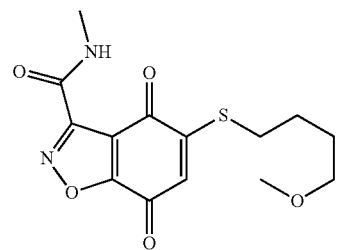 [SMILES: CNC(=O)c1noc2c1C(=O)C(SCCCCOC)=CC2=O]
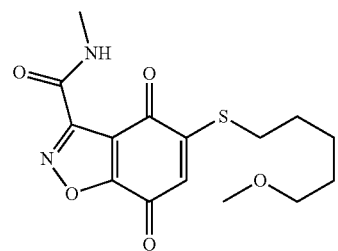 [SMILES: CNC(=O)c1noc2c1C(=O)C(SCCCCCOC)=CC2=O]
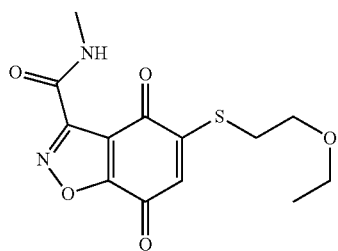 [SMILES: CCOCCSC1=CC(=O)c2onc(C(=O)NC)c2C1=O]
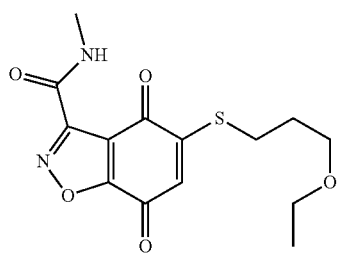 [SMILES: CCOCCCSC1=CC(=O)c2onc(C(=O)NC)c2C1=O]
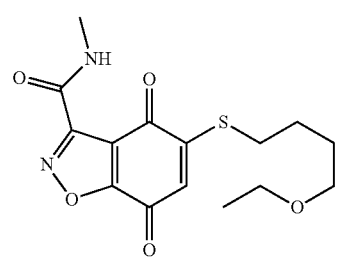 [SMILES: CCOCCCCSC1=CC(=O)c2onc(C(=O)NC)c2C1=O]
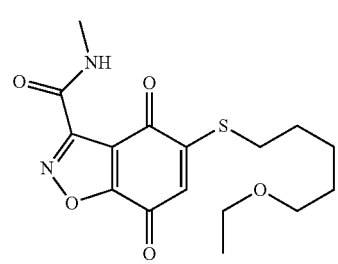 [SMILES: CCOCCCCCSC1=CC(=O)c2onc(C(=O)NC)c2C1=O]
TABLE 1-continued
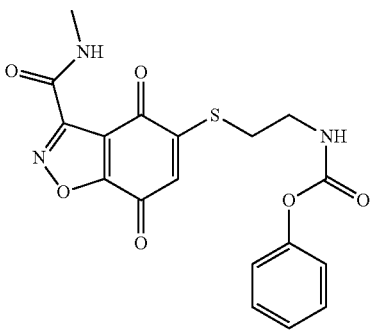 [SMILES: CNC(=O)c1noc2c1C(=O)C(SCCNC(=O)Oc1ccccc1)=CC2=O]
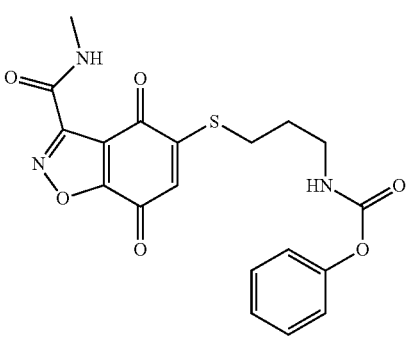
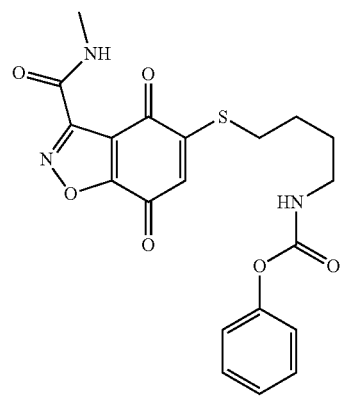
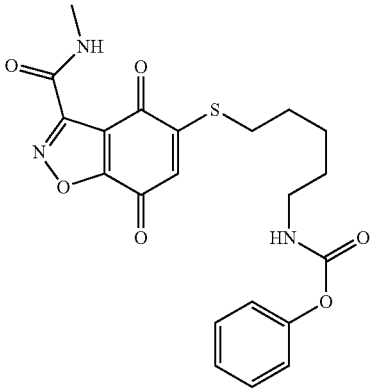 [SMILES: CNC(=O)c1noc2c1C(=O)C(SCCCCCNC(=O)Oc1ccccc1)=CC2=O]

TABLE 1-continued
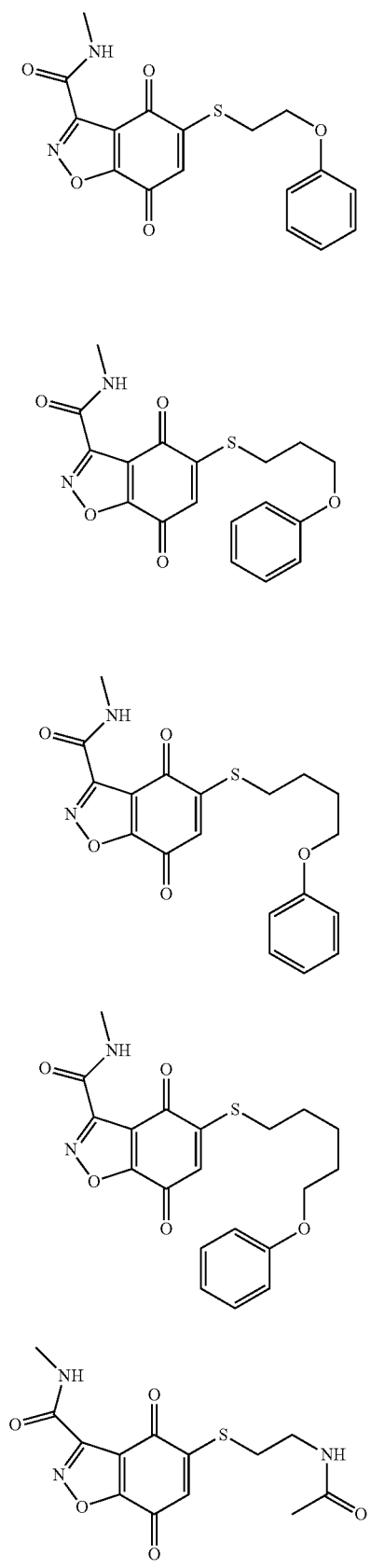
TABLE 1-continued
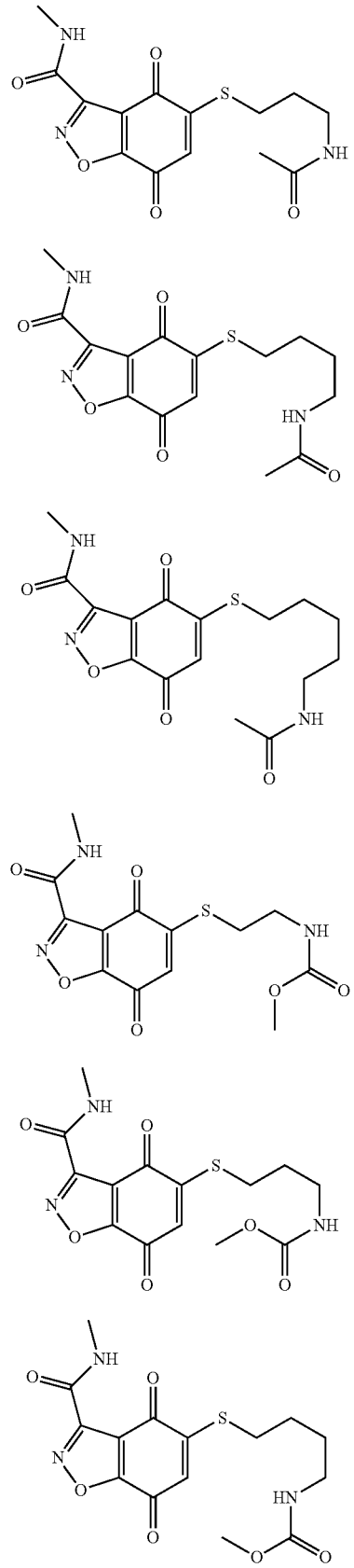

TABLE 1-continued
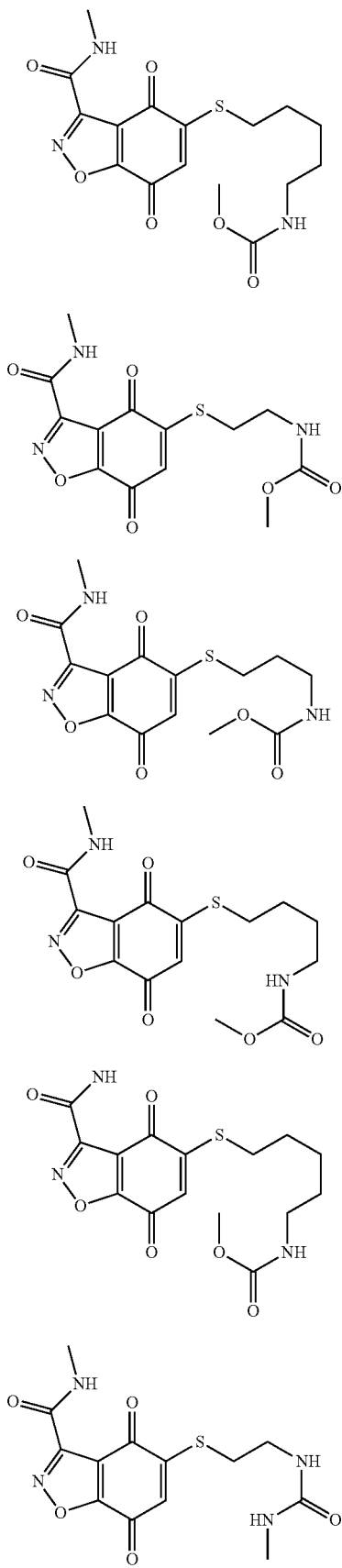
TABLE 1-continued
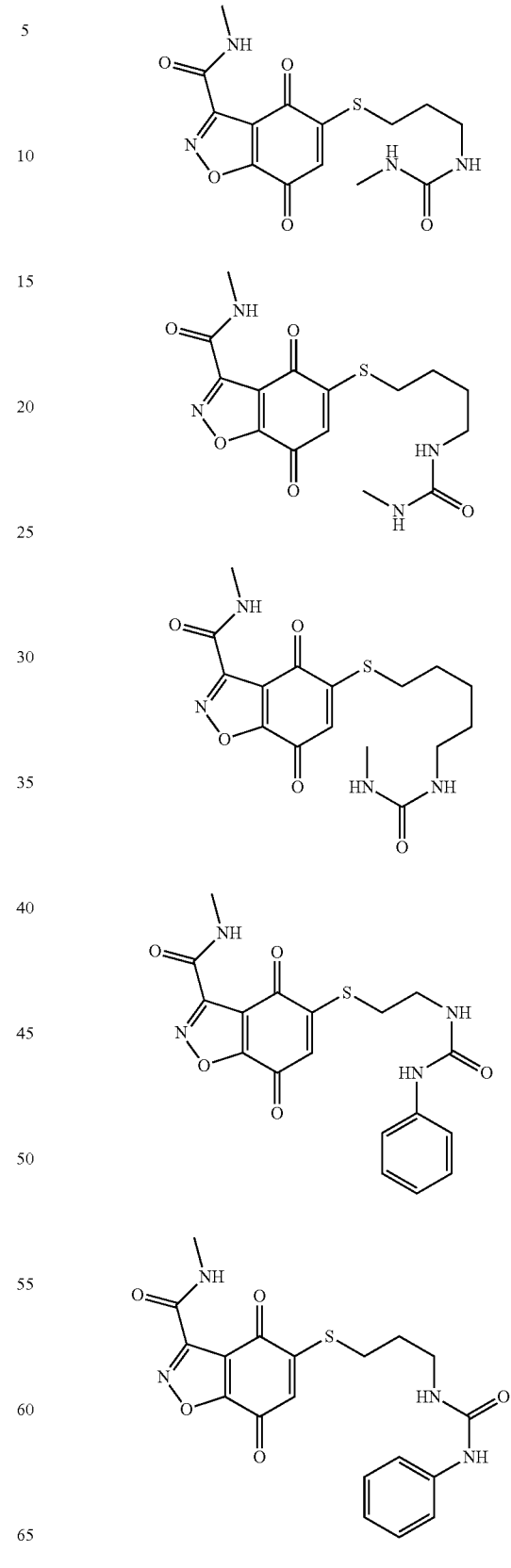

TABLE 1-continued
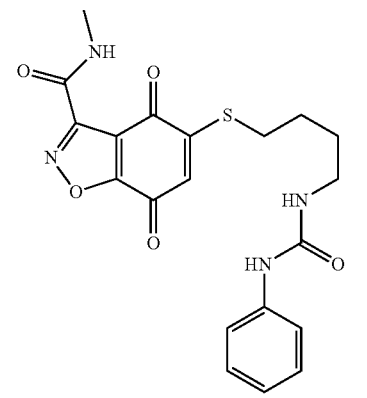 [SMILES: CNC(=O)c1noc2c1C(=O)C(SCCCCNC(=O)Nc1ccccc1)=CC2=O]
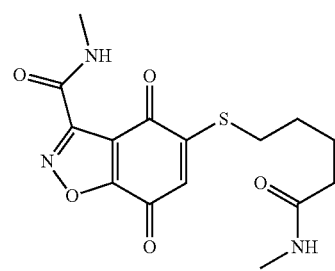 [SMILES: CNC(=O)CCCCSC1=CC(=O)c2onc(C(=O)NC)c2C1=O]
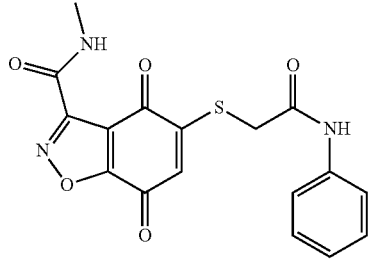 [SMILES: CNC(=O)c1noc2c1C(=O)C(SCC(=O)Nc1ccccc1)=CC2=O]
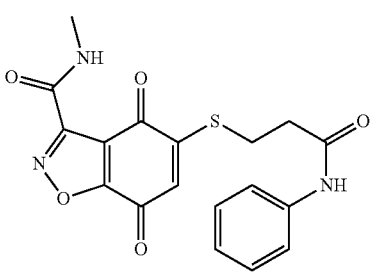 [SMILES: CNC(=O)c1noc2c1C(=O)C(SCCC(=O)Nc1ccccc1)=CC2=O]
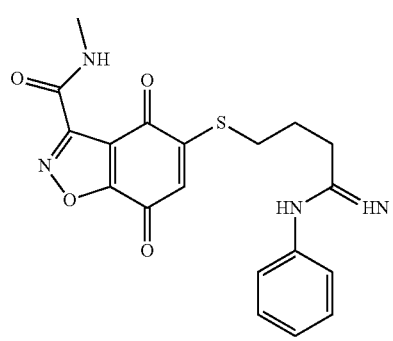 [SMILES: CNC(=O)c1noc2c1C(=O)C(SCCCC(=N)Nc1ccccc1)=CC2=O]
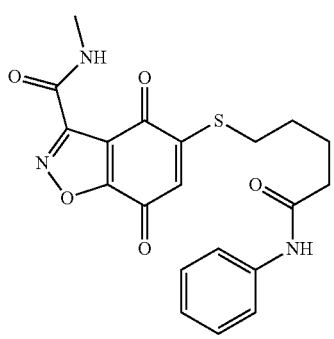 [SMILES: CNC(=O)c1noc2c1C(=O)C(SCCCCC(=O)Nc1ccccc1)=CC2=O]

TABLE 1-continued
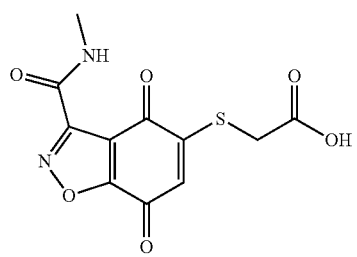
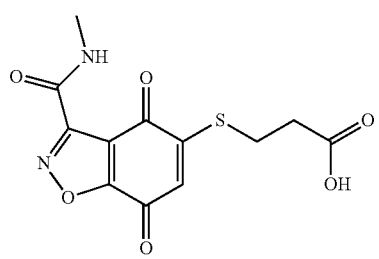 [SMILES: CNC(=O)c1noc2c1C(=O)C(SCCC(=O)O)=CC2=O]
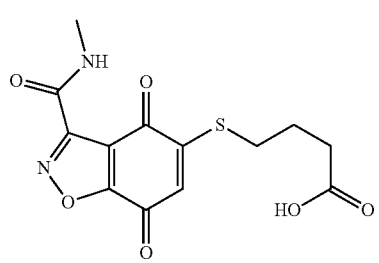 [SMILES: CNC(=O)c1noc2c1C(=O)C(SCCCC(=O)O)=CC2=O]
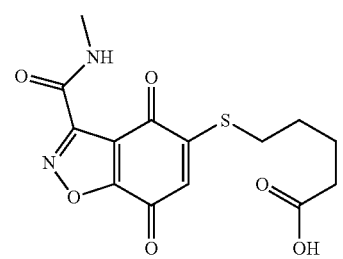 [SMILES: CNC(=O)c1noc2c1C(=O)C(SCCCCC(=O)O)=CC2=O]
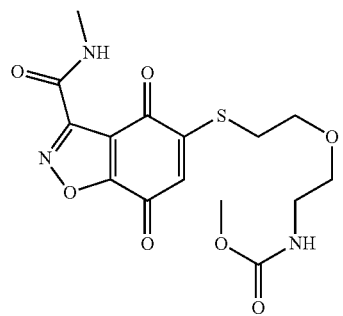 [SMILES: CNC(=O)c1noc2c1C(=O)C(SCCOCCNC(=O)OC)=CC2=O]
TABLE 1-continued
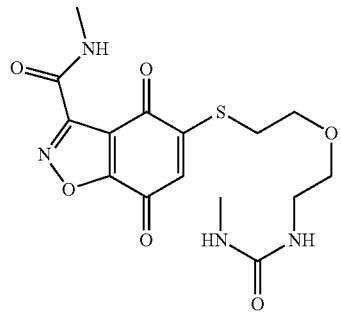
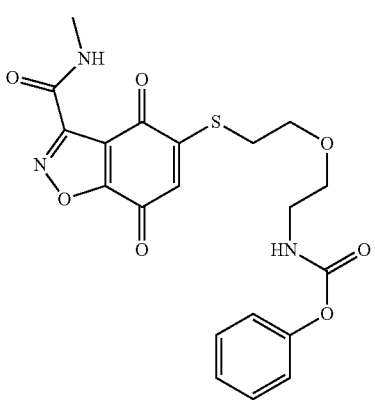 [SMILES: CNC(=O)c1noc2c1C(=O)C(SCCOCCNC(=O)Oc1ccccc1)=CC2=O]
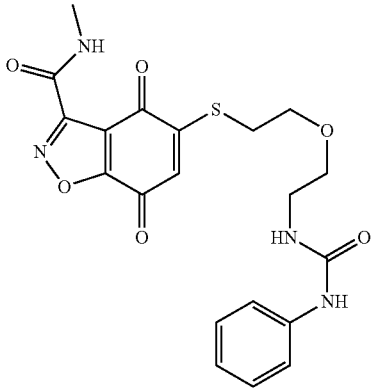 [SMILES: CNC(=O)c1noc2c1C(=O)C(SCCOCCNC(=O)Nc1ccccc1)=CC2=O]
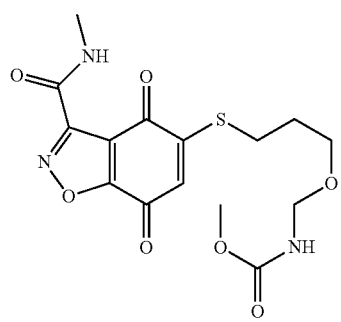

US 10,071,076 B2
| 239 | 240 |
|---|---|
| TABLE 1-continued | TABLE 1-continued |
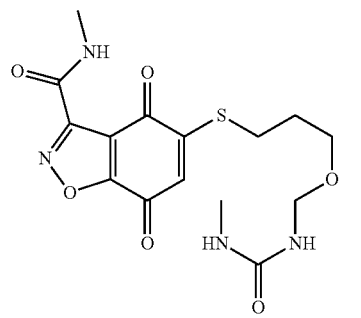 [SMILES: CNC(=O)NCOCCCSC1=CC(=O)c2onc(C(=O)NC)c2C1=O]
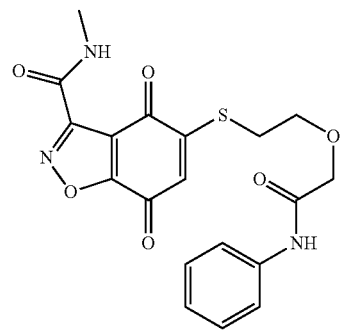
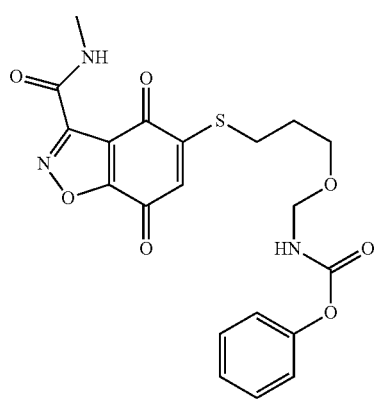 [SMILES: CNC(=O)c1noc2c1C(=O)C(SCCCOCNC(=O)Oc1ccccc1)=CC2=O]
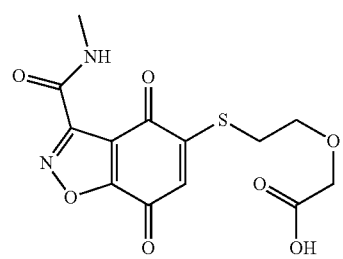
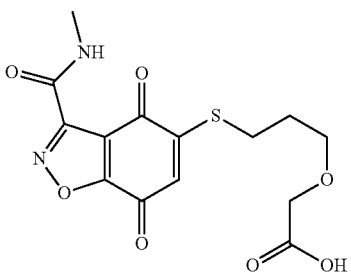
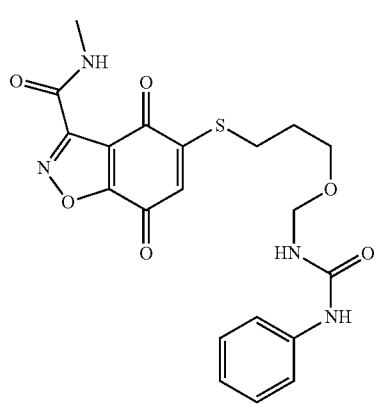 [SMILES: CNC(=O)c1noc2c1C(=O)C(SCCCOCNC(=O)Nc1ccccc1)=CC2=O]
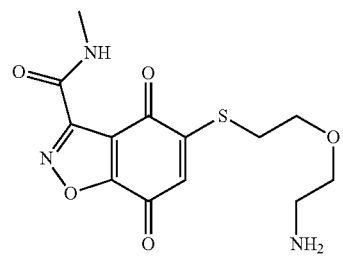
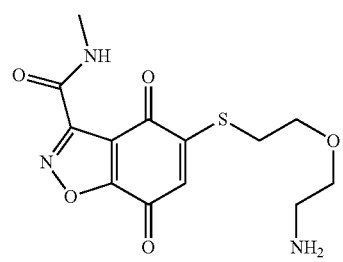
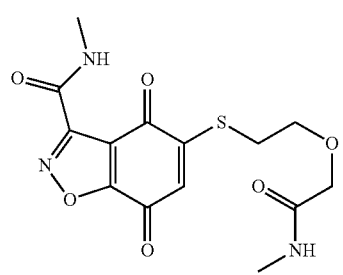 [SMILES: CNC(=O)COCCSC1=CC(=O)c2onc(C(=O)NC)c2C1=O]
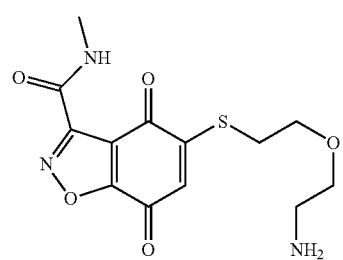

TABLE 1-continued

TABLE 1-continued
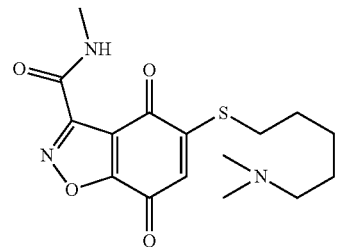 [SMILES: CNC(=O)c1noc2c1C(=O)C(SCCCCCN(C)C)=CC2=O]
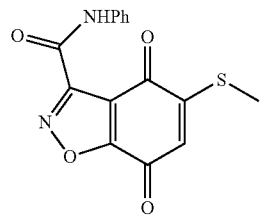
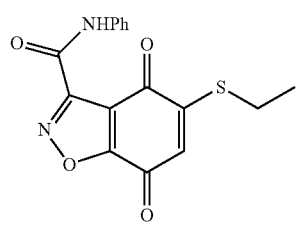
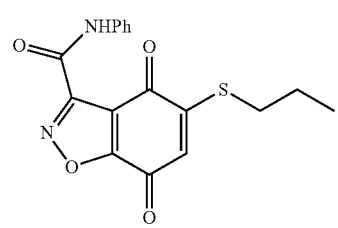
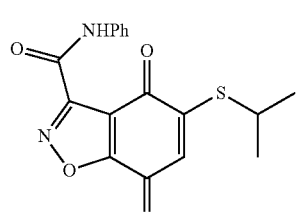
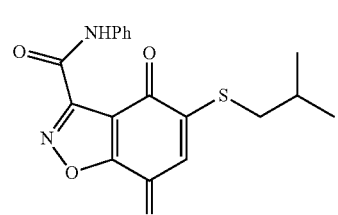
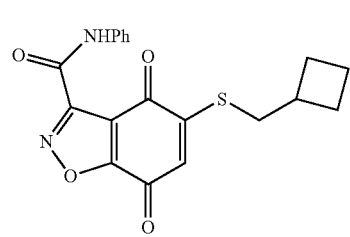
TABLE 1-continued
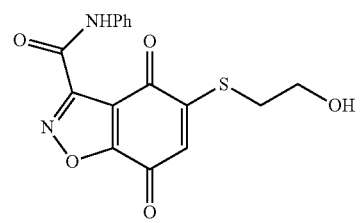
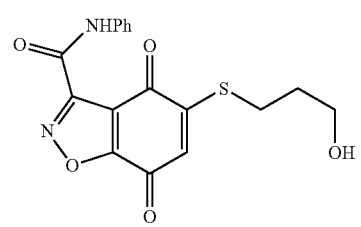
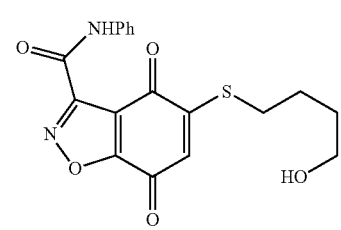
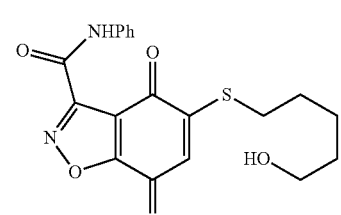
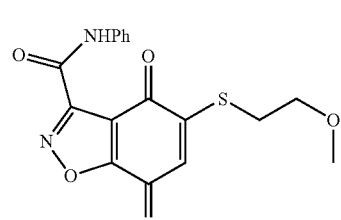
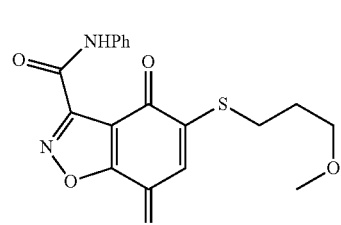
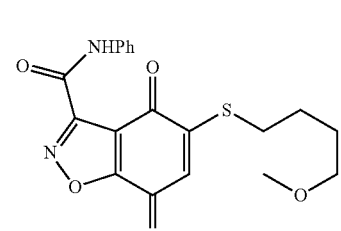

TABLE 1-continued
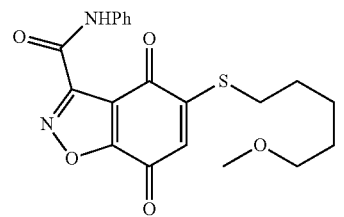
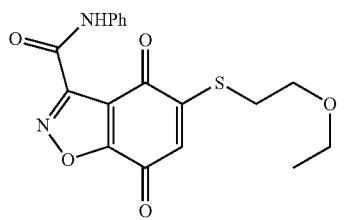
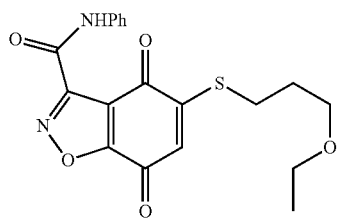
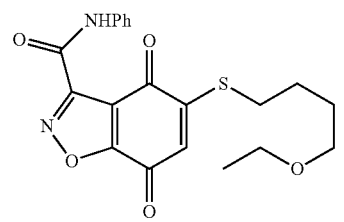
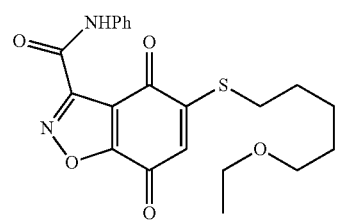
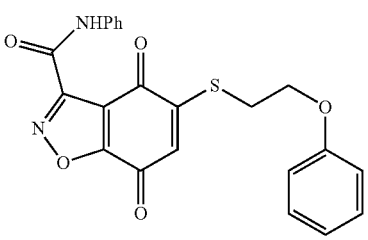
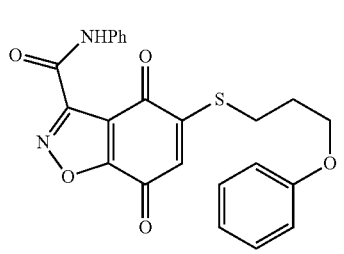
TABLE 1-continued
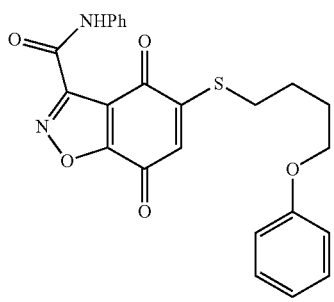
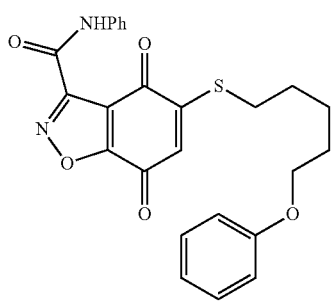
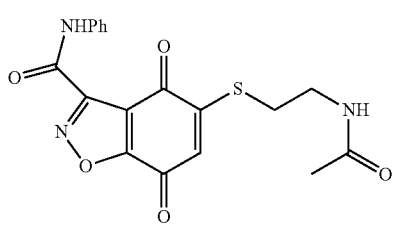
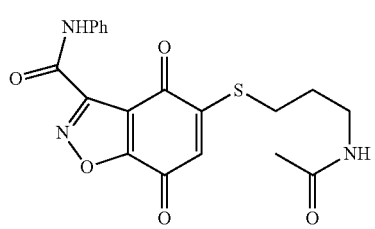
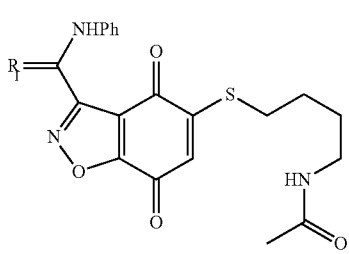
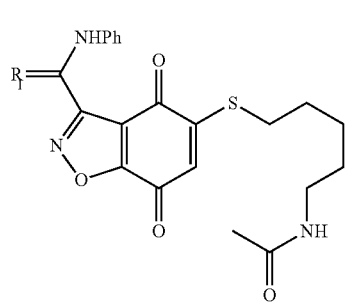

TABLE 1-continued
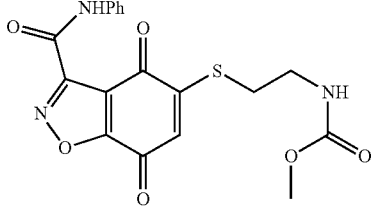
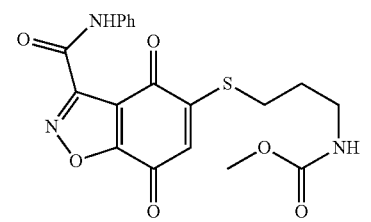
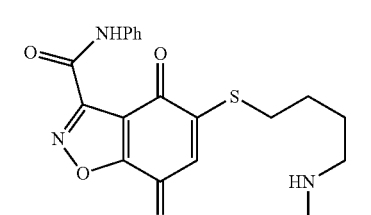
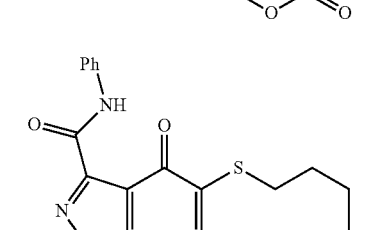
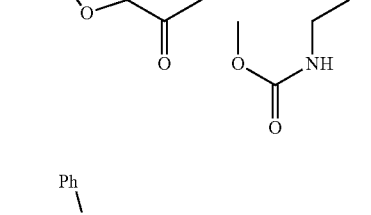
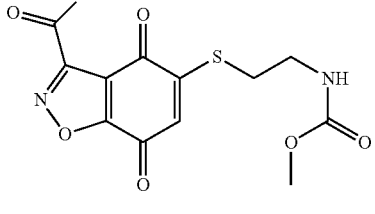
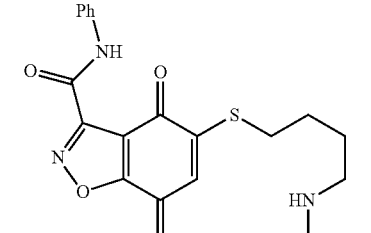

TABLE 1-continued
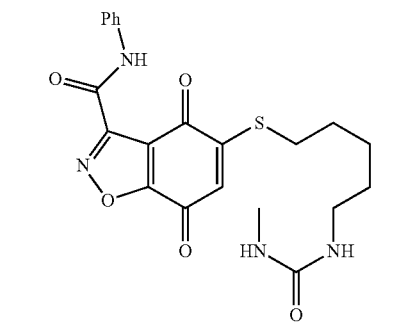 [SMILES: CNC(=O)NCCCCCSC1=CC(=O)c2onc(C(=O)Nc3ccccc3)c2C1=O]
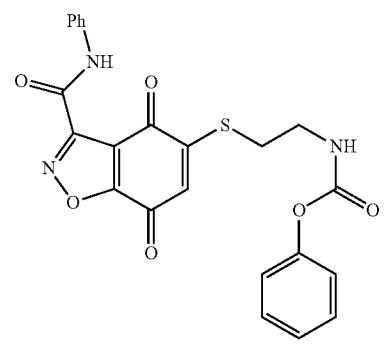 [SMILES: O=C(NCCSC1=CC(=O)c2onc(C(=O)Nc3ccccc3)c2C1=O)Oc1ccccc1]
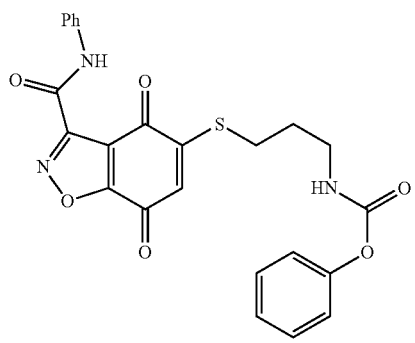 [SMILES: O=C(NCCCSC1=CC(=O)c2onc(C(=O)Nc3ccccc3)c2C1=O)Oc1ccccc1]
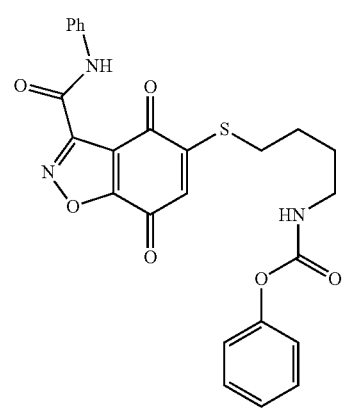 [SMILES: O=C(NCCCCSC1=CC(=O)c2onc(C(=O)Nc3ccccc3)c2C1=O)Oc1ccccc1]
TABLE 1-continued
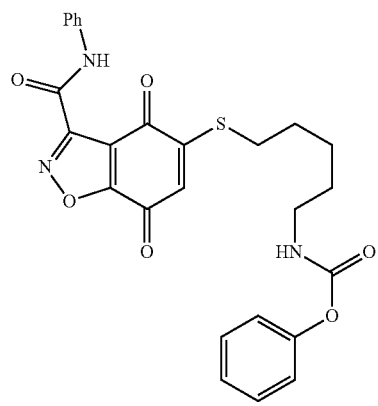 [SMILES: O=C(NCCCCCSC1=CC(=O)c2onc(C(=O)Nc3ccccc3)c2C1=O)Oc1ccccc1]
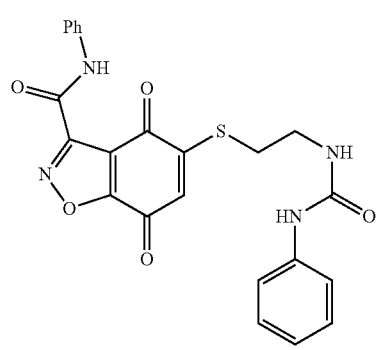
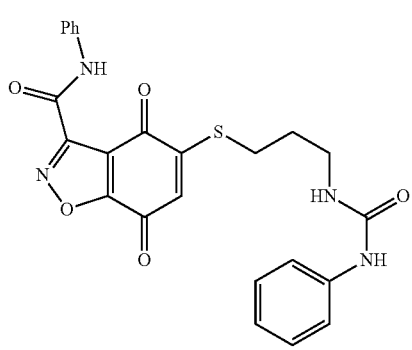 [SMILES: O=C(NCCCSC1=CC(=O)c2onc(C(=O)Nc3ccccc3)c2C1=O)Nc1ccccc1]
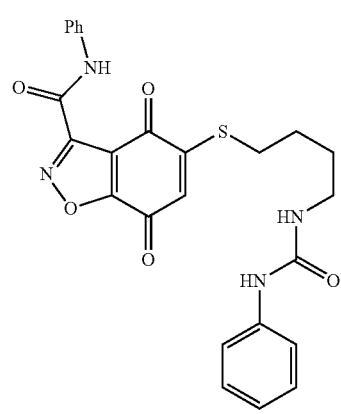

TABLE 1-continued
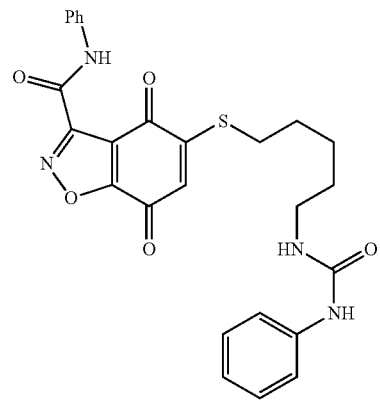 [SMILES: O=C(NCCCCCSC1=CC(=O)c2onc(C(=O)Nc3ccccc3)c2C1=O)Nc1ccccc1]
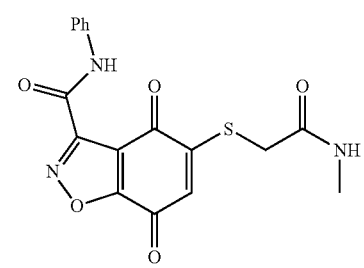 [SMILES: CNC(=O)CSC1=CC(=O)c2onc(C(=O)Nc3ccccc3)c2C1=O]
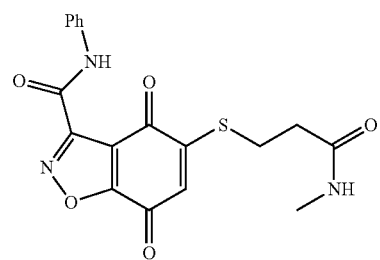 [SMILES: CNC(=O)CCSC1=CC(=O)c2onc(C(=O)Nc3ccccc3)c2C1=O]
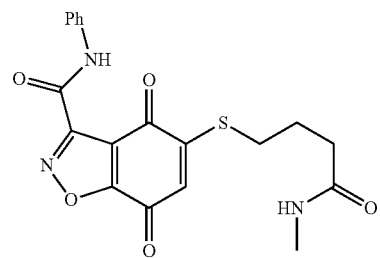 [SMILES: CNC(=O)CCCSC1=CC(=O)c2onc(C(=O)Nc3ccccc3)c2C1=O]
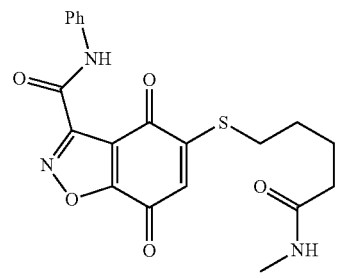 [SMILES: CNC(=O)CCCCSC1=CC(=O)c2onc(C(=O)Nc3ccccc3)c2C1=O]
TABLE 1-continued
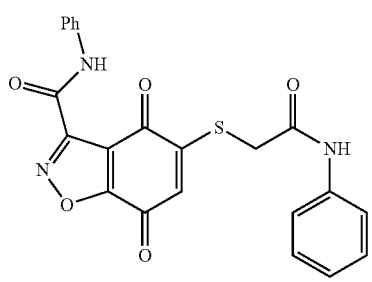 [SMILES: O=C(CSC1=CC(=O)c2onc(C(=O)Nc3ccccc3)c2C1=O)Nc1ccccc1]
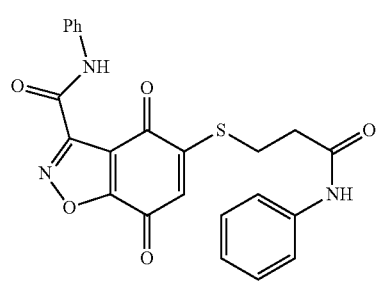 [SMILES: O=C(CCSC1=CC(=O)c2onc(C(=O)Nc3ccccc3)c2C1=O)Nc1ccccc1]
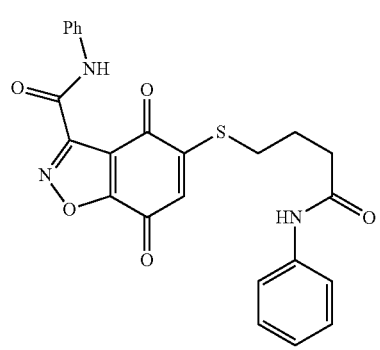 [SMILES: O=C(CCCSC1=CC(=O)c2onc(C(=O)Nc3ccccc3)c2C1=O)Nc1ccccc1]
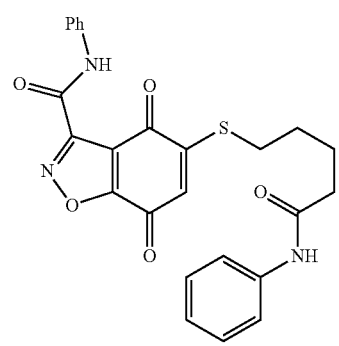 [SMILES: O=C(CCCCSC1=CC(=O)c2onc(C(=O)Nc3ccccc3)c2C1=O)Nc1ccccc1]
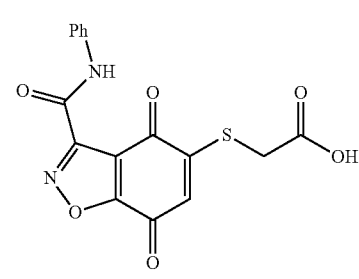 [SMILES: O=C(O)CSC1=CC(=O)c2onc(C(=O)Nc3ccccc3)c2C1=O]

TABLE 1-continued
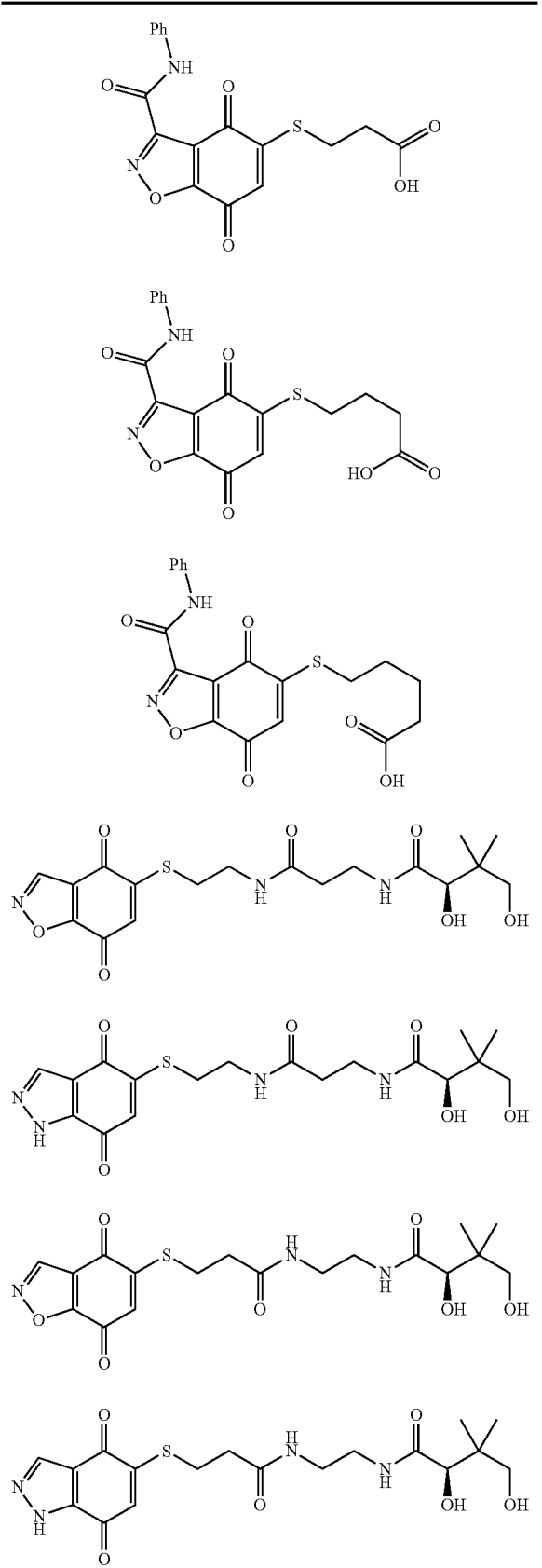
TABLE 1-continued
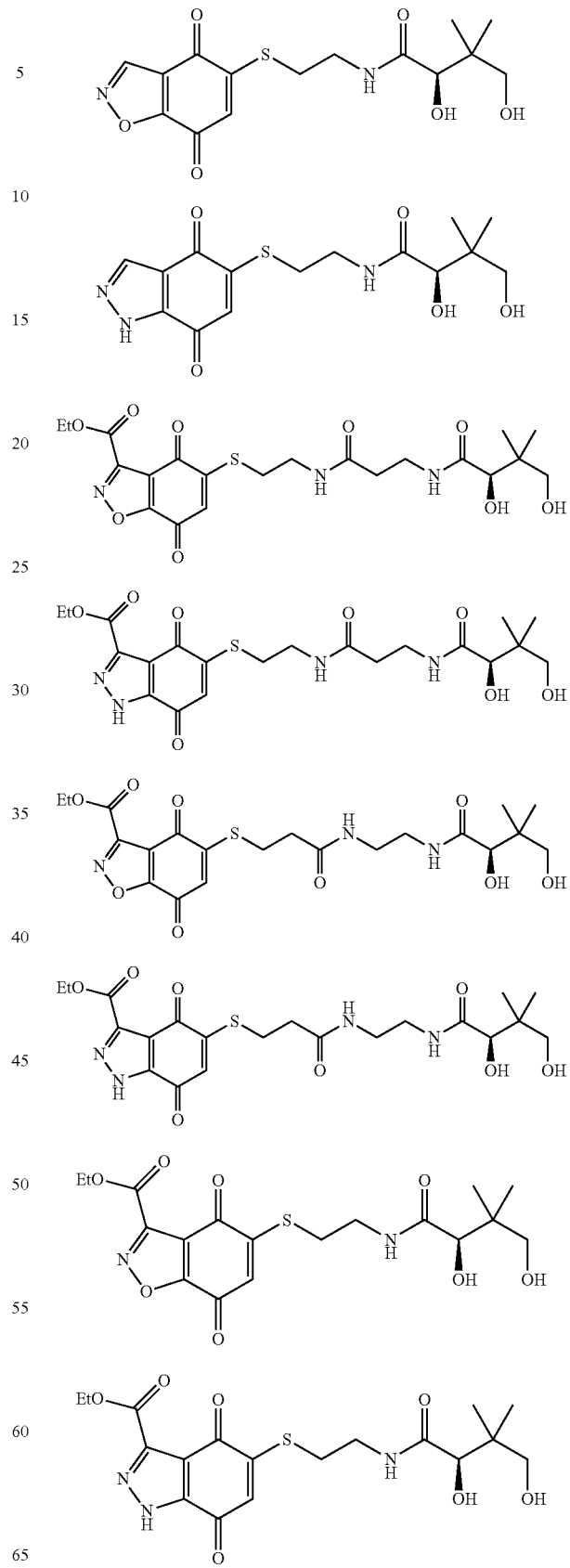

TABLE 1-continued

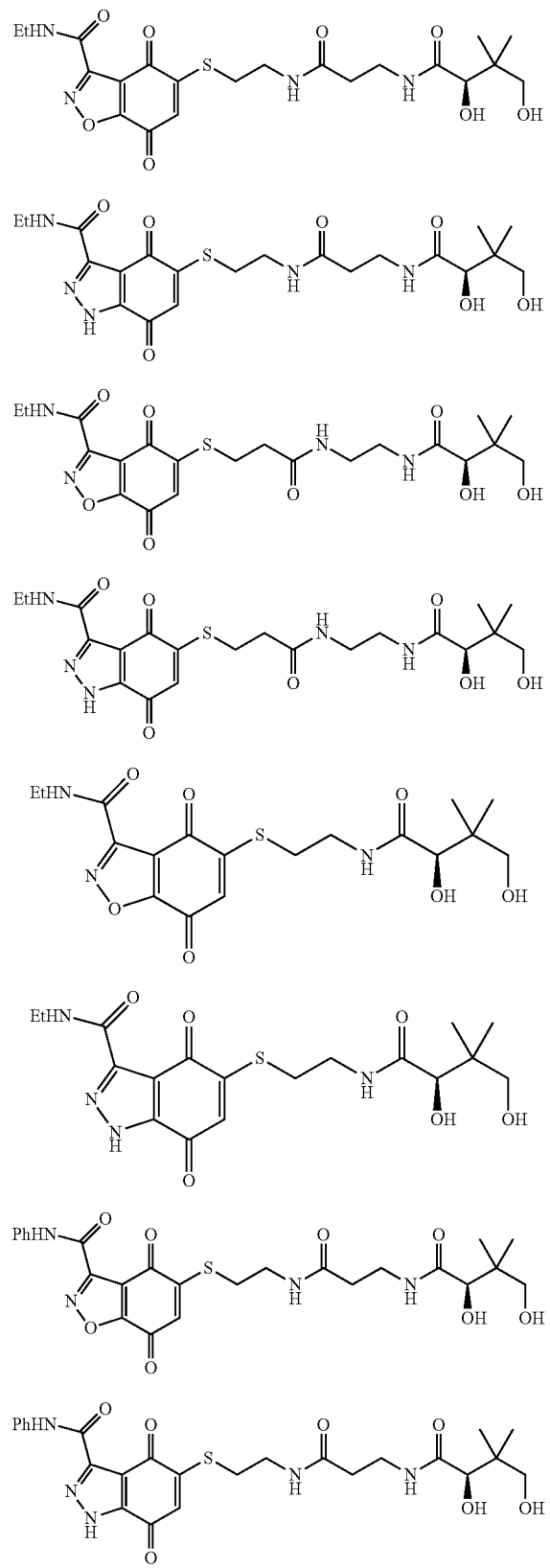

TABLE 1-continued

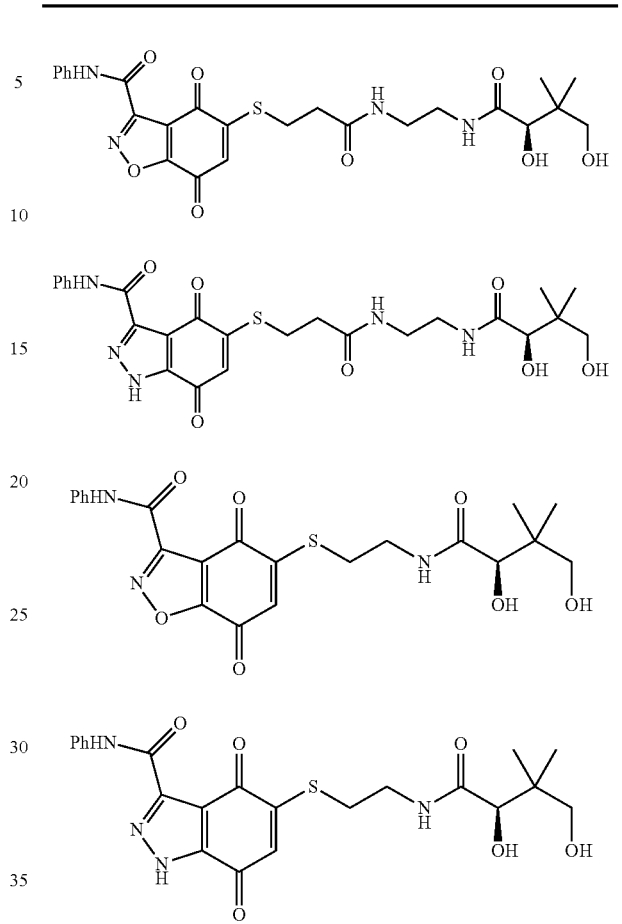

and pharmaceutically acceptable salts or prodrugs thereof.

10. The method of claim 1, wherein said active compound is a compound Formula Ia.

11. The method of claim 1, wherein said active compound is a compound Formula Ib.

12. The method of claim 1, wherein said active compound is a compound Formula Ic.

13. The method of claim 2, wherein said cancer exhibits elevated levels of fatty acid synthase.

14. The method of claim 1, wherein said active compound has the following structure:

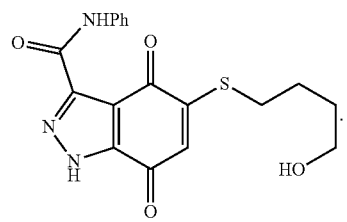

* * * * *

UNITED STATES PATENT AND TRADEMARK OFFICE
CERTIFICATE OF CORRECTION

Page 1 of 2

PATENT NO. : 10,071,076 B2
APPLICATION NO. : 15/193793
DATED : September 11, 2018
INVENTOR(S) : Kridel et al.

It is certified that error appears in the above-identified patent and that said Letters Patent is hereby corrected as shown below:

In the Specification

Column 7, Line 14: Please correct "$N(R_e)C(O)NR_aR_b$" to read -- $N(R_c)C(O)NR_aR_b$ --

In the Claims

Claim 9, Column 146, Lines 15-25: Please correct

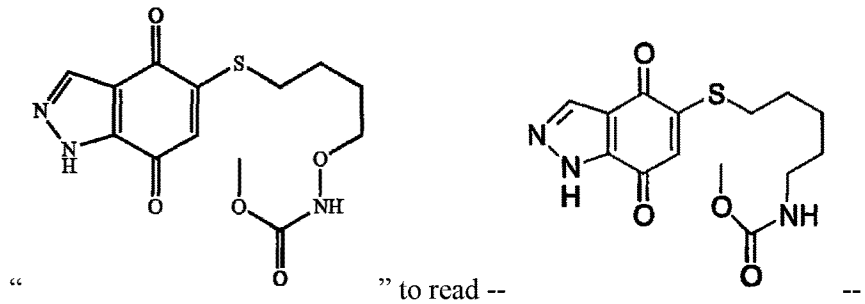

" to read --                                    --

Claim 9, Column 208, Lines 1-10: Please correct

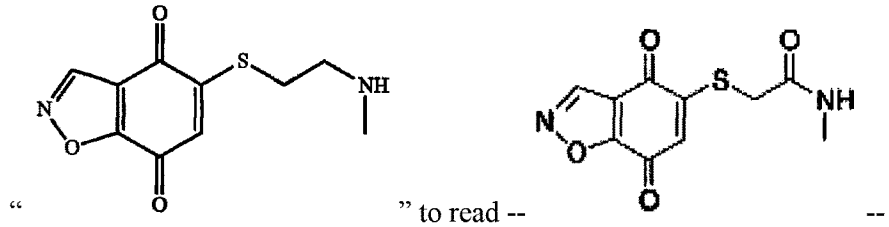

" to read --                                    --

Signed and Sealed this
Nineteenth Day of February, 2019

Andrei Iancu
*Director of the United States Patent and Trademark Office*

CERTIFICATE OF CORRECTION (continued)
U.S. Pat. No. 10,071,076 B2

Claim 9, Column 236, Lines 40-50: Please correct

" 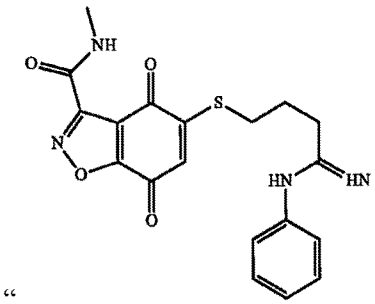 " to read -- 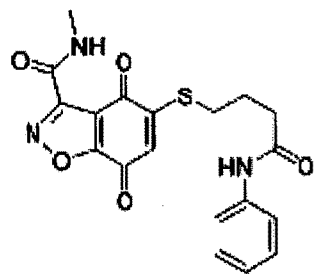 --

Claim 9, Column 246, Lines 45-65: Please correct

" 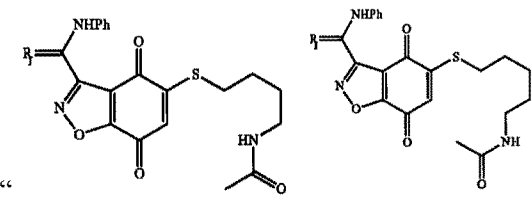 " to read

-- 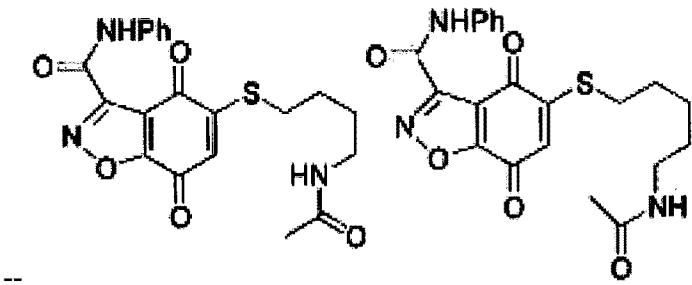 --